United States Patent
Hamilton

(10) Patent No.: US 9,416,389 B2
(45) Date of Patent: Aug. 16, 2016

(54) METHODS FOR REDUCING MANNOSYLTRANSFERASE ACTIVITY IN LOWER EUKARYOTES

(71) Applicant: Merck Sharp & Dohme Corp., Rahway, NJ (US)

(72) Inventor: Stephen R. Hamilton, Enfield, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/375,800

(22) PCT Filed: Feb. 13, 2013

(86) PCT No.: PCT/US2013/025917
§ 371 (c)(1),
(2) Date: Jul. 31, 2014

(87) PCT Pub. No.: WO2013/123034
PCT Pub. Date: Aug. 22, 2013

(65) Prior Publication Data
US 2015/0017686 A1    Jan. 15, 2015

Related U.S. Application Data

(60) Provisional application No. 61/599,616, filed on Feb. 16, 2012.

(51) Int. Cl.
| | | |
|---|---|---|
| *C12P 21/00* | (2006.01) | |
| *C07K 14/39* | (2006.01) | |
| *C12N 15/81* | (2006.01) | |
| *C07K 16/28* | (2006.01) | |
| *C07K 14/715* | (2006.01) | |

(52) U.S. Cl.
CPC .............. *C12P 21/005* (2013.01); *C07K 14/39* (2013.01); *C07K 16/2878* (2013.01); *C12N 15/815* (2013.01); *C07K 14/7151* (2013.01); *C07K 2317/14* (2013.01); *C07K 2319/30* (2013.01)

(58) Field of Classification Search
None
See application file for complete search history.

(56) References Cited

U.S. PATENT DOCUMENTS

2011/0207214 A1    8/2011    Helenius et al.

FOREIGN PATENT DOCUMENTS

| WO | WO0009550 | 2/2000 | |
|---|---|---|---|
| WO | WO 2013/062940 A1 * | 5/2013 | ............. C12N 15/09 |

OTHER PUBLICATIONS

Dean et al., The VRG4 gene is required for GDP-mannose transport into the lumen of the Golgi in the yeast., J. Biol. Chem., 1997, No. 50, pp. 31908-31914, 272.
Gao et al., Identification of a conserved motif in the yeast golgi GDP-mannose transporter required for binding to nucleotide sugar, J. Biol. Chem., 2001, No. 6, pp. 4424-4432, 276.
Nishikawa et al., Molecular and phenotypic analysis of CaVRG4, J. Bacteriol., 2002, No. 1, pp. 29-42, 184.
International Search Report—Mailing Date: Apr. 24, 2013.
Written Opinion—mailing date: Apr. 24, 2013.
Poster et al., The Journal of Biological Chemistry, vol. 27, Issue of Feb. 16, 1996, pp. 3837-3845.
Li et al., Letters, Nature Biotechnology, vol. 24, No. 2, 2006, pp. 210-215.
Ha, et al., mAbs—Biochemical and Biophysical Characterization of Humanized IgG1 Produced in Pichia Pastoris, vol. 3, issue 5, pp. 453-460.
Hopkins et al., Elimination of Beta-mannose glycan structures in Pichia Pastoris—Glycobiology, vol. 21, No. 12, 2011, pp. 1616-1626.
Arakawa et al., J. Gen. Appl. Microbiol. vol. 52, 2006, pp. 137-145.

* cited by examiner

*Primary Examiner* — Suzanne M Noakes
(74) *Attorney, Agent, or Firm* — John David Reilly; Gloria Fuentes

(57) ABSTRACT

Disclosed are methods for reducing detectable mannosylation of N-linked and O-linked oligosaccharides in lower eukaryote host cells. In particular, recombinant lower eukaryote host cells are provided in which expression of the GDP-mannose transporter encoded by the Vanadate Resistant Glycosylation 4 (VRG4) gene has been disrupted. In general, the VRG4 gene is essential for cell viability; however, the present invention provides host cells that are viable when expression of the VRG4 gene therein has been disrupted. The host cells are capable of producing proteins or glycoproteins that have reduced or no detectable α-linked mannose, β-linked mannose or phosphomannose containing N- and/or O-glycans.

15 Claims, 34 Drawing Sheets

VRG4 deletions in various glycoengineered strain backgrounds

| Strain | | Clones obtained | Transporters present | Translocated nucleotide-sugar |
|---|---|---|---|---|
| WT | NRRL-Y11430 → pGLY6 | 0 | | |
| | YGLY1-3 [ura5Δ::ScSUC2] → pGLY40 | | | |
| GFI 1.0 | YGLY2-3 [ura5Δ::ScSUC2 och1Δ::lacZ-URA5-lacZ] c/s + pGLY43a → | 1 | | |
| | YGLY6-3 [ura5Δ::ScSUC2 och1Δ::lacZ bmt2Δ::lacZ-URA5-lacZ/KlMNN2-2] c/s + pGLY48 → | 1 | KlMNN2-2 | UDP-GlcNAc |
| | YGLY10-3 [ura5Δ::ScSUC2 och1Δ::lacZ bmt2Δ::lacZ/KlMNN2-2 mnn4L1Δ::lacZ-URA5-lacZ/MmSLC35A3] c/s + pGLY45 → | 1 | MmSLC35A3 | UDP-GlcNAc |
| | YGLY14-3 (YGLY28269*) [ura5Δ::ScSUC2 och1Δ::lacZ bmt2Δ::lacZ/KlMNN2-2 mnn4L1Δ::lacZ/MmSLC35A3 pno1Δmnn4Δ::lacZ-URA5-lacZ] c/s + pGLY1430 → | 0 (3) | | |

FIG.2-1

| | | | |
|---|---|---|---|
| GFI 3.0 | YGLY2798<br>[ura5Δ::ScSUC2 och1Δ::lacZ bmt2Δ::lacZ/KlMNN2-2<br>mnn4L1Δ::lacZ/MmSLC35A3 pno1Δ mnn4Δ::lacZ<br>ADE1::lacZ-URA5-lacZ/NA10/MmSLC35A3/FB8] | MmSLC35A3 | UDP-GlcNAc |
| | ↓ c/s + pGLY582 | | |
| GFI 3.5 | YGLY3853<br>[ura5Δ::ScSUC2 och1Δ::lacZ bmt2Δ::lacZ/KlMNN2-2<br>mnn4L1Δ::lacZ/MmSLC35A3 pno1Δ mnn4Δ::lacZ<br>ADE1::lacZ/NA10/MmSLC35A3/FB8<br>his1Δ::lacZ-URA5-lacZ/ScGAL10/XB33/DmUGT] | DmUGT | UDP-Gal |
| | ↓ pGLY167b | 6 | |
| GFI 5.0 | YGLY4754<br>[ura5Δ::ScSUC2 och1Δ::lacZ bmt2Δ::lacZ/KlMNN2-2<br>mnn4L1Δ::lacZ/MmSLC35A3 pno1Δ mnn4Δ::lacZ<br>ADE1::lacZ/NA10/MmSLC35A3/FB8<br>his1Δ::lacZ-URA5-lacZ/ScGAL10/XB33/DmUGT<br>arg1Δ::HIS1/KD53/TC54] | 5 | |

*PCR knock-out of VRG4 could not be confirmed in YGLY14-3, consequently this strain was remade from the YGLY10-3. The resultant strain YGLY28269 gave three VRG4 knock-out strains YGLY29175 to 29177.

c/s – counterselected in the presence of 5-fluoroorotic acid (5-FOA) to produce a number of strains in which the URA5 gene has been lost and only the lacZ repeats

FIG.2-2

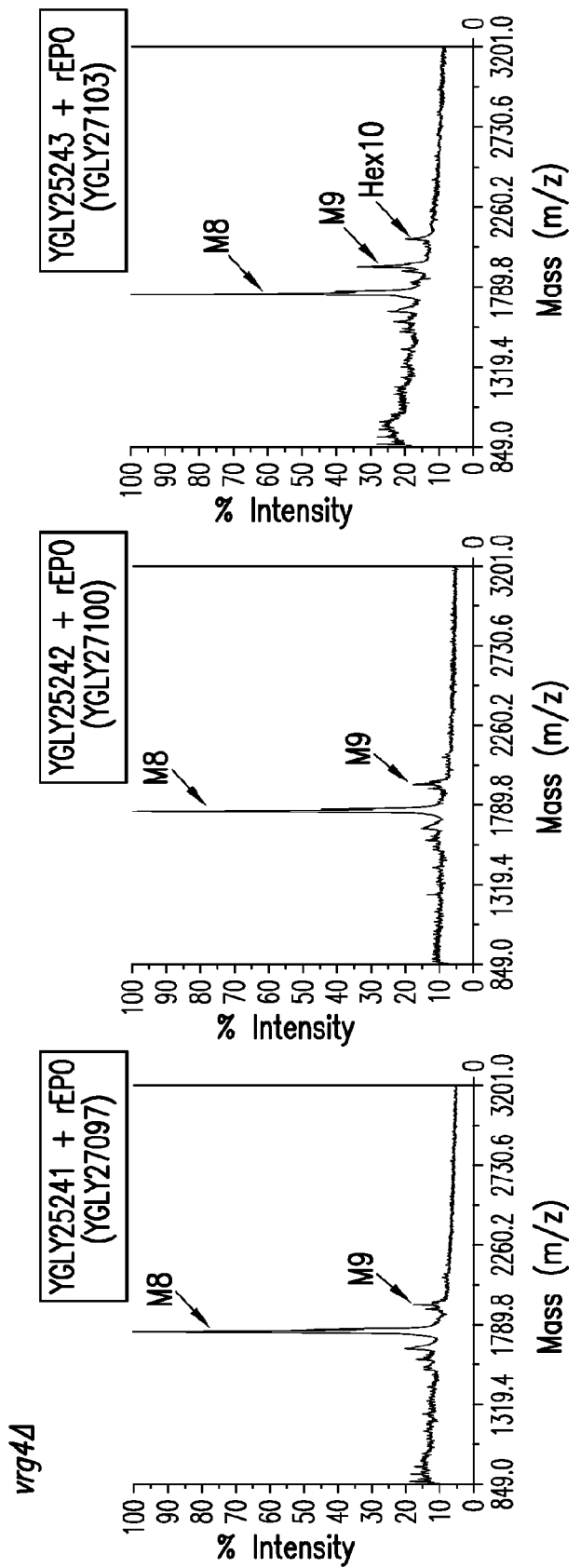

SEQUENCE LISTING

<160> NUMBER OF SEQ ID NOS: 77

<210> SEQ ID NO 1
<211> LENGTH: 968
<212> TYPE: DNA
<213> ORGANISM: Artificial
<220> FEATURE:
<223> OTHER INFORMATION: Pichia pastoris VRG4 5' knock-out region

<400> SEQUENCE: 1

```
gcgagctcgt ctacaaacag tatcactgtt cgtcaggatc cagaaatcga acgggagatg      60
gagttgaaaa ggcagcaaga agaacaggaa aagatggaac tgactgatat gatcaagact     120
gctctacgag accaggtaga gcatatgcct gctgccaaaa cgatcgatgt taacaaaatg     180
acgacagaag atttgctaaa ctggcacctg ggagatcagt ccacaaaaaa cagttctatc     240
catcgtgaat ttgatccatc agagcaagaa gagtttaata ggctagcaca aaagattgcc     300
aaagttaaga taaagaacga tctgaaggaa aaatttggca aatcaaaacc gaaaccttct     360
ggaaaagttc tccaattgaa cacttcaaat gacggatcca aatatcaaaa ggctctacaa     420
aaggagttgg cagatctttc cttcaaggag aaattcagcg tagctactga gatcaacgat     480
gatctgagtg agttactcgg cgagaacatt ttcgtttcag actctgtttc aagagatgat     540
gcgaccgaag atattgacgc gttgttgaag gacagctcag ctaaaaagcc cgaaacaata     600
gagagacaaa gcgttgcgcc gacttctcaa aagcttaatt ccatcgatcc cgaggccgat     660
aaatttctcg atgatctact cggctaaatc tcgtacctat tctgctcttt tcgtgtcgtc     720
ttccggttca cccctatctg cattcttatc cataactaat ttatttcatg tatattgcca     780
attacaattg cgcgcaccag cctcgcgttt cattccacag ctgtgcaacc attagggaaa     840
cgtttttcca tcgcgctttc ctcctaatcc tactgaaaaa ctaaaaaaaa acaagttgct     900
tcagtacttt ttctcttttg tggacgtgtt ctaatactta tcatcaaagc aagacatcgg     960
ccggccgc                                                              968
```

<210> SEQ ID NO 2
<211> LENGTH: 1135
<212> TYPE: DNA
<213> ORGANISM: Artificial
<220> FEATURE:
<223> OTHER INFORMATION: Pichia pastoris VRG4 3' knock-out region

<400> SEQUENCE: 2

```
ccactagtgc tttgaacaag cttccaattg ccctgtctgg tttgctattt ttcaaggctc       60
```

```
ctatcaactt ctattctatc agccctatct ttattggttt tgccgctggt ctagtctatg      120
ccattgccaa gcagaagcaa aagaaggaag acgagttgca gttaccaact gacaagagct      180
agattataag gaaagaaac actctatata tggtttattt attgattttc agactgaagt       240
ccactatacc gactccctga tggatcgaag aagtactata gatatcaatt tcattgcaca      300
gataatcctt tatattatcc aaagtcaaac ctccactgca ctccaaatag aatttcttgt      360
ttgtgttagc ccacttgttc ttcaaattga tggctgcgac tttcagcccc tcaccggtga      420
aattgtccaa catgataata tcggctcctg ctgctatggc ctcattggct tcagcttcgt      480
cttgcacttc cacctcaatc ttagtgctaa atccaatcac tttttgagca ctttcaatgg      540
ccttggtgat cgaaccagtt gaccagatat ggttgtcttt cagcataatc atagaactta      600
gatcataacg gtgactgtcg catccaccaa cgagcattga gtattttcc aacaatcgta       660 atcctggagt agtctttctg gttcccgcaa tgattccttt gtatccagct tctctagccc      720
tttttatagt aatatagctt tgagtagcga ccccagagca tcttgctaga atattcagcg      780
ataaccgttc agcgaggagg atgtttcgaa cagggccctt aacgagtgca actttcactt      840
taccctcgtc tccaccacaa atgtaatccc cttcctttag aaaccactcg acctccaaac      900
cgcattgttt gtaaacctct tgtgcaaacg gtactccact aatgactccg ttggacttta      960
tccatagagt agcactctgc aggttttcac ccaccacata tcctccgtaa tcaaaagaag     1020
gggtatcctc gtctagccag ctggtgatat cttctcttcca ttttccgtcc acaggtaaaa     1080
gatgggcaaa ttcggggttg gggttggaga aactcatagt cgtctacgtc gaccc          1135

<210> SEQ ID NO 3
<211> LENGTH: 2990
<212> TYPE: DNA
<213> ORGANISM: Pichia pastoris

<400> SEQUENCE: 3
aaatatgcca gaaggccgat gatagataat tcatacagat atggtttgga gtctacaaac      60
agtatcactg ttcgtcagga tccagaaatc gaacgggaga tggagttgaa aaggcagcaa     120
gaagaacagg aaaagatgga actgactgat atgatcaaga ctgctctacg agaccaggta     180
gagcatatgc ctgctgccaa aacgatcgat gttaacaaaa tgacgacaga agatttgcta     240
aactggcacc tgggagatca gtccacaaaa aacagttcta tccatcgtga atttgatcca     300
tcagagcaag aagagtttaa taggctagca caaaagattg ccaaagttaa gataaagaac     360
gatctgaagg aaaaatttgg caaatcaaaa ccgaaacctt ctggaaaagt tctccaattg     420
aacacttcaa atgacggatc caaatatcaa aaggctctac aaaaggagtt ggcagatctt     480
tccttcaagg agaaattcag cgtagctact gagatcaacg atgatctgag tgagttactc     540
ggcgagaaca ttttcgtttc agactctgtt tcaagagatg atgcgaccga agatattgac     600
gcgttgttga aggacagctc agctaaaaag cccgaaacaa tagagagaca aagcgttgcg     660
ccgacttctc aaaagcttaa ttccatcgat cccgaggccg ataaatttct cgatgatcta     720
ctcggctaaa tctcgtacct attctgctct tttcgtgtcg tcttccggtt caccctatc      780 tgcattctta tccataacta attatttca tgtatattgc caattacaat gcgcgcacc       840 agcctcgcgt ttcattccac agctgtgcaa ccattaggga aacgttttc catcgcgctt      900 tcctcctaat cctactgaaa aactaaaaaa aaacaagttg cttcagtact ttttctcttt      960
tgtggacgtg ttctaatact tatcatcaaa gcaagacatc atggctgaca aaggatcggt    1020
```

```
agcggctaaa tcgcttacca actctgcacc cttatccatc ttttcttact gtgctgcatc    1080
aattctgatg acagttacca ataagtatgc cgtgtccggt gtcgatttca actttaactt    1140 cttttttgctt gccgttcagg gaatcgtttg tattaccttg attagctcgt tgaagcaatt    1200
gaatgttatc acctttagag agttcaacaa ggttgaagca agaaatggt tcccaatcgc    1260 cgtgctgtta gttgtcatga tttataccctc ctccaaggct ctacagtatc tgagcattcc    1320
aatttacacg atattcaaaa acttgaccat tatccttatt gcttatggtg aagtcatctg    1380
gttcggaggc cgtgtgacca acttggctct gggctcgttt gtattgatgg tgctctcctc    1440
tgcagtggct tcttatggtg attctaatgt tgacactgga aaactcaatt ttaacattgg    1500
ctatttctgg atgttcacca actgtttctc ctctgccgca tttgtgttgt tcatgagaaa    1560
gagaataaag ttgaccaact tcaaagactt tgacaccatg tattacaaca accttctctc    1620
cattccaatt ttgctctttg catctttgac tactgaagac tggtccgcta aaaacatagc    1680
tcagaacttc cctgaagaca ccaaatacgc tgtcatcgct tccatgatta tttcaggaat    1740
gtctgccgtg ggtatctcat acacatctgc atggtgtgtc cgtgtgacat cttccacgac    1800
atactcgatg gttggtgctt tgaacaagct tccaattgcc ctgtctggtt tgctattttt    1860
caaggctcct atcaacttct attctatcag ctctatcttt attggttttg ccgctggtct    1920
agtctatgcc attgccaagc agaagcaaaa gaaggaagac gagttgcagt taccaactga    1980
caagagctag attataagga aaagaaacac tctatatatg gtttatttat tgattttcag    2040
actgaagtcc actataccga ctccctgatg gatcgaagaa gtactataga tatcaatttc    2100
attgcacaga taatccttta tattatccaa agtcaaacct ccactgcact ccaaatagaa    2160
tttcttgttt gtgttagccc acttgttctt caaattgatg gctgcgactt tcagcccctc    2220
accggtgaaa ttgtccaaca tgataatatc ggctcctgct gctatggcct cattggcttc    2280
agcttcgtct tgcacttcca cctcaatctt agtgctaaat ccaatcactt tttgagcact    2340
ttcaatggcc ttggtgatcg aaccagttga ccagatatgg ttgtctttca gcataatcat    2400
agaacttaga tcataacggt gactgtcgca tccaccaacg agcattgagt attttttccaa    2460 caatcgtaat cctggagtag tctttctggt tcccgcaatg attcctttgt atccagcttc    2520 tctagcccctt tttatagtaa tatagctttg agtagcgacc ccagagcatc ttgctagaat    2580
attcagcgat aaccgttcag cgaggaggat gtttcgaaca gggcccttaa cgagtgcaac    2640 tttcactta ccctcgtctc caccacaaat gtaatcccct tcctttagaa accactcgac    2700
ctccaaaccg cattgtttgt aaacctcttg tgcaaacggt actccactaa tgactccgtt    2760
ggactttatc catagagtag cactctgcag gttttcaccc accacatatc ctccgtaatc    2820
aaaagaaggg gtatcctcgt ctagccagct ggtgatatct ttcttccatt ttccgtccac    2880
aggtaaaaga tgggcaaatt cggggttggg gttggagaaa ctccatagtcg tctacaaatg    2940 tgaaggaaat ggatgatatt gttaggccat tctccgcgag tcattccggg                2990
```

<210> SEQ ID NO 4  
<211> LENGTH: 484  
<212> TYPE: PRT  
<213> ORGANISM: Artificial  
<220> FEATURE:  
<223> OTHER INFORMATION: HSA-TNFR-Fc double mutein ORF

<400> SEQUENCE: 4

```
Met Lys Trp Val Thr Phe Ile Ser Leu Leu Phe Leu Phe Ser Ser Ala
1               5                   10                  15
```

-continued

```
Tyr Ser Leu Pro Ala Gln Val Ala Phe Thr Pro Tyr Ala Pro Glu Pro
             20                  25                  30

Gly Ser Thr Cys Arg Leu Arg Glu Tyr Asp Gln Thr Ala Gln Met
         35                  40                  45

Cys Cys Ser Lys Cys Ser Pro Gly Gln His Ala Lys Val Phe Cys Thr
     50                  55                  60

Lys Thr Ser Asp Thr Val Cys Asp Ser Cys Glu Asp Ser Thr Tyr Thr
 65                  70                  75                  80

Gln Leu Trp Asn Trp Val Pro Glu Cys Leu Ser Cys Gly Ser Arg Cys
                 85                  90                  95

Ser Ser Asp Gln Val Glu Thr Gln Ala Cys Thr Arg Glu Gln Asn Arg
             100                 105                 110

Ile Cys Thr Cys Arg Pro Gly Trp Tyr Cys Ala Leu Ser Lys Gln Glu
         115                 120                 125

Gly Cys Arg Leu Cys Ala Pro Leu Arg Lys Cys Arg Pro Gly Phe Gly
     130                 135                 140

Val Ala Arg Pro Gly Thr Glu Thr Ser Asp Val Val Cys Lys Pro Cys
145                 150                 155                 160

Ala Pro Gly Thr Phe Ser Asn Thr Thr Ser Ser Thr Asp Ile Cys Arg
                 165                 170                 175

Pro His Gln Ile Cys Asn Val Val Ala Ile Pro Gly Asn Ala Ser Met
             180                 185                 190

Asp Ala Val Cys Thr Ser Thr Ser Pro Thr Arg Ser Met Ala Pro Gly
         195                 200                 205

Ala Val His Leu Pro Gln Pro Val Ser Thr Arg Ser Gln His Thr Gln
     210                 215                 220

Pro Thr Pro Glu Pro Ser Thr Ala Pro Ser Thr Ser Phe Leu Leu Pro
225                 230                 235                 240

Met Gly Pro Ser Pro Ala Glu Gly Ser Thr Gly Asp Glu Pro Lys
                 245                 250                 255

Ser Cys Asp Lys Thr His Thr Cys Pro Pro Cys Pro Ala Pro Glu Leu
             260                 265                 270

Leu Gly Gly Pro Ser Val Phe Leu Ala Pro Pro Lys Pro Lys Asp Thr
         275                 280                 285

Leu Met Ile Ser Arg Thr Pro Glu Val Thr Cys Val Val Ala Asp Val
     290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                 325                 330                 335

Thr Tyr Arg Val Val Ser Val Leu Thr Val Leu His Gln Asp Trp Leu
             340                 345                 350

Asn Gly Lys Glu Tyr Lys Cys Lys Val Ser Asn Lys Ala Leu Pro Ala
         355                 360                 365

Pro Ile Glu Lys Thr Ile Ser Lys Ala Lys Gly Gln Pro Arg Glu Pro
     370                 375                 380

Gln Val Tyr Thr Leu Pro Pro Ser Arg Glu Glu Met Thr Lys Asn Gln
385                 390                 395                 400

Val Ser Leu Thr Cys Leu Val Lys Gly Phe Tyr Pro Ser Asp Ile Ala
                 405                 410                 415

Val Glu Trp Glu Ser Asn Gly Gln Pro Glu Asn Asn Tyr Lys Thr Thr
             420                 425                 430

Pro Pro Val Leu Asp Ser Asp Gly Ser Phe Phe Leu Tyr Ser Lys Leu
```

```
          435                 440                 445
Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly
```

<210> SEQ ID NO 5
<211> LENGTH: 1455
<212> TYPE: DNA
<213> ORGANISM: Artificial
<220> FEATURE:
<223> OTHER INFORMATION: DNA sequence encoding HSA-TNFR-Fc double mutein
      ORF

<400> SEQUENCE: 5

```
atgaagtggg ttacctttat ctctttgttg tttcttttct cttctgctta ctctctgcca     60
gctcaagttg cttttactcc atacgctcca gaaccaggtt ctacttgtag attgagagag    120
tactacgacc aaactgctca gatgtgttgt tccaagtgtt ctccaggtca acacgctaag    180
gttttctgta ctaagacttc cgacactgtt tgtgactctt gtgaggactc cacttacact    240
caattgtgga actgggttcc agaatgtttg tcctgtggtt ccagatgttc ttccgaccaa    300
gttgagactc aggcttgtac tagagagcag aacagaatct gtacttgtag acctggttgg    360
tactgtgctt tgtccaagca gagggttgt agattgtgtg ctccattgag aaagtgtaga    420
ccaggtttcg gtgttgctag accaggtaca gaaacttccg acgttgtttg taagccatgt    480
gctccaggaa ctttctccaa cactacttcc tccactgaca tctgtagacc acaccaaatc    540
tgtaacgttg ttgctatccc aggtaacgct tctatggacg ctgtttgtac ttctacttcc    600
ccaactagat ccatggctcc aggtgctgtt catttgccac agccagtttc cactagatcc    660
caacacactc aaccaactcc agaaccatct actgctccat ccacttcctt tttgttgcca    720
atgggaccat ctccacctgc tgaaggttct actggtgacg agccaaagtc ctgtgacaag    780
acacatactt gtccaccatg tccagctcca gaattgttgg gtggtccatc cgttttcttg    840
gccccaccaa agccaaagga cactttgatg atctccagaa ctccagaggt tacatgtgtt    900
gttgctgacg tttctcacga ggacccagag gttaagttca actggtacgt gacggtgtt    960
gaagttcaca acgctaagac taagccaaga gaagagcagt acaactccac ttacagagtt   1020
gtttccgttt tgactgtttt gcaccaggat tggttgaacg gtaaagaata caagtgtaag   1080
gtttccaaca aggctttgcc agctccaatc gaaaagacaa tctccaaggc taagggtcaa   1140
ccaagagagc cacaggttta cactttgcca ccatccagag aagagatgac taagaaccag   1200
gtttccttga cttgtttggt taaggattac acccatccg acattgctgt tgaatgggaa   1260
tctaacggtc aaccagagaa caactacaag actactccac cagttttgga ttctgacggt   1320
tccttcttct tgtactccaa gttgactgtt gacaagtcca gatggcaaca gggtaacgtt   1380
ttctcctgtt ccgttatgca tgaggctttg cacaaccact acactcaaaa gtccttgtct   1440
ttgtccccag gttag                                                    1455
```

<210> SEQ ID NO 6
<211> LENGTH: 280
<212> TYPE: PRT
<213> ORGANISM: Artificial
<220> FEATURE:
<223> OTHER INFORMATION: alpha-mating factor prepro EPO ORF

<400> SEQUENCE: 6

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Ala Pro Pro Arg Leu
                85                  90                  95

Ile Cys Asp Ser Arg Val Leu Glu Arg Tyr Ile Leu Glu Ala Lys Glu
                100                 105                 110

Ala Glu Asn Val Thr Met Gly Cys Ala Glu Gly Pro Arg Leu Ser Glu
            115                 120                 125

Asn Ile Thr Val Pro Asp Thr Lys Val Asn Phe Tyr Ala Trp Lys Arg
130                 135                 140

Met Lys Val Glu Glu Gln Ala Val Glu Val Trp Gln Gly Leu Ser Leu
145                 150                 155                 160

Leu Ser Glu Ala Ile Leu Gln Ala Gln Ala Leu Gln Ala Asn Ser Ser
                165                 170                 175

Gln Pro Pro Glu Ser Leu Gln Leu His Ile Asp Lys Ala Ile Ser Gly
            180                 185                 190

Leu Arg Ser Leu Thr Ser Leu Leu Arg Val Leu Gly Ala Gln Lys Glu
        195                 200                 205

Leu Met Ser Pro Pro Asp Ala Thr Gln Ala Ala Pro Leu Arg Thr Leu
    210                 215                 220

Thr Ala Asp Thr Phe Cys Lys Leu Phe Arg Val Tyr Ser Asn Phe Leu
225                 230                 235                 240

Arg Gly Lys Leu Lys Leu Tyr Thr Gly Glu Ala Cys Arg Arg Gly Asp
                245                 250                 255

Arg Gly Leu Glu Gln Lys Leu Ile Ser Glu Glu Asp Leu Asn Ser Ala
            260                 265                 270

Val Asp His His His His His His
            275                 280
```

<210> SEQ ID NO 7
<211> LENGTH: 843
<212> TYPE: DNA
<213> ORGANISM: Artificial
<220> FEATURE:
<223> OTHER INFORMATION: DNA sequence encoding alpha-mating factor
      prepro EPO ORF

<400> SEQUENCE: 7

| atgagatttc cttcaatttt tactgctgtt ttattcgcag catcctccgc attagctgct | 60 |
| ccagtcaaca ctacaacaga agatgaaacg gcacaaattc cggctgaagc tgtcatcggt | 120 |
| tactcagatt tagaagggga tttcgatgtt gctgttttgc catttccaa cagcacaaat | 180 |
| aacgggttat tgtttataaa tactactatt gccagcattg ctgctaaaga agaaggggta | 240 |
| tctctggaga aaagagaggc tgaagctgag ttcgctcccc cacgcctcat ttgcgacagt | 300 |
| cgcgttctgg agaggtacat cttggaggcc aaggaggcag aaaatgtcac aatgggctgt | 360 |

```
gcagaaggtc ccagactgag tgagaatatt accgtcccag ataccaaagt caacttctac    420
gcttggaaaa gaatgaaggt ggaagaacag gctgtagaag tttggcaagg cctgtctctg    480
ctctcagaag ccatcctgca ggcccaggct ctgcaggcca attcctccca gccaccagag    540
agtcttcagc ttcatataga caaagccatc agtgggctac gtagcctcac ttcactgctt    600
cgggtgctgg gagctcagaa ggaattgatg tcgcctccag acgccaccca agccgctcca    660
ctccgaacac tcacagcgga tactttctgc aagctcttcc gggtctactc caacttcctc    720
cgggggaaac tgaagctgta cacggggag gcctgcagga gagggacag gggtctggaa     780 caaaaactca tctcagaaga ggatctgaat agcgccgtcg accatcatca tcatcatcat    840
tga                                                                 843
```

<210> SEQ ID NO 8
<211> LENGTH: 2250
<212> TYPE: DNA
<213> ORGANISM: Pichia pastoris

<400> SEQUENCE: 8

```
caatacaagg ttgtcttgga gtttacattg accagatgat ttggcttttt ctctgttcaa     60
ttcacatttt tcagcgagaa tcggattgac ggagaaatgg cggggtgtgg ggtggataga    120
tggcagaaat gctcgcaatc accgcgaaag aaagacttta tggaatagaa ctactgggtg    180
gtgtaaggat tacatagcta gtccaatgga gtccgttgga aaggtaagaa gaagctaaaa    240
ccggctaagt aactagggaa gaatgatcag actttgattt gatgaggtct gaaaatactc    300
tgctgctttt tcagttgctt tttccctgca acctatcatt ttccttttca taagcctgcc    360
ttttctgttt tcacttatat gagttccgcc gagacttccc caaattctct cctggaacat    420
tctctatcgc tctccttcca agttgcgccc ctggcactg cctagtaata ttaccacgcg     480
acttatattc agttccacaa tttccagtgt tcgtagcaaa tatcatcagc catggcgaag    540
gcagatggca gtttgctcta ctataatcct cacaatccac ccagaaggta ttacttctac    600
atggctatat tcgccgtttc tgtcatttgc gttttgtacg daccctcaca acaattatca    660
tctccaaaaa tagactatga tccattgacg ctccgatcac ttgatttgaa gactttggaa    720
gctccttcac agttgagtcc aggcaccgta gaagataatc ttcgaagaca attggagttt    780
cattttcctt accgcagtta cgaaccttttt ccccaacata tttggcaaac gtggaaagtt    840
tctccctctg atagttcctt tccgaaaaac ttcaaagact taggtgaaag ttggctgcaa    900
aggtccccaa attatgatca ttttgtgata cccgatgatg cagcatggga acttattcac    960
catgaatacg aacgtgtacc agaagtcttg gaagctttcc acctgctacc agagcccatt   1020
ctaaaggccg attttttcag gtatttgatt ctttttgccc gtggaggact gtatgctgac   1080
atggacacta tgttattaaa accaatagaa tcgtggctga ctttcaatga aactattggt   1140
ggagtaaaaa acaatgctgg gttggtcatt ggtattgagg ctgatcctga tagacctgat   1200
tggcacgact ggtatgctag aaggatacaa ttttgccaat gggcaattca gtccaaacga   1260
ggacacccag cactgcgtga actgattgta agagttgtca gcacgacttt acggaaagag   1320
aaaagcggtt acttgaacat ggtggaagga aaggatcgtg gaagtgatgt gatggactgg   1380
acgggtccag gaatatttac agacactcta tttgattata tgactaatgt caatacaaca   1440
ggccactcag gccaaggaat tggagctggc tcagcgtatt acaatgcctt atcgttggaa   1500
gaacgtgatg ccctctctgc ccgcccgaac ggagagatgt aaaagagaa agtcccaggt   1560 aaatatgcac agcaggttgt tttatgggaa caatttacca acctgcgctc ccccaaatta   1620
```

```
atcgacgata ttcttattct tccgatcacc agcttcagtc cagggattgg ccacagtgga    1680
gctggagatt tgaaccatca ccttgcatat attaggcata catttgaagg aagttggaag    1740
gactaaagaa agctagagta aaatagatat agcgagatta gagaatgaat accttcttct    1800
aagcgatcgt ccgtcatcat agaatatcat ggactgtata gttttttttt tgtacatata    1860
atgattaaac ggtcatccaa catctcgttg acagatctct cagtacgcga aatccctgac    1920
tatcaaagca agaaccgatg aagaaaaaaa caacagtaac ccaaacacca caacaaacac    1980
tttatcttct ccccccaac accaatcatc aaagagatgt cggaaccaaa caccaagaag     2040
caaaaactaa ccccatataa aaacatcctg gtagataatg ctggtaaccc gctctccttc    2100
catattctgg gctacttcac gaagtctgac cggtctcagt tgatcaacat gatcctcgaa    2160
atgggtggca agatcgttcc agacctgcct cctctggtag atggagtgtt gttttttgaca   2220 ggggattaca agtctattga tgaagatacc                                     2250
```

```
<210> SEQ ID NO 9
<211> LENGTH: 3029
<212> TYPE: DNA
<213> ORGANISM: Saccharomyces cerevisiae

<400> SEQUENCE: 9
```

```
aggcctcgca acaacctata attgagttaa gtgccttttcc aagctaaaaa gtttgaggtt     60
ataggggctt agcatccaca cgtcacaatc tcgggtatcg agtatagtat gtagaattac    120
ggcaggaggt ttcccaatga acaaggaca ggggcacggt gagctgtcga aggtatccat     180
tttatcatgt ttcgtttgta caagcacgac atactaagac atttaccgta tgggagttgt    240
tgtcctagcg tagttctcgc tcccccagca aagctcaaaa aagtacgtca tttagaatag    300
tttgtgagca aattaccagt cggtatgcta cgttagaaag gcccacagta ttcttctacc    360
aaaggcgtgc ctttgttgaa ctcgatccat tatgagggct tccattattc cccgcatttt    420
tattactctg aacaggaata aaaagaaaaa acccagttta ggaaattatc cgggggcgaa    480
gaaatacgcg tagcgttaat cgaccccacg tccaggggtt ttccatggag gtttctggaa    540
aaactgacga ggaatgtgat tataaatccc tttatgtgat gtctaagact tttaaggtac    600
gcccgatgtt tgcctattac catcatagag acgtttcttt tcgaggaatg cttaaacgac    660
tttgtttgac aaaaatgttg cctaagggct ctatagtaaa ccatttggaa gaaagatttg    720 acgactttt ttttttggat ttcgatccta taatccttcc tcctgaaaag aaacatataa      780
atagatatgt attattcttc aaaacattct cttgttcttg tgctttttttt ttaccatata   840 tcttactttt tttttctct cagagaaaca agcaaaacaa aaagcttttc ttttcactaa      900
cgtatatgat gcttttgcaa gctttccttt tccttttggc tggttttgca gccaaaatat    960
ctgcatcaat gacaaacgaa actagcgata gacctttggt ccacttcaca cccaacaagg   1020
gctggatgaa tgacccaaat gggttgtggt acgatgaaaa agatgccaaa tggcatctgt   1080
actttcaata caacccaaat gacaccgtat ggggtacgcc attgttttgg ggccatgcta   1140
cttccgatga tttgactaat tgggaagatc aacccattgc tatcgctccc aagcgtaacg   1200
attcaggtgc tttctctggc tccatggtgg ttgattacaa caacacgagt gggttttttca   1260 atgatactat tgatccaaga caaagatgcg ttgcgatttg gacttataac actcctgaaa   1320
gtgaagagca atacattagc tattctcttg atggtggtta cactttttact gaataccaaa   1380 agaaccctgt tttagctgcc aactccactc aattcagaga tccaaaggtg ttctggtatg   1440
```

```
aaccttctca aaaatggatt atgacggctg ccaaatcaca agactacaaa attgaaattt    1500
actcctctga tgacttgaag tcctggaagc tagaatctgc atttgccaat gaaggtttct    1560
taggctacca atacgaatgt ccaggtttga ttgaagtccc aactgagcaa gatccttcca    1620
aatcttattg ggtcatgttt atttctatca acccaggtgc acctgctggc ggttccttca    1680
accaatattt tgttggatcc ttcaatggta ctcattttga agcgtttgac aatcaatcta    1740
gagtggtaga ttttggtaag gactactatg ccttgcaaac tttcttcaac actgacccaa    1800
cctacggttc agcattaggt attgcctggg cttcaaactg ggagtacagt gcctttgtcc    1860
caactaaccc atggagatca tccatgtctt tggtccgcaa gttttctttg aacactgaat    1920
atcaagctaa tccagagact gaattgatca atttgaaagc cgaaccaata ttgaacatta    1980
gtaatgctgg tccctggtct cgttttgcta ctaacacaac tctaactaag gccaattctt    2040
acaatgtcga tttgagcaac tcgactggta ccctagagtt tgagttggtt tacgctgtta    2100
acaccacaca aaccatatcc aaatccgtct ttgccgactt atcactttgg ttcaagggtt    2160
tagaagatcc tgaagaatat ttgagaatgg gttttgaagt cagtgcttct tccttctttt    2220
tggaccgtgg taactctaag gtcaagtttg tcaaggagaa cccatatttc acaaacagaa    2280
tgtctgtcaa caaccaacca ttcaagtctg agaacgacct aagttactat aaagtgtacg    2340
gcctactgga tcaaaacatc ttggaattgt acttcaacga tggagatgtg gtttctacaa    2400 ataccctactt catgaccacc ggtaacgctc taggatctgt gaacatgacc actggtgtcg    2460
ataatttgtt ctacattgac aagttccaag taagggaagt aaaatagagg ttataaaact    2520
tattgtcttt tttattttt tcaaaagcca ttctaaaggg ctttagctaa cgagtgacga    2580
atgtaaaact ttatgatttc aaagaatacc tccaaaccat tgaaaatgta ttttatttt    2640 tatttctcc cgaccccagt tacctggaat ttgttctta tgtactttat ataagtataa    2700
ttctcttaaa aatttttact actttgcaat agacatcatt ttttcacgta ataaacccac    2760
aatcgtaatg tagttgcctt acactactag gatggacctt tttgccttta tctgttttgt    2820
tactgacaca atgaaaccgg gtaaagtatt agttatgtga aaatttaaaa gcattaagta    2880
gaagtatacc atattgtaaa aaaaaaaagc gttgtcttct acgtaaaagt gttctcaaaa    2940
agaagtagtg agggaaatgg ataccaagct atctgtaaca ggagctaaaa aatctcaggg    3000
aaaagcttct ggtttgggaa acggtcgac                                     3029

<210> SEQ ID NO 10
<211> LENGTH: 898
<212> TYPE: DNA
<213> ORGANISM: Artificial
<220> FEATURE:
<223> OTHER INFORMATION: Sequence of the 5'-Region used for knock out of
      PpURA5

<400> SEQUENCE: 10
atcggccttt gttgatgcaa gttttacgtg gatcatggac taaggagttt tatttggacc      60
aagttcatcg tcctagacat tacggaaagg gttctgctcc tcttttttgga aacttttttgg    120 aacctctgag tatgacagct tggtggattg tacccatggt atggcttcct gtgaatttct     180
attttttcta cattggattc accaatcaaa acaaattagt cgccatggct ttttggcttt     240
tgggtctatt tgtttggacc ttcttggaat atgctttgca tagattttttg ttccacttgg     300 actactatct tccagagaat caattgcatt ttaccattca tttcttattg catgggatac      360
accactattt accaatggat aaatacagat tggtgatgcc acctacactt ttcattgtac      420
```

```
tttgctaccc aatcaagacg ctcgtctttt ctgttctacc atattacatg gcttgttctg    480
gatttgcagg tggattcctg ggctatatca tgtatgatgt cactcattac gttctgcatc    540
actccaagct gcctcgttat ttccaagagt tgaagaaata tcatttggaa catcactaca    600
agaattacga gttaggcttt ggtgtcactt ccaaattctg gacaaagtc tttgggactt     660 atctgggtcc agacgatgtg tatcaaaaga caaattagag tatttataaa gttatgtaag    720
caaatagggg ctaataggga agaaaaaatt tggttctttt atcagagctg gctcgcgcgc    780
agtgtttttc gtgctccttt gtaatagtca tttttgacta ctgttcagat tgaaatcaca    840
ttgaagatgt cactcgaggg gtaccaaaaa aggttttttgg atgctgcagt ggcttcgc     898
```

<210> SEQ ID NO 11
<211> LENGTH: 1060
<212> TYPE: DNA
<213> ORGANISM: Artificial
<220> FEATURE:
<223> OTHER INFORMATION: Sequence of the 3'-Region used for knock out of
      PpURA5

<400> SEQUENCE: 11

```
ggtcttttca acaaagctcc attagtgagt cagctggctg aatcttatgc acaggccatc     60
attaacagca acctggagat agacgttgta tttggaccag cttataaagg tattcctttg    120
gctgctatta ccgtgttgaa gttgtacgag ctcggcggca aaaatacga aaatgtcgga    180 tatgcgttca atagaaaaga aagaaagac cacgagaag gtggaagcat cgttggagaa    240
agtctaaaga ataaaagagt actgattatc gatgatgtga tgactgcagg tactgctatc    300
aacgaagcat ttgctataat tggagctgaa ggtgggagag ttgaaggtag tattattgcc    360
ctagatagaa tggagactac aggagatgac tcaaatacca gtgctaccca ggctgttagt    420
cagagatatg gtaccctgt cttgagtata gtgacattgg accatattgt ggcccatttg    480
ggcgaaactt tcacagcaga cgagaaatct caaatgaaaa cgtatagaaa aaagtatttg    540
cccaaataag tatgaatctg cttcgaatga atgaattaat ccaattatct tctcaccatt    600
attttcttct gtttcggagc tttgggcacg gcggcgggtg gtgcgggctc aggttccctt    660
tcataaacag atttagtact tggatgctta atagtgaatg gcgaatgcaa aggaacaatt    720
tcgttcatct ttaacccttt cactcggggt acacgttctg gaatgtaccc gccctgttgc    780
aactcaggtg gaccgggcaa ttcttgaact ttctgtaacg ttgttggatg ttcaaccaga    840
aattgtccta ccaactgtat tagttttcctt ttggtcttat attgttcatc gagatacttc    900
ccactctcct tgatagccac tctcactctt cctggattac caaaatcttg aggatgagtc    960
ttttcaggct ccaggatgca aggtatatcc aagtacctgc aagcatctaa tattgtcttt   1020
gccagggggt tctccacacc atactccttt tggcgcatgc                         1060
```

<210> SEQ ID NO 12
<211> LENGTH: 957
<212> TYPE: DNA
<213> ORGANISM: Artificial
<220> FEATURE:
<223> OTHER INFORMATION: Sequence of the PpURA5 auxotrophic marker

<400> SEQUENCE: 12

```
tctagaggga cttatctggg tccagacgat gtgtatcaaa agacaaatta gagtatttat     60
aaagttatgt aagcaaatag gggctaatag ggaaagaaaa attttggttc tttatcagag    120
ctggctcgcg cgcagtgttt ttcgtgctcc ttttgtaatag tcattttga ctactgttca    180
```

```
gattgaaatc acattgaaga tgtcactgga ggggtaccaa aaaaggtttt tggatgctgc    240
agtggcttcg caggccttga agtttggaac tttcaccttg aaaagtggaa gacagtctcc    300
atacttcttt aacatgggtc ttttcaacaa agctccatta gtgagtcagc tggctgaatc    360
ttatgctcag gccatcatta acagcaacct ggagatagac gttgtatttg accagctta    420 taaaggtatt cctttggctg ctattaccgt gttgaagttg tacgagctgg gcggcaaaaa    480
atacgaaaat gtcggatatg cgttcaatag aaaagaaaag aaagaccacg agaaggtgg    540 aagcatcgtt ggagaaagtc taagaataaa agagtactg attatcgatg atgtgatgac    600
tgcaggtact gctatcaacg aagcatttgc tataattgga gctgaaggtg ggagagttga    660
aggttgtatt attgccctag atagaatgga gactacagga gatgactcaa ataccagtgc    720
tacccaggct gttagtcaga gatatggtac ccctgtcttg agtatagtga cattggacca    780
tattgtggcc catttgggcg aaactttcac agcagacgag aaatctcaaa tggaaacgta    840
tagaaaaaag tatttgccca ataagtatg aatctgcttc gaatgaatga attaatccaa    900
ttatcttctc accattattt tcttctgttt cggagctttg ggcacggcgg cggatcc      957

<210> SEQ ID NO 13
<211> LENGTH: 709
<212> TYPE: DNA
<213> ORGANISM: Artificial
<220> FEATURE:
<223> OTHER INFORMATION: Sequence of the part of the Ec lacZ gene that
      was used to construct the PpURA5 blaster (recyclable auxotrophic
      marker)

<400> SEQUENCE: 13
cctgcactgg atggtggcgc tggatggtaa gccgctggca agcggtgaag tgcctctgga    60
tgtcgctcca caaggtaaac agttgattga actgcctgaa ctaccgcagc cggagagcgc    120
cgggcaactc tggctcacag tacgcgtagt gcaaccgaac gcgaccgcat ggtcagaagc    180
cgggcacatc agcgcctggc agcagtggcg tctggcggaa aacctcagtg tgacgctccc    240
cgccgcgtcc cacgccatcc cgcatctgac caccagcgaa atggattttt gcatcgagct    300
gggtaataag cgttggcaat ttaaccgcca gtcaggcttt cttttcacaga gtgtggattgg    360 cgataaaaaa caactgctga cgccgctgcg cgatcagttc acccgtgcac cgctggataa    420
cgacattggc gtaagtgaag cgacccgcat tgaccctaac gcctgggtcg aacgctggaa    480
ggcggcgggc cattaccagg ccgaagcagc gttgttgcag tgcacggcag atacacttgc    540
tgatgcggtg ctgattacga ccgctcacgc gtggcagcat caggggaaaa ccttatttat    600
cagccggaaa acctaccgga ttgatggtag tggtcaaatg gcgattaccg ttgatgttga    660
agtggcgagc gatacaccgc atccggcgcg gattggcctg aactgccag                709

<210> SEQ ID NO 14
<211> LENGTH: 2875
<212> TYPE: DNA
<213> ORGANISM: Artificial
<220> FEATURE:
<223> OTHER INFORMATION: Sequence of the 5'-Region used for knock out of
      PpOCH1

<400> SEQUENCE: 14 aaaaccttt ttcctattca aacacaaggc attgcttcaa cacgtgtgcg tatccttaac    60
acagatactc catacttcta ataatgtgat agacgaatac aaagatgttc actctgtgtt    120
gtgtctacaa gcatttctta ttctgattgg ggatattcta gttacagcac taaacaactg    180
```

```
gcgatacaaa cttaaattaa ataatccgaa tctagaaaat gaacttttgg atggtccgcc      240
tgttggttgg ataaatcaat accgattaaa tggattctat tccaatgaga gagtaatcca      300
agacactctg atgtcaataa tcatttgctt gcaacaacaa acccgtcatc taatcaaagg      360
gtttgatgag gcttaccttc aattgcagat aaactcattg ctgtccactg ctgtattatg      420
tgagaatatg ggtgatgaat ctggtcttct ccactcagct aacatggctg tttgggcaaa      480
ggtggtacaa ttatacggag atcaggcaat agtgaaattg ttgaatatgg ctactggacg      540
atgcttcaag gatgtacgtc tagtaggagc cgtgggaaga ttgctggcag aaccagttgg      600
cacgtcgcaa caatccccaa gaaatgaaat aagtgaaaac gtaacgtcaa agacagcaat      660
ggagtcaata ttgataacac cactggcaga gcggttcgta cgtcgttttg gagccgatat      720
gaggctcagc gtgctaacag cacgattgac aagaagactc tcgagtgaca gtaggttgag      780
taaagtattc gcttagattc ccaaccttcg ttttattctt tcgtagacaa agaagctgca      840
tgcgaacata gggacaactt ttataaatcc aattgtcaaa ccaacgtaaa accctctggc      900
accattttca acatatattt gtgaagcagt acgcaatatc gataaatact caccgttgtt      960
tgtaacagcc ccaacttgca tacgccttct aatgacctca aatggataag ccgcagcttg     1020
tgctaacata ccagcagcac cgcccgcggt cagctgcgcc cacacatata aaggcaatct     1080
acgatcatgg gaggaattag ttttgaccgt caggtcttca agagttttga actcttcttc     1140
ttgaactgtg taaccttta atgacggga tctaaatacg tcatggatga gatcatgtgt     1200
gtaaaaactg actccagcat atggaatcat tccaaagatt gtaggagcga acccacgata     1260
aaagtttccc aaccttgcca aagtgtctaa tgctgtgact tgaaatctgg gttcctcgtt     1320
gaagaccctg cgtactatgc ccaaaaactt tcctccacga gccctattaa cttctctatg     1380
agtttcaaat gccaaacgga cacggattag gtccaatggg taagtgaaaa acacagagca     1440
aaccccagct aatgagccgg ccagtaaccg tcttggagct gtttcataag agtcattagg     1500
gatcaataac gttctaatct gttcataaca tacaaatttt atggctgcat agggaaaaat     1560
tctcaacagg gtagccgaat gaccctgata tagacctgcg acaccatcat acccatagat     1620
ctgcctgaca gccttaaaga gcccgctaaa agacccggaa aaccgagaga actctggatt     1680
agcagtctga aaaagaatct tcactctgtc tagtggagca attaatgtct tagcggcact     1740
tcctgctact ccgccagcta ctcctgaata gatcacatac tgcaaagact gcttgtcgat     1800
gaccttgggg ttatttagct tcaagggcaa ttttttggac attttggaca caggagactc     1860
agaaacagac acagagcgtt ctgagtcctg gtgctcctga cgtaggccta gaacaggaat     1920
tattggcttt atttgtttgt ccatttcata ggcttggggt aatagataga tgacagagaa     1980
atagagaaga cctaatattt tttgttcatg gcaaatcgcg ggttcgcggt cgggtcacac     2040
acggagaagt aatgagaaga gctggtaatc tggggtaaaa gggttcaaaa gaaggtcgcc     2100
tggtagggat gcaatacaag gttgtcttgg agtttacatt gaccagatga tttggctttt     2160
tctctgttca attcacattt ttcagcgaga atcggattga cggagaaatg gcggggtgtg     2220
gggtggatag atggcagaaa tgctcgcaat caccgcgaaa gaaagacttt atggaataga     2280
actactgggt ggtgtaagga ttacatagct agtccaatgg agtccgttgg aaaggtaaga     2340
agaagctaaa accggctaag taactaggga agaatgatca gactttgatt tgatgaggtc     2400
tgaaaatact ctgctgcttt ttcagttgct ttttccctgc aacctatcat tttccttttc     2460
ataagcctgc cttttctgtt ttcacttata tgagttccgc cgagacttcc ccaaattctc     2520
tcctggaaca ttctctatcg ctctccttcc aagttgcgcc ccctggcact gcctagtaat     2580
```

```
attaccacgc gacttatatt cagttccaca atttccagtg ttcgtagcaa atatcatcag    2640
ccatggcgaa ggcagatggc agtttgctct actataatcc tcacaatcca cccagaaggt    2700
attacttcta catggctata ttcgccgttt ctgtcatttg cgttttgtac ggaccctcac    2760
aacaattatc atctccaaaa atagactatg atccattgac gctccgatca cttgatttga    2820
agactttgga agctccttca cagttgagtc caggcaccgt agaagataat cttcg         2875
```

<210> SEQ ID NO 15
<211> LENGTH: 997
<212> TYPE: DNA
<213> ORGANISM: Artificial
<220> FEATURE:
<223> OTHER INFORMATION: Sequence of the 3'-Region used for knock out of PpOCH1

<400> SEQUENCE: 15

```
aaagctagag taaaatagat atagcgagat tagagaatga ataccttctt ctaagcgatc    60
gtccgtcatc atagaatatc atggactgta tagtttttttt tttgtacata taatgattaa   120
acggtcatcc aacatctcgt tgacagatct ctcagtacgc gaaatccctg actatcaaag   180
caagaaccga tgaagaaaaa aacaacagta acccaaacac cacaacaaac actttatctt   240
ctccccccca acaccaatca tcaaagagat gtcggaacca acaccaaga agcaaaaact   300 aaccccatat aaaaacatcc tggtagataa tgctggtaac ccgctctcct tccatattct   360
gggctacttc acgaagtctg accggtctca gttgatcaac atgatcctcg aaatgggtgg   420
caagatcgtt ccagacctgc ctcctctggt agatggagtg ttgttttttga cagggatta   480 caagtctatt gatgaagata ccctaaagca actgggggac gttccaatat acagagactc   540
cttcatctac cagtgttttg tgcacaagac atctcttccc attgacactt tccgaattga   600
caagaacgtc gacttggctc aagatttgat caatagggcc cttcaagagt ctgtggatca   660
tgtcacttct gccagcacag ctgcagctgc tgctgttgtt gtcgctacca acggcctgtc   720
ttctaaacca gacgctcgta ctagcaaaat acagttcact cccgaagaag atcgttttat   780
tcttgacttt gttaggagaa atcctaaacg aagaaacaca catcaactgt acactgagct   840
cgctcagcac atgaaaaacc atacgaatca ttctatccgc cacagatttc gtcgtaatct   900
ttccgctcaa cttgattggg tttatgatat cgatccattg accaaccaac ctcgaaaaga   960
tgaaaacggg aactacatca aggtacaagg ccttcca                            997
```

<210> SEQ ID NO 16
<211> LENGTH: 2159
<212> TYPE: DNA
<213> ORGANISM: Artificial
<220> FEATURE:
<223> OTHER INFORMATION: K. lactis UDP-GlcNAc transporter gene (KlMNN2-2)

<400> SEQUENCE: 16

```
aaacgtaacg cctggcactc tatttttctca aacttctggg acggaagagc taaatattgt    60
gttgcttgaa caaacccaaa aaaacaaaaa aatgaacaaa ctaaaactac acctaaataa   120
accgtgtgta aaacgtagta ccatattact agaaaagatc acaagtgtat cacacatgtg   180
catctcatat tacatctttt atccaatcca ttctctctat cccgtctgtt cctgtcagat   240 tcttttttcca taaaagaag aagacccccga atctcaccgg tacaatgcaa aactgctgaa   300
aaaaaaagaa agttcactgg atacgggaac agtgccagta ggcttcacca catggacaaa   360
```

```
acaattgacg ataaaataag caggtgagct tcttttcaa gtcacgatcc ctttatgtct      420
cagaaacaat atatcaagc taaacccttt tgaaccagtt ctctcttcat agttatgttc      480
acataaattg cgggaacaag actccgctgg ctgtcaggta cacgttgtaa cgttttcgtc    540
cgcccaatta ttagcacaac attggcaaaa agaaaaactg ctcgttttct ctacaggtaa    600
attacaattt ttttcagtaa ttttcgctga aaaatttaaa gggcaggaaa aaaagacgat    660
ctcgactttg catagatgca agaactgtgg tcaaaacttg aaatagtaat tttgctgtgc    720
gtgaactaat aaatatatat atatatatat atatatattt gtgtattttg tatatgtaat    780
tgtgcacgtc ttggctattg gatataagat tttcgcgggt tgatgacata gagcgtgtac   840
tactgtaata gttgtatatt caaaagctgc tgcgtggaga aagactaaaa tagataaaaa   900
gcacacattt tgacttcggt accgtcaact tagtgggaca gtcttttata tttggtgtaa   960
gctcatttct ggtactattc gaaacagaac agtgttttct gtattaccgt ccaatcgttt    1020
gtcatgagtt ttgtattgat tttgtcgtta gtgttcggag gatgttgttc caatgtgatt    1080
agtttcgagc acatggtgca aggcagcaat ataaatttgg gaaatattgt tacattcact   1140
caattcgtgt ctgtgacgct aattcagttg cccaatgctt tggacttctc tcactttccg   1200
tttaggttgc gacctagaca cattcctctt aagatccata tgttagctgt gttttgttc   1260 tttaccagtt cagtcgccaa taacagtgtg tttaaatttg acatttccgt tccgattcat   1320
attatcatta gattttcagg taccactttg acgatgataa taggttgggc tgtttgtaat   1380
aagaggtact ccaaacttca ggtgcaatct gccatcatta tgacgcttgg tgcgattgtc    1440
gcatcattat accgtgacaa agaattttca atggacagtt taaagttgaa tacggattca   1500
gtgggtatga cccaaaaatc tatgtttggt atctttgttg tgctagtggc cactgccttg    1560
atgtcattgt tgtcgttgct caacgaatgg acgtataaca agtacgggaa acattggaaa    1620
gaaactttgt tctattcgca tttcttggct ctaccgttgt ttatgttggg gtacacaagg   1680
ctcagagacg aattcagaga cctcttaatt tcctcagact caatggatat tcctattgtt    1740
aaattaccaa ttgctacgaa acttttcatg ctaatagcaa ataacgtgac ccagttcatt    1800
tgtatcaaag gtgttaacat gctagctagt aacacggatg ctttgacact ttctgtcgtg   1860
cttctagtgc gtaaatttgt tagtctttta ctcagtgtct acatctacaa gaacgtccta    1920
tccgtgactg catacctagg gaccatcacc gtgttcctgg gagctggttt gtattcatat   1980
ggttcggtca aaactgcact gcctcgctga aacaatccac gtctgtatga tactcgtttc   2040
agaatttttt tgatttttctg ccggatatgg tttctcatct ttacaatcgc attcttaatt   2100
ataccagaac gtaattcaat gatcccagtg actcgtaact cttatatgtc aatttaagc    2159
```

<210> SEQ ID NO 17
<211> LENGTH: 870
<212> TYPE: DNA
<213> ORGANISM: Artificial
<220> FEATURE:
<223> OTHER INFORMATION: Sequence of the 5'-Region used for knock out of PpBMT2

<400> SEQUENCE: 17

```
ggccgagcgg gcctagattt tcactacaaa tttcaaaact acgcggattt attgtctcag     60
agagcaattt ggcatttctg agcgtagcag gaggcttcat aagattgtat aggaccgtac    120
caacaaattg ccgaggcaca acacggtatg ctgtgcactt atgtggctac ttccctacaa   180
cggaatgaaa ccttcctctt tccgcttaaa cgagaaagtg tgtcgcaatt gaatgcaggt    240
```

```
gcctgtgcgc cttggtgtat tgtttttgag ggcccaattt atcaggcgcc ttttttcttg      300
gttgttttcc cttagcctca agcaaggttg gtctatttca tctccgcttc tataccgtgc      360
ctgatactgt tggatgagaa cacgactcaa cttcctgctg ctctgtattg ccagtgtttt      420
gtctgtgatt tggatcggag tcctccttac ttggaatgat aataatcttg gcggaatctc      480
cctaaacgga ggcaaggatt ctgcctatga tgatctgcta tcattgggaa gcttcaacga      540
catggaggtc gactcctatg tcaccaacat ctacgacaat gctccagtgc taggatgtac      600
ggatttgtct tatcatggat tgttgaaagt caccccaaag catgacttag cttgcgattt      660
ggagttcata agagctcaga tttggacat tgacgtttac tccgccataa aagacttaga       720
agataaagcc ttgactgtaa acaaaaggt tgaaaaacac tggtttacgt tttatggtag      780
ttcagtcttt ctgcccgaac acgatgtgca ttacctggtt agacgagtca tcttttcggc      840
tgaaggaaag gcgaactctc cagtaacatc                                       870
```

<210> SEQ ID NO 18
<211> LENGTH: 1733
<212> TYPE: DNA
<213> ORGANISM: Artificial
<220> FEATURE:
<223> OTHER INFORMATION: Sequence of the 3'-Region used for knock out of PpBMT2

<400> SEQUENCE: 18

```
ccatatgatg ggtgtttgct cactcgtatg gatcaaaatt ccatggtttc ttctgtacaa       60
cttgtacact tatttggact tttctaacgg ttttctggt gatttgagaa gtccttattt       120
tggtgttcgc agcttatccg tgattgaacc atcagaaata ctgcagctcg ttatctagtt      180
tcagaatgtg ttgtagaata caatcaattc tgagtctagt ttgggtgggt cttggcgacg      240
ggaccgttat atgcatctat gcagtgttaa ggtacataga atgaaaatgt aggggttaat      300
cgaaagcatc gttaatttca gtagaacgta gttctattcc ctacccaaat aatttgccaa      360
gaatgcttcg tatccacata cgcagtggac gtagcaaatt tcactttgga ctgtgacctc      420
aagtcgttat cttctacttg gacattgatg gtcattacgt aatccacaaa gaattggata      480
gcctctcgtt ttatctagtg cacagcctaa tagcacttaa gtaagagcaa tggacaaatt      540
tgcatagaca ttgagctaga tacgtaactc agatcttgtt cactcatggt gtactcgaag      600
tactgctgga accgttacct cttatcattt cgctactggc tcgtgaaact actggatgaa      660
aaaaaaaaaa gagctgaaag cgagatcatc ccattttgtc atcatacaaa ttcacgcttg      720
cagttttgct tcgttaacaa gacaagatgt ctttatcaaa gacccgtttt tcttcttga      780 agaatacttc cctgttgagc acatgcaaac catatttatc tcagatttca ctcaacttgg      840
gtgcttccaa gagaagtaaa attcttccca ctgcatcaac ttccaagaaa cccgtagacc      900
agtttctctt cagccaaaag aagttgctcg ccgatcaccg cggtaacaga ggagtcagaa      960
ggtttcacac ccttccatcc cgatttcaaa gtcaaagtgc tgcgttgaac caaggttttc     1020
aggttgccaa agcccagtct gcaaaaacta gttccaaatg gcctattaat tcccataaaa     1080
gtgttggcta cgtatgtatc ggtacctcca ttctggtatt tgctattgtt gtcgttggtg     1140
ggttgactag actgaccgaa tccggtcttt ccataacgga gtggaaacct atcactggtt     1200
cggttccccc actgactgag gaagactgga agttggaatt tgaaaaatac aaacaaagcc     1260
ctgagtttca ggaactaaat tctcacataa cattggaaga gttcaagttt atattttcca     1320
tggaatgggg acatagattg ttgggaaggg tcatcggcct gtcgtttgtt cttcccacgt     1380
```

| tttacttcat tgcccgtcga aagtgttcca aagatgttgc attgaaactg cttgcaatat | 1440 |
| gctctatgat aggattccaa ggtttcatcg gctggtggat ggtgtattcc ggattggaca | 1500 |
| aacagcaatt ggctgaacgt aactccaaac caactgtgtc tccatatcgc ttaactaccc | 1560 |
| atcttggaac tgcatttgtt atttactgtt acatgattta cacagggctt caagttttga | 1620 |
| agaactataa gatcatgaaa cagcctgaag cgtatgttca aattttcaag caaattgcgt | 1680 |
| ctccaaaatt gaaaactttc aagagactct cttcagttct attaggcctg gtg | 1733 |

<210> SEQ ID NO 19
<211> LENGTH: 981
<212> TYPE: DNA
<213> ORGANISM: Artificial
<220> FEATURE:
<223> OTHER INFORMATION: DNA encodes MmSLC35A3 UDP-GlcNAc transporter; DNA

<400> SEQUENCE: 19

| atgtctgcca acctaaaata tctttccttg ggaattttgg tgtttcagac taccagtctg | 60 |
| gttctaacga tgcggtattc taggacttta aaagaggagg ggcctcgtta tctgtcttct | 120 |
| acagcagtgg ttgtggctga attttttgaag ataatggcct gcatcttttt agtctacaaa | 180 |
| gacagtaagt gtagtgtgag agcactgaat agagtactgc atgatgaaat tcttaataag | 240 |
| cccatggaaa ccctgaagct cgctatcccg tcagggatat atactcttca gaacaactta | 300 |
| ctctatgtgg cactgtcaaa cctagatgca gccacttacc aggttacata tcagttgaaa | 360 |
| atacttacaa cagcattatt ttctgtgtct atgcttggta aaaaattagg tgtgtaccag | 420 |
| tggctctccc tagtaattct gatggcagga gttgcttttg tacagtggcc ttcagattct | 480 |
| caagagctga actctaagga cctttcaaca ggctcacagt ttgtaggcct catggcagtt | 540 |
| ctcacagcct gtttttcaag tggctttgct ggagtttatt ttgagaaaat cttaaaagaa | 600 |
| acaaaacagt cagtatggat aaggaacatt caacttggtt tctttggaag tatatttgga | 660 |
| ttaatgggtg tatacgttta tgatggagaa ttggtctcaa agaatggatt tttttcaggga | 720 |
| tataatcaac tgacgtggat agttgttgct ctgcaggcac ttggaggcct tgtaatagct | 780 |
| gctgtcatca aatatgcaga taacatttta aaaggatttg cgacctcctt atccataata | 840 |
| ttgtcaacaa taatatctta ttttggttg caagattttg tgccaaccag tgtctttttc | 900 |
| cttggagcca tccttgtaat agcagctact ttcttgtatg gttacgatcc caaacctgca | 960 |
| ggaaatccca ctaaagcata g | 981 |

<210> SEQ ID NO 20
<211> LENGTH: 486
<212> TYPE: DNA
<213> ORGANISM: Artificial
<220> FEATURE:
<223> OTHER INFORMATION: PpGAPDH promoter

<400> SEQUENCE: 20

| tttttgtaga aatgtcttgg tgtcctcgtc caatcaggta gccatctctg aaatatctgg | 60 |
| ctccgttgca actccgaacg acctgctggc aacgtaaaat tctccggggt aaaacttaaa | 120 |
| tgtggagtaa tggaaccaga aacgtctctt cccttctctc tccttccacc gcccgttacc | 180 |
| gtccctagga aatttttactc tgctggagag cttcttctac ggccccttg cagcaatgct | 240 |
| cttcccagca ttacgtttgcg ggtaaaacgg aggtcgtgta cccgacctag cagcccaggg | 300 |
| atggaaaagt cccggccgtc gctggcaata atagcgggcg gacgcatgtc atgagattat | 360 |

| | |
|---|---|
| tggaaaccac cagaatcgaa tataaaaggc gaacaccttt cccaattttg gtttctcctg | 420 |
| acccaaagac tttaaattta atttatttgt ccctatttca atcaattgaa caactatcaa | 480 |
| aacaca | 486 |

<210> SEQ ID NO 21
<211> LENGTH: 293
<212> TYPE: DNA
<213> ORGANISM: Artificial
<220> FEATURE:
<223> OTHER INFORMATION: ScCYC TT

<400> SEQUENCE: 21

| | |
|---|---|
| acaggcccct tttcctttgt cgatatcatg taattagtta tgtcacgctt acattcacgc | 60 |
| cctcctccca catccgctct aaccgaaaag gaaggagtta gacaacctga agtctaggtc | 120 |
| cctatttatt ttttttaata gttatgttag tattaagaac gttatttata tttcaaattt | 180 |
| ttcttttttt tctgtacaaa cgcgtgtacg catgtaacat tatactgaaa accttgcttg | 240 |
| agaaggtttt gggacgctcg aaggctttaa tttgcaagct gccggctctt aag | 293 |

<210> SEQ ID NO 22
<211> LENGTH: 1128
<212> TYPE: DNA
<213> ORGANISM: Artificial
<220> FEATURE:
<223> OTHER INFORMATION: Sequence of the 5'-Region used for knock out of
    PpMNN4L1

<400> SEQUENCE: 22

| | |
|---|---|
| gatctggcca ttgtgaaact tgacactaaa gacaaaactc ttagagtttc caatcactta | 60 |
| ggagacgatg tttcctacaa cgagtacgat ccctcattga tcatgagcaa tttgtatgtg | 120 |
| aaaaaagtca tcgaccttga caccttggat aaaagggctg gaggaggtgg aaccacctgt | 180 |
| gcaggcggtc tgaaagtgtt caagtacgga tctactacca aatatacatc tggtaacctg | 240 |
| aacggcgtca ggttagtata ctggaacgaa ggaaagttgc aaagctccaa atttgtggtt | 300 |
| cgatcctcta attactctca aaagcttgga ggaaacagca acgccgaatc aattgacaac | 360 |
| aatggtgtgg gttttgcctc agctggagac tcaggcgcat ggattctttc caagctacaa | 420 |
| gatgttaggg agtaccagtc attcactgaa aagctaggtg aagctacgat gagcattttc | 480 |
| gatttccacg gtcttaaaca ggagacttct actacagggc ttgggggtagt tggtatgatt | 540 |
| cattcttacg acggtgagtt caaacagttt ggtttgttca ctccaatgac atctattcta | 600 |
| caaagacttc aacgagtgac caatgtagaa tggtgtgtag cggggttgcga agatggggat | 660 |
| gtggacactg aaggagaaca cgaattgagt gatttggaac aactgcatat gcatagtgat | 720 |
| tccgactagt caggcaagag agagccctca aatttacctc tctgccccctc ctcactcctt | 780 |
| ttggtacgca taattgcagt ataaagaact tgctgccagc cagtaatctt atttcatacg | 840 |
| cagttctata tagcacataa tcttgcttgt atgtatgaaa tttaccgcgt ttagttgaa | 900 |
| attgtttatg ttgtgtgcct tgcatgaaat ctctcgttag ccctatcctt acatttaact | 960 |
| ggtctcaaaa cctctaccaa ttccattgct gtacaacaat atgaggcggc attactgtag | 1020 |
| ggttggaaaa aaattgtcat tccagctaga gatcacacga cttcatcacg cttattgctc | 1080 |
| ctcattgcta aatcatttac tcttgacttc gacccagaaa agttcgcc | 1128 |

<210> SEQ ID NO 23
<211> LENGTH: 1231
<212> TYPE: DNA

<213> ORGANISM: Artificial
<220> FEATURE:
<223> OTHER INFORMATION: Sequence of the 3'-Region used for knock out of PpMNN4L1

<400> SEQUENCE: 23

```
gcatgtcaaa cttgaacaca acgactagat agttgttttt tctatataaa acgaaacgtt      60
atcatcttta ataatcattg aggtttaccc ttatagttcc gtattttcgt ttccaaactt     120
agtaatcttt tggaaatatc atcaaagctg gtgccaatct tcttgtttga agtttcaaac     180
tgctccacca agctacttag agactgttct aggtctgaag caacttcgaa cacagagaca     240
gctgccgccg attgttcttt tttgtgtttt tcttctggaa gaggggcatc atcttgtatg     300
tccaatgccc gtatcctttc tgagttgtcc gacacattgt ccttcgaaga gtttcctgac     360
attgggcttc ttctatccgt gtattaattt tgggttaagt tcctcgtttg catagcagtg     420
gataccctcga tttttttggc tcctatttac ctgacataat attctactat aatccaactt    480
ggacgcgtca tctatgataa ctaggctctc ctttgttcaa aggggacgtc ttcataatcc     540
actggcacga agtaagtctg caacgaggcg gcttttgcaa cagaacgata gtgtcgtttc     600
gtacttggac tatgctaaac aaaaggatct gtcaaacatt tcaaccgtgt ttcaaggcac     660
tcttttacgaa ttatcgacca agaccttcct agacgaacat ttcaacatat ccaggctact   720
gcttcaaggt ggtgcaaatg ataaaggtat agatattaga tgtgtttggg acctaaaaca    780
gttcttgcct gaagattccc ttgagcaaca ggcttcaata gccaagttag agaagcagta    840
ccaaatcggt aacaaaaggg ggaagcatat aaaaccttta ctattgcgac aaaatccatc    900
cttgaaagta agctgtttg ttcaatgtaa agcatacgaa acgaaggagg tagatcctaa    960
gatggttaga gaacttaacg ggacatactc cagctgcatc ccatattacg atcgctggaa  1020
gactttttc atgtacgtat cgcccaccaa cctttcaaag caagctaggt atgatttga   1080
cagttctcac aatccattgg ttttcatgca acttgaaaaa acccaactca aacttcatgg  1140
ggatccatac aatgtaaatc attacgagag ggcgaggttg aaaagtttcc attgcaatca  1200
cgtcgcatca tggctactga aaggccttaa c                                 1231
```

<210> SEQ ID NO 24
<211> LENGTH: 937
<212> TYPE: DNA
<213> ORGANISM: Artificial
<220> FEATURE:
<223> OTHER INFORMATION: Sequence of the 5'-Region used for knock out of PpPNO1 and PpMNN4

<400> SEQUENCE: 24

```
tcattctata tgttcaagaa aagggtagtg aaaggaaaga aaaggcatat aggcgaggga      60
gagttagcta gcatacaaga taatgaagga tcaatagcgg tagttaaagt gcacaagaaa    120
agagcacctg ttgaggctga tgataaagct ccaattacat tgccacagag aaacacagta    180
acagaaatag gagggatgc accacgagaa gagcattcag tgaacaactt tgccaaattc     240
ataacccccaa gcgctaataa gccaatgtca aagtcggcta ctaacattaa tagtacaaca    300
actatcgatt tcaaccagaa tgtttgcaag gactacaaac agacaggtta ctgcggatat    360
ggtgacactt gtaagttttt gcacctgagg gatgatttca acagggatg gaaattagat    420
agggagtggg aaaatgtcca aaagaagaag cataatactc tcaaagggt taaggagatc    480
caaatgttta atgaagatga gctcaaagat atcccgttta aatgcattat atgcaaagga    540
gattacaaat cacccgtgaa aacttcttgc aatcattatt tttgcgaaca atgtttcctg    600
```

```
caacggtcaa gaagaaaacc aaattgtatt atatgtggca gagacacttt aggagttgct      660
ttaccagcaa agaagttgtc ccaatttctg gctaagatac ataataatga agtaataaaa      720
gtttagtaat tgcattgcgt tgactattga ttgcattgat gtcgtgtgat actttcaccg      780
aaaaaaaaca cgaagcgcaa taggagcggt tgcatattag tccccaaagc tatttaattg      840
tgcctgaaac tgttttttaa gctcatcaag cataattgta tgcattgcga cgtaaccaac      900
gtttaggcgc agtttaatca tagcccactg ctaagcc                               937

<210> SEQ ID NO 25
<211> LENGTH: 1906
<212> TYPE: DNA
<213> ORGANISM: Artificial
<220> FEATURE:
<223> OTHER INFORMATION: Sequence of the 3'-Region used for knock out of
      PpPNO1 and PpMNN4

<400> SEQUENCE: 25
cggaggaatg caataataa tctccttaat tacccactga taagctcaag agacgcggtt       60
tgaaaacgat ataatgaatc atttggattt tataataaac cctgacagtt tttccactgt      120
attgttttaa cactcattgg aagctgtatt gattctaaga agctagaaat caatacggcc      180
atacaaaaga tgacattgaa taagcaccgg cttttttgat tagcatatac cttaaagcat      240
gcattcatgg ctacatagtt gttaaagggc ttcttccatt atcagtataa tgaattacat      300
aatcatgcac ttatatttgc ccatctctgt tctctcactc ttgcctgggt atattctatg      360
aaattgcgta tagcgtgtct ccagttgaac cccaagcttg gcgagtttga agagaatgct      420
aaccttgcgt attccttgct tcaggaaaca ttcaaggaga acaggtcaa gaagccaaac       480 attttgatcc ttcccgagtt agcattgact ggctacaatt tcaaagcca gcagcggata      540 gagcctttttt tggaggaaac aaccaaggga gctagtaccc aatgggctca aaaagtatcc    600
aagacgtggg attgctttac tttaatagga tacccagaaa aagtttaga gagccctccc      660 cgtatttaca acagtgcggt acttgtatcg cctcaggaa agtaatgaa caactacaga       720 aagtccttct tgtatgaagc tgatgaacat tggggatgtt cggaatcttc tgatgggttt     780
caaacagtag atttattaat tgaaggaaag actgtaaaga catcatttgg aatttgcatg    840
gatttgaatc cttataaatt tgaagctcca ttcacagact tcgagttcag tggccattgc   900
ttgaaaaccg gtacaagact cattttgtgc ccaatggcct ggttgtcccc tctatcgcct    960
tccattaaaa aggatcttag tgatatagag aaaagcagac ttcaaaagtt ctaccttgaa    1020
aaaatagata ccccggaatt tgacgttaat tacgaattga aaaagatga agtattgccc    1080 acccgtatga atgaaacgtt ggaaacaatt gactttgagc cttcaaaacc ggactactct   1140
aatataaatt attggatact aaggtttttt ccctttctga ctcatgtcta taaacgagat   1200
gtgctcaaag agaatgcagt tgcagtctta tgcaaccgag ttggcattga gagtgatgtc    1260
ttgtacggag gatcaaccac gattctaaac ttcaatggta agttagcatc gacacaagag   1320
gagctggagt tgtacgggca gactaatagt ctcaaccca gtgtggaagt attggggcc     1380 cttggcatgg gtcaacaggg aattctagta cgagacattg aattaacata atatacaata  1440
tacaataaac acaaataaag aatacaagcc tgacaaaaat tcacaaatta ttgcctagac  1500
ttgtcgttat cagcagcgac cttttttccaa tgctcaattt cacgatatgc cttttctagc   1560
tctgctttaa gcttctcatt ggaattggct aactcgttga ctgcttggtc agtgatgagt   1620
ttctccaagg tccatttctc gatgttgttg ttttcgtttt cctttaatct cttgatataa  1680
```

```
tcaacagcct tctttaatat ctgagccttg ttcgagtccc ctgttggcaa cagagcggcc   1740
agttccttta ttccgtggtt tatattttct cttctacgcc tttctacttc tttgtgattc   1800
tctttacgca tcttatgcca ttcttcagaa ccagtggctg gcttaaccga atagccagag   1860
cctgaagaag ccgcactaga agaagcagtg gcattgttga ctatgg                  1906
```

<210> SEQ ID NO 26
<211> LENGTH: 1224
<212> TYPE: DNA
<213> ORGANISM: Artificial
<220> FEATURE:
<223> OTHER INFORMATION: DNA encodes human GnTI catalytic domain (NA)
      Codon-optimized

<400> SEQUENCE: 26

```
tcagtcagtg ctcttgatgg tgacccagca agtttgacca gagaagtgat tagattggcc     60
caagacgcag aggtggagtt ggagagacaa cgtggactgc tgcagcaaat cggagatgca    120
ttgtctagtc aaagaggtag ggtgcctacc gcagctcctc cagcacagcc tagagtgcat    180 gtgaccctg caccagctgt gattcctatc ttggtcatcg cctgtgacag atctactgtt    240
agaagatgtc tggacaagct gttgcattac agaccatctg ctgagttgtt ccctatcatc    300
gttagtcaag actgtggtca cgaggagact gcccaagcca tcgcctccta cggatctgct    360
gtcactcaca tcagacagcc tgacctgtca tctattgctg tgccaccaga ccacagaaag    420
ttccaaggtt actacaagat cgctagacac tacagatggg cattgggtca agtcttcaga    480
cagtttagat tccctgctgc tgtggtggtg gaggatgact ggaggtggc tcctgacttc    540 tttgagtact tagagcaac ctatccattg ctgaaggcag acccatccct gtggtgtgtc    600
tctgcctgga tgacaacgg taaggagcaa atggtgacg cttctaggcc tgagctgttg    660
tacagaaccg acttctttcc tggtctggga tggttgctgt tggctgagtt gtgggctgag    720
ttggagccta gtggccaaa ggcattctgg gacgactgga tgagaagacc tgagcaaaga    780
cagggtagag cctgtatcag acctgagatc tcaagaacca tgaccttgg tagaaaggga    840 gtgtctcacg tcaattctt tgaccaacac ttgaagttta tcaagctgaa ccagcaattt    900
gtgcacttca cccaactgga cctgtcttac ttgcagagag aggcctatga cagagatttc    960
ctagctagag tctacggagc tcctcaactg caagtggaga agtgaggac caatgacaga   1020 aaggagttgg gagaggtgag agtgcagtac actggtaggg actccttaa ggctttcgct   1080 aaggctctgg gtgtcatgga tgaccttaag tctggagttc ctagagctgg ttacagaggt   1140
attgtcacct ttcaattcag aggtagaaga gtccacttgg ctcctccacc tacttgggag   1200
ggttatgatc cttcttggaa ttag                                         1224
```

<210> SEQ ID NO 27
<211> LENGTH: 99
<212> TYPE: DNA
<213> ORGANISM: Artificial
<220> FEATURE:
<223> OTHER INFORMATION: DNA encodes Pp SEC12 (10)

<400> SEQUENCE: 27

```
atgcccagaa aaatatttaa ctacttcatt ttgactgtat tcatggcaat tcttgctatt     60
gttttacaat ggtctataga gaatggacat gggcgcgcc                           99
```

<210> SEQ ID NO 28
<211> LENGTH: 435

```
<212> TYPE: DNA
<213> ORGANISM: Artificial
<220> FEATURE:
<223> OTHER INFORMATION: Sequence of the PpSEC4 promoter

<400> SEQUENCE: 28
gaagtaaagt tggcgaaact ttgggaacct ttggttaaaa ctttgtaatt tttgtcgcta      60
cccattaggc agaatctgca tcttgggagg gggatgtggt ggcgttctga gatgtacgcg     120
aagaatgaag agccagtggt aacaacaggc tagagagat acgggcataa tgggtataac      180
ctacaagtta agaatgtagc agccctggaa accagattga acgaaaaac gaaatcattt      240 aaactgtagg atgttttggc tcattgtctg gaaggctggc tgtttattgc cctgttcttt     300
gcatgggaat aagctattat atccctcaca taatcccaga aaatagattg aagcaacgcg     360
aaatccttac gtatcgaagt agccttctta cacattcacg ttgtacggat aagaaaacta    420
ctcaaacgaa caatc                                                      435

<210> SEQ ID NO 29
<211> LENGTH: 404
<212> TYPE: DNA
<213> ORGANISM: Artificial
<220> FEATURE:
<223> OTHER INFORMATION: Sequence of the PpOCH1 terminator

<400> SEQUENCE: 29
aatagatata gcgagattag agaatgaata ccttcttcta agcgatcgtc cgtcatcata      60
gaatatcatg gactgtatag ttttttttt gtacatataa tgattaaacg gtcatccaac     120
atctcgttga cagatctctc agtacgcgaa atccctgact atcaaagcaa gaaccgatga    180
agaaaaaaac aacagtaacc caaacaccac aacaaacact ttatcttctc ccccccaaca    240
ccaatcatca aagagatgtc ggaacacaaa caccaagaag caaaaactaa ccccatataa    300
aaacatcctg gtagataatg ctggtaaccc gctctccttc catattctgg gctacttcac    360
gaagtctgac cggtctcagt tgatcaacat gatcctcgaa atgg                     404

<210> SEQ ID NO 30
<211> LENGTH: 1407
<212> TYPE: DNA
<213> ORGANISM: Artificial
<220> FEATURE:
<223> OTHER INFORMATION: DNA encodes Mm ManI catalytic domain (FB)

<400> SEQUENCE: 30
gagcccgctg acgccaccat ccgtgagaag agggcaaaga tcaaagagat gatgacccat      60
gcttggaata attataaacg ctatgcgtgg ggcttgaacg aactgaaacc tatatcaaaa     120
gaaggccatt caagcagttt gtttggcaac atcaaaggag ctacaatagt agatgccctg    180
gatacccttt tcattatggg catgaagact gaatttcaag aagctaaatc gtggattaaa    240
aaatatttag attttaatgt gaatgctgaa gtttctgttt ttgaagtcaa catacgcttc    300
gtcggtggac tgctgtcagc ctactatttg tccggagagg agatatttcg aaagaaagca    360
gtggaacttg gggtaaaatt gctacctgca tttcatactc cctctggaat accttgggca    420
ttgctgaata tgaaaagtgg gatcgggcgg aactggccct gggcctctgg aggcagcagt    480
atcctggccg aatttggaac tctgcattta gagtttatgc acttgtccca cttatcagga    540
gacccagtct ttgccgaaaa ggttatgaaa attcgaacag tgttgaacaa actggacaaa    600
ccagaaggcc tttatcctaa ctatctgaac cccagtagtg acagtggggg tcaacatcat    660
```

```
gtgtcggttg gaggacttgg agacagcttt tatgaatatt tgcttaaggc gtggttaatg      720
tctgacaaga cagatctcga agccaagaag atgtatttg atgctgttca ggccatcgag       780
actcacttga tccgcaagtc aagtggggga ctaacgtaca tcgcagagtg aagggggggc      840
ctcctggaac acaagatggg ccacctgacg tgctttgcag gaggcatgtt tgcacttggg      900
gcagatggag ctccggaagc ccgggcccaa cactaccttg aactcggagc tgaaattgcc     960
cgcacttgtc atgaatctta taatcgtaca tatgtgaagt tgggaccgga agcgtttcga     1020
tttgatggcg gtgtggaagc tattgccacg aggcaaaatg aaaagtatta catcttacgg    1080
cccgaggtca tcgagacata catgtacatg tggcgactga ctcacgaccc caagtacagg    1140
acctgggcct gggaagccgt ggaggctcta gaaagtcact gcagagtgaa cggaggctac    1200
tcaggcttac gggatgttta cattgcccgt gagagttatg acgatgtcca gcaaagtttc    1260
ttcctggcag agacactgaa gtatttgtac ttgatatttt ccgatgatga ccttcttcca    1320
ctagaacact ggatcttcaa caccgaggct catcctttcc ctatactccg tgaacagaag    1380
aaggaaattg atggcaaaga gaaatga                                          1407

<210> SEQ ID NO 31
<211> LENGTH: 318
<212> TYPE: DNA
<213> ORGANISM: Artificial
<220> FEATURE:
<223> OTHER INFORMATION: DNA encodes ScSEC12 (8)

<400> SEQUENCE: 31
atgaacacta tccacataat aaaattaccg cttaactacg ccaactacac ctcaatgaaa       60
caaaaaatct ctaaattttt caccaacttc atccttattg tgctgctttc ttacatttta      120
cagttctcct ataagcacaa tttgcattcc atgcttttca attacgcgaa ggacaatttt      180
ctaacgaaaa gagacaccat ctcttcgccc tacgtagttg atgaagactt acatcaaaca      240
actttgtttg gcaaccacgg tacaaaaaca tctgtaccta gcgtagattc cataaaagtg      300
catggcgtgg ggcgcgcc                                                      318

<210> SEQ ID NO 32
<211> LENGTH: 1250
<212> TYPE: DNA
<213> ORGANISM: Artificial
<220> FEATURE:
<223> OTHER INFORMATION: Sequence of the 5'-region that was used to
      knock into the PpADE1 locus

<400> SEQUENCE: 32
gagtcggcca agagatgata actgttacta agcttctccg taattagtgg tattttgtaa       60
cttttaccaa taatcgttta tgaatacgga tattttcga ccttatccag tgccaaatca       120
cgtaacttaa tcatggttta aatactccac ttgaacgatt cattattcag aaaaaagtca      180
ggttggcaga aacacttggg cgctttgaag agtataagag tattaagcat aaacatctg       240 aactttcacc gccccaatat actactctag gaaactcgaa aaattccttt ccatgtgtca      300
tcgcttccaa cacactttgc tgtatccttc caagtatgtc cattgtgaac actgatctgg      360
acggaatcct acctttaatc gccaaaggaa aggttagaga catttatgca gtcgatgaga      420
acaacttgct gttcgtcgca actgaccgta tctccgctta cgatgtgatt atgacaaacg      480
gtattcctga taagggaaag attttgactc agctctcagt tttctggttt gattttttgg      540
caccctacat aaagaatcat ttggttgctt ctaatgacaa ggaagtcttt gctttactac      600
```

```
catcaaaact gtctgaagaa aaatacaaat ctcaattaga gggacgatcc ttgatagtaa    660
aaaagcacag actgatacct ttggaagcca ttgtcagagg ttacatcact ggaagtgcat    720
ggaaagagta caagaactca aaaactgtcc atggagtcaa ggttgaaaac gagaaccttc    780
aagagagcga cgcctttcca actccgattt tcacaccttc aacgaaagct gaacagggtg    840
aacacgatga aacatctct attgaacaag ctgctgagat tgtaggtaaa gacatttgtg    900
agaaggtcgc tgtcaaggcg gtcgagttgt attctgctgc aaaaaacctc gcccttttga    960
aggggatcat tattgctgat acgaaattcg aatttggact ggacgaaaac aatgaattgg   1020
tactagtaga tgaagtttta actccagatt cttctagatt ttggaatcaa aagacttacc   1080
aagtgggtaa atcgcaagag agttacgata agcagtttct cagagattgg ttgacggcca   1140
acggattgaa tggcaaagag ggcgtagcca tggatgcaga aattgctatc aagagtaaag   1200
aaaagtatat tgaagcttat gaagcaatta ctggcaagaa atgggcttga              1250
```

<210> SEQ ID NO 33
<211> LENGTH: 376
<212> TYPE: DNA
<213> ORGANISM: Artificial
<220> FEATURE:
<223> OTHER INFORMATION: PpALG3 TT

<400> SEQUENCE: 33

```
atttacaatt agtaatatta aggtggtaaa acattcgta gaattgaaat gaattaatat     60
agtatgacaa tggttcatgt ctataaatct ccggcttcgg taccttctcc ccaattgaat    120
acattgtcaa aatgaatggt tgaactatta ggttcgccag tttcgttatt aagaaaactg    180
ttaaaatcaa attccatatc atcggttcca gtgggaggac cagttccatc gccaaaatcc    240
tgtaagaatc cattgtcaga acctgtaaag tcagtttgag atgaaatttt tccggtcttt    300
gttgacttgg aagcttcgtt aaggttaggt gaaacagttt gatcaaccag cggctcccgt    360
tttcgtcgct tagtag                                                    376
```

<210> SEQ ID NO 34
<211> LENGTH: 882
<212> TYPE: DNA
<213> ORGANISM: Artificial
<220> FEATURE:
<223> OTHER INFORMATION: Sequence of the 3'-region that was used to
      knock into the PpADE1 locus

<400> SEQUENCE: 34

```
atgattagta ccctcctcgc cttttcaga catctgaaat ttcccttatt cttccaattc     60
catataaaat cctatttagg taattagtaa acaatgatca taaagtgaaa tcattcaagt    120
aaccattccg tttatcgttg atttaaaatc aataacgaat gaatgtcggt ctgagtagtc    180
aatttgttgc cttggagctc attggcaggg ggtcttttgg ctcagtatgg aaggttgaaa    240
ggaaaacaga tggaaagtgg ttcgtcagaa aagaggtatc ctacatgaag atgaatgcca    300
aagagatatc tcaagtgata gctgagttca gaattcttag tgagttaagc catcccaaca    360
ttgtgaagta ccttcatcac gaacatattt ctgagaataa aactgtcaat ttatacatgg    420
aatactgtga tggtggagat ctctccaagc tgattcgaac acatagaagg aacaaagagt    480
acatttcaga agaaaaaata tggagtattt ttacgcaggt tttattagca ttgtatcgtt    540
gtcattatgg aactgatttc acggcttcaa aggagtttga atcgctcaat aaaggtaata    600
gacgaaccca gaatccttcg tgggtagact cgacaagagt tattattcac agggatataa    660
```

```
aacccgacaa catctttctg atgaacaatt caaaccttgt caaactggga gattttggat    720
tagcaaaaat tctggaccaa gaaaacgatt ttgccaaaac atacgtcggt acgccgtatt    780
acatgtctcc tgaagtgctg ttggaccaac cctactcacc attatgtgat atatggtctc    840
ttgggtgcgt catgtatgag ctatgtgcat tgaggcctcc tt                       882

<210> SEQ ID NO 35
<211> LENGTH: 2100
<212> TYPE: DNA
<213> ORGANISM: Artificial
<220> FEATURE:
<223> OTHER INFORMATION: DNA encodes ScGAL10

<400> SEQUENCE: 35
atgacagctc agttacaaag tgaaagtact tctaaaattg ttttggttac aggtggtgct     60
ggatacattg gttcacacac tgtggtagag ctaattgaga atggatatga ctgtgttgtt    120
gctgataacc tgtcgaattc aacttatgat tctgtagcca ggttagaggt cttgaccaag    180
catcacattc ccttctatga ggttgatttg tgtgaccgaa aaggtctgga aaaggttttc    240
aaagaatata aaattgattc ggtaattcac tttgctggtt taaaggctgt aggtgaatct    300
acacaaatcc cgctgagata ctatcacaat aacattttgg gaactgtcgt tttattagag    360
ttaatgcaac aatacaacgt ttccaaattt gttttttcat cttctgctac tgtctatggt    420
gatgctacga gattcccaaa tatgattcct atcccagaag aatgtccctt agggcctact    480
aatccgtatg gtcatacgaa atacgccatt gagaatatct tgaatgatct ttacaatagc    540
gacaaaaaaa gttggaagtt tgctatcttg cgttatttta acccaattgg cgcacatccc    600
tctggattaa tcggagaaga tccgctaggt ataccaaaca atttgttgcc atatatggct    660
caagtagctg ttggtaggcg cgagaagctt tacatcttcg gagacgatta tgattccaga    720
gatggtaccc cgatcaggga ttatatccac gtagttgatc tagcaaaagg tcatattgca    780
gccctgcaat acctagaggc ctacaatgaa aatgaaggtt tgtgtcgtga gtggaacttg    840
ggttccggta aaggttctac agttttgaa gtttatcatg cattctgcaa agcttctggt    900
attgatcttc catacaaagt tacgggcaga agagcaggtc atgttttgaa cttgacggct    960
aaaccagata gggccaaacg cgaactgaaa tggcagaccg agttgcaggt tgaagactcc   1020
tgcaaggatt tatggaaatg gactactgag aatccttttg ttaccagtt aaggggtgtc   1080 gaggccagat tttccgctga agatatgcgt tatgacgcaa gatttgtgac tattggtgcc   1140
ggcaccagat tcaagccac gtttgccaat ttgggcgcca gcattgttga cctgaaagtg   1200
aacggacaat cagttgttct tggctatgaa aatgaggaag ggtatttgaa tcctgatagt   1260
gcttatatag gcgccacgat cggcaggtat gctaatcgta tttcgaaggg taagtttagt   1320
ttatgcaaca aagactatca gttaaccgtt aataacggcg ttaatgcgaa tcatagtagt   1380
atcggttctt ccacagaaa aagattttttg ggacccatca ttcaaaatcc ttcaaaggat   1440 gttttttaccg ccgagtacat gctgatagat aatgagaagg acaccgaatt tccaggtgat   1500
ctattggtaa ccatacagta tactgtgaac gttgcccaaa aaagtttgga aatggtatat   1560
aaaggtaaat tgactgctgg tgaagcgacg ccaataaatt taacaaatca tagttatttc   1620
aatctgaaca agccatatgg agacactatt gagggtacgg agattatggt gcgttcaaaa   1680
aaatctgttg atgtcgacaa aaacatgatt cctacgggta atatcgtcga tagagaaatt   1740 gctacccttta actctacaaa gccaacggtc ttaggcccca aaaatcccca gtttgattgt   1800
tgttttgtgg tggatgaaaa tgctaagcca agtcaaatca atactctaaa caatgaattg   1860
```

```
acgcttattg tcaaggcttt tcatcccgat tccaatatta cattagaagt tttaagtaca    1920
gagccaactt atcaatttta taccggtgat ttcttgtctg ctggttacga agcaagacaa    1980
ggttttgcaa ttgagcctgg tagatacatt gatgctatca atcaagagaa ctggaaagat    2040
tgtgtaacct tgaaaaacgg tgaaacttac gggtccaaga ttgtctacag attttcctga   2100
```

<210> SEQ ID NO 36
<211> LENGTH: 1037
<212> TYPE: DNA
<213> ORGANISM: Artificial
<220> FEATURE:
<223> OTHER INFORMATION: Sequence of the PpPMA1 promoter

<400> SEQUENCE: 36

```
aaatgcgtac ctcttctacg agattcaagc gaatgagaat aatgtaatat gcaagatcag      60
aaagaatgaa aggagttgaa aaaaaaaacc gttgcgtttt gaccttgaat ggggtggagg     120
tttccattca agtaaagcc tgtgtcttgg tattttcggc ggcacaagaa atcgtaattt      180
tcatcttcta aacgatgaag atcgcagccc aacctgtatg tagttaaccg gtcggaatta    240
taagaaagat tttcgatcaa caaaccctag caaatagaaa gcagggttac aactttaaac    300
cgaagtcaca aacgataaac cactcagctc ccacccaaat tcattcccac tagcagaaag    360
gaattattta tccctcagg aaacctcgat gattctcccg ttcttccatg ggcgggtatc     420
gcaaaatgag gaattttca aatttctcta ttgtcaagac tgtttattat ctaagaaata    480
gcccaatccg aagctcagtt ttgaaaaaat cacttccgcg tttctttttt acagcccgat    540
gaatatccaa atttggaata tggattactc tatcgggact gcagataata tgacaacaac    600
gcagattaca ttttaggtaa ggcataaaca ccagccagaa atgaaacgcc cactagccat    660
ggtcgaatag tccaatgaat tcagatagct atggtctaaa agctgatgtt ttttattggg    720
taatggcgaa gagtccagta cgacttccag cagagctgag atggccattt ttgggggtat    780
tagtaacttt ttgagctctt ttcacttcga tgaagtgtcc cattcgggat ataatcggat    840
cgcgtcgttt tctcgaaaat acagcttagc gtcgtccgct tgttgtaaaa gcagcaccac    900
attcctaatc tcttatataa acaaaacaac ccaaattatc agtgctgttt tcccaccaga    960
tataagtttc ttttctcttc cgcttttttga ttttttatct cttttcctta aaaacttctt   1020
taccttaaag ggcggcc                                                   1037
```

<210> SEQ ID NO 37
<211> LENGTH: 512
<212> TYPE: DNA
<213> ORGANISM: Artificial
<220> FEATURE:
<223> OTHER INFORMATION: Sequence of the PpPMA1 terminator

<400> SEQUENCE: 37

```
taagcttcac gatttgtgtt ccagtttatc cccccttttat ataccgttaa ccctttccct     60
gttgagctga ctgttgttgt attaccgcaa tttttccaag tttgccatgc ttttcgtgtt    120
atttgaccga tgtctttttt cccaaatcaa actatatttg ttaccattta aaccaagtta    180
tcttttgtat taagagtcta agtttgttcc caggcttcat gtgagagtga taaccatcca    240
gactatgatt cttgtttttt attgggtttg tttgtgtgat acatctgagt tgtgattcgt    300
aaagtatgtc agtctatcta gatttttaat agttaattgg taatcaatga cttgtttgtt    360 ttaacttta aattgtgggt cgtatccacg cgtttagtat agctgttcat ggctgttaga    420
```

```
ggagggcgat gtttatatac agaggacaag aatgaggagg cggcgtgtat ttttaaaatg    480
gagacgcgac tcctgtacac cttatcggtt gg                                  512
```

<210> SEQ ID NO 38
<211> LENGTH: 1068
<212> TYPE: DNA
<213> ORGANISM: Artificial
<220> FEATURE:
<223> OTHER INFORMATION: hGalT codon optimized (XB)

<400> SEQUENCE: 38

```
ggtagagatt tgtctagatt gccacagttg gttggtgttt ccactccatt gcaaggaggt     60
tctaactctg ctgctgctat tggtcaatct tccggtgagt tgagaactgg tggagctaga   120
ccacctccac cattgggagc ttcctctcaa ccaagaccag gtggtgattc ttctccagtt   180
gttgactctg gtccaggtcc agcttctaac ttgacttccg ttccagttcc acacactact   240
gctttgtcct tgccagcttg tccagaagaa tccccattgt tggttggtcc aatgttgatc   300
gagttcaaca tgccagttga cttggagttg gttgctaagc agaacccaaa cgttaagatg   360
ggtggtagat acgctccaag agactgtgtt tccccacaca agttgctat catcatccca   420 ttcagaaaca gacaggagca cttgaagtac tggttgtact acttgcaccc agttttgcaa   480
agacagcagt tggactacgg tatctacgtt atcaaccagg ctggtgacac tattttcaac   540
agagctaagt gttgaatgt tggtttccag gaggctttga aggattacga ctacacttgt   600
ttcgttttct ccgacgttga cttgattcca atgaacgacc acaacgctta cagatgtttc   660
tcccagccaa gacacatttc tgttgctatg gacaagttcg gtttctcctt gccatacgtt   720
caatacttcg gtggtgtttc cgctttgtcc aagcagcagt tcttgactat caacggtttc   780
ccaaacaatt actggggatg gggtggtgaa gatgacgaca tctttaacag attggttttc   840
agaggaatgt ccatctctag accaaacgct gttgttggta gatgtagaat gatcagacac   900
tccagagaca gaagaacga gccaaaccca caaagattcg acagaatcgc tcacactaag   960
gaaactatgt tgtccgacgg attgaactcc ttgacttacc aggttttgga cgttcagaga  1020
tacccattgt acactcagat cactgttgac atcggtactc catcctag              1068
```

<210> SEQ ID NO 39
<211> LENGTH: 183
<212> TYPE: DNA
<213> ORGANISM: Artificial
<220> FEATURE:
<223> OTHER INFORMATION: DNA encodes ScMnt1 (Kre2) (33)

<400> SEQUENCE: 39

```
atggccctct ttctcagtaa agactgttg agatttaccg tcattgcagg tgcggttatt     60
gttctcctcc taacattgaa ttccaacagt agaactcagc aatatattcc gagttccatc   120
tccgctgcat ttgattttac ctcaggatct atatcccctg aacaacaagt catcgggcgc   180
gcc                                                                  183
```

<210> SEQ ID NO 40
<211> LENGTH: 1074
<212> TYPE: DNA
<213> ORGANISM: Artificial
<220> FEATURE:
<223> OTHER INFORMATION: DNA encodes DmUGT

<400> SEQUENCE: 40

```
atgaatagca tacacatgaa cgccaatacg ctgaagtaca tcagcctgct gacgctgacc     60
```

```
ctgcagaatg ccatcctggg cctcagcatg cgctacgccc gcaccggcc aggcgacatc      120 ttcctcagct ccacggccgt actcatggca gagttcgcca aactgatcac gtgcctgttc      180
ctggtcttca acgaggaggg caaggatgcc cagaagtttg tacgctcgct gcacaagacc      240
atcattgcga atcccatgga cacgctgaag gtgtgcgtcc cctcgctggt ctatatcgtt      300
caaaacaatc tgctgtacgt ctctgcctcc catttggatg cggccaccta ccaggtgacg      360
taccagctga agattctcac cacggccatg ttcgcggttg tcattctgcg ccgcaagctg      420
ctgaacacgc agtggggtgc gctgctgctc ctggtgatgg gcatcgtcct ggtgcagttg      480
gcccaaacgg agggtccgac gagtggctca gccggtggtg ccgcagctgc agccacggcc      540
gcctcctctg gcggtgctcc cgagcagaac aggatgctcg gactgtgggc cgcactgggc      600
gcctgcttcc tctccggatt cgcgggcatc tactttgaga gatcctcaa gggtgccgag      660 atctccgtgt ggatgcggaa tgtgcagttg agtctgctca gcattccctt cggcctgctc      720
acctgtttcg ttaacgacgg cagtaggatc ttcgaccagg gattcttcaa gggctacgat      780
ctgtttgtct ggtacctggt cctgctgcag gccggcggtg gattgatcgt tgccgtggtg      840
gtcaagtacg cggataacat tctcaagggc ttcgccacct cgctggccat catcatctcg      900
tgcgtggcct ccatatacat cttcgacttc aatctcacgc tgcagttcag cttcggagct      960
ggcctggtca tcgcctccat atttctctac ggctacgatc cggccaggtc ggcgccgaag     1020
ccaactatgc atggtcctgg cggcgatgag gagaagctgc tgccgcgcgt ctag           1074

<210> SEQ ID NO 41
<211> LENGTH: 798
<212> TYPE: DNA
<213> ORGANISM: Artificial
<220> FEATURE:
<223> OTHER INFORMATION: Sequence of the PpOCH1 promoter

<400> SEQUENCE: 41
tggacacagg agactcagaa acagacacag agcgttctga gtcctggtgc tcctgacgta       60
ggcctagaac aggaattatt ggctttattt gtttgtccat ttcataggct tggggtaata      120
gatagatgac agagaaatag agaagaccta atatttttg ttcatggcaa atcgcgggtt      180
cgcggtcggg tcacacacgg agaagtaatg agaagagctg gtaatctggg gtaaagggt      240 tcaaaagaag gtcgcctggt agggatgcaa tacaaggttg tcttggagtt tacattgacc      300
agatgatttg gcttttctc tgttcaattc acatttttca gcgagaatcg gattgacgga      360
gaaatggcgg ggtgtggggt ggatagatgg cagaaatgct cgcaatcacc gcgaaagaaa      420
gactttatgg aatagaacta ctgggtggtg taaggattac atagctagtc caatggagtc      480
cgttggaaag gtaagaagaa gctaaaaccg gctaagtaac tagggaagaa tgatcagact      540
ttgatttgat gaggtctgaa aatactctgc tgcttttca gttgctttt ccctgcaacc      600 tatcattttc cttttcataa gcctgccttt tctgttttca cttatatgag ttccgccgag      660
acttccccaa attctctcct ggaacattct ctatcgctct ccttccaagt tgcgcccct      720 ggcactgcct agtaatatta ccacgcgact tatattcagt tccacaattt ccagtgttcg      780
tagcaaatat catcagcc                                                    798

<210> SEQ ID NO 42
<211> LENGTH: 302
<212> TYPE: DNA
<213> ORGANISM: Artificial
<220> FEATURE:
```

<223> OTHER INFORMATION: Sequence of the PpALG12 terminator

<400> SEQUENCE: 42

```
aatatatacc tcatttgttc aatttggtgt aaagagtgtg gcggatagac ttcttgtaaa      60
tcaggaaagc tacaattcca attgctgcaa aaaataccaa tgcccataaa ccagtatgag     120
cggtgccttc gacggattgc ttactttccg acccttttgtc gtttgattct tctgcctttg    180
gtgagtcagt tgtttcgac tttatatctg actcatcaac ttcctttacg gttgcgtttt     240
taatcataat tttagccgtt ggcttattat cccttgagtt ggtaggagtt ttgatgatgc    300
tg                                                                    302
```

<210> SEQ ID NO 43
<211> LENGTH: 461
<212> TYPE: DNA
<213> ORGANISM: Artificial
<220> FEATURE:
<223> OTHER INFORMATION: Sequence of the 5'-Region used for knock out of PpHIS1

<400> SEQUENCE: 43

```
taactggccc tttgacgttt ctgacaatag ttctagagga gtcgtccaaa aactcaactc      60
tgacttgggt gacaccacca cgggatccgg ttcttccgag gaccttgatg accttggcta    120
atgtaactgg agttttagta tccattttaa gatgtgtgtt tctgtaggtt ctgggttgga    180
aaaaaatttt agacaccaga agagaggagt gaactggttt gcgtgggttt agactgtgta    240
aggcactact ctgtcgaagt tttagatagg ggttacccgc tccgatgcat gggaagcgat    300
tagcccggct gttgcccgtt tggttttttga agggtaattt tcaatatctc tgtttgagtc    360
atcaattcca tattcaaaga ttcaaaaaca aaatctggtc caaggagcgc atttaggatt    420
atggagttgg cgaatcactt gaacgataga ctattatttg c                        461
```

<210> SEQ ID NO 44
<211> LENGTH: 1841
<212> TYPE: DNA
<213> ORGANISM: Artificial
<220> FEATURE:
<223> OTHER INFORMATION: Sequence of the 3'-Region used for knock out of PpHIS1

<400> SEQUENCE: 44

```
gtgacattct tgtctttgag atcagtaatt gtagagcata gatagaataa tattcaagac      60
caacggcttc tcttcggaag ctccaagtag cttatagtga tgagtaccgg catatattta    120
taggcttaaa atttcgaggg ttcactatat tcgtttagtg ggaagagttc ctttcactct    180
tgttatctat attgtcagcg tggactgttt ataactgtac caacttagtt tctttcaact    240
ccaggttaag agacataaat gtcctttgat gctgacaata atcagtggaa ttcaaggaag    300
gacaatcccg acctcaatct gttcattaat gaagagttcg aatcgtcctt aaatcaagcg    360
ctagactcaa ttgtcaatga gaacccttc tttgaccaag aaactataaa tagatcgaat    420
gacaaagttg gaaatgagtc cattagctta catgatattg agcaggcaga ccaaaataaa    480
ccgtcctttg agagcgatat tgatggttcg gcgccgttga taagagacga caaattgcca    540
aagaaacaaa gctgggggct gagcaatttt ttttcaagaa gaaatagcat atgtttacca    600
ctacatgaaa atgattcaag tgttgttaag accgaaagat ctattgcagt gggaacaccc    660
catcttcaat actgcttcaa tggaatctcc aatgccaagt acaatgcatt tacccttttc    720
ccagtcatcc tatacgagca attcaaattt tttttcaatt tatactttac tttagtggct    780
```

```
ctctctcaag cgataccgca acttcgcatt ggatatcttt cttcgtatgt cgtcccactt      840
ttgtttgtac tcatagtgac catgtcaaaa gaggcgatgg atgatattca acgccgaaga      900
agggatagag aacagaacaa tgaaccatat gaggttctgt ccagcccatc accagttttg      960
tccaaaaact taaaatgtgg tcacttggtt cgattgcata agggaatgag agtgcccgca     1020
gatatggttc ttgtccagtc aagcgaatcc accggagagt catttatcaa gacagatcag     1080
ctggatggtg agactgattg gaagcttcgg attgtttctc cagttacaca atcgttacca     1140
atgactgaac ttcaaaatgt cgccatcact gcaagcgcac cctcaaaatc aattcactcc     1200
tttcttggaa gattgaccta caatgggcaa tcatatggtc ttacgataga caacacaatg     1260
tggtgtaata ctgtattagc ttctggttca gcaattggtt gtataattta cacaggtaaa     1320
gatactcgac aatcgatgaa cacaactcag cccaaactga aaacgggctt gttagaactg     1380
gaaatcaata gtttgtccaa gatcttatgt gtttgtgtgt ttgcattatc tgtcatctta     1440
gtgctattcc aaggaatagc tgatgattgg tacgtcgata tcatgcggtt tctcattcta     1500
ttctccacta ttatcccagt gtctctgaga gttaaccttg atcttggaaa gtcagtccat     1560
gctcatcaaa tagaaactga tagctcaata cctgaaaccg ttgttagaac tagtacaata     1620
ccggaagacc tgggaagaat tgaataccta ttaagtgaca aaactggaac tcttactcaa     1680
aatgatatgg aaatgaaaaa actacaccta ggaacagtct cttatgctgg tgataccatg     1740
gatattattt ctgatcatgt taaggtctt aataacgcta aacatcgag gaaagatctt     1800 ggtatgagaa taagagattt ggttacaact ctggccatct g                         1841
```

<210> SEQ ID NO 45
<211> LENGTH: 3105
<212> TYPE: DNA
<213> ORGANISM: Artificial
<220> FEATURE:
<223> OTHER INFORMATION: DNA encodes Drosophila melanogaster ManII
      codon-optimized (KD)

<400> SEQUENCE: 45

```
agagacgatc caattagacc tccattgaag gttgctagat ccccaagacc aggtcaatgt       60
caagatgttg ttcaggacgt cccaaacgtt gatgtccaga tgttggagtt gtacgataga      120
atgtccttca aggacattga tggtggtgtt tggaagcagg gttggaacat taagtacgat      180
ccattgaagt acaacgctca tcacaagttg aaggtcttcg ttgtcccaca ctcccacaac      240
gatcctggtt ggattcagac cttcgaggaa tactaccagc acgacaccaa gcacatcttg      300
tccaacgctt tgagacattt gcacgacaac ccagagatga agttcatctg gctgaaatc      360 tcctacttcg ctagattcta ccacgatttg ggtgagaaca agaagttgca gatgaagtcc      420
atcgtcaaga acggtcagtt ggaattcgtc actggtggat gggtcatgcc agacgaggct      480
aactcccact ggagaaacgt tttgttgcag ttgaccgaag gtcaaacttg gttgaagcaa      540
ttcatgaacg tcactccaac tgcttcctgg gctatcgatc cattcggaca ctctccaact      600
atgccataca ttttgcagaa gtctggtttc aagaatatgt tgatccagag aacccactac      660
tccgttaaga aggagttggc tcaacagaga cagttggagt tcttgtggag acagatctgg      720
gacaacaaag gtgacactgc tttgttcacc cacatgatgc cattctactc ttacgacatt      780
cctcatacct gtggtccaga tccaaaggtt tgttgtcagt tcgatttcaa aagaatgggt      840
tccttcggtt tgtcttgtcc atggaaggtt ccacctagaa ctatctctga tcaaaatgtt      900
gctgctagat ccgatttgtt ggttgatcag tggaagaaga aggctgagtt gtacagaacc      960
```

-continued

```
aacgtcttgt tgattccatt gggtgacgac ttcagattca agcagaacac cgagtgggat    1020
gttcagagag tcaactacga aagattgttc gaacacatca actctcaggc tcacttcaat    1080
gtccaggctc agttcggtac tttgcaggaa tacttcgatg ctgttcacca ggctgaaaga    1140
gctggacaag ctgagttccc aaccttgtct ggtgacttct tcacttacgc tgatagatct    1200
gataactact ggtctggtta ctacacttcc agaccatacc ataagagaat ggacagagtc    1260
ttgatgcact acgttagagc tgctgaaatg ttgtccgctt ggcactcctg gacggtatg     1320 gctagaatcg aggaaagatt ggagcaggct agaagagagt tgtccttgtt ccagcaccac    1380
gacggtatta ctggtactgc taaaactcac gttgtcgtcg actacgagca agaatgcag     1440 gaagctttga aagcttgtca aatggtcatg caacagtctg tctacagatt gttgactaag    1500
ccatccatct actctccaga cttctccttc tcctacttca ctttggacga ctccagatgg    1560
ccaggttctg gtgttgagga ctctagaact accatcatct gggtgagga tatcttgcca    1620 tccaagcatg ttgtcatgca caacaccttg ccacactgga gagagcagtt ggttgacttc    1680
tacgtctcct ctccattcgt ttctgttacc gacttggcta acaatccagt tgaggctcag    1740
gtttctccag tttggtcttg gcaccacgac actttgacta agactatcca cccacaaggt    1800
tccaccacca agtacagaat catcttcaag gctagagttc accaatgggt tttggctacc    1860
tacgttttga ccatctccga ttccaagcca gagcacacct cctacgcttc aatttgttg     1920 cttagaaaga acccaacttc cttgccattg ggtcaatacc cagaggatgt caagttcggt    1980
gatccaagag agatctcctt gagagttggt aacggtccaa ccttggcttt ctctgagcag    2040
ggtttgttga agtccattca gttgactcag gattctccac atgttccagt tcacttcaag    2100
ttcttgaagt acggtgttag atctcatggt gatagatctg gtgcttactt gttcttgcca    2160
aatggtccag cttctccagt cgagttgggt cagccagttg tcttggtcac taagggtaaa    2220
ttggagtctt ccgtttctgt tggttttgcca tctgtcgttc accagaccat catgagaggt    2280
ggtgctccag agattagaaa tttggtcgat attggttctt tggacaacac tgagatcgtc    2340
atgagattgg agactcatat cgactctggt gatatcttct acactgattt gaatggattg    2400
caattcatca agaggagaag attggacaag ttgccattgc aggctaacta ctacccaatt    2460
ccatctggta tgttcattga ggatgctaat accagattga cttttgttgac cggtcaacca    2520 ttgggtggat cttctttggc ttctggtgag ttggagatta tgcaagatag aagattggct    2580
tctgatgatg aaagaggttt gggtcagggt gttttggaca caagccagt tttgcatatt     2640 tacagattgg tcttggagaa ggttaacaac tgtgtcagac catctaagtt gcatccagct    2700
ggttacttga cttctgctgc tcacaaagct tctcagtctt tgttggatcc attggacaag    2760
ttcatcttcg ctgaaaatga gtggatcggt gctcagggtc aattcggtgg tgatcatcca    2820
tctgctagag aggatttgga tgtctctgtc atgagaagat tgaccaagtc ttctgctaaa    2880
acccagagag ttggttacgt tttgcacaga accaatttga tgcaatgtgg tactccagag    2940
gagcatactc agaagttgga tgtctgtcac ttgttgccaa atgttgctag atgtgagaga    3000
actaccttga cttttcttgca gaatttggag cacttggatg gtatggttgc tccagaagtt    3060
tgtccaatga aaaccgctgc ttacgtctct tctcactctt cttga                   3105
```

<210> SEQ ID NO 46
<211> LENGTH: 108
<212> TYPE: DNA
<213> ORGANISM: Artificial
<220> FEATURE:

<223> OTHER INFORMATION: DNA encodes Mnn2 leader (53)

<400> SEQUENCE: 46

```
atgctgctta ccaaaaggtt ttcaaagctg ttcaagctga cgttcatagt tttgatattg    60
tgcgggctgt tcgtcattac aaacaaatac atggatgaga acacgtcg              108
```

<210> SEQ ID NO 47
<211> LENGTH: 1729
<212> TYPE: DNA
<213> ORGANISM: Artificial
<220> FEATURE:
<223> OTHER INFORMATION: Sequence of the PpHIS1 auxotrophic marker

<400> SEQUENCE: 47

```
caagttgcgt ccggtatacg taacgtctca cgatgatcaa agataatact taatcttcat     60
ggtctactga ataactcatt taaacaattg actaattgta cattatattg aacttatgca    120
tcctattaac gtaatcttct ggcttctctc tcagactcca tcagacacag aatatcgttc    180
tctctaactg gtcctttgac gtttctgaca atagttctag aggagtcgtc caaaaactca    240
actctgactt gggtgacacc accacgggat ccggttcttc cgaggacctt gatgaccttg    300
gctaatgtaa ctggagtttt agtatccatt ttaagatgtg tgtttctgta ggttctgggt    360
tggaaaaaaa ttttagacac cagaagagag gagtgaactg gtttgcgtgg gtttagactg    420
tgtaaggcac tactctgtcg aagttttaga taggggttac ccgctccgat gcatgggaag    480
cgattagccc ggctgttgcc cgtttggttt ttgaagggta attttcaata tctctgtttg    540
agtcatcaat ttcatattca aagattcaaa acaaaatct ggtccaagga gcgcatttag    600
gattatggag ttggcgaatc acttgaacga tagactatta tttgctgttc ctaaagaggg    660
cagattgtat gagaaatgcg ttgaattact taggggatca gatattcagt ttcgaagatc    720
cagtagattg gatatagctt tgtgcactaa cctgcccctg gcattggttt tccttccagc    780
tgctgacatt cccacgtttg taggagaggg taaatgtgat ttgggtataa ctggtattga    840
ccaggttcag gaaagtgacg tagatgtcat acctttatta gacttgaatt tcggtaagtg    900
caagttgcag attcaagttc ccgagaatgg tgacttgaaa gaacctaaac agctaattgg    960
taaagaaatt gtttcctcct ttactagctt aaccaccagg tactttgaac aactggaagg   1020
agttaagcct ggtgagccac taaagacaaa aatcaaatat gttggagggt ctgttgaggc   1080
ctcttgtgcc ctaggagttg ccgatgctat tgtggatctt gttgagagtg gagaaaccat   1140
gaaagcggca gggctgatcg atattgaaac tgttcttct acttccgctt acctgatctc   1200
ttcgaagcat cctcaacacc cagaactgat ggatactatc aaggagagaa ttgaaggtgt   1260
actgactgct cagaagtatg tcttgtgtaa ttacaacgca cctagaggta accttcctca   1320
gctgctaaaa ctgactccag caagagagc tgctaccgtt tctccattag atgaagaaga   1380
ttgggtggga gtgtcctcga tggtagagaa gaaagatgtt ggaagaatca tggacgaatt   1440
aaagaaacaa ggtgccagtg acattcttgt ctttgagatc agtaattgta gagcatagat   1500
agaataatat tcaagaccaa cggcttctct tcggaagctc caagtagctt atagtgatga   1560
gtaccggcat atatttatag gcttaaaatt tcgaggggtc actatattcg tttagtgcga   1620
agagttcctt tcactcttgt tatctatatt gtcagcgtgg actgtttata actgtaccaa   1680
cttagtttct ttcaactcca ggttaagaga cataaatgtc ctttgatgc                1729
```

<210> SEQ ID NO 48
<211> LENGTH: 1068

```
<212> TYPE: DNA
<213> ORGANISM: Artificial
<220> FEATURE:
<223> OTHER INFORMATION: DNA encodes Rat GnT II (TC) Codon-optimized

<400> SEQUENCE: 48
tccttggttt accaattgaa cttcgaccag atgttgagaa acgttgacaa ggacggtact      60
tggtctcctg gtgagttggt tttggttgtt caggttcaca acagaccaga gtacttgaga     120
ttgttgatcg actccttgag aaaggctcaa ggtatcagag aggttttggt tatcttctcc     180
cacgatttct ggtctgctga gatcaactcc ttgatctcct ccgttgactt ctgtccagtt     240
ttgcaggttt tcttcccatt ctccatccaa ttgtacccat ctgagttccc aggttctgat     300
ccaagagact gtccaagaga cttgaagaag aacgctgctt tgaagttggg ttgtatcaac     360
gctgaatacc cagattcttt cggtcactac agagaggcta agttctccca aactaagcat     420
cattggtggt ggaagttgca ctttgtttgg gagagagtta aggttttgca ggactacact     480
ggattgatct tgttcttgga ggaggatcat tacttggctc cagacttcta ccacgttttc     540
aagaagatgt ggaagttgaa gcaacaagag tgtccaggtt gtgacgtttt gtccttggga     600
acttacacta ctatcagatc cttctacggt atcgctgaca aggttgacgt taagacttgg     660
aagtccactg aacacaacat gggattggct ttgactagag atgcttacca agaagttgatc    720
gagtgtactg acactttctg tacttacgac gactacaact gggactggac tttgcagtac     780
ttgactttgg cttgtttgcc aaaagtttgg aaggttttgg ttccacaggc tccaagaatt     840
ttccacgctg gtgactgtgg aatgcaccac aagaaaactt gtagaccatc cactcagtcc     900
gctcaaattg agtccttgtt gaacaacaac aagcagtact tgttcccaga cttttggtt      960
atcggagaga agtttccaat ggctgctatt tccccaccaa gaaagaatgg tggatggggt    1020
gatattgaga accacgagtt gtgtaaatcc tacagaagat tgcagtag                 1068

<210> SEQ ID NO 49
<211> LENGTH: 300
<212> TYPE: DNA
<213> ORGANISM: Artificial
<220> FEATURE:
<223> OTHER INFORMATION: DNA encodes Mnn2 leader (54)

<400> SEQUENCE: 49
atgctgctta ccaaaaggtt ttcaaagctg ttcaagctga cgttcatagt tttgatattg      60
tgcgggctgt tcgtcattac aaacaaatac atggatgaga acacgtcggt caaggagtac     120
aaggagtact tagacagata tgtccagagt tactccaata gtattcatc ttcctcagac      180
gccgccagcg ctgacgattc aaccccattg agggacaatg atgaggcagg caatgaaaag    240
ttgaaaagct tctacaacaa cgttttcaac tttctaatgg ttgattcgcc cgggcgcgcc    300

<210> SEQ ID NO 50
<211> LENGTH: 1373
<212> TYPE: DNA
<213> ORGANISM: Artificial
<220> FEATURE:
<223> OTHER INFORMATION: Sequence of the 5'-Region used for knock out of
      PpARG1

<400> SEQUENCE: 50
gatctggcct tccctgaatt tttacgtcca gctatacgat ccgttgtgac tgtatttcct      60
gaaatgaagt ttcaacctaa agttttggtt gtacttgctc cacctaccac ggaaactaat    120
atcgaaacca atgaaaaagt agaactggaa tcgtcaatcg aaattcgcaa ccaagtggaa    180
```

```
cccaaagact tgaatctttc taaagtctat tctagtgaca ctaatggcaa cagaagattt      240
gagctgactt ttcaaatgaa tctcaataat gcaatatcaa catcagacaa tcaatgggct      300
ttgtctagtg acacaggatc aattatagta gtgtcttctg caggaagaat aacttccccg      360
atcctagaag tcggggcatc cgtctgtgtc ttaagatcgt acaacgaaca ccttttggca      420
ataacttgtg aaggaacatg cttttcatgg aatttaaaga agcaagaatg tgttctaaac      480
agcatttcat tagcacctat agtcaattca cacatgctag ttaagaaagt tggagatgca      540
aggaactatt ctattgtatc tgccgaagga acaacaatc cgttacccca gattctagac        600
tgcgaacttt ccaaaaatgg cgctccaatt gtggctctta gcacgaaaga catctactct      660
tattcaaaga aaatgaaatg ctggatccat tgattgatt cgaaatactt tgaattgttg        720
ggtgctgaca atgcactgtt tgagtgtgtg aagcgctag aaggtccaat tggaatgcta        780
attcatagat tggtagatga gttcttccat gaaaacactg ccggtaaaaa actcaaactt      840
tacaacaagc gagtactgga ggacctttca aattcacttg aagaactagg tgaaaatgcg      900
tctcaattaa gagagaaact tgacaaactc tatggtgatg aggttgaggc ttcttgacct      960
cttctctcta tctgcgtttc tttttttttt tttttttttt tttttttcag ttgagccaga      1020
ccgcgctaaa cgcataccaa ttgccaaatc aggcaattgt gagacagtgg taaaaaagat      1080
gcctgcaaag ttagattcac acagtaagag agatcctact cataaatgag gcgcttattt      1140
agtagctagt gatagccact gcggttctgc tttatgctat tgttgtatg ccttactatc        1200 tttgtttggc tccttttct tgacgttttc cgttggaggg actccctatt ctgagtcatg        1260
agccgcacag attatcgccc aaaattgaca aaatcttctg gcgaaaaaag tataaaagga      1320
gaaaaaagct cacccttttc cagcgtagaa agtatatatc agtcattgaa gac            1373

<210> SEQ ID NO 51
<211> LENGTH: 1470
<212> TYPE: DNA
<213> ORGANISM: Artificial
<220> FEATURE:
<223> OTHER INFORMATION: Sequence of the 3'-Region used for knock out of
      PpARG1

<400> SEQUENCE: 51
gggactttaa ctcaagtaaa aggatagttg tacaattata tatacgaaga ataaatcatt       60
acaaaaagta ttcgtttctt tgattcttaa caggattcat tttctgggtg tcatcaggta      120
cagcgctgaa tatcttgaag ttaacatcga gctcatcatc gacgttcatc acactagcca      180
cgtttccgca acggtagcaa taattaggag cggaccacac agtgacgaca tctttctctt      240
tgaaatggta tctgaagcct tccatgacca attgatgggc tctagcgatg agttgcaagt      300
tattaatgtg gttgaactca cgtgctactc gagcaccgaa taaccagcca gctccacgag      360
gagaaacagc ccaactgtcg acttcatctg ggtcagacca aaccaagtca caaaatcctc      420
cttcatgagg gacctcttgc gctcggctga gaactctgat ttgatctaac atgcgaatat      480
cgggagagag accaccatgg atacataata ttttaccatc aatgatggca ctaagggtta      540
aaaagtcgaa cacctggcaa cagtacttcc agacagtggt ggaaccatat ttattgagac      600
attcctcata aaatccataa acctgagtga tctgtctgga ttcatgattt ccccttacca      660
atgtgatatg ttgaggaaac ttaattttta aaatcatgag taacgtgaac gtctccaacg      720
agaaatagcc tctatccaca tagtctccta ggaagatata gttctgtttt attccattag      780
aggaggatcc gggaaaccca ccactaatct tgaaaagttc cagtagatcg tgaaattggc      840
```

```
cgtgaatatc tccgcatact gtcactggac tctgcactgg ctgtatattg gattcctcca      900
tcagcaaatc cttcacccgt tcgcaaagat gcttcatatc attttcactt aaagccttgc      960
agcttttgac ttcttcaaac cactgatctg gtcctctttc tggcatgatt aaggtctata     1020
atatttctga gctgagatgt aaaaaaaaat aataaaaatg gggagtgaaa agtgtgtag      1080 cttttaggag tttgggattg atacccccaaa atgatcttta tgagaattaa aaggtagata    1140
cgcttttaat aagaacacct atctatagta ctttgtggtc ttgagtaatt gagatgttca     1200
gcttctgagg tttgccgtta ttctgggata gtagtgcgcg accaaacaac ccgccaggca    1260
aagtgtgttg tgctcgaaga cgattgccag aagagtaagt ccgtcctgcc tcagatgtta   1320
cacactttct tccctagaca gtcgatgcat catcggattt aaacctgaaa ctttgatgcc    1380
atgatacgcc tagtcacgtc gactgagatt ttagataagc cccgatccct ttagtacatt   1440
cctgttatcc atggatggaa tggcctgata                                      1470

<210> SEQ ID NO 52
<211> LENGTH: 1666
<212> TYPE: DNA
<213> ORGANISM: Artificial
<220> FEATURE:
<223> OTHER INFORMATION: HYGR resistance cassette

<400> SEQUENCE: 52
gatctgttta gcttgcctcg tccccgccgg gtcacccggc cagcgacatg gaggcccaga       60
ataccctcct tgacagtctt gacgtgcgca gctcagggc atgatgtgac tgtcgcccgt     120
acatttagcc catacatccc catgtataat catttgcatc catacatttt gatggccgca     180
cggcgcgaag caaaaattac ggctcctcgc tgcggacctg cgagcaggga aacgctcccc     240
tcacagacgc gttgaattgt ccccacgccg cgcccctgta gagaaatata aaaggttagg    300
atttgccact gaggttcttc tttcatatac ttccttttaa aatcttgcta ggatacagtt     360
ctcacatcac atccgaacat aaacaaccat gggtaaaaag cctgaactca ccgcgacgtc     420
tgtcgagaag tttctgatcg aaaagttcga cagcgtctcc gacctgatgc agctctcgga    480
gggcgaagaa tctcgtgctt tcagcttcga tgtaggaggg cgtggatatg tcctgcgggt    540
aaatagctgc gccgatggtt tctacaaaga tcgttatgtt tatcggcact ttgcatcggc    600
cgcgctcccg attccggaag tgcttgacat tggggaattc agcgagagcc tgacctattg    660
catctcccgc cgtgcacagg gtgtcacgtt gcaagacctg cctgaaaccg aactgcccgc   720
tgttctgcag ccggtcgcgg aggccatgga tgcgatcgct gcggccgatc ttagccagac    780
gagcgggttc ggcccattcg gaccgcaagg aatcggtcaa tacactacat ggcgtgattt     840
catatgcgcg attgctgatc cccatgtgta tcactggcaa actgtgatgg acgacaccgt     900
cagtgcgtcc gtcgcgcagg ctctcgatga gctgatgctt tgggccgagg actgccccga    960
agtccggcac ctcgtgcacg cggatttcgg ctccaacaat gtcctgacgg acaatggccg    1020
cataacagcg gtcattgact ggagcgaggc gatgttcggg gattcccaat acgaggtcgc    1080
caacatcttc ttctggaggc cgtggttggc ttgtatggag cagcagacgc gctacttcga    1140
gcggaggcat ccggagcttg caggatcgcc gcggctccgg gcgtatatgc tccgcattgg    1200
tcttgaccaa ctctatcaga gcttggttga cggcaatttc gatgatgcag cttgggcgca    1260
gggtcgatgc gacgcaatcg tccgatccgg agccgggact gtcgggcgta cacaaatcgc    1320
ccgcagaagc gcggccgtct ggaccgatgg ctgtgtagaa gtactcgccg atagtggaaa    1380
```

```
ccgacgcccc agcactcgtc cgagggcaaa ggaataatca gtactgacaa taaaaagatt      1440
cttgttttca agaacttgtc atttgtatag ttttttttata ttgtagttgt tctattttaa      1500
tcaaatgtta gcgtgattta tattttttttt cgcctcgaca tcatctgccc agatgcgaag     1560
ttaagtgcgc agaaagtaat atcatgcgtc aatcgtatgt gaatgctggt cgctatactg      1620
ctgtcgattc gatactaacg ccgccatcca gtgtcgaaaa cgagct                     1666

<210> SEQ ID NO 53
<211> LENGTH: 388
<212> TYPE: DNA
<213> ORGANISM: Artificial
<220> FEATURE:
<223> OTHER INFORMATION: Ashbya gossypii TEF1 promoter

<400> SEQUENCE: 53
gatctgttta gcttgcctcg tccccgccgg gtcacccggc cagcgacatg gaggcccaga       60 atacccctcct tgacagtctt gacgtgcgca gctcaggggc atgatgtgac tgtcgcccgt    120
acatttagcc catacatccc catgtataat catttgcatc catacatttt gatggccgca     180
cggcgcgaag caaaaattac ggctcctcgc tgcagacctg cgagcaggga acgctcccc      240 tcacagacgc gttgaattgt ccccacgccg cgccctgta gagaaatata aaaggttagg      300
atttgccact gaggttcttc tttcatatac ttccttttaa aatcttgcta ggatacagtt      360
ctcacatcac atccgaacat aaacaacc                                        388

<210> SEQ ID NO 54
<211> LENGTH: 247
<212> TYPE: DNA
<213> ORGANISM: Artificial
<220> FEATURE:
<223> OTHER INFORMATION: Ashbya gossypii TEF1 termination sequence

<400> SEQUENCE: 54
taatcagtac tgacaataaa aagattcttg ttttcaagaa cttgtcattt gtatagtttt      60
tttatattgt agttgttcta ttttaatcaa atgttagcgt gatttatatt ttttttcgcc     120
tcgacatcat ctgcccagat gcgaagttaa gtgcgcagaa agtaatatca tgcgtcaatc     180
gtatgtgaat gctggtcgct atactgctgt cgattcgata ctaacgccgc catccagtgt     240
cgaaaac                                                              247

<210> SEQ ID NO 55
<211> LENGTH: 34
<212> TYPE: DNA
<213> ORGANISM: Artificial
<220> FEATURE:
<223> OTHER INFORMATION: Primer SH512

<400> SEQUENCE: 55
gagacgatag acggtgagga ttcagaagat cctg                                  34

<210> SEQ ID NO 56
<211> LENGTH: 24
<212> TYPE: DNA
<213> ORGANISM: Artificial
<220> FEATURE:
<223> OTHER INFORMATION: Primer SH97

<400> SEQUENCE: 56
ggggagaagg taccgaagcc ggag                                             24
```

```
<210> SEQ ID NO 57
<211> LENGTH: 32
<212> TYPE: DNA
<213> ORGANISM: Artificial
<220> FEATURE:
<223> OTHER INFORMATION: Primer SH515

<400> SEQUENCE: 57
ccatacacca gatgtatctc aaaaatgtca ac                                32

<210> SEQ ID NO 58
<211> LENGTH: 26
<212> TYPE: DNA
<213> ORGANISM: Artificial
<220> FEATURE:
<223> OTHER INFORMATION: Primer SH379

<400> SEQUENCE: 58
catgcccctg agctgcgcac gtcaag                                       26

<210> SEQ ID NO 59
<211> LENGTH: 28
<212> TYPE: DNA
<213> ORGANISM: Artificial
<220> FEATURE:
<223> OTHER INFORMATION: Primer SH520

<400> SEQUENCE: 59
caacttggct ctgggctcgt ttgtattg                                     28

<210> SEQ ID NO 60
<211> LENGTH: 28
<212> TYPE: DNA
<213> ORGANISM: Artificial
<220> FEATURE:
<223> OTHER INFORMATION: Primer SH521

<400> SEQUENCE: 60
ggtgtcttca gggaagttct gagctatg                                     28

<210> SEQ ID NO 61
<211> LENGTH: 934
<212> TYPE: DNA
<213> ORGANISM: Artificial
<220> FEATURE:
<223> OTHER INFORMATION: Pp AOX1 promoter

<400> SEQUENCE: 61
aacatccaaa gacgaaaggt tgaatgaaac cttttttgcca tccgacatcc acaggtccat   60
tctcacacat aagtgccaaa cgcaacagga ggggatacac tagcagcaga ccgttgcaaa  120
cgcaggacct ccactcctct tctcctcaac acccactttt gccatcgaaa accagccca   180 gttattgggc ttgattggag ctcgctcatt ccaattcctt ctattaggct actaacacca  240
tgactttatt agcctgtcta tcctggcccc cctggcgagg ttcatgtttg tttatttccg  300
aatgcaacaa gctccgcatt acacccgaac atcactccag atgagggctt tctgagtgtg  360
gggtcaaata gtttcatgtt ccccaaatgg cccaaaactg acagtttaaa cgctgtcttg  420
gaacctaata tgacaaaagc gtgatctcat ccaagatgaa ctaagtttgg ttcgttgaaa  480
tgctaacggc cagttggtca aaaagaaact tccaaaagtc ggcataccgt ttgtcttgtt  540
tggtattgat tgacgaatgc tcaaaaataa tctcattaat gcttagcgca gtctctctat  600
cgcttctgaa ccccggtgca cctgtgccga aacgcaaatg gggaaacacc cgcttttttgg  660
```

```
atgattatgc attgtctcca cattgtatgc ttccaagatt ctggtgggaa tactgctgat      720
agcctaacgt tcatgatcaa aatttaactg ttctaacccc tacttgacag caatatataa      780
acagaaggaa gctgccctgt cttaaacctt ttttttttatc atcattatta gcttactttc     840
ataattgcga ctggttccaa ttgacaagct tttgatttta cgacttttta acgacaactt     900
gagaagatca aaaacaact aattattcga aacg                                   934

<210> SEQ ID NO 62
<211> LENGTH: 375
<212> TYPE: DNA
<213> ORGANISM: Artificial
<220> FEATURE:
<223> OTHER INFORMATION: Sequence of the Sh ble ORF (Zeocin resistance
      marker)

<400> SEQUENCE: 62
atggccaagt tgaccagtgc cgttccggtg ctcaccgcgc gcgacgtcgc cggagcggtc      60
gagttctgga ccgaccggct cgggttctcc cggacttcg tggaggacga cttcgccggt      120
gtggtccggg acgacgtgac cctgttcatc agcgcggtcc aggaccaggt ggtgccggac      180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300 ccgtggggc gggagttcgc cctgcgcgac cggccggca actgcgtgca cttcgtggcc       360
gaggagcagg actga                                                       375

<210> SEQ ID NO 63
<211> LENGTH: 427
<212> TYPE: DNA
<213> ORGANISM: Artificial
<220> FEATURE:
<223> OTHER INFORMATION: ScTEF1 promoter

<400> SEQUENCE: 63
gatcccccac acaccatagc ttcaaaatgt ttctactcct ttttttactct tccagatttt     60 ctcggactcc gcgcatcgcc gtaccacttc aaaacaccca agcacagcat actaaatttc      120 ccctcttttct tcctctaggg tgtcgttaat tacccgtact aaaggtttgg aaaagaaaaa    180
agagaccgcc tcgtttctttt tcttcgtcg aaaaaggcaa taaaaatttt tatcacgttt      240 cttttttcttg aaaattttttt ttttttgattt ttttttctcttt cgatgacctc ccattgatat  300
ttaagttaat aaacggtctt caatttctca agtttcagtt tcatttttct tgttctatta     360
caactttttt tacttcttgc tcattagaaa gaaagcatag caatctaatc taagttttaa     420
ttacaaa                                                                427

<210> SEQ ID NO 64
<211> LENGTH: 1936
<212> TYPE: DNA
<213> ORGANISM: Pichia pastoris

<400> SEQUENCE: 64
ggccagccca tcaccatgaa tgcttaaaac gccaactcct tccatctcat tttcgtacca      60
gattatgact cttaggcggg gagaatcccg tccagcatag cgaacatttc tttttttttt     120
ttttttcgtt tcgcatctct ctatcgcatt cagaaaaaaa tacatataat tcttccagtt     180
tccgtcattc attacgttta aaactacgaa agttttagct ctcttttgtt tttgtttcct    240
agattcgaaa tattttcttt attgagttta atttgtgtgg cagacaatgg ttagatcttt    300
```

-continued

| | |
|---|---|
| caccatcaaa gtgcctgctt cctcagcaaa tataggaccg gggtttgacg ttctgggaat | 360 |
| tggtctcaac ctttacttgg aactacaagt caccattgat cccaaaattg atacctcaag | 420 |
| cgatccagaa aatgtgttat tgtcgtatga aggtgagggg gctgatgagg tgtcattgaa | 480 |
| aagtgacgaa aacttgatta cgcgcacagc tctctatgtt ctacgttgtg acgacgtcag | 540 |
| gactttccct aagggaacca agattcacgt cattaaccct attcctctag aagaggctt | 600 |
| gggatcttcg ggtgctgcag ttgtcgccgg tgcattgctc ggaaattcca tcggacagct | 660 |
| tggatactcc aaacaacgtt tactggatta ctgtttgatg atagaacgtc atccagataa | 720 |
| catcaccgca gctatggtgg gtggtttcgt tggatcttat cttagagatc tttcaccaga | 780 |
| agacacccag agaaaagaga ttccattagc agaagtcctg ccagaacctc aaggtggtat | 840 |
| taacaccggt ctcaacccac cagtgcctcc aaaaaacatt gggcaccaca tcaaatacgg | 900 |
| ctgggcaaaa gagatcaaat gtattgccat tattccagac tttgaagtat caaccgcttc | 960 |
| atctagaggc gttcttccaa ccacttacga gagacatgac attattttca acctgcaaag | 1020 |
| gatagccgtt cttaccactg ccctgacaca atctccacca gatccaagct tgatataccc | 1080 |
| agctatgcag gacaggattc accaaccctta caggaaaact ttgatccacg gactgactga | 1140 |
| aatactgtct tcattcaccc cagaattaca caaaggtttg ttgggaatct gtctttccgg | 1200 |
| tgctgggccc acaatattag ccctcgcaac tgaaaacttc gatcagattg ctaaggacat | 1260 |
| cattgccaga tttgctgtcg aagacatcac ctgtagttgg aaactcttga ccccagctct | 1320 |
| tgaaggttct gttgttgagg agcttgctta atagaaatta gaacatcctc tttagattat | 1380 |
| gataatacgt ttttaacttt tcccctaact gtagtgatgg tatctgaccc tcttagacct | 1440 |
| taggttggac cttctcgaat ttcctgcctc tatcaaaaat ccgaccctcg acatcgttta | 1500 |
| cgtactttgc aaccaattaa ctagtaccgg cagacgttca gtgatcatgg ctctctatac | 1560 |
| aaatacctg ataacgtttg cattcctgac agtcggagga tgtacgtgct tatttcttg | 1620 |
| ctagtcccaa atgttttgag attgctccaa tcgtttttc aacaatacta actgccaaca | 1680 |
| aatagatctt ttattcaacg gaaatgggga acaattcaac gtgggtgact ttttggagac | 1740 |
| tacatctccc tatatgtggg caaatctggg tatagcaagt tgcattggat tctcggtcat | 1800 |
| tggtgctgca tggggaattt tcataacagg ttcttcgatc atcggtgcag gtgtcaaagc | 1860 |
| tcccagaatc acaacaaaaa atttaatctc catcattttc tgtgaggtgg tggctatta | 1920 |
| tgggcttatt atggcc | 1936 |

<210> SEQ ID NO 65
<211> LENGTH: 672
<212> TYPE: DNA
<213> ORGANISM: Artificial
<220> FEATURE:
<223> OTHER INFORMATION: PpTRP1 5' region and ORF

<400> SEQUENCE: 65

| | |
|---|---|
| gcggaaacgg cagtaaacaa tggagcttca ttagtgggtg ttattatggt ccctggccgg | 60 |
| gaacgaacgg tgaaacaaga ggttgcgagg gaaatttcgc agatggtgcg ggaaaagaga | 120 |
| atttcaaagg gctcaaaata cttggattcc agacaactga ggaaagagtg ggacgactgt | 180 |
| cctctggaag actggtttga gtacaacgtg aaagaaataa acagcagtgg tccattttta | 240 |
| gttggagttt ttcgtaatca agtatagat gaaatccagc aagctatcca cactcatggt | 300 |
| ttggatttcg tccaactaca tgggtctgag gattttgatt cgtatatacg caatatccca | 360 |
| gttcctgtga ttaccagata cacagataat gccgtcgatg gtcttaccgg agaagacctc | 420 |

```
gctataaata gggccctggt gctactggac agcgagcaag gaggtgaagg aaaaaccatc    480
gattgggctc gtgcacaaaa atttggagaa cgtagaggaa aatatttact agccggaggt    540
ttgacacctg ataatgttgc tcatgctcga tctcatactg gctgtattgg tgttgacgtc    600
tctggtgggg tagaaacaaa tgcctcaaaa gatatggaca agatcacaca atttatcaga    660
aacgctacat aa                                                        672
```

<210> SEQ ID NO 66
<211> LENGTH: 834
<212> TYPE: DNA
<213> ORGANISM: Artificial
<220> FEATURE:
<223> OTHER INFORMATION: PpTRP1 3' region

<400> SEQUENCE: 66

```
aagtcaatta aatacacgct tgaaaggaca ttacatagct ttcgatttaa gcagaaccag     60
aaatgtagaa ccacttgtca atagattggt caatcttagc aggagcggct gggctagcag    120
ttggaacagc agaggttgct gaaggtgaga aggatggagt ggattgcaaa gtggtgttgg    180
ttaagtcaat ctcaccaggg ctggttttgc caaaaatcaa cttctcccag gcttcacggc    240
attcttgaat gacctcttct gcatacttct tgttcttgca ttcaccagag aaagcaaact    300
ggttctcagg ttttccatca gggatcttgt aaattctgaa ccattcgttg gtagctctca    360
acaagcccgg catgtgcttt tcaacatcct cgatgtcatt gagcttagga gccaatgggt    420
cgttgatgtc gatgacgatg accttccagt cagtctctcc ctcatccaac aaagccataa    480
caccgaggac cttgacttgc ttgacctgtc cagtgtaacc tacggcttca ccaatttcgc    540
aaacgtccaa tggatcattg tcaccctggg ccttggtctc tggatgagtg acgttagggt    600
cttcccatgt ctgagggaag gcaccgtagt tgtgaatgta tccgtggtga gggaaacagt    660
tacgaacgaa acgaagtttt cccttctttg tgtcctgaag aattgggttc agtttctcct    720
ccttggaaat ctccaacttg gcgttggtcc aacggggac  ttcaacaacc atgttgagaa    780
ccttcttgga ttcgtcagca taaagtggga tgtcgtggaa aggagatacg actt          834
```

<210> SEQ ID NO 67
<211> LENGTH: 1400
<212> TYPE: DNA
<213> ORGANISM: Artificial
<220> FEATURE:
<223> OTHER INFORMATION: NatR expression cassette

<400> SEQUENCE: 67

```
gagttaggtt cacatacgat ttaggtgaca ctatagaacg cggccgccag ctgaagcttc     60
gtacgctgca ggtcgacgga tccccgggtt aattaaggcg cgccagatct gtttagcttg    120
cctcgtcccc gccgggtcac ccggccagcg acatggaggc ccagaatacc ctccttgaca    180
gtcttgacgt gcgcagctca ggggcatgat gtgactgtcg cccgtacatt tagcccatac    240
atccccatgt ataatcattt gcatccatac attttgatgg ccgcacggcg cgaagcaaaa    300
attacggctc ctcgctgcag acctgcgagc agggaaacgc tccctcaca  gacgcgttga    360 attgtcccca cgccgcgccc ctgtagagaa atataaaagg ttaggatttg ccactgaggt    420
tcttctttca tatacttcct tttaaaatct tgctaggata cagttctcac atcacatccg    480
aacataaaca accatgggta ccactcttga cgacacggct taccgtacc  gcaccagtgt    540 cccggggac  gccgaggcca tcgaggcact ggatgggtcc ttcaccaccg acaccgtctt    600
```

```
ccgcgtcacc gccaccgggg acggcttcac cctgcgggag gtgccggtgg acccgcccct    660
gaccaaggtg ttccccgacg acgaatcgga cgacgaatcg gacgacgggg aggacggcga    720
cccggactcc cggacgttcg tcgcgtacgg ggacgacggc gacctggcgg gcttcgtggt    780
catctcgtac tcggcgtgga accgccggct gaccgtcgag gacatcgagg tcgccccgga    840
gcaccggggg cacggggtcg ggcgcgcgtt gatggggctc gcgacggagt tcgccggcga    900
gcggggcgcc gggcacctct ggctggaggt caccaacgtc aacgcaccgg cgatccacgc    960
gtaccggcgg atggggttca ccctctgcgg cctggacacc gccctgtacg acggcaccgc   1020
ctcggacggc gagcggcagg cgctctacat gagcatgccc tgcccctaat cagtactgac   1080
aataaaaaga ttcttgtttt caagaacttg tcatttgtat agttttttta tattgtagtt   1140
gttctatttt aatcaaatgt tagcgtgatt tatattttt ttcgcctcga catcatctgc    1200
ccagatgcga agttaagtgc gcagaaagta atatcatgcg tcaatcgtat gtgaatgctg   1260
gtcgctatac tgctgtcgat tcgatactaa cgccgccatc cagtgtcgaa aacgagctcg   1320
aattcatcga tgatatcaga tccactagtg gcctatgcgg ccgcggatct gccggtctcc   1380
ctatagtgag tcgtattcac                                               1400
```

<210> SEQ ID NO 68
<211> LENGTH: 25
<212> TYPE: DNA
<213> ORGANISM: Artificial
<220> FEATURE:
<223> OTHER INFORMATION: Primer SH1406

<400> SEQUENCE: 68
gtttcgcgtt ctcacttaga tggag                                          25

<210> SEQ ID NO 69
<211> LENGTH: 27
<212> TYPE: DNA
<213> ORGANISM: Artificial
<220> FEATURE:
<223> OTHER INFORMATION: Primer SH1420

<400> SEQUENCE: 69
ccatttctcc gtcaatccga ttctcgc                                        27

<210> SEQ ID NO 70
<211> LENGTH: 30
<212> TYPE: DNA
<213> ORGANISM: Artificial
<220> FEATURE:
<223> OTHER INFORMATION: Primer SH1407

<400> SEQUENCE: 70
ccactcgcca gatcggagct gcaaacactc                                     30

<210> SEQ ID NO 71
<211> LENGTH: 25
<212> TYPE: DNA
<213> ORGANISM: Artificial
<220> FEATURE:
<223> OTHER INFORMATION: Primer SH1421

<400> SEQUENCE: 71
ccgccctgta cgacggcacc gcctc                                          25

<210> SEQ ID NO 72
<211> LENGTH: 31

```
<212> TYPE: DNA
<213> ORGANISM: Artificial
<220> FEATURE:
<223> OTHER INFORMATION: Primer SH1417

<400> SEQUENCE: 72
cgaacctttt ccccaacata tttggcaaac g                               31

<210> SEQ ID NO 73
<211> LENGTH: 31
<212> TYPE: DNA
<213> ORGANISM: Artificial
<220> FEATURE:
<223> OTHER INFORMATION: Primer SH1418

<400> SEQUENCE: 73
gcaaggtgat ggttcaaatc tccagctcca c                               31

<210> SEQ ID NO 74
<211> LENGTH: 2004
<212> TYPE: DNA
<213> ORGANISM: Artificial
<220> FEATURE:
<223> OTHER INFORMATION: Pichia pastoris ATT1 5' region in pGLY5933

<400> SEQUENCE: 74
ggccgggact acatgaggcc gattcttcaa gccagggaaa ttaattgctt gaaccggaaa      60
atcattaagg caggcaacga aaatccaac  tccttggttg aattgactca aaagtttatc    120
ttacggagaa aagctaaaga catcaatacg aatttccttc cgccaaaaac tgaactgata    180
ctgatggttc caatgactga attacaacag gagctataca aggatataat tgaaactaac    240
caagccaagc ttggcttgat caacgacaga aactttttc  ttcaaaaaat tttgattctt    300
cgtaaaatat gcaattcacc ctccctgctg aaagacgaac ctgattttgc cagatacaat    360
ctcggcaata gattcaatag cggtaagatc aagctaacag tactgctttt acgaaagctg    420
tttgaaacca ccaatgagaa gtgtgtgatt gtttcaaact tcactaaaac tttggacgta    480
cttcagctaa tcatagagca caacaattgg aaataccacc gactagatgg ttcgagtaaa    540
ggacgggaca aaatcgtacg agattttaac gagtcgcctc aaaaagatcg attcatcatg    600
ttgctttctt ccaaggcagg gggagtgggg ctcaacttaa ttggagcctc acgcttaatt    660
cttttttgata cgactggaa  tcccagtgtt gacattcaag caatggctag agtgcatcga    720
gacgggcaga aaaggcacac ctttatctat cgtttgtata cgaaaggcac aattgacgaa    780
aagatcctac aaaggcaatt gatgaaacaa aatctgagcg acaaattcct ggatgataat    840
gatagcagca aggatgatgt gtttaacgac tacgatctca agatttgtt  tactgtagat    900
cttgacacga attgtagtac acacgatttg atggaatgtt tatgtaatgg gcggctgaga    960
gatccgactc ccgtcttgga agcagaagaa tgcaagacaa aaccgttgga ggccgttgac   1020
gacacgatg  atggttggat gtcagctctg gatttcaaac agttatcaca aaaagaggag   1080
acaggtgctg tgtcaacaat gcgtcaatgt ctgctcggat atcaacacat tgatccaaag   1140
attttggaac caacagaacc tgtagggggac gatttggtat tggcaaacat cctcgcggag   1200
tcctcaggct tggctaaatc tgcattgtca tctgaaaaga aacccaagaa accagtggtg   1260
aactttatct ttgtgtcagg ccaagactaa gctggaagaa cggaacttta atcgaaggaa   1320
aaattaaatg tcaaagtggg tcgatcagga gataatccat gcttcacgtg atttttctta   1380
ataaacgccg gaaaaacttt cttttttgtg accaaaatta tccgatctga aaaaaaatta   1440
```

| | |
|---|---|
| cgcatgcgtg aagtaggatg agagacttac tgttgaactt tgtgagacga ggggaaaagg | 1500 |
| aatatcctga tcgtaaacaa aaaagttttc cagcccaatc gggaacatct gcgaagtgtt | 1560 |
| ggaattcaac ccctctttcg aaaatgttcc attttaccca aaattattgt tattaaataa | 1620 |
| tacatgtgtt actagcaaag tctgcgcttt ccatgtctca gattcggcag ataacaaagt | 1680 |
| tgacacgttc ttgcgagata cgcatgaatc ttttggctgc ttttgtgaa agagaaatgg | 1740 |
| tgccatatat tgcagacgcc cctgaaagat tagtgtgcgg ctgagtcttt ttttttctc | 1800 |
| aaccagcttt ttcttttat tgggtaccat cgcgcacgca ggactcatgc tccattagac | 1860 |
| ttctgaacca cctgacttaa tattcatgga cggacgcttt tatccttaaa ttgttcatcc | 1920 |
| attcctcaat ttttccgttt gccctccctg tactattaaa ttacaaaagc tgatctttt | 1980 |
| caagtgtttc tctttgaatc gctc | 2004 |

<210> SEQ ID NO 75
<211> LENGTH: 1854
<212> TYPE: DNA
<213> ORGANISM: Artificial
<220> FEATURE:
<223> OTHER INFORMATION: Pichia pastoris ATT1 3' region in pGLY5933

<400> SEQUENCE: 75

| | |
|---|---|
| ggaccctgaa gacgaagaca tgtctgcctt agagtttacc gcagttcgat tccccaactt | 60 |
| ttcagctacg acaacagccc cgcctcctac tccagtcaat tgcaacagtc ctgaaaacat | 120 |
| caagacctcc actgtggacg attttttgaa agctactcaa gatccaaata caaagagat | 180 |
| actcaacgac atttacagtt tgatttttga tgactccatg gatcctatga gcttcggaag | 240 |
| tatggaacca agaaacgatt tggaagttcc ggacactata atggattaat ttgcagcggg | 300 |
| cctgttttgta tagtctttga ttgtgtataa tagaattact acgcgtatat cccgatctgg | 360 |
| aagtaacatg gaagtttccc attttcgcgc agtctcctac tcgtatcctc cccaccccctt | 420 |
| accgatgacg caaaaggtca ctagataagc atagcatagt ttcatccctt gctcttttcct | 480 |
| tgtaccaaca gatcatggct gggaatctca aggatattct atccttgtcg aggaagacag | 540 |
| caaggaatct gaagcaggct ctggatgagc ttgcggagca ggtgatcaac caccaacgga | 600 |
| gacgaccagc tctggtccga gttcctatca acaacaacct taggcgcaag agccagcagt | 660 |
| cctttttgaa tcgcaggtca ttccatcttt ggaccagcaa gtacaaccca tacttttgga | 720 |
| ggggaggcag aagcaacgtt ctggaccagc ttaaccgtga agctttaagg tacagatcgt | 780 |
| cttttgcgaa acccggattt tatccaagtg ggctgtatca gtcaactttc cctcaaagag | 840 |
| gtagtaggat gttttccacc tgcgcctact catgtcagca ggaggcagtc aaaaacttga | 900 |
| cttccgctgt tcgtgctttg ttacaaagtg gtgctaattt cggcagtcaa atgaaacaaa | 960 |
| tgaaacactg ttcgcaaaag aagaagcact tctctaaatt ttctaagagg cttacttctt | 1020 |
| ccactgccgc tgggtctggc aagaatgctg aacaagctcc ttctggtttg gccgaaggat | 1080 |
| ccgctgttgt tttagcctt gaacgtcaaa gtcacaatac tgagttggaa ggaatcttgg | 1140 |
| atcaagaaac ttcttccatt ctcgaggaag aaatggttca acatgagcgt cacctggcta | 1200 |
| ttattagaga agaaatccag agaattagtg agaatctagg atcattacca ttaatcatgt | 1260 |
| ctggtcacaa gattgaggta ttttttcccca attgtgacac tgttaaatgt gagcaactga | 1320 |
| tgagagattt ggctattacg aaagggggttg tgaggcgtca tgattctact gctgagcatt | 1380 |
| caagctccag gtcattgtt ccagaagatt gcttgtattc ctcagggtca agttcaccga | 1440 |
| atcctttatc ctcaacttct tcgaaatcat ttgatagagt ctcattggac tacatttcct | 1500 |

```
ctcggtctac atctgatcaa accactggtt ctgagtacac atctctgtct caacaatatc    1560
acctggttag caattacaac cctgtactat cctcagcccc gggttcttcg agggtcttgg    1620
agctgaatac tcccgagtcc actatggaag gcagtacaga tctggagtat ttaacgcgag    1680
acgatgtgtt gctgttaaat gtctaatcta gacctatcct tcattctata tagcttagtt    1740
gagttttacg taagccctag ttttttgttaa ttcttatcga tttatggtta gtgtaccact    1800
caactcacga tgatatatcc caggagctgt tgtgcatta taactaccaa tcct           1854
```

<210> SEQ ID NO 76
<211> LENGTH: 987
<212> TYPE: DNA
<213> ORGANISM: Pichia pastoris

<400> SEQUENCE: 76

```
atggctgaca aaggatcggt agcggctaaa tcgcttacca actctgcacc cttatccatc     60 tttcttact gtgctgcatc aattctgatg acagttacca ataagtatgc cgtgtccggt    120
gtcgatttca actttaactt cttttttgctt gccgttcagg gaatcgtttg tattaccttg    180
attagctcgt tgaagcaatt gaatgttatc acctttagag agttcaacaa ggttgaagca    240
aagaaatggt tcccaatcgc cgtgctgtta gttgtcatga tttatacctc ctccaaggct    300
ctacagtatc tgagcattcc aatttacacg atattcaaaa acttgaccat tatccttatt    360
gcttatggtg aagtcatctg gttcggaggc cgtgtgacca acttggctct gggctcgttt    420
gtattgatgg tgctctcctc tgcagtggct tcttatggtg attctaatgt tgacactggt    480
aaactcaatt ttaacattgg ctatttctgg atgttcacca actgtttctc ctctgccgca    540
tttgtgttgt tcatgagaaa agagaataaag ttgaccaact tcaaagactt tgacaccatg    600
tattacaaca accttctctc cattccaatt ttgctctttg catctttgac tactgaagac    660
tggtccgcta aaaacatagc tcagaacttc cctgaagaca ccaaatacgc tgtcatcgct    720
tccatgatta tttcaggaat gtctgccgtg ggtatctcat acacatctgc atggtgtgtc    780
cgtgtgacat cttccacgac atactcgatg gttggtgctt tgaacaagct tccaattgcc    840
ctgtctggtt tgctatttt caaggctcct atcaacttct attctatcag ctctatcttt    900
attggttttg ccgctggtct agtctatgcc attgccaagc agaagcaaaa gaaggaagac    960
gagttgcagt taccaactga caagagc                                        987
```

<210> SEQ ID NO 77
<211> LENGTH: 329
<212> TYPE: PRT
<213> ORGANISM: Pichia pastoris

<400> SEQUENCE: 77

```
Met Ala Asp Lys Gly Ser Val Ala Ala Lys Ser Leu Thr Asn Ser Ala
1               5                   10                  15

Pro Leu Ser Ile Phe Ser Tyr Cys Ala Ala Ser Ile Leu Met Thr Val
            20                  25                  30

Thr Asn Lys Tyr Ala Val Ser Gly Val Asp Phe Asn Phe Asn Phe Phe
        35                  40                  45

Leu Leu Ala Val Gln Gly Ile Val Cys Ile Thr Leu Ile Ser Ser Leu
    50                  55                  60

Lys Gln Leu Asn Val Ile Thr Phe Arg Glu Phe Asn Lys Val Glu Ala
65                  70                  75                  80

Lys Lys Trp Phe Pro Ile Ala Val Leu Leu Val Val Met Ile Tyr Thr
```

-continued

```
                    85                  90                  95
Ser Ser Lys Ala Leu Gln Tyr Leu Ser Ile Pro Ile Tyr Thr Ile Phe
            100                 105                 110

Lys Asn Leu Thr Ile Ile Leu Ile Ala Tyr Gly Glu Val Ile Trp Phe
            115                 120                 125

Gly Gly Arg Val Thr Asn Leu Ala Leu Gly Ser Phe Val Leu Met Val
            130                 135                 140

Leu Ser Ser Ala Val Ala Ser Tyr Gly Asp Ser Asn Val Asp Thr Gly
145                 150                 155                 160

Lys Leu Asn Phe Asn Ile Gly Tyr Phe Trp Met Phe Thr Asn Cys Phe
            165                 170                 175

Ser Ser Ala Ala Phe Val Leu Phe Met Arg Lys Arg Ile Lys Leu Thr
            180                 185                 190

Asn Phe Lys Asp Phe Asp Thr Met Tyr Tyr Asn Asn Leu Leu Ser Ile
            195                 200                 205

Pro Ile Leu Leu Phe Ala Ser Leu Thr Thr Glu Asp Trp Ser Ala Lys
            210                 215                 220

Asn Ile Ala Gln Asn Phe Pro Glu Asp Thr Lys Tyr Ala Val Ile Ala
225                 230                 235                 240

Ser Met Ile Ile Ser Gly Met Ser Ala Val Gly Ile Ser Tyr Thr Ser
            245                 250                 255

Ala Trp Cys Val Arg Val Thr Ser Ser Thr Thr Tyr Ser Met Val Gly
            260                 265                 270

Ala Leu Asn Lys Leu Pro Ile Ala Leu Ser Gly Leu Leu Phe Phe Lys
            275                 280                 285

Ala Pro Ile Asn Phe Tyr Ser Ile Ser Ser Ile Phe Ile Gly Phe Ala
            290                 295                 300

Ala Gly Leu Val Tyr Ala Ile Ala Lys Gln Lys Gln Lys Lys Glu Asp
305                 310                 315                 320

Glu Leu Gln Leu Pro Thr Asp Lys Ser
            325
```

METHODS FOR REDUCING MANNOSYLTRANSFERASE ACTIVITY IN LOWER EUKARYOTES

CROSS REFERENCE TO RELATED APPLICATIONS

This application is the National Stage of International Application No. PCT/US2013/025917 filed on Feb. 13, 2013, which claims the benefit under 35 U.S.C. 119(e) of U.S. Provisional Application No. 61/599,616, filed Feb. 16, 2013.

REFERENCE TO SEQUENCE LISTING SUBMITTED ELECTRONICALLY

The sequence listing of the present application is submitted electronically via EFS-Web as an ASCII formatted sequence listing with a file name "23193-US-PCT-SEQLIST.txt", creation date of Jul. 10, 2014, and a size of 83 KB. This sequence listing submitted via EFS-Web is part of the specification and is herein incorporated by reference in its entirety.

BACKGROUND OF THE INVENTION (1) Field of the Invention

The present invention relates to methods for reducing detectable mannosylation of N-linked and O-linked oligosaccharides in yeast. In particular, the present invention provides recombinant yeast host cells in which expression of the GDP-mannose transporter encoded by the Vanadate Resistant Glycosylation 4 (VRG4) gene has been disrupted. In general, the VRG4 gene is essential for cell viability; however, the present invention provides host cells that are viable when expression of the VRG4 gene therein has been disrupted.

(2) Description of Related Art

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (e.g., CHO cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as the methylotrophic yeast *Pichia pastoris* have distinct advantages for therapeutic protein expression, for example, they do not secrete high amounts of endogenous proteins, strong inducible promoters for producing heterologous proteins are available, they can be grown in defined chemical media and without the use of animal sera, and they can produce high titers of recombinant proteins (Cregg et al., FEMS Microbiol. Rev. 24: 45-66 (2000)). However, glycosylated proteins expressed in *P. pastoris* generally contain additional mannose sugars resulting in "high mannose" glycans, as well as mannosylphosphate groups which impart a negative charge onto glycoproteins. Glycoproteins with either high mannose glycans or charged mannans present the risk of eliciting an unwanted immune response in humans (Takeuchi, Trends in Glycosci. Glycotechnol. 9:S29-S35 (1997); Rosenfeld and Ballou, J. Biol. Chem. 249: 2319-2321 (1974)). Accordingly, it is desirable to produce therapeutic glycoproteins in fungal host cells wherein the pattern of glycosylation on the glycoprotein is identical to or similar to that which occurs on glycoproteins produced in humans and which do not have detectable yeast glycosylation.

BRIEF SUMMARY OF THE INVENTION

The present invention provides methods for reducing detectable mannosylation of N-linked and O-linked oligosaccharides in lower eukaryotes, for example, yeast and filamentous fungi. In particular, recombinant lower eukaryote host cells are provided in which expression of the GDP-mannose transmembrane transporter protein encoded by the Vanadate Resistant Glycosylation 4 (VRG4) gene or homologue thereof has been disrupted. Various publications in the scientific literature have suggested that the VRG4 gene is essential for cell viability; however, inventor has discovered that lower eukaryote host cells, for example *Pichia pastoris*, can be constructed in which expression of the VRG4 gene has been disrupted. The inventor has discovered that host cells lacking expression of the VRG4 gene are viable and may be used to produce recombinant or heterologous proteins or glycoproteins that have reduced or no detectable mannosylation on N- and/or O-glycans compared to proteins or glycoproteins produced in host cells that express the VRG4 gene and produce a fully functional GDP-mannose transmembrane transporter protein.

Therefore, the present invention provides a lower eukaryote host cell comprising (a) a disruption of expression of the Vanadate Resistance Glycosylation (VRG4) gene or homologue thereof; and (b) a nucleic acid molecule encoding a recombinant or heterologous, non-endogenous protein or glycoprotein, wherein the host cell is viable. Disruption of expression of the VRG4 gene or homologue thereof may be achieved by providing an inhibitor selected from the group consisting of a chemical compound that binds or antagonizes the function of the encoded GDP-mannose transmembrane transporter protein (Vrg4p), an antisense DNA to an mRNA encoding the Vrg4p, and an siRNA to an mRNA encoding the Vrg4p. Disruption of expression of the VRG4 gene or homologue thereof may be achieved by deleting the VRG4 gene or the open reading frame (ORF) encoding the Vrg4p or by deleting one or more nucleotides within the gene or ORF encoding the Vrg4p or by inserting a heterologous nucleic acid molecule into the gene or ORF encoding the Vrg4p. In particular embodiments, disruption of expression of the VRG4 gene may be accomplished by introducing one or more mutations into the ORF encoding the vrg4p, the mutations of which result in the disruption, abrogation, or reduction of the activity of the Vrg4p. A further means of disrupting gene expression is to alter expression levels by placing the ORF under the regulatory control of a heterologous promoter and/or terminator. Such expression control can be constitutive, inducible or repressible expression of the native or mutated ORF or a part thereof. Therefore, in particular embodiments, the host cell does not produce a functional GDP-mannose transmembrane transporter protein (Vrg4p) or produces a GDP-mannose transmembrane transporter protein (Vrg4p) with reduced activity, or does not produce a GDP-mannose transmembrane transporter protein (Vrg4p) at all. As used herein the term Vrg4p refers to the protein encoded by VRG4 gene or homologue thereof.

The present invention further provides a method for producing a recombinant heterologous, non-endogenous protein or glycoprotein in a lower eukaryote host cell comprising expressing a nucleic acid molecule encoding the recombinant heterologous, non-endogenous protein glycoprotein in a lower eukaryote host cell in which expression of the Vanadate Resistance Glycosylation (VRG4) gene or homologue thereof encoding the GDP-mannose transmembrane transporter has been disrupted. In particular aspects, the nucleic acid molecule encoding the heterologous, non-endogenous protein or glycoprotein may be integrated into a region of the VRG4 gene or replace the VRG4 gene or replace the ORF encoding the Vrg4p or homologue thereof.

The present invention further provides a method for reducing the amount of mannosylation on N- and O-glycans on a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter has been disrupted, wherein the amount of mannosylation on N- and O-glycans is less than the amount of mannose present on N- and O-glycans on the recombinant heterologous, non-endogenous protein or glycoprotein produced in a lower eukaryote host that expresses the GDP-mannose transmembrane transporter. For example, in an OCH1 wild-type host strain wherein the number of mannose residues is reduced to having no more than nine or ten mannose residues.

The inventor has also discovered that the lower eukaryote host cells that lack expression of the VRG4 gene produce proteins or glycoproteins that have reduced α-linked mannose addition to N- and/or O-glycans compared to the amount of α-linked mannose on N- and O-glycans on proteins or glycoproteins produced in host cells that produce a functional GDP-mannose transmembrane transporter protein. Therefore, the present invention further provides a method for reducing the amount of α-linked mannose on a heterologous heterologous, non-endogenous recombinant protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter protein has been disrupted, wherein the amount of α-linked mannose is less than the amount of α-linked mannose on the recombinant heterologous, non-endogenous protein or glycoprotein produced in a lower eukaryote host that expresses the GDP-mannose transmembrane transporter protein.

The present invention further provides a method for reducing the amount of α-linked mannose addition to N- and/or O-glycans of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter protein has been disrupted, wherein the amount of α-linked mannose addition is less than the α-linked mannoseaddition on the recombinant heterologous, non-endogenous protein or glycoprotein produced in a lower eukaryote host that expresses the GDP-mannose transmembrane transporter protein.

Thus, in a further aspect, the present invention provides a method for reducing the amount of high mannose N-glycans on a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter has been disrupted, wherein the amount of high mannose N-glycans is less than the amount of high mannose N-glycans on the recombinant heterologous, non-endogenous protein or glycoprotein produced in a lower eukaryote host that expresses the GDP-mannose transmembrane transporter. In general, the host cells are capable of producing proteins or glycoproteins wherein the number of mannose residues on an N-glycan is no more than nine or ten mannose residues compared to N-glycans in a host cell that expresses a functional GDP-mannose transmembrane transferease.

The inventor has also discovered that the lower eukaryote host cells that lack expression of the VRG4 gene produce proteins or glycoproteins that have O-glycans in which the number of mannose residues is reduced compared to the number of mannose residues comprising O-glycans on proteins or glycoproteins produced in host cells that produce a functional GDP-mannose transmembrane transporter protein. These mannose residues are linked in α1,2-linkages. Therefore, the present invention further provides a method for reducing the amount of O-glycan chain length of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter protein has been disrupted, wherein the O-glycan chain length is less than the p O-glycan chain length on the recombinant heterologous, non-endogenous protein or glycoprotein produced in a lower eukaryote host that expresses the GDP-mannose transmembrane transporter protein. Thus, these host cells are capable of producing proteins and glycoproteins having O-glycans with reduced amounts of α-linked mannose residues thereon.

The inventor has also discovered that the lower eukaryote host cells that lack expression of the VRG4 gene produce proteins or glycoproteins that have reduced β-linked mannose addition to N- and/or O-glycans compared to the amount of β-linked mannose on N- and/or O-glycans on proteins or glycoproteins produced in host cells that produce a functional GDP-mannose transmembrane transporter protein. Therefore, the present invention further provides a method for reducing the amount of β-linked mannose on a heterologous heterologous, non-endogenous recombinant protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter protein has been disrupted, wherein the amount of β-linked mannose is less than the amount of β-linked mannose on the recombinant heterologous, non-endogenous protein or glycoprotein produced in a lower eukaryote host that expresses the GDP-mannose transmembrane transporter protein.

The present invention further provides a method for reducing the amount of β-linked mannose addition to N- and/or O-glycans of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter protein has been disrupted, wherein the amount of β-linked mannose addition is less than the β-linked mannoseaddition on the recombinant heterologous, non-endogenous protein or glycoprotein produced in a lower eukaryote host that expresses the GDP-mannose transmembrane transporter protein.

The inventor has also discovered that the lower eukaryote host cells that lack expression of the VRG4 gene produce proteins or glycoproteins that have reduced phosphomannosylation of N- and/or O-glycans compared to amount phosphomannosylation of N- and/or O-glycans on proteins or glycoproteins produced in host cells that produce a functional GDP-mannose transmembrane transporter protein. Therefore, the present invention further provides a method for reducing the amount of phosphomannosylation of N- and/or O-glycans of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter protein has been disrupted, wherein the amount of phosphomanosylation is less than the phosphomannosylation on the recombinant heterologous, non-endogenous protein or glycoprotein produced in a lower eukaryote host that expresses the GDP-mannose transmembrane transporter protein.

The inventor has also discovered that the lower eukaryote host cells that lack expression of the VRG4 gene produce proteins or glycoproteins that have reduced amounts of hybrid N-glycans compared to the amount of hybrid N-glycans on proteins or glycoproteins produced in host cells that produce a functional GDP-mannose transmembrane transporter protein. Therefore, the present invention further provides a method for reducing the amount of hybrid N-glycans on a heterologous, non-endogenous recombinant protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or homologue thereof encoding the GDP-mannose transmembrane transporter has been disrupted, wherein the amount of hybrid N-glycans is less than the amount of hybrid N-glycans on the recombinant heterologous, non-endogenous protein or glycoprotein produced in a lower eukaryote host that expresses the GDP-mannose transmembrane transporter.

In further aspects of the aforementioned the lower eukaryote host cell, expression of at least one β-mannosyltransferase (BMT) gene or homologue thereof selected from the group consisting of BMT1, BMT2, BMT3, and BMT4 is disrupted. In particular embodiments, disruption of expression of the β-mannosyltransferase gene or homologue thereof may be achieved by providing an inhibitor selected from the group consisting of a chemical compound that binds or antagonizes the β-mannosyltransferase, an antisense DNA to an mRNA encoding the β-mannosyltransferase, and siRNA to one or more mRNA encoding the β-mannosyltransferase. Disruption of expression of the β-mannosyltransferase gene may be achieved by disrupting or deleting the β-mannosyltransferase gene or inserting mutations into the BMT gene that reduce or abrogate the activity of the encoded β-mannosyltransferase.

In particular aspects, the lower eukaryote host cell has a disruption of the expression of the Outer Chain (OCH1) gene or homologue thereof, the Acquired Thermo-Tolerance 1 (ATT1) gene or homologue thereof, or both. Disruption of expression includes but is not limited to deletion or disruption of the OCH1 gene or ORF encoding the Och1p and/or deletion or disruption of the ATT1 gene or ORF encoding the Att1p.

In particular aspects, the lower eukaryote host cell is a yeast or filamentous fungus host cell. In further aspects, the yeast or filamentous fungus host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. In further aspects, the lower eukaryote host cell is a yeast host cell selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica*, and *Pichia* sp. In further aspects, the lower eukaryote host cell is *Pichia pastoris*.

In further aspects, the lower eukaryote host cell has been genetically engineered to produce human-like N-glycans.

In further embodiments of any one of the above, the lower eukaryote host cell is genetically engineered to produce glycoproteins comprising one or more mammalian- or human-like complex N-glycans selected from G0, G1, G2, A1, or A2. In further embodiments, the host cell is genetically engineered to produce glycoproteins comprising one or more mammalian- or human-like complex N-glycans that have bisected N-glycans or have multiantennary N-glycans. In other embodiments, the host cell is genetically engineered to produce glycoproteins comprising one or more mammalian- or human-like N-glycans selected from the G-1 structure GlcNAcMan$_3$GlcNAc$_2$; the G-2 structure Man$_3$GlcNAc$_2$, or a high mannose N-glycan having six, seven, eight, nine, or ten mannose residues. The N-glycans may be fucosylated, that is include one or more fucose residues, or be non-fucosylated or fucose free and lack any fucose residues.

In particular aspects of any one of the above, the lower eukaryote host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, GnT IX, UDP-galactosyltransferase (GalT), fucosyltransferase, and sialyltransferase. In particular embodiments, the mannosidase is selected from the group consisting of *C. elegans* mannosidase IA, *C. elegans* mannosidase IB, *D. melanogaster* mannosidase IA, *H. sapiens* mannosidase IB, *P. citrinum* mannosidase I, mouse mannosidase IA, mouse mannosidase IB, *A. nidulans* mannosidase IA, *A. nidulans* mannosidase IB, *A. nidulans* mannosidase IC, mouse mannosidase II, *C. elegans* mannosidase II, *H. sapiens* mannosidase II, and mannosidase III.

In certain aspects of any one of the above, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases, and phospho-mannosyltransferases.

In particular aspects of any one of the above, the lower eukaryote host cell further includes one or more nucleic acid molecules encode one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above, the lower eukaryote host cell includes one or more nucleic acid molecules encoding an α1,2-mannosidase activity, a UDP-GlcNAc transferase (GnT) I activity, a mannosidase II activity, and a GnT II activity.

In further still aspects of any one of the above, the lower eukaryote host cell includes one or more nucleic acid molecules encoding an α1,2-mannosidase activity, a UDP-GlcNAc transferase (GnT) I activity, a mannosidase II activity, a GnT II activity, and a UDP-galactosyltransferase (GalT) activity.

In further still aspects of any one of the above, the lower eukaryote host cell includes one or more nucleic acid molecules encoding an α1,2-mannosidase activity, a UDP-GlcNAc transferase (GnT) I activity, a mannosidase II activity, a GnT II activity, a UDP-galactosyltransferase (GalT) activity and a silayltransferase activity.

In further still aspects of any one of the above, the lower eukaryote host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

The present invention provides protein glycoprotein compositions wherein the composition lacks detectable amounts of the addition of more than one mannose residue that is typically characterized by post-endoplasmic reticulum processing wherein detection of N-glycans is by MALDI-TOF or HPLC. Such mannose addition can either be in the α-linked mannose, β-linked mannose or phosphomannose configuration.

The present invention provides protein or glycoprotein compositions wherein the composition lacks detectable amounts of mannotetraose O-glycans wherein detection of O-glycans is by MALDI-TOF or HPLC.

In further aspects, the compositions comprise a therapeutic protein or glycoprotein. Examples of therapeutic glycoproteins include but are not limited to the therapeutic proteins glycoproteins recited supra.

The present invention provides a plasmid vector comprising a nucleic acid molecule encoding at least 25, 50, 75, or 100 contiguous nucleotides of SEQ ID NO:1, SEQ ID NO:2, or SEQ ID NO:3. In further embodiments, the plasmid vector further includes a nucleic acid molecule encoding a selection marker. In particular embodiments the selection marker is a nucleic acid molecule encoding hygromycin resistance, Ura5p, Ura3p, Zeocin resistance, arsenite resistance or nourseothricin resistance.

The present invention further provides a method for producing a lower eukaryote host cell in which expression of the VRG4 gene or homologue thereof is disrupted comprising (a) providing a plasmid vector comprising a first nucleic acid molecule encoding a selection marker flanked on one side by a second nucleic acid molecule comprising a 5' region of the VRG4 gene or homologue thereof and on the other side by a third nucleic molecule comprising a 3' region of the VRG4 gene or homologue thereof; (b) transforming the lower eukaryote host cell with the plasmid vector wherein the selection marker is integrated into the VRG4 gene or homologue thereof by double-crossover homologous recombination to produce a lower eukaryote host cell in which the first nucleic acid molecule encoding the selection marker is integrated into the VRG4 gene or homologue thereof between the 5' region and the 3' region of the VRG4 gene or homologue thereof that are homologous or have identity to the second and third nucleic acid molecules, respectively, and (c) selecting the lower eukaryote host cell comprising the nucleic acid molecule encoding the selection marker integrated into the VRG4 gene or homologue thereof to produce the lower eukaryote host cell in which expression of the VRG4 gene or homologue thereof is disrupted.

In particular aspects, the second nucleic acid molecule comprising the 5' region of the VRG4 gene or homologue thereof and the third nucleic acid molecule comprising 3' region of the VRG4 gene or homologue thereof are noncontiguous and the first nucleic acid encoding the selection marker when integrated into the VRG4 gene or homologue thereof replaces the region between the 5' and 3' regions of the VRG4 gene or homologue thereof in the host cell to produce the host cell in which expression of the VRG4 gene or homologue thereof is disrupted. In a further aspect, the first nucleic acid molecule encoding the selection marker replaces the open reading frame (ORF) in the VRG4 gene or homologue thereof encoding the Vrg4p. Further provided are lower eukaryote host cells produced by the aforementioned method.

In particular aspects, the lower eukaryote host cell is a yeast or filamentous fungus host cell. In further aspects, the yeast or filamentous fungus host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*. In further aspects, the lower eukaryote host cell is a yeast host cell selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica*, and *Pichia sp*. In further aspects, the lower eukaryote host cell is *Pichia pastoris*.

In particular aspects the lower eukaryote host cell has a disruption of the expression of the Outer Chain (OCH1) gene or homologue thereof, the Acquired Thermo-Tolerance 1 (ATT1) gene or homologue thereof, or both.

In particular embodiments of any one of the above embodiments or aspects of the present invention, the heterologous, non-endogenous protein or glycoprotein may be a therapeutic protein or glycoprotein. Therapeutic proteins and glycoproteins are included in compositions for administering to a mammal or human to treat a disease or condition. Examples of therapeutic proteins or glycoproteins, human or mammalian, include but are not limited to, erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; insulin and analogs thereof, GLP1 receptor agonists such as GLP1 and analogs thereof, oxyntomodulin and analogs thereof, exendin-4 and analogs thereof, and the like; glucagon receptor agonists or antagonists; fibroblast growth factors such as FGF-21 and analogs thereof, FGF-19 and analogs thereof, and the like; leptin and analogs thereof; amylin and analogs thereof; IL-2 receptor agonist, or analog or mutein thereof.

In further embodiments of any one of the above, the therapeutic glycoprotein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

The present invention further provides for the use of any one of the lower eukaryote host cells disclosed herein for the production of a medicament for treating a disease or disorder. For example, the present invention provides for the use of a lower eukaryote host cell comprising a disruption of the expression of the VRG4 gene or homologue thereof for producing a medicament for treating a disease or disorder.

DEFINITIONS

As used herein, the term "glycoprotein" refers to any protein having one or more N-glycan or O-glycans attached thereto. The term refers both to proteins that are generally recognized in the art as a glycoprotein and to proteins not generally recognized as glycoproteins in the art but which have been modified or genetically engineered to contain one or more N-linked and/or O-linked glycosylation sites. The term also refers to proteins that are not generally recognized in the art as having N-glycans and/or O-glycans but which when expressed as a recombinant heterologous, non-endogenous protein in a particular host cell are glycosylated. For example, insulin is not generally recognized as a glycoprotein; however, it has been found that in certain cases when a nucleic acid molecule encoding human insulin is expressed in *Saccharomyces cerevisiae* or *Pichia pastoris*, a portion of the insulin molecules produced are glycosylated (See for example, Published International Application No. WO2009/104199 and U.S. Pat. No. 6,180,757).

As used herein, an "N-linked glycosylation site" refers to the tri-peptide amino acid sequence NX(S/T) or AsnXaa(Ser/Thr) wherein "N" represents an asparagine (Asn) residue, "X" represents any amino acid (Xaa) except proline (Pro), "S" represents a serine (Ser) residue, and "T" represents a threonine (Thr) residue.

As used herein, the term "N-glycan" and "glycoform" are used interchangeably and refer to the oligosaccharide group per se that is attached by an asparagine-N-acetylglucosamine linkage to an attachment group comprising an N-linked glycosylation site. The N-glycan oligosaccharide group may be attached in vitro to any amino acid residue other than asparagine or in vivo to an asparagine residue comprising an N-linked glycosylation site.

The term "N-linked glycan" refers to an N-glycan in which the N-acetylglucosamine residue at the reducing end is linked in a β1 linkage to the amide nitrogen of an asparagine residue of an attachment group in the protein.

As used herein, the terms "N-linked glycosylated" and "N-glycosylated" are used interchangeably and refer to an N-glycan attached to an attachment group comprising an asparagine residue or an N-linked glycosylation site or motif.

As used herein, the term "in vivo glycosylation" or "in vivo N-glycosylation" or "in vivo N-linked glycosylation" refers to the attachment of an oligosaccharide or glycan moiety to an asparagine residue of an N-linked glycosylation site occurring in vivo, i.e., during posttranslational processing in a glycosylating cell expressing the polypeptide by way of N-linked glycosylation. The exact oligosaccharide structure depends, to a large extent, on the host cell used to produce the glycosylated protein or polypeptide.

The term "attachment group" is intended to indicate a functional group of the polypeptide, in particular of an amino acid residue thereof, capable of being covalently linked to a macromolecular substance such as an oligosaccharide or glycan, a polymer molecule, a lipophilic molecule, or an organic derivatizing agent.

For in vivo N-glycosylation, the term "attachment group" is used in an unconventional way to indicate the amino acid residues constituting an "N-linked glycosylation site" or "N-glycosylation site" comprising N—X—S/T, wherein X is any amino acid except proline. Although the asparagine (N) residue of the N-glycosylation site is where the oligosaccharide or glycan moiety is attached during glycosylation, such attachment cannot be achieved unless the other amino acid residues of the N-glycosylation site are present. While the N-linked glycosylated insulin analogue precursor will include all three amino acids comprising the "attachment group" to enable in vivo N-glycosylation, the N-linked glycosylated insulin analogue may be processed subsequently to lack X and/or S/T. Accordingly, when the conjugation is to be achieved by N-glycosylation, the term "amino acid residue comprising an attachment group for the oligosaccharide or glycan" as used in connection with alterations of the amino acid sequence of the polypeptide is to be understood as meaning that one or more amino acid residues constituting an N-glycosylation site are to be altered in such a manner that a functional N-glycosylation site is introduced into the amino acid sequence. The attachment group may be present in the insulin analogue precursor but in the heterodimer insulin analogue one or two of the amino acid residues comprising the attachment site but not the asparagine (N) residue linked to the oligosaccharide or glycan may be removed. For example, an insulin analogue precursor may comprise an attachment group consisting of NKT at positions B28, 29, and 30, respectively, but the mature heterodimer of the analogue may be a desB30 insulin analogue wherein the T at position 30 has been removed.

As used herein, "N-glycans" have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid ("Sia") or derivatives (e.g., "NANA" or "NeuAc" where "Neu" refers to neuraminic acid and "Ac" refers to acetyl, or the derivative NGNA, which refers to N-glycolylneuraminic acid). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. N-glycans consisting of a $Man_3GlcNAc_2$ structure are called paucimannose. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $SiaGal_2GlcNAc_2Man_3GlcNAc_2$; and, the term "A2" refers to an N-glycan structure that can be characterized as $Sia_2Gal_2GlcNAc_2Man_3GlcNAc_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contain a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $Sia_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the inner most, β-linked mannose of the trimannose core of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Abbreviations used herein are of common usage in the art, see, e.g., abbreviations of sugars, above. Other common abbreviations include "PNGase", or "glycanase" which all refer to glycopeptide N-glycosidase; glycopeptidase; N-oligosaccharide glycopeptidase; N-glycanase; glycopeptidase; Jack-bean glycopeptidase; PNGase A; PNGase F; glycopeptide N-glycosidase (EC 3.5.1.52, formerly EC 3.2.2.18).

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Host cells may be yeast, fungi, mammalian cells, plant cells, insect cells, and prokaryotes and archaea that have been genetically engineered to produce glycoproteins.

When referring to "mole percent" or "mole %" of a glycan present in a preparation of a glycoprotein, the term means the molar percent of a particular glycan present in the pool of N-linked oligosaccharides released when the protein preparation is treated with PNGase and then quantified by a method that is not affected by glycoform composition, (for instance, labeling a PNGase released glycan pool with a fluorescent tag such as 2-aminobenzamide and then separating by high performance liquid chromatography or capillary electrophoresis and then quantifying glycans by fluorescence intensity). For example, 50 mole percent $NANA_2Gal_2GlcNAc_2Man_3GlcNAc_2$ means that 50 percent of the released glycans are $NANA_2Gal_2GlcNAc_2Man_3GlcNAc_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences that are necessary to affect the expression of coding sequences to which they are operably linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", "transfection", "transfecting" and the like refer to the introduction of a heterologous nucleic acid into eukaryote cells, both higher and lower eukaryote cells. Historically, the term "transformation" has been used to describe the introduction of a nucleic acid into a prokaryote, yeast, or fungal cell; however, the term "transfection" is also used to refer to the introduction of a nucleic acid into any prokaryotic or eukaryote cell, including yeast and fungal cells. Furthermore, introduction of a heterologous nucleic acid into prokaryotic or eukaryotic cells may also occur by viral or bacterial infection or ballistic DNA transfer, and the term "transfection" is also used to refer to these methods in appropriate host cells.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharomyces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp., *Yarrowia lipolytica*, and *Neurospora crassa*.

As used herein, the term "consisting essentially of" will be understood to imply the inclusion of a stated integer or group of integers; while excluding modifications or other integers that would materially affect or alter the stated integer. For example, with respect to a species of N-glycans attached to an insulin or insulin analogue, the term "consisting essentially of" a stated N-glycan will be understood to include the N-glycan whether or not that N-glycan is fucosylated at the N-acetylglucosamine (GlcNAc) which is directly linked to the asparagine residue of the glycoprotein provided that for the particular N-glycan species the fucose does not materially affect the glycosylated insulin or insulin analogue compared to the glycosylated insulin or insulin analogue in which the N-glycan lacks the fucose.

As used herein, the term "predominantly" or variations such as "the predominant" or "which is predominant" will be understood to mean the glycan species that has the highest mole percent (%) of total N-glycans after the glycoprotein has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A at 40 mole percent, species B at 35 mole percent and species C at 25 mole percent, the composition comprises predominantly species A, and species B would be the next most predominant species. Some host cells may produce compositions comprising neutral N-glycans and charged N-glycans such as mannosylphosphate or sialic acid. Therefore, a composition of glycoproteins can include a plurality of charged and uncharged or neutral N-glycans. In the present invention, it is within the context of the total plurality of N-glycans in the composition in which the predominant N-glycan determined. Thus, as used herein, "predominant N-glycan" means that of the total plurality of neutral N-glycans in the composition, the predominant N-glycan is of a particular structure.

As used herein, the term "essentially free of" a particular sugar residue, such as fucose, or galactose and the like, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast (for example, *Pichia* sp.; *Saccharomyces* sp.; *Kluyveromyces* sp.; *Aspergillus* sp.), and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

As used herein, the term "leader peptide" refers to a polypeptide comprising a pre-peptide (the signal peptide) and a propeptide.

As used herein, the term "signal peptide" refers to a pre-peptide which is present as an N-terminal peptide on a precursor form of a protein. The function of the signal peptide is to enable or facilitate translocation of the expressed polypeptide to which it is attached into the endoplasmic reticulum. The signal peptide is normally cleaved off in the course of this process. The signal peptide may be heterologous or homologous to the organism used to produce the polypeptide. A number of signal peptides which may be used include the yeast aspartic protease 3 (YAP3) signal peptide or any functional analog (Egel-Mitani et al. YEAST 6:127 137 (1990) and U.S. Pat. No. 5,726,038) and the signal peptide of the *Saccharomyces cerevisiae* mating factor al gene (ScMF α 1) gene (Thorner (1981) in The Molecular Biology of the Yeast *Saccharomyces cerevisiae*, Strathern et al., eds., pp 143 180, Cold Spring Harbor Laboratory, NY and U.S. Pat. No. 4,870,008.

As used herein, the term "propeptide" refers to a peptide whose function is to allow the expressed polypeptide to which it is attached to be directed from the endoplasmic reticulum to the Golgi apparatus and further to a secretory vesicle for secretion into the culture medium (i.e., exportation of the polypeptide across the cell wall or at least through the cellular membrane into the periplasmic space of the yeast cell). The propeptide may be the ScMF al (See U.S. Pat. Nos. 4,546,082 and 4,870,008). Alternatively, the pro-peptide may be a synthetic propeptide, which is to say a propeptide not found in nature, including but not limited to those disclosed in U.S. Pat. Nos. 5,395,922; 5,795,746; and 5,162,498 and in WO 9832867. The propeptide will preferably contain an endopeptidase processing site at the C-terminal end, such as a Lys-Arg sequence or any functional analog thereof.

As used herein an amino acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

BRIEF DESCRIPTION OF THE DRAWINGS

FIGS. 2-1 and 2-2 shows schematically the construction of several vrg4 deletion mutants in various glycoengineered *Pichia pastoris* cells, the number of vrg4 deletion (vrg4Δ) clones obtained, and the sugar transporters that had been integrated into the host cell genome by homologous recombination.

FIGS. 3-1 and 3-2 shows MALDI-TOF (matrix assisted laser desorption/ionization-time of flight mass spectroscopy) analyses of N-glycans extracted from the total cell mass from VRG4 and vrg4Δ GFI 1.0 glycoengineered strains.

FIGS. 4-1 and 4-2 shows MALDI-TOF analyses of N-glycans extracted from the total cell mass from VRG4 and vrg4Δ GFI 3.5 and 5.0 glycoengineered strains.

FIGS. 6-1 and 6-2 shows MALDI-TOF analyses of cell N-glycans extracted from the total cell mass obtained from VRG4 and vrg4Δ GFI 1.0 and 5.0 glycoengineered strains that further express TNFRII-Fc.

FIGS. 11-1 and 11-2 shows a MALDI-TOF analysis of cell N-glycans extracted from the total cell mass obtained from VRG4 cells and vrg4Δ GFI 1.0 glycoengineered strains further expressing rEPO.

FIGS. 12-1 and 12-2 shows MALDI-TOF analyses of compositions of rEPO N-glycans from compositions of rEPO obtained from VRG4 cells and vrg4Δ GFI 1.0 glycoengineered strains.

FIGS. 16-1 and 16-2 shows a MALDI-TOF analysis of cell N-glycans extracted from the total cell mass obtained from VRG4 cells and vrg4Δ GFI 1.0 glycoengineered strains in which the OCH1 gene has been re-introduced and thus, OCH1 compared to strains that are och1Δ.

FIGS. 17-1 and 17-2 shows a MALDI-TOF analysis of cell N-glycans extracted from the total cell mass obtained from VRG4 cells and vrg4Δ GFI 1.0 glycoengineered strains in which the OCH1 gene has been re-introduced and thus, OCH1 compared to strains that are och1Δ. The strains further express TNFRII-Fc as a reporter protein.

FIGS. 18-1 and 18-2 shows a MALDI-TOF analysis of N-glycans extracted from TNFRII-Fc compositions obtained from VRG4 cells and vrg4Δ GFI 1.0 glycoengineered strains in which the OCH1 gene has been re-introduced and thus, OCH1 compared to strains that are och1Δ. The strains express TNFRII-Fc as a reporter protein.

FIGS. 22-1 and 22-2 shows schematically the construction of VRG4 and vrg4Δ strains engineered in both OCH1 and och1Δ strains. In the example of the OCH1 strain lineage the knock-out of ATT1 was incorporated prior to VRG4 knockout.

FIGS. 23-1 and 23-2 shows MALDI-TOF analyses of N-glycans extracted from the total cell mass from strain YGLY29170 (och1Δ/vrg4Δ) grown in shake flasks compared to strains YGLY25241 (och1Δ/vrg4Δ) grown in shake flasks. Also shown is the comparison of the glycans from YGLY27836 (OCH1/att1Δ) and YGLY29170 (OCH1/att1Δ/vrg4Δ) which indicates that the extent of mannosylation is greatly reduced on knock-out of VRG4 in a wild-type OCH1 background.

DETAILED DESCRIPTION OF THE INVENTION

Figure 1:
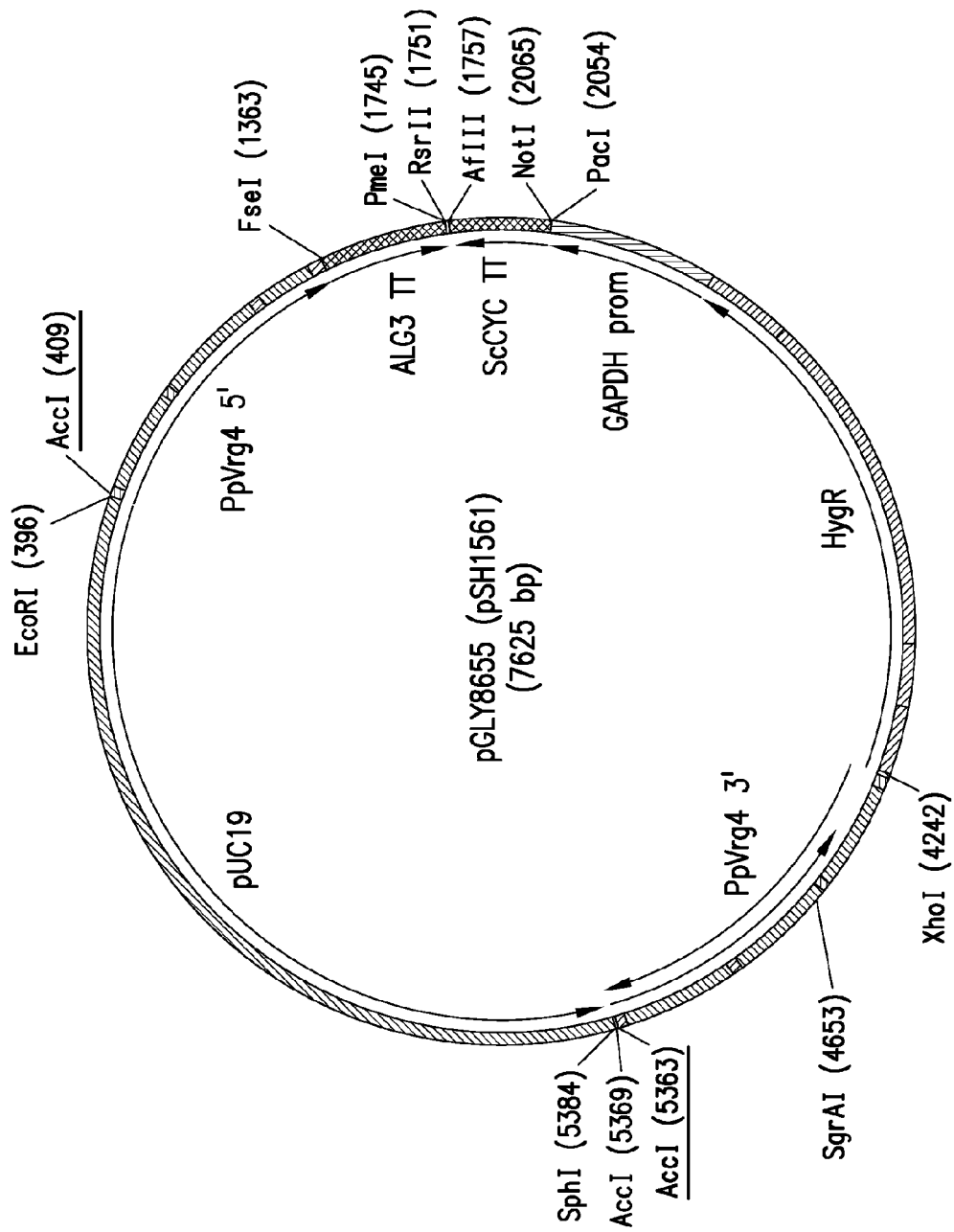
FIG. 1 shows a map of plasmid vector pGLY8655 for disrupting the VRG4 locus by homologous recombination, resulting in the deletion of the open reading frame encoding the Vrg4p. The vector further includes an expression cassette encoding the selectable marker hygromycin (HygR) resistance.

The present invention provides methods for reducing or eliminating detectable mannosylation of N-linked and/or O-linked oligosaccharides of recombinant heterologous, non-endogenous proteins and glycoproteins produced in lower eukaryote host cells, including but not limited to yeast and filamentous fungi host cells. In particular, the present invention provides recombinant lower eukaryote host cells in which expression of the GDP-mannose transporter protein encoded by the Vanadate-Resistant Glycosylation 4 (VRG4) gene or homologue thereof has been disrupted. When these host cells are used to produce recombinant heterologous, non-endogenous proteins or glycoproteins, the amount of hybrid and high mannose N-glycans thereon is reduced compared to the amount of hybrid and high mannose N-glycans on the corresponding proteins or glycoproteins produced in a host cell that expresses the endogenous VRG4 gene and produces a functional GDP-mannose transporter protein. In general, the N- and/or O-glycans in the host cells lacking VRG4 gene expression as disclosed herein have significantly lower post-endoplasmic reticulum mannose addition to glycans whereas host cells expressing the VRG4 gene produce N- and/or O-glycans in which significant mannosylation, including the incorporation of α-linked mannose, β-linked mannose and/or phosphomannose, occurs. In addition, when these host cells are used to produce recombinant heterologous, non-endogenous proteins or glycoproteins, the amount of mannosylation, including α-linked mannose, β-linked mannose and/or phosphomannose incorporation, on N-glycans and/or 0-glycans thereon is reduced compared to the amount of mannosylation N-glycans and O-glycans on the corresponding proteins or glycoproteins produced in a host cell that expresses the endogenous VRG4 gene and a functional GDP-mannose transporter protein. As such, O-glycan mannosylation (i.e., the number of mannose residues in an O-glycan) thereon is reduced compared to O-glycan mannosylation produced in a host cell that expresses the endogenous VRG4 gene and a functional GDP-mannose transporter protein. In general, the amount or proportion of mannotriose and mannotetraose O-glycans relative to the amount or proportion of mannose and mannobiose O-glycans on a protein or glycoprotein produced in the host cells of the present invention is reduced or decreased so that mannose and mannobiose O-glycans are the predominant O-glycan species on the protein or glycoprotein. In particular embodiments of the present invention, the proteins or glycoproteins produced in the host cells of the present invention have predominantly mannose and mannobiose O-glycans with no detectable mannotriose or mannotetraose O-glycans. Furthermore, the invention demonstrates that the disruption of the VRG4 gene can significantly reduce the mannobiose O-glycans to O-glycans with predominantly a single mannose in strains from several backgrounds.

The VRG4 gene or homologue thereof encodes a GDP-mannose transporter, which facilitates the transport of GDP-mannose from the cytoplasm into the Golgi apparatus where the GDP-mannose is made available to Golgi-resident mannosyltransferases. The Golgi-resident mannosyltransferases effect the transfer of mannose from the GDP-mannose to the N-glycan or O-glycan of a glycoprotein or to a phosphoinositol-containing sphingolipid. The transferred mannose may be incorporated into the glycan or sphingolipid in an α1,2; α1,3; α1,6; or β1,2 linkage. Alternatively, the mannose may be transferred to the N-glycan or O-glycan as a phosphomannose, which then introduces a charge to the glycoprotein or sphingolipid.

The VRG4 gene was identified in *Saccharomyces cerevisiae* by Poster and Dean (J. Biol. Chem. 271: 3837-3845 (1996)) who also showed that vrg4 mutants lack outer chain glycosylation of N-glycans of glycoproteins that are normally extended during passage of the glycoprotein through the Golgi. Dean et al. (J. Biol. Chem. 272: 31908-31914 (1997) showed the Vrg4p protein is a GDP-mannose transmembrane transporter protein and that its presence is essential for cell growth. Abe et al. (FEBS Letts. 458: 309-312 (1999) showed that the Vrg4p or GDP-mannose transmembrane transporter protein has multiple transmembrane domains and is essential for transport of GDP-mannose across the Golgi membrane.

The *Pichia pastoris* VRG4 gene comprises the nucleotide sequence shown in SEQ ID NO:3 or at least the open reading frame (ORF) encoding the *Pichia pastoris* GDP-mannose transmembrane transporter protein (Vrg4p) having the amino acid sequence shown in SEQ ID NO: 77, which is encoded by nucleotides 1001 to 1987 of SEQ ID NO:3 with the stop codon TAG including nucleotides 1988-1990. The nucleic acid sequence encoding Vrg4p is shown in SEQ ID NO:76. The present invention further provides nucleic acid molecules comprising 70%, 75%, 80%, 85%, 90%, 95%, 98%, or more identity to the nucleotide sequence shown in SEQ ID NO:1, 2, 3, or 76. The present invention further provides nucleic acid molecules encoding a GDP-mannose transmembrane transporter protein having 70%, 75%, 80%, 85%, 90%, 95%, 98%, or more identity to the polypeptide sequence shown in SEQ ID NO:77. The present invention further provides plasmid vectors comprising a nucleic acid molecule comprising 70%, 75%, 80%, 85%, 90%, 95%, 98%, or more identity to the nucleotide sequence shown in SEQ ID NO:1. The present invention further provides plasmid vectors comprising a nucleic acid molecule comprising 70%, 75%, 80%, 85%, 90%, 95%, 98%, or more identity to the nucleotide sequence shown in SEQ ID NO:2. The present invention further provides plasmid vectors comprising a nucleic acid molecule comprising 70%, 75%, 80%, 85%, 90%, 95%, 98%, or more identity to the nucleotide sequence shown in SEQ ID NO:1 and a nucleic acid molecule comprising 70%, 75%, 80%, 85%, 90%, 95%, 98%, or more identity to the nucleotide sequence shown in SEQ ID NO:2. The present invention further provides a plasmid vector comprising a nucleic acid molecule comprising 70%, 75%, 80%, 85%, 90%, 95%, 98%, or more identity to the nucleotide sequence shown in SEQ ID NO:76. The present invention further provides a plasmid vector comprising a nucleic acid molecule encoding a GDP-mannose transmembrane transporter protein comprising 70%, 75%, 80%, 85%, 90%, 95%, 98%, or more identity to the polypeptide sequence shown in SEQ ID NO:77.

Fungi such as yeasts are attractive hosts for producing proteins because they are capable of producing proteins of high quality in high yield. However, the glycosylation pathway of yeast produces glycoproteins with a glycosylation pattern very different from the glycosylation pattern produced by mammalian and human host cells. Yeasts produce glycoproteins that have hypermannosylated or high mannose N-glycans. Lower eukaryotes such as yeast lack the ability to synthesize N-glycans that have galactose, fucose, and terminal sialic acid: sugars that are commonly found in mammalian and human N-glycans. Therefore, to use yeast host cells to produce glycoproteins that have human-like N-glycans, the host cells are genetically engineered to lack mannosyltransferase activities that enable the host cell to produce glycoproteins that have high mannose or hypermannosylated N-glycans and then modified to include one or more nucleic acid molecules encoding sugar transporters and glycosyltransferase activities from mammalian or human sources, which have been modified to include a localization peptide that targets the glycosyltransferase activity to a location in the endoplasmic reticulum or Golgi apparatus that enables the glycosyltransferase activity to modify the N-glycans on a glycoprotein as it traverses the secretory pathway to have a mammalian-like or human-like glycosylation pattern. U.S. Pat. No. 7,029,872 discloses methods for making recombinant lower eukaryote host cells that make glycoproteins with mammalian-like or human-like N-glycans.

For example, to reduce outer chain glycosylation of N-glycans in *Pichia pastoris* and *Saccharomyces cerevisiae*, expression of the OCH1 gene encoding an α1,6-mannosyltransferase (Och1p) is disrupted (See U.S. Pat. No. 7,029,872). While disrupting expression of the OCH1 gene significantly reduces outer chain glycosylation and thus, hypermannosylation, yeast host cells express other mannosyltransferases that may act in the Golgi to effect transfer of mannose residues to N-glycans. For example, FIGS. 4-1, 6-1, and 11-1 each show that *Pichia pastoris* host cells genetically engineered to lack expression of OCH1 and further modified to produce mammalian-like or human-like N-glycans may still produce detectable high mannose N-glycans, i.e., N-glycans containing more than nine mannose residues. These mannosyltransferases reside in the Golgi and rely upon Vrg4p or GDP-mannose transmembrane transporter protein to transport sufficient GDP-mannose into Golgi for transfer to the N-glycan.

To further reduce the occurrence of proteins or glycoproteins that have yeast N-glycan structures, the yeast host cells are further modified to lack β-mannosyltransferase activities and phosphomannosyltransferase activities. To reduce the occurrence of N-glycans and O-glycans that have β-linked mannose residues, expression of one or more of the β-mannosyltransferase genes (e.g., BMT1, BMT2, BMT3, and BMT4)(See, U.S. Pat. No. 7,465,577, U.S. Pat. No. 7,713,719, and Published International Application No. WO2011046855) is disrupted. To enable the cell to make proteins or glycoproteins that have mammalian-like or human-like N-glycans, the host cell is then modified to include one or more nucleic acid molecules encoding glycosylation enzyme activities from mammalian-like or human sources modified to include a localization peptide that targets the glycosylation activity to a location in the endoplasmic reticulum or Golgi apparatus that enables the glycosylation enzyme activity to modify N-glycans on a glycoprotein. To reduce the occurrence of N-glycans and O-glycans that have phosphorylated mannose residues, expression of the PNO1 and MNN4 genes is disrupted (U.S. Pat. Nos. 7,198,921 and 7,259,007). In *Saccharomyces cerevisiae*, the MNN4 gene is disrupted (Chiba et al. J. Biol. Chem. 273: 26298-26304 (1998)).

However, it has been found that in some cases these host cells may continue to display residual mannosylation activity. Therefore, a composition of proteins or glycoproteins produced in these host cells may in some cases include a population or subset of glycoproteins that have detectable amounts of high mannose, phosphomannose, or β-mannose structures. For the production of therapeutic proteins or glycoproteins, the presence of these structures, even in very low amounts, is undesirable because protein or glycoprotein compositions that comprise even very low amounts of glycoproteins with such structures may still elicit an unwanted immune response when the composition is administered to some patients. In addition, these unwanted or improper glycosylation structures may modify the activity of the protein or glycoprotein to an extent that inters with the activity of the protein or glycoprotein. For example, the unwanted or improper glycosylation may render the protein or glycoprotein in active.

The inventor has discovered that *Pichia pastoris* host cells in which expression of the endogenous VRG4 gene has been disrupted, are not only viable and but also capable of producing glycoproteins wherein the amount of hybrid and high mannose N-glycans is reduced compared to the amount of hybrid and high mannose N-glycans produced in a host cell that expresses the endogenous VRG4 gene and produces a functional GDP-mannose transmembrane transporter protein; the amount of phosphomannose N-glycans and O-glycans is reduced compared to the amount of phosphomannose N-glycans and O-glycans produced in a host cell that expresses the endogenous VRG4 gene and produces a functional GDP-mannose transmembrane transporter protein; and O-glycan mannosylation (i.e., the number of mannose residues in an O-glycan) is reduced compared to that produced in a host cell that expresses the endogenous VRG4 gene and produces a functional GDP-mannose transmembrane transporter protein. For example, FIGS. 4-2, 6-2, and 11-2 each show that *Pichia pastoris* host cells genetically engineered to lack expression of OCH1 and VRG4 and further modified to produce mammalian-like or human-like N-glycans do not produce detectable high mannose N-glycans, i.e., N-glycans containing more than nine mannose residues. As shown in the Examples, the reduction in phosphomannosylation may even be achieved in host cells that express the PNO1, MNN4 and MNN4L1 genes, genes known to be involved in phosphomannosylation of N-glycans and O-glycans.

The inventor has found that *Pichia pastoris* strains in which expression of the Outer Chain (OCH1) gene or homologue, the Acquired Thermo-Tolerance 1 (ATT1) gene or homologue, or both has been disrupted can tolerate disruption of expression of the VRG4 gene. Viable recombinant host cells that lack expression of the VRG4 gene may also be constructed by random mutagenesis followed by transformation of the mutagenized host cells with a plasmid vector designed to disrupt expression of the VRG4 gene or a plasmid vector that encodes an siRNA to inhibit expression of the VRG4 gene and screening the transformed host cells for viable recombinant host cells. The viable recombinant host cells may be used as disclosed herein to produce recombinant glycoproteins.

By disrupting expression of the VRG4 gene or homologue thereof, vrg4 host cells are provided that lack a secretory pathway GDP-mannose pool. Since mannosylatransferases in the secretory pathway use GDP-mannose as the sugar donor to transfer mannose to an N- or O-glycan, the lack of a secretory pathway GDP-mannose pool in the vrg4 host cells results in the inhibition or elimination of the extension of N- and/or O-glycans on glycoproteins as they traverse the secretory. In addition, disrupting expression of the VRG4 gene or homologue thereof also inhibits the synthesis of N-glycans that are phosphorylated or have one or more mannose residues linked in a β1,2-linkages.

As discussed above, prior art methods for inhibiting or reducing the occurrence of undesirable glycoforms, e.g, high mannose and phosphorylated N-glycans and N-glycans that have β1,2-linked mannose residues, involve constructing recombinant host cells in which the expression of a number of genes encoding mannosyltransferases are disrupted. For example, to produce a recombinant *Pichia pastoris* host cell in which the synthesis of high mannose and phosphorylated N-glycans and N-glycans containing β1,2-linked mannose residues is inhibited or eliminated, expression of up to seven host genes encoding various mannosyltransferases is inhibited. The ability to achieve a similar effect in a host by disrupting expression of just one gene, the VRG4 gene, is a significant improvement over prior art methods for inhibiting or eliminating many of the undesirable glycoforms that may occur in particular host cells expressing particular recombinant heterologous, non-endogenous proteins or glycoproteins. This is of particular interest when further genetic engineering of the host cell is desired to produce host cells that are capable of producing proteins or glycoproteins with mammalian-like or human-like glycoforms. For example, in the production of host cells that can make predominantly any one of the glycoforms shown in FIG. 19, competing mannosylation may occur, which is often growth or culture condition related and which affects overall quality of the glycoproteins produced. One such undesirable mannosylation activity is the addition of mannose residues to the N-glycan in an α1,2 linkage. The gene family responsible for the transfer of these mannose residues to an N- or O-glycan possesses several members. Therefore, elimination of this undesirable activity may potentially require disruption of the expression of each of the family members. Disrupting expression of the VRG4 gene achieves this end goal without the need to identify all the members of the gene family and then disrupting expression of all the family members.

Therefore, in particular embodiments, provided is a lower eukaryote host cell comprising (a) a disruption of Vanadate Resistance Glycosylation (VRG4) gene or homologue thereof expression; and (b) a nucleic acid molecule encoding a recombinant heterologous, non-endogenous glycoprotein, wherein the host cell does not produce a functional GDP-mannose transmembrane transporter protein (Vrg4p) and wherein the host cell is viable. Disruption of expression of the VRG4 gene or homologue thereof may be achieved by providing an inhibitor selected from the group consisting of a chemical compound that binds or antagonizes the function of the encoded GDP-mannose transmembrane transporter protein (Vrg4p), an antisense DNA to an mRNA encoding the Vrg4p, and an siRNA to an mRNA encoding the Vrg4p. Disruption of expression of the VRG4 gene or homologue thereof may be achieved by deleting the VRG4 gene or the open reading frame (ORF) encoding the Vrg4p or by deleting one or more nucleotides within the ORF encoding the Vrg4p or by inserting a heterologous nucleic acid molecule into the ORF encoding the Vrg4p. In particular embodiments, disruption of expression of the VRG4 gene may be accomplished by introducing one or more mutations into the ORF encoding the vrg4p, the mutations of which result in the disruption, abrogation, or reduction of the activity of the Vrg4p. A further means of disrupting gene expression is to alter expression levels by placing the ORF under the regulatory control of a heterologous promoter and/or terminator. Such expression control can be constitutive, inducible or repressible expression of the native or mutated ORF or a part thereof. Therefore, in particular embodiments, the host cell does not produce a functional GDP-mannose transmembrane transporter protein (Vrg4p) or produces a GDP-mannose transmembrane transporter protein (Vrg4p) with reduced activity, or does not produce a GDP-mannose transmembrane transporter protein (Vrg4p) at all. As used herein the term Vrg4p refers to the protein encoded by VRG4 gene or homologue thereof.

The lower eukaryote host cell may further include embodiments wherein expression of at least one β-mannosyltransferase (BMT) gene selected from the group consisting of BMT1, BMT2, BMT3, and BMT4 is disrupted, which may include embodiments, wherein the BMT gene or ORF encoding the Bmt protein is deleted or disrupted.

In particular aspects, the lower eukaryote host cell has a disruption of the expression of the Outer Chain (OCH1) gene or homologue thereof, the Acquired Thermo-Tolerance 1 (ATT1) gene or homologue thereof, or both. Disruption of expression includes but is not limited to deletion or disruption of the OCH1 gene or ORF encoding the Och1p and/or deletion or disruption of the ATT1 gene or ORF encoding the Att1p.

The lower eukaryote host cell may be a yeast or filamentous fungus host cell. The yeast or filamentous fungus host cell may be selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*. In particular aspects, the host cell is a yeast host cell selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica,* and *Pichia* sp. In particular aspects, the lower eukaryote host cell is *Pichia pastoris*.

Further provided is a method for producing a recombinant glycoprotein in a lower eukaryote host cell comprising expressing a nucleic acid molecule encoding the recombinant glycoprotein in a lower eukaryote host cell in which expression of the Vanadate Resistance Glycosylation (VRG4) gene or analogue thereof encoding the GDP-mannose transmembrane transporter protein has been disrupted. In further embodiments, the disruption of VRG4 gene expression comprises a deletion or disruption of the VRG4 gene or ORF encoding the GDP-mannose transmembrane transporter protein (Vrg4p).

Further provided is a method for reducing the amount of phosphomannosylation of N- and/or O-glycans of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or analogue thereof encoding the GDP-mannose transmembrane transporter protein has been disrupted, wherein the amount of phosphomanosylation is less than the phosphomannosylation on the recombinant heterologous, non-endogenous protein or glycoprotein produced in a lower eukaryote host that expresses the GDP-mannose transmembrane transporter protein. In further embodiments, the disruption of VRG4 gene expression comprises a deletion or disruption of the VRG4 gene or the ORF encoding the GDP-mannose transmembrane transporter protein (Vrg4p).

Further provided is a method for reducing the amount of α-linked mannose incorporation of N- and/or O-glycans of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or analogue thereof encoding the GDP-mannose transmembrane transporter protein has been disrupted, wherein the amount of α-linked mannose incorporation is less than the α-linked mannose incorporation on the recombinant heterologous, non-endogenous protein or glycoprotein produced in a lower eukaryote host that expresses the GDP-mannose transmembrane transporter protein. In further embodiments, the disruption of VRG4 gene expression comprises a deletion or disruption of the VRG4 gene or the ORF encoding the GDP-mannose transmembrane transporter protein (Vrg4p).

Further provided is a method for reducing the amount of β-linked mannose incorporation of N- and/or O-glycans of a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene or analogue thereof encoding the GDP-mannose transmembrane transporter protein has been disrupted, wherein the amount of β-linked mannose incorporation is less than the β-linked mannose incorporation on the recombinant heterologous, non-endogenous protein or glycoprotein produced in a lower eukaryote host that expresses the GDP-mannose transmembrane transporter protein. In further embodiments, the disruption of VRG4 gene expression comprises a deletion or disruption of the VRG4 gene or the ORF encoding the GDP-mannose transmembrane transporter protein (Vrg4p).

Further provided is a method for reducing the amount of high mannose N-glycans on a recombinant heterologous, non-endogenous protein or glycoprotein produced in a lower eukaryote host cell comprising expressing a nucleic acid molecule encoding the recombinant heterologous, non-endogenous protein or glycoprotein in a lower eukaryote host cell in which expression of the Vanadate Resistance Glycosylation (VRG4) gene encoding the GDP-mannose transmembrane transporter protein has been disrupted, wherein the amount of high mannose N-glycans is less than the amount of high mannose N-glycans on the recombinant heterologous, non-endogenous protein or glycoprotein produced in a lower eukaryote host that expresses the GDP-mannose transmembrane transporter protein. In further embodiments, the disruption of VRG4 gene expression comprises a deletion or disruption of the VRG4 gene or ORF encoding the or ORF encoding the GDP-mannose transmembrane transporter protein (Vrg4p).

Further provided is a method for reducing the amount of mannosylation of hybrid N-glycans on a recombinant glycoprotein produced in a yeast host cell comprising expressing a nucleic acid molecule encoding the recombinant glycoprotein in a lower eukaryote host cell in which expression of the Vanadate Resistance Glycosylation (VRG4) gene encoding the GDP-mannose transmembrane transporter protein has been disrupted, wherein the extent (or amount) of mannosylation of hybrid N-glycans is less than the amount of of mannosylation hybrid N-glycans on the recombinant glycoprotein produced in a lower eukaryote host that expresses the GDP-mannose transmembrane transporter protein. In further embodiments, the disruption of VRG4 gene expression comprises a deletion or disruption of the VRG4 gene or ORF encoding the or ORF encoding the GDP-mannose transmembrane transporter protein (Vrg4p).

Any one of the aforementioned methods may further include embodiments wherein expression of at least one β-mannosyltransferase (BMT) gene selected from the group consisting of BMT1, BMT2, BMT3, and BMT4 is disrupted, which may include embodiments wherein the BMT gene or ORF encoding the Bmtp is deleted or disrupted.

Any one of the aforementioned methods further includes embodiments in which the lower eukaryote host cell has a disruption of the expression of the Outer Chain (OCH1) gene or homologue thereof, the Acquired Thermo-Tolerance 1 (ATT1) gene or homologue thereof, or both. Disruption of expression includes but is not limited to deletion or disruption of the OCH1 gene or ORF encoding the Och1p and/or deletion or disruption of the ATT1 gene or ORF encoding the Att1p.

Any one of the aforementioned methods may further includes embodiments wherein the lower eukaryote host cell is a yeast or filamentous fungus host cell. In further aspects, the host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*. In further aspects, the host cell is a yeast host cell selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica*, and *Pichia* sp. In further aspects, the host cell is *Pichia pastoris*.

The above host cells and thus the methods that use the lower eukaryote host cells further include embodiments, wherein the host cell has been genetically engineered to produce proteins or glycoproteins that have human-like N-glycans, in particular, recombinant heterologous, non-endogenous proteins or glycoproteins. Thus, the above recombinant host cells may further include any combination of the following genetic manipulations to provide host cells that are capable of expressing proteins or glycoproteins in which the N-glycosylation pattern is mammalian-like or human-like or humanized or where a particular N-glycan species is predominant. This may be achieved by eliminating selected endogenous glycosylation enzymes and/or supplying exogenous enzymes as described by Gerngross et al., U.S. Pat. No. 7,449,308, the disclosure of which is incorporated herein by reference, and general methods for reducing O-glycosylation in yeast have been described in International Application No. WO2007061631. In this manner, protein or glycoprotein compositions can be produced in which a specific desired glycoform is predominant in the composition. If desired, additional genetic engineering of the glycosylation can be performed, such that the protein or glycoprotein can be produced with or without core fucosylation. Use of lower eukaryotic host cells such as yeast are further advantageous in that these cells are able to produce relatively homogenous compositions of protein or glycoprotein, such that the predominant glycoform of the protein or glycoprotein may be present as greater than thirty mole percent of the protein or glycoprotein in the composition. In particular aspects, the predominant glycoform may be present in greater than forty mole percent, fifty mole percent, sixty mole percent, seventy mole percent and, most preferably, greater than eighty mole percent of the protein or glycoprotein present in the composition. Such can be achieved by eliminating selected endogenous glycosylation enzymes and/or supplying exogenous enzymes as described by Gerngross et al., U.S. Pat. No. 7,029,872 and U.S. Pat. No. 7,449,308, the disclosures of which are incorporated herein by reference. For example, a host cell can be selected or engineered to be depleted in $\alpha 1,6$-mannosyl transferase activities, which would otherwise add mannose residues onto the N-glycan on a glycoprotein. For example, in yeast such an $\alpha 1,6$-mannosyltransferase activity is encoded by the OCH1 gene and deletion or disruption of the OCH1 inhibits the production of high mannose or hypermannosylated N-glycans in yeast such as *Pichia pastoris* or *Saccharomyces cerevisiae*. (See for example, Gerngross et al. in U.S. Pat. No. 7,029,872; Contreras et al. in U.S. Pat. No. 6,803,225; and Chiba et al. in EP1211310B1 the disclosures of which are incorporated herein by reference).

In one embodiment, the host cell further includes an $\alpha 1,2$-mannosidase catalytic domain fused to a cellular targeting signal peptide not normally associated with the catalytic domain and selected to target the $\alpha 1,2$-mannosidase activity to the ER or Golgi apparatus of the host cell. Passage of a recombinant heterologous, non-endogenous protein or glycoprotein through the ER or Golgi apparatus of the host cell produces a recombinant protein or glycoprotein comprising a $Man_5GlcNAc_2$ glycoform, for example, a recombinant protein or glycoprotein composition comprising predominantly a $Man_5GlcNAc_2$ glycoform. For example, U.S. Pat. No. 7,029,872, U.S. Pat. No. 7,449,308, and U.S. Published Patent Application No. 2005/0170452, the disclosures of which are all incorporated herein by reference, disclose lower eukaryote host cells capable of producing a recombinant heterologous, non-endogenous protein or protein glycoprotein comprising a $Man_5GlcNAc_2$ glycoform.

In a further embodiment, the immediately preceding host cell further includes an N-acetylglucosaminyltransferase I (GlcNAc transferase I or GnT I) catalytic domain fused to a cellular targeting signal peptide not normally associated with the catalytic domain and selected to target GlcNAc transferase I activity to the ER or Golgi apparatus of the host cell. Passage of the recombinant heterologous, non-endogenous protein or glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a $GlcNAcMan_5GlcNAc_2$ glycoform. U.S. Pat. No. 7,029,872, U.S. Pat. No. 7,449,308, and U.S. Published Patent Application No. 2005/0170452, the disclosures of which are all incorporated herein by reference, disclose lower eukaryote host cells capable of producing a recombinant heterologous, non-endogenous protein or glycoprotein comprising a $GlcNAcMan_5GlcNAc_2$ glycoform. The glycoprotein produced in the above cells can be treated in vitro with a hexaminidase to produce a recombinant protein or glycoprotein comprising a $Man_5GlcNAc_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant heterologous, non-endogenous protein or glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872 and U.S. Pat. No. 7,625,756, the disclosures of which are all incorporated herein by reference, discloses lower eukaryote host cells that express mannosidase II enzymes and are capable of producing glycoproteins having predominantly a $GlcNAcMan_3GlcNAc_2$ glycoform. The glycoprotein produced in the above cells can be treated in vitro with a hexosaminidase that removes the terminal GlcNAc residue to produce a recombinant heterologous, non-endogenous protein or glycoprotein comprising a $Man_3GlcNAc_2$ glycoform or the hexosaminidase can be co-expressed with the glycoprotein in the host cell to produce a recombinant glycoprotein comprising a $Man_3GlcNAc_2$ glycoform.

In a further embodiment, the immediately preceding host cell further includes N-acetylglucosaminyltransferase II (GlcNAc transferase II or GnT II) catalytic domain fused to a cellular targeting signal peptide not normally associated with the catalytic domain and selected to target GlcNAc transferase II activity to the ER or Golgi apparatus of the host cell. Passage of the recombinant heterologous, non-endogenous protein or glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform. U.S. Pat. Nos. 7,029,872 and 7,449,308 and U.S. Published Patent Application No. 2005/0170452, the disclosures of which are all incorporated herein by reference, disclose lower eukaryote host cells capable of producing a recombinant heterologous, non-endogenous protein or glycoprotein comprising a $GlcNAc_2Man_3GlcNAc_2$ glycoform. The glycoprotein produced in the above cells can be treated in vitro with a hexosaminidase that removes the terminal GlcNAc residues to produce a recombinant protein or glycoprotein comprising a $Man_3GlcNAc_2$ glycoform or the hexosaminidase can be co-expressed with the glycoprotein in the host cell to produce a recombinant protein or glycoprotein comprising a $Man_3GlcNAc_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant heterologous, non-endogenous protein or glycoprotein through the ER or Golgi apparatus of the host cell produces a recombinant glycoprotein comprising a $GalGlcNAc_2Man_3GlcNAc_2$ or $Gal_2GlcNAc_2Man_3GlcNAc_2$ glycoform, or mixture thereof for example a recombinant protein or glycoprotein composition comprising predominantly a $GalGlcNAc_2Man_3GlcNAc_2$ glycoform or $Gal_2GlcNAc_2Man_3GlcNAc_2$ glycoform or mixture thereof. U.S. Pat. No. 7,029,872 and U.S. Published Patent Application No. 2006/0040353, the disclosures of which are incorporated herein by reference, discloses lower eukaryote host cells capable of producing a recombinant heterologous, non-endogenous protein or glycoprotein comprising a Gal$_2$GlcNAc$_2$Man$_3$GlcNAc$_2$ glycoform. The protein or glycoprotein produced in the above cells can be treated in vitro with a galactosidase to produce a recombinant protein or glycoprotein comprising a GlcNAc$_2$Man$_3$GlcNAc$_2$ glycoform, for example a recombinant protein or glycoprotein composition comprising predominantly a GlcNAc$_2$Man$_3$GlcNAc$_2$ glycoform or the galactosidase can be co-expressed with the glycoprotein in the host cell to produce a recombinant protein or glycoprotein comprising the GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. Passage of the recombinant heterologous, non-endogenous protein or glycoprotein through the ER or Golgi apparatus of the host cell produces a recombinant glycoprotein comprising predominantly a Sia$_2$Gal$_2$GlcNAc$_2$Man$_3$GlcNAc$_2$ glycoform or SiaGalGlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729, the disclosure of which is incorporated herein by reference, discloses a method for genetically engineering lower eukaryotes to have a CMP-sialic acid synthesis pathway and U.S. Published Patent Application No. 2006/0286637, the disclosure of which is incorporated herein by reference, discloses a method for genetically engineering lower eukaryotes to produce sialylated glycoproteins. The protein or glycoprotein produced in the above cells can be treated in vitro with a neuraminidase to produce a recombinant protein or glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof or the neuraminidase can be co-expressed with the protein or glycoprotein in the host cell to produce a recombinant protein or glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

In a further aspect, the above host cell capable of making proteins or glycoproteins having a Man$_5$GlcNAc$_2$ glycoform can further include a mannosidase III catalytic domain fused to a cellular targeting signal peptide not normally associated with the catalytic domain and selected to target the mannosidase III activity to the ER or Golgi apparatus of the host cell. Passage of the recombinant heterologous, non-endogenous protein or glycoprotein through the ER or Golgi apparatus of the host cell produces a recombinant protein or glycoprotein comprising a Man$_3$GlcNAc$_2$ glycoform, for example a recombinant protein or glycoprotein composition comprising predominantly a Man$_3$GlcNAc$_2$ glycoform. U.S. Pat. No. 7,625,756, the disclosures of which are all incorporated herein by reference, discloses the use of lower eukaryote host cells that express mannosidase III enzymes and are capable of producing recombinant heterologous, non-endogenous protein or glycoproteins having predominantly a Man$_3$GlcNAc$_2$ glycoform.

Any one of the preceding host cells can further include one or more GlcNAc transferase selected from the group consisting of GnT III, GnT IV, GnT V, GnT VI, and GnT IX to produce recombinant heterologous, non-endogenous protein or glycoproteins having bisected (GnT III) and/or multiantennary (GnT IV, V, VI, and IX) N-glycan structures such as disclosed in U.S. Pat. No. 7,598,055 and U.S. Published Patent Application No. 2007/0037248, the disclosures of which are all incorporated herein by reference.

In further embodiments, the host cell that produces recombinant heterologous, non-endogenous protein or glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target galactosyltransferase activity to the ER or Golgi apparatus of the host cell. Passage of the recombinant heterologous, non-endogenous protein or glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced recombinant heterologous, non-endogenous proteins or glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialytransferase activity to the ER or Golgi apparatus of the host cell. Passage of the recombinant heterologous, non-endogenous protein or glycoprotein through the ER or Golgi apparatus of the host cell produces a recombinant protein or glycoprotein comprising a SiaGalGlcNAcMan$_5$GlcNAc$_2$ glycoform.

In general yeast and filamentous fungi are not able to make proteins or glycoproteins that have N-glycans that include fucose. Therefore, the N-glycans disclosed herein will lack fucose unless the host cell is specifically modified to include a pathway for synthesizing GDP-fucose and a fucosyltransferase. Therefore, in particular aspects where it is desirable to have glycoproteins in which the N-glycan includes fucose, any one of the aforementioned host cells is further modified to include a fucosyltransferase and a pathway for producing fucose and transporting fucose into the ER or Golgi. Examples of methods for modifying *Pichia pastoris* to render it capable of producing proteins or glycoproteins in which one or more of the N-glycans thereon are fucosylated are disclosed in Published International Application No. WO 2008112092, the disclosure of which is incorporated herein by reference. In particular aspects of the invention, the *Pichia pastoris* host cell is further modified to include a fucosylation pathway comprising a GDP-mannose-4,6-dehydratase, GDP-keto-deoxy-mannose-epimerase/GDP-keto-deoxy-galactose-reductase, GDP-fucose transporter, and a fucosyltransferase. In particular aspects, the fucosyltransferase is selected from the group consisting of α1,2-fucosyltransferase, α1,3-fucosyltransferase, α1,4-fucosyltransferase, and α1,6-fucosyltransferase.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include *Pichia pastoris* that are genetically engineered to produce proteins or glycoproteins having few or no detectable phosphomannose residues by deleting or disrupting expression of one or both of the phosphomannosyltransferase genes PNO1 and MNN4 (also referred to as MNN4B) (See for example, U.S. Pat. Nos. 7,198,921 and 7,259,007; the disclosures of which are all incorporated herein by reference), which in further aspects can also include deleting or disrupting the MNN4L1 (also referred to as MNN4A) gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

To reduce or eliminate the likelihood of the host cell being capable of producing recombinant heterologous, non-endogenous proteins or glycoproteins that have N-glycans and O-glycans with β-linked mannose residues, which are resistant to α-mannosidases, the recombinant glycoengineered host cells are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Pat. No. 7,465,577, U.S. Pat. No. 7,713,719, and Published International Application No. WO2011046855, each of which is incorporated herein by reference). The deletion or disruption of BMT2 and one or more of BMT1, BMT3, and BMT4 also reduces or eliminates detectable cross reactivity to antibodies against host cell protein.

Yield of protein or glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO2009105357 and WO2010019487 (the disclosures of which are incorporated herein by reference).

Host cells further include lower eukaryote cells (e.g., yeast such as *Pichia pastoris*) that are genetically modified to control O-glycosylation of the recombinant heterologous, non-endogenous protein or glycoprotein by deleting or disrupting one or more of the protein 0-mannosyltransferase (Dol-P-Man:Protein (Ser/Thr) Mannosyl Transferase genes) (PMTs) (See U.S. Pat. No. 5,714,377; the disclosure of which is incorporated herein by reference) or grown in the presence of Pmtp inhibitors and/or an α1,2 mannosidase as disclosed in Published International Application No. WO 2007061631 the disclosure of which is incorporated herein by reference. Disruption includes disrupting the open reading frame encoding the Pmtp or disrupting expression of the open reading frame or abrogating translation of RNAs encoding one or more of the Pmtps using interfering RNA, antisense RNA, or the like.

The host cells can further include any one of the aforementioned host cells modified to produce particular N-glycan structures.

Examples of Pmtp inhibitors include but are not limited to a benzylidene thiazolidinediones such as those disclosed in U.S. Pat. No. 7,105,554 and U.S. Published Application No. 20110076721. Examples of benzylidene thiazolidinediones that can be used are 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; 5-[[3-(1-Phenyl-2-hydroxy)ethoxy)-4-(2-phenylethoxy)]phenyl]methylene]-4-oxo-2-thioxo-3-thiazolidineacetic Acid; and, Example 4 compound in U.S. Published Application No. 20110076721). However, while these methods have been successful in controlling O-glycosylation, these PMT inhibitors do reduce cell viability which in turn affects recombinant protein yields.

Figure 19:
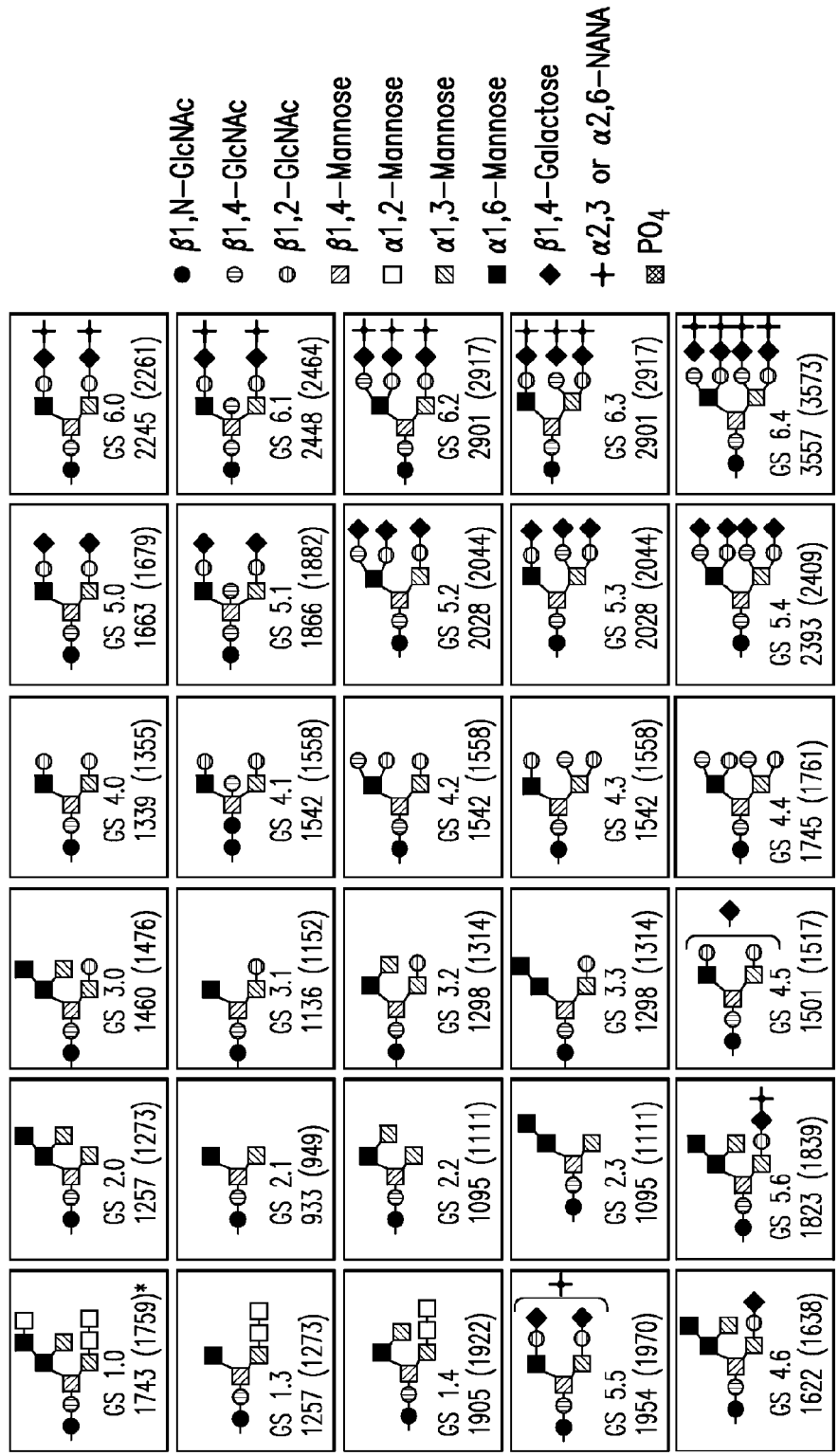
FIG. 19 shows examples of N-glycan structures that can be attached to the asparagine residue in the motif Asn-Xaa-Ser/Thr wherein Xaa is any amino acid other than proline of a glycoprotein.

In particular embodiments, the host cells do not display Alg3p protein activity or have a disruption of expression from the ALG3 gene as described in Published U.S. Application No. 20050170452 or US20100227363, which are incorporated herein by reference. Alg3p is $Man_5GlcNAc_2$-PP-dolichyl alpha-1,3 mannosyltransferase that transfers a mannose residue to the mannose residue of the alpha-1,6 arm of lipid-linked $Man_5GlcNAc_2$ (FIG. 19, GS 1.3) in an alpha-1,3 linkage to produce lipid-linked $Man_6GlcNAc_2$ (FIG. 19, GS 1.4), a precursor for the synthesis of lipid-linked $Glc_3Man_9GlcNAc_2$, which is then transferred by an oligosaccharyltransferase to an aspargine residue of a glycoprotein followed by removal of the glucose (Glc) residues. In host cells that lack Alg3p protein activity, the lipid-linked $Man_5GlcNAc_2$ oligosaccharide may be transferred by an oligosaccharyltransferase to an aspargine residue of a glycoprotein. In such host cells that further include an α1,2-mannosidase, the $Man_5GlcNAc_2$ oligosaccharide attached to the protein or glycoprotein is trimmed to a trimannose (paucimannose) $Man_3GlcNAc_2$ structure (FIG. 19, GS 2.1). The $Man_5GlcNAc_2$ (GS 1.3) structure is distinguishable from the $Man_5GlcNAc_2$ (GS 2.0) shown in FIG. 19, and which is produced in host cells that express the $Man_5GlcNAc_2$-PP-dolichyl alpha-1,3 mannosyltransferase (Alg3p).

Therefore, the methods disclose herein can use any host cell that has been genetically modified to produce proteins or glycoproteins comprising at least N-glycan shown in FIG. 19. The methods disclose herein can use any host cell that has been genetically modified to produce glycoproteins wherein the predominant N-glycan is selected from the group consisting of complex N-glycans, hybrid N-glycans, and high mannose N-glycans wherein complex N-glycans are selected from the group consisting of $Man_3GlcNAc_2$ (paucimannose), $GlcNAc_{(1-4)}Man_3GlcNAc_2$, $Gal_{(1-4)}GlcNAc_{(1-4)}Man_3GlcNAc_2$, and $Sia_{(1-4)}Gal_{(1-4)}GlcNAc_2Man_3GlcNAc_2$; hybrid N-glycans are selected from the group consisting of $GlcNAcMan_5GlcNAc_2$, $GalGlcNAcMan_5GlcNAc_2$, and $SiaGalGlcNAcMan_5GlcNAc_2$; and high Mannose N-glycans are selected from the group consisting of $Man_5GlcNAc_2$, (GS 2.0), $Man_6GlcNAc_2$, $Man_7GlcNAc_2$, $Man_8GlcNAc_2$, and $Man_9GlcNAc_2$. In further embodiments, the host cell produces glycoproteins that have predominantly an N-glycan structure consisting of the $Man_5GlcNAc_2$ (GS 1.3) structure.

To increase the N-glycosylation site occupancy on a glycoprotein produced in a recombinant host cell, a nucleic acid molecule encoding a heterologous single-subunit oligosaccharyltransferase, which is capable of functionally suppressing a lethal mutation of one or more essential subunits comprising the endogenous host cell hetero-oligomeric oligosaccharyltransferase (OTase) complex, is overexpressed in the recombinant host cell either before or simultaneously with the expression of the glycoprotein in the host cell. The *Leishmania major* STT3A protein, *Leishmania major* STT3B protein, and *Leishmania major* STT3D protein, are single-subunit oligosaccharyltransferases that have been shown to suppress the lethal phenotype of a deletion of the STT3 locus in *Saccharomyces cerevisiae* (Naseb et al., Molec. Biol. Cell 19: 3758-3768 (2008)). Naseb et al. (ibid.) further showed that the *Leishmania major* STT3D protein could suppress the lethal phenotype of a deletion of the WBP1, OST1, SWP1, or OST2 loci. Hese et al. (Glycobiology 19: 160-171 (2009)) teaches that the *Leishmania major* STT3A (STT3-1), STT3B (STT3-2), and STT3D (STT3-4) proteins can functionally complement deletions of the OST2, SWP1, and WBP1 loci. As shown in Published International Application No. WO2011106389, which is incorporated herein by reference in its entirety, the *Leishmania major* STT3D (LmSTT3D) protein is a heterologous single-subunit oligosaccharyltransferases that is capable of suppressing a lethal phenotype of a Δstt3 mutation and at least one lethal phenotype of a Δwbp1, Δost1, Δswp1, and Δost2 mutation that is shown in the examples herein to be capable of enhancing the N-glycosylation site occupancy of heterologous glycoproteins, for example antibodies, produced by the host cell.

Therefore, in a further aspect of the methods herein, provided are yeast or filamentous fungus host cells genetically engineered to be capable of producing proteins glycoproteins with mammalian- or human-like complex or hybrid N-glycans wherein the host cell further includes a nucleic acid molecule encoding a heterologous single-subunit oligosaccharyltransferase (OTase) complex.

In general, in the above methods and host cells, the single-subunit oligosaccharyltransferase is capable of functionally suppressing the lethal phenotype of a mutation of at least one essential protein of the OTase complex. In further aspects, the essential protein of the OTase complex is encoded by the STT3 locus, WBP1 locus, OST1 locus, SWP1 locus, or OST2 locus, or homologue thereof. In further aspects, the for example single-subunit oligosaccharyltransferase is the *Leishmania major* STT3D protein.

For genetically engineering yeast, selectable markers can be used to construct the recombinant host cells include drug resistance markers and genetic functions which allow the yeast host cell to synthesize essential cellular nutrients, e.g. amino acids. Drug resistance markers that are commonly used in yeast include chloramphenicol, kanamycin, methotrexate, G418 (geneticin), Zeocin, and the like. Genetic functions that allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al., J. Biol. Chem. 272:30061-30066 (1997)). A number of suitable integration sites include those enumerated in U.S. Pat. No. 7,479,389 (the disclosure of which is incorporated herein by reference) and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135; the disclosures of which are all incorporated herein by reference).

Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700 (the disclosure of which is incorporated herein by reference), the HIS3 and TRP1 genes have been described in Cosano et al., Yeast 14:861-867 (1998), HIS4 has been described in GenBank Accession No. X56180.

In further still aspects, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above host cells, the host cell is *Pichia pastoris* or *Saccharomyces cerevisiae*. In a further aspect, the host cell is an och1 mutant of *Pichia pastoris* or *Saccharomyces cerevisiae*.

In further aspects, provided is a plasmid vector comprising a nucleic acid molecule having at least 25, 50, 75, or 100 contiguous nucleotides of SEQ ID NO:1, SEQ ID NO:2, or SEQ ID NO:3. In further embodiments, the plasmid vector further includes a nucleic acid molecule encoding a selection marker. In particular embodiments the selection marker is a nucleic acid molecule encoding hygromycin resistance, Ura5p, Ura3p, zeocin resistance, arsenite resistance or nourseothricin resistance. In a further embodiment, the plasmid vector comprises a first nucleic acid molecule encoding a selection marker flanked on one side by a second nucleic acid molecule comprising a 5' region of the VRG4 gene and on the other side by a third nucleic molecule comprising a 3' region of the VRG4 gene. In a further embodiment, the second nucleic acid molecule comprises at least 25, 50, 75, or 100 contiguous nucleotides of SEQ ID NO:1 and the third nucleic acid molecule comprises at least 25, 50, 75, or 100 contiguous nucleotides of SEQ ID NO:2. In particular aspects, the second nucleic acid molecule comprising the 5' region of the VRG4 gene and the third nucleic acid molecule comprising 3' region of the VRG4 gene are noncontiguous and the first nucleic acid molecule encoding the selection marker is located between the second and third nucleic acid molecules.

Further provided is a method for producing a lower eukaryote host cell in which expression of the VRG4 gene is disrupted comprising (a) providing a plasmid vector comprising a first nucleic acid molecule encoding a selection marker flanked on one side by a second nucleic acid molecule comprising a 5' region of the VRG4 gene and on the other side by a third nucleic molecule comprising a 3' region of the VRG4 gene; (b) transforming the host cell with the plasmid vector wherein the selection marker is integrated into the VRG4 gene by double-crossover homologous recombination to produce a host cell in which the first nucleic acid molecule encoding the selection marker is integrated into the VRG4 gene between the 5' region and the 3' region of the VRG4 gene that are homologous or have identity to the second and third nucleic acid molecules, respectively, and (c) selecting the host cell comprising the nucleic acid molecule encoding the selection marker integrated into the VRG4 gene to produce the host cell in which expression of the VRG4 gene is disrupted. In particular aspects, the second nucleic acid molecule comprising the 5' region of the VRG4 gene and the third nucleic acid molecule comprising 3' region of the VRG4 gene are noncontiguous and the first nucleic acid encoding the selection marker when integrated into the VRG4 gene replaces the region between the 5' and 3' regions of the VRG4 gene in the host cell to produce the host cell in which expression of the VRG4 gene is disrupted. In a further aspect, the first nucleic acid molecule encoding the selection marker replaces the open reading frame (ORF) in the VRG4 gene encoding the Vrg4p. Further provided are host cells produced by the aforementioned method.

The aforementioned host cells may be a host cell that has a disruption of the expression of the Outer Chain (OCH1) gene or homologue thereof, the Acquired Thermo-Tolerance 1 (ATT1) gene or homologue thereof, or both. Disruption of expression includes but is not limited to deletion or disruption of the OCH1 gene or ORF encoding the Och1p and/or deletion or disruption of the ATT1 gene or ORF encoding the Att1p. Host cells comprising either of the aforementioned disruptions have been shown in the examples to support disruption of expression of the VRG4 gene (See for example, strains YGLY2-3 (och1Δ and ATT1) or YGLY27836 (att1Δ and OCH1)). In particular aspects, the host cell may have the genotype of or similar to YGLY2-3 or YGLY27836 or is a host cell descendant from YGLY2-3 or YGLY27836 or a strain of a similar genotype to YGLY2-3 or YGLY27836.

Host cells that are viable following disruption of expression of the VRG4 gene may also be provided by random mutagenesis of a host cell to produce a host cell that is viable following disruption of the VRG4 gene. For example, a host cell may be transformed with the aforementioned plasmid vector and the transformed host cell mutagenized by UV mutagenesis as described by Winston (Curr. Protoc. Mol. Biol. 82: 13.3B.1-13.3B.5 (2008)). The transformation of the yeast cells is well known in the art and may for instance be effected by protoplast formation followed by transformation in a manner known per se. The medium used to cultivate the cells may be any conventional medium suitable for growing yeast organisms. In one embodiment, a transformed host cell is grown in YSD liquid medium over night at 24° C. Upon reaching an $OD_{600}$ of about five, an aliquot of culture is transferred into an empty Petri dish and treated, with the lid off, with about 12 $mJ/cm^2$ of UV irradiation. After the UV treatment, the Petri dish is immediately covered with aluminum foil (to prevent photo-induced DNA repair). The mutagenized cells are allowed to recover at 24° C. for three hours in the dark. Then the transformed, mutagenized cells are concentrated and cultivated for a time in a liquid broth (e.g., BMGY media) and then plated onto agar plates (e.g., YSD agar plates) under selective conditions to identify and select clones that are viable. Clones are analyzed to confirm disruption of expression of the VRG4 gene.

In particular embodiments of any one of the above embodiments or aspects of the present invention, the heterologous, non-endogenous protein or glycoprotein may be a therapeutic protein or glycoprotein. Therapeutic proteins and glycoproteins are included in compositions for administering to a mammal or human to treat a disease or condition. Examples of therapeutic proteins or glycoproteins, human or mammalian, include but are not limited to, erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fe fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; insulin and analogs thereof, GLP1 receptor agonists such as GLP1 and analogs thereof, oxyntomodulin and analogs thereof, exendin-4 and analogs thereof, and the like; glucagon receptor agonists or antagonists; fibroblast growth factors such as FGF-21 and analogs thereof, FGF-19 and analogs thereof, and the like; leptin and analogs thereof; amylin and analogs thereof; IL-2 receptor agonist, or analog or mutein thereof.

In further embodiments of any one of the above host cells, the therapeutic glycoprotein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

The following examples are intended to promote a further understanding of the present invention.

Example 1

This example describes the strains that were constructed to demonstrate the present invention. The strains were constructed from wild-type *Pichia pastoris* strain NRRL-Y 11430 using methods described earlier (See for example, U.S. Pat. No. 7,449,308; U.S. Pat. No. 7,479,389; U.S. Published Application No. 20090124000; Published PCT Application No. WO2009085135; Nett and Gerngross, Yeast 20:1279 (2003); Choi et al., Proc. Natl. Acad. Sci. USA 100:5022 (2003); Hamilton et al., Science 301:1244 (2003)). All plasmids were made in a pUC19 plasmid using standard molecular biology procedures. For nucleotide sequences that were optimized for expression in *P. pastoris*, the native nucleotide sequences were analyzed by the GENEOPTIMIZER software (GeneArt, Regensburg, Germany) and the results used to generate nucleotide sequences in which the codons were optimized for *P. pastoris* expression. Yeast strains were transformed by electroporation (using standard techniques as recommended by the manufacturer of the electroporator BioRad).

NRR-Y 11430 was transformed with plasmid pGLY6, an integration vector that targets the URA5 locus. The plasmid contains a nucleic acid molecule comprising the *S. cerevisiae* invertase gene or transcription unit (ScSUC2; SEQ ID NO:9) flanked on one side by a nucleic acid molecule comprising a nucleotide sequence from the 5' region of the *P. pastoris* URA5 gene (SEQ ID NO:10) and on the other side by a nucleic acid molecule comprising the nucleotide sequence from the 3' region of the *P. pastoris* URA5 gene (SEQ ID NO:11). Plasmid pGLY6 was linearized and the linearized plasmid transformed into wild-type strain NRRL-Y 11430 to produce a number of strains in which the ScSUC2 gene was inserted into the URA5 locus by double-crossover homologous recombination. Strain YGLY1-3 was selected from the strains produced and is auxotrophic for uracil.

Strain YGLY1-3 was transformed with plasmid pGLY40, an integration vector that targets the OCH1 locus and contains a nucleic acid molecule comprising the *P. pastoris* URA5 gene or transcription unit (SEQ ID NO:12) flanked by nucleic acid molecules comprising lacZ repeats (SEQ ID NO:13) which in turn is flanked on one side by a nucleic acid molecule comprising a nucleotide sequence from the 5' region of the OCH1 gene (SEQ ID NO:14) and on the other side by a nucleic acid molecule comprising a nucleotide sequence from the 3' region of the OCH1 gene (SEQ ID NO:15). Plasmid pGLY40 was linearized with SfiI and the linearized plasmid transformed into strain YGLY1-3 to produce a number of strains in which the URA5 gene flanked by the lacZ repeats has been inserted into the OCH1 locus by double-crossover homologous recombination. Strain YGLY2-3 was selected from the strains produced and is prototrophic for URA5. Strain YGLY2-3 was counterselected in the presence of 5-fluoroorotic acid (5-FOA) to produce a number of strains in which the URA5 gene has been lost and only the lacZ repeats remain in the OCH1 locus. This renders the strain auxotrophic for uracil. Strain YGLY4-3 was selected. Strains YGLY2-3 and YGLY4-3 produce glycoproteins with a GS 1.0 glycoform ($Man_8GlcNAc_2$ and $Man_9GlcNAc_2$ N-glycans).

Strain YGLY4-3 was transformed with pasmid pGLY43a, an integration vector that targets the BMT2 locus and contains a nucleic acid molecule comprising the K. lactis UDP-N-acetylglucosamine (UDP-GlcNAc) transporter gene or transcription unit (KlMNN2-2, SEQ ID NO:16) adjacent to a nucleic acid molecule comprising the P. pastoris URA5 gene or transcription unit flanked by nucleic acid molecules comprising lacZ repeats. The adjacent genes are flanked on one side by a nucleic acid molecule comprising a nucleotide sequence from the 5' region of the BMT2 gene (SEQ ID NO: 17) and on the other side by a nucleic acid molecule comprising a nucleotide sequence from the 3' region of the BMT2 gene (SEQ ID NO:18). Plasmid pGLY43a was linearized with SfiI and the linearized plasmid transformed into strain YGLY4-3 to produce to produce a number of strains in which the KlMNN2-2 gene and URA5 gene flanked by the lacZ repeats has been inserted into the BMT2 locus by double-crossover homologous recombination. The BMT2 gene has been disclosed in Mille et al., J. Biol. Chem. 283: 9724-9736 (2008) and U.S. Pat. No. 7,465,557. Strain YGLY6-3 was selected from the strains produced and is prototrophic for uracil. Strain YGLY6-3 was counterselected in the presence of 5-FOA to produce strains in which the URA5 gene has been lost and only the lacZ repeats remain. This renders the strain auxotrophic for uracil. Strain YGLY8-3 was selected. Strains YGLY6-3 and YGLY8-3 produce glycoproteins with a GS 1.0 glycoform ($Man_8GlcNAc_2$ and $Man_9GlcNAc_2$ N-glycans).

Strain YGLY8-3 was transformed with plasmid pGLY48, an integration vector that targets the MNN4L1 locus and contains an expression cassette comprising a nucleic acid molecule encoding the mouse homologue of the UDP-GlcNAc transporter (SEQ ID NO:19) open reading frame (ORF) operably linked at the 5' end to a nucleic acid molecule comprising the P. pastoris GAPDH promoter (SEQ ID NO:20) and at the 3' end to a nucleic acid molecule comprising the S. cerevisiae CYC termination sequences (SEQ ID NO:21) adjacent to a nucleic acid molecule comprising the P. pastoris URA5 gene flanked by lacZ repeats and in which the expression cassettes together are flanked on one side by a nucleic acid molecule comprising a nucleotide sequence from the 5' region of the P. pastoris MNN4L1 gene (SEQ ID NO:22) and on the other side by a nucleic acid molecule comprising a nucleotide sequence from the 3' region of the MNN4L1 gene (SEQ ID NO:23). Plasmid pGLY48 was linearized with SfiI and the linearized plasmid transformed into strain YGLY8-3 to produce a number of strains in which the expression cassette encoding the mouse UDP-GlcNAc transporter and the URA5 gene have been inserted into the MNN4L1 locus by double-crossover homologous recombination. The MNN4L1 gene (also referred to as MNN4B) has been disclosed in U.S. Pat. No. 7,259,007. Strain YGLY10-3 was selected from the strains produced and then counterselected in the presence of 5-FOA to produce a number of strains in which the URA5 gene has been lost and only the lacZ repeats remain. Strain YGLY12-3 was selected. Strains YGLY10-3 and YGLY12-3 produce glycoproteins with a GS 1.0 glycoform ($Man_8GlcNAc_2$ and $Man_9GlcNAc_2$ N-glycans).

Strain YGLY12-3 was transformed with plasmid pGLY45, an integration vector that targets the PNO1/MNN4 loci and contains a nucleic acid molecule comprising the P. pastoris URA5 gene or transcription unit flanked by nucleic acid molecules comprising lacZ repeats which in turn is flanked on one side by a nucleic acid molecule comprising a nucleotide sequence from the 5' region of the PNO1 gene (SEQ ID NO:24) and on the other side by a nucleic acid molecule comprising a nucleotide sequence from the 3' region of the MNN4 gene (SEQ ID NO:25). Plasmid pGLY45 was linearized with SfiI and the linearized plasmid transformed into strain YGLY12-3 to produce a number of strains in which the URA5 gene flanked by the lacZ repeats has been inserted into the PNO1/MNN4 loci by double-crossover homologous recombination. The PNO1 gene has been disclosed in U.S. Pat. No. 7,198,921 and the MNN4 gene (also referred to as MNN4B) has been disclosed in U.S. Pat. No. 7,259,007. Strain YGLY14-3 was selected from the strains produced and then counterselected in the presence of 5-FOA to produce a number of strains in which the URA5 gene has been lost and only the lacZ repeats remain. Strain YGLY16-3 was selected. Strains YGLY14-3 and YGLY16-3 produce glycoproteins with a GS1.0 glycoform ($Man_8GlcNAc_2$ and $Man_9GlcNAc_2$ N-glycans).

Strain YGLY16-3 was transformed with plasmid pGLY1430, a KINKO integration vector that targets the ADE1 locus without disrupting expression of the locus and contains in tandem four expression cassettes encoding (1) the human GlcNAc transferase I catalytic domain (NA) fused at the N-terminus to P. pastoris SEC12 leader peptide (10) to target the chimeric enzyme to the ER or Golgi, (2) mouse homologue of the UDP-GlcNAc transporter (MmTr), (3) the mouse mannosidase IA catalytic domain (FB) fused at the N-terminus to S. cerevisiae SEC12 leader peptide (8) to target the chimeric enzyme to the ER or Golgi, and (4) the P. pastoris URA5 gene or transcription unit. KINKO (Knock-In with little or No Knock-Out) integration vectors enable insertion of heterologous DNA into a targeted locus without disrupting expression of the gene at the targeted locus and have been described in U.S. Published Application No. 20090124000. The expression cassette encoding the NA10 comprises a nucleic acid molecule encoding the human GlcNAc transferase I catalytic domain codon-optimized for expression in P. pastoris (SEQ ID NO:26) fused at the 5' end to a nucleic acid molecule encoding the SEC12 leader 10 (SEQ ID NO:27), which is operably linked at the 5' end to a nucleic acid molecule comprising the P. pastoris PMA1 promoter and at the 3' end to a nucleic acid molecule comprising the P. pastoris PMA1 transcription termination sequence. The expression cassette encoding MmTr comprises a nucleic acid molecule encoding the mouse homologue of the UDP-GlcNAc transporter ORF operably linked at the 5' end to a nucleic acid molecule comprising the P. pastoris SEC4 promoter (SEQ ID NO:28) and at the 3' end to a nucleic acid molecule comprising the P. pastoris OCH1 termination sequences (SEQ ID NO:29). The expression cassette encoding the FB8 comprises a nucleic acid molecule encoding the mouse mannosidase IA catalytic domain (SEQ ID NO:30) fused at the 5' end to a nucleic acid molecule encoding the SEC12-m leader 8 (SEQ ID NO:31), which is operably linked at the 5' end to a nucleic acid molecule comprising the P. pastoris GADPH promoter and at the 3' end to a nucleic acid molecule comprising the S. cerevisiae CYC transcription termination sequence. The URA5 expression cassette comprises a nucleic acid molecule comprising the P. pastoris URA5 gene or transcription unit flanked by nucleic acid molecules comprising lacZ repeats. The four tandem cassettes are flanked on one side by a nucleic acid molecule comprising a nucleotide sequence from the 5' region and complete ORF of the ADE1 gene (SEQ ID NO:32) followed by a P. pastoris ALG3 termination sequence (SEQ ID NO:33) and on the other side by a nucleic acid molecule comprising a nucleotide sequence from the 3' region of the ADE1 gene (SEQ ID NO:34). Plasmid pGLY1430 was linearized with SfiI and the linearized plasmid transformed into strain YGLY16-3 to produce a number of strains in which the four tandem expression cassette have been inserted into the ADE1 locus immediately following the ADE1 ORF by double-crossover homologous recombination. The strain YGLY2798 was selected from the strains produced and is auxotrophic for arginine and now prototrophic for uridine, histidine, and adenine. The strain was then counterselected in the presence of 5-FOA to produce a number of strains now auxotrophic for uridine. Strains YGLY2798 and YGLY3794 were selected and are capable of making glycoproteins that have predominantly a GS3.0 glycoform (GlcNAcMan$_5$GlcNAc$_2$ N-glycans).

Strain YGLY3794 was transformed with plasmid pGLY582, an integration vector that targets the HIS1 locus and contains in tandem four expression cassettes encoding (1) the S. cerevisiae UDP-glucose epimerase (ScGAL10), (2) the human galactosyltransferase I (hGalT) catalytic domain fused at the N-terminus to the S. cerevisiae KRE2-s leader peptide (33) to target the chimeric enzyme to the ER or Golgi, (3) the P. pastoris URA5 gene or transcription unit flanked by lacZ repeats, and (4) the D. melanogaster UDP-galactose transporter (DmUGT). The expression cassette encoding the ScGAL10 comprises a nucleic acid molecule encoding the ScGAL10 ORF (SEQ ID NO:35) operably linked at the 5' end to a nucleic acid molecule comprising the P. pastoris PMA1 promoter (SEQ ID NO:36) and operably linked at the 3' end to a nucleic acid molecule comprising the P. pastoris PMA1 transcription termination sequence (SEQ ID NO:37). The expression cassette encoding the chimeric galactosyltransferase I comprises a nucleic acid molecule encoding the hGalT catalytic domain codon optimized for expression in P. pastoris (SEQ ID NO:38) fused at the 5' end to a nucleic acid molecule encoding the KRE2-s leader 33 (SEQ ID NO:39), which is operably linked at the 5' end to a nucleic acid molecule comprising the P. pastoris GAPDH promoter and at the 3' end to a nucleic acid molecule comprising the S. cerevisiae CYC transcription termination sequence. The URA5 expression cassette comprises a nucleic acid molecule comprising the P. pastoris URA5 gene or transcription unit flanked by nucleic acid molecules comprising lacZ repeats. The expression cassette encoding the DmUGT comprises a nucleic acid molecule encoding the DmUGT ORF (SEQ ID NO:40) operably linked at the 5' end to a nucleic acid molecule comprising the P. pastoris OCH1 promoter (SEQ ID NO:41) and operably linked at the 3' end to a nucleic acid molecule comprising the P. pastoris ALG12 transcription termination sequence (SEQ ID NO:42). The four tandem cassettes are flanked on one side by a nucleic acid molecule comprising a nucleotide sequence from the 5' region of the HIS1 gene (SEQ ID NO:43) and on the other side by a nucleic acid molecule comprising a nucleotide sequence from the 3' region of the HIS1 gene (SEQ ID NO:44). Plasmid pGLY582 was linearized and the linearized plasmid transformed into strain YGLY3794 to produce a number of strains in which the four tandem expression cassette have been inserted into the HIS1 locus by homologous recombination. Strain YGLY3853 was selected and is auxotrophic for histidine and prototrophic for uridine. Strain YGLY3853 is capable of making glycoproteins that have predominantly a GS3.5 glycoform (GalGlcNAcMan$_5$GlcNAc$_2$ N-glycans).

Strain YGLY3853 was transformed with plasmid pGLY167b, an integration vector that targets the ARG1 locus and contains in tandem three expression cassettes encoding (1) the D. melanogaster mannosidase II catalytic domain (KD) fused at the N-terminus to S. cerevisiae MNN2 leader peptide (53) to target the chimeric enzyme to the ER or Golgi, (2) the P. pastoris HIS1 gene or transcription unit, and (3) the rat N-acetylglucosamine (GlcNAc) transferase II catalytic domain (TC) fused at the N-terminus to S. cerevisiae MNN2 leader peptide (54) to target the chimeric enzyme to the ER or Golgi. The expression cassette encoding the KD53 comprises a nucleic acid molecule encoding the D. melanogaster mannosidase II catalytic domain codon-optimized for expression in P. pastoris (SEQ ID NO:45) fused at the 5' end to a nucleic acid molecule encoding the MNN2 leader 53 (SEQ ID NO:46), which is operably linked at the 5' end to a nucleic acid molecule comprising the P. pastoris GAPDH promoter and at the 3' end to a nucleic acid molecule comprising the S. cerevisiae CYC transcription termination sequence. The HIS1 expression cassette comprises a nucleic acid molecule comprising the P. pastoris HIS1 gene or transcription unit (SEQ ID NO:47). The expression cassette encoding the TC54 comprises a nucleic acid molecule encoding the rat GlcNAc transferase II catalytic domain codon-optimized for expression in P. pastoris (SEQ ID NO:48) fused at the 5' end to a nucleic acid molecule encoding the MNN2 leader 54 (SEQ ID NO:49), which is operably linked at the 5' end to a nucleic acid molecule comprising the P. pastoris PMA1 promoter and at the 3' end to a nucleic acid molecule comprising the P. pastoris PMA1 transcription termination sequence. The three tandem cassettes are flanked on one side by a nucleic acid molecule comprising a nucleotide sequence from the 5' region of the ARG1 gene (SEQ ID NO:50) and on the other side by a nucleic acid molecule comprising a nucleotide sequence from the 3' region of the ARG1 gene (SEQ ID NO:51). Plasmid pGLY167b was linearized with SfiI and the linearized plasmid transformed into strain YGLY3853 to produce a number of strains (in which the three tandem expression cassette have been inserted into the ARG1 locus by double-crossover homologous recombination. The strain YGLY4754 was selected from the strains produced and is auxotrophic for arginine and prototrophic for uridine and histidine. Strain YGLY4754 produces glycoproteins with predominantly a GS5.0 glycoform (GalGlcNAc$_2$Man$_3$GlcNAc$_2$ and Gal$_2$GlcNAc$_2$Man$_3$GlcNAc$_2$ complex N-glycans).

Example 2

This example provides several Pichia pastoris strains in which the VRG4 gene has been disrupted and shows that these mutant strains have substantially reduced Golgi-associated mannosylation, which renders the strains capable of producing glycoproteins that have reduced amounts of high mannose N-glycans.

Plasmid vector pGLY8655 (FIG. 1) for disrupting the VRG4 gene in *Pichia pastoris* comprises a nucleic acid molecule containing the 5' region of the VRG4 gene (SEQ ID NO:1) and a nucleic acid molecule containing the 3' region of the VRG4 gene (SEQ ID NO:2). The two nucleic acid fragments flank an expression cassette encoding hygromycin resistance (HygR) (nucleotide sequence of cassette is shown in SEQ ID NO:52). The ORF encoding HYG$^R$ in the expression cassette is operably linked to the *Ashbya gossypii* TEF1 promoter and *A. gossypii* TEF1 termination sequences, which also shown in SEQ ID NOs:53 and 54, respectively. The HygR expression cassette has been described in Goldstein et al., Yeast 15: 1541 (1999)). The nucleotide sequence of the VRG4 gene is shown in SEQ ID NO:3. The open reading frame (ORF) encoding Vrg4p is nucleotides 1001 to 1987. Prototrophic *Pichia pastoris* host strains NRRL-Y 11430, YGLY2-3, YGLY6-3, YGLY10-3, YGLY14-3, YGLY3853, and YGLY4754 were each transformed with 10 μg of pGLY8655 linearized with with AccI using transformation methods as described in Choi et al. PNAS USA. 100:5022-5027 (2003) and Hamilton et al. Science 301: 1244-1246 (2003). The transformants were plated on 100 μg/mL hygromycin YSD plates to select for incorporation of the transformed vectors. Successful knock-out of the VRG4 gene was confirmed by PCR using the 5', 3' and knock-out primer sets listed below. The nucleotide sequences for the PCR primers are SH512-GAGACGATAGACGGTGAGGATTCAGAA-GATCCTG (SEQ ID NO:55); SH97-GGGGAGAAGGTAC-CGAAGCCGGAG (SEQ ID NO:56); SH515-CCATACAC-CAGATGTATCTCAAAAATGTCAAC (SEQ ID NO:57); SH379-CATGCCCCTGAGCTGCGCACGTCAAG (SEQ ID NO:58); SH520-CAACTTGGCTCTGGGCTCGTTTG-TATTG (SEQ ID NO:59); and SH521-GGTGTCTTCAGG-GAAGTTCTGAGCTATG (SEQ ID NO:60). The SH512 and SH97 primer pair was used to PCR amplify a 1.1 kbp nucleic acid fragment from the 5' crossover region. The SH515 and SH379 PCR primer pairs were used to PCR amplify a 1.3 kbp nucleic acid fragment from the 3' crossover region. The SH520 and SH521 PCR primer pair was used to PCR amplify a 300 bp nucleic acid fragment from within the ORF encoding Vrg4p. The 300 bp fragment may be amplified from strains that encode Vrg4p but is absent in strains in which the VRG4 gene has been deleted (knocked-out (KO)).

Under Shake-flask growth conditions, the yeast strains were grown in 50 mL BSGY for approximately 65 hours at 24° C. Subsequently, the cultures were induced in 5 mL BSMY (BSGY containing 1% MeOH in place of glycerol) and grown for at least another 24 hours. The culture was centrifuged at 2400 rpm for five minutes to pellet the cells.

Figures 1, 3:
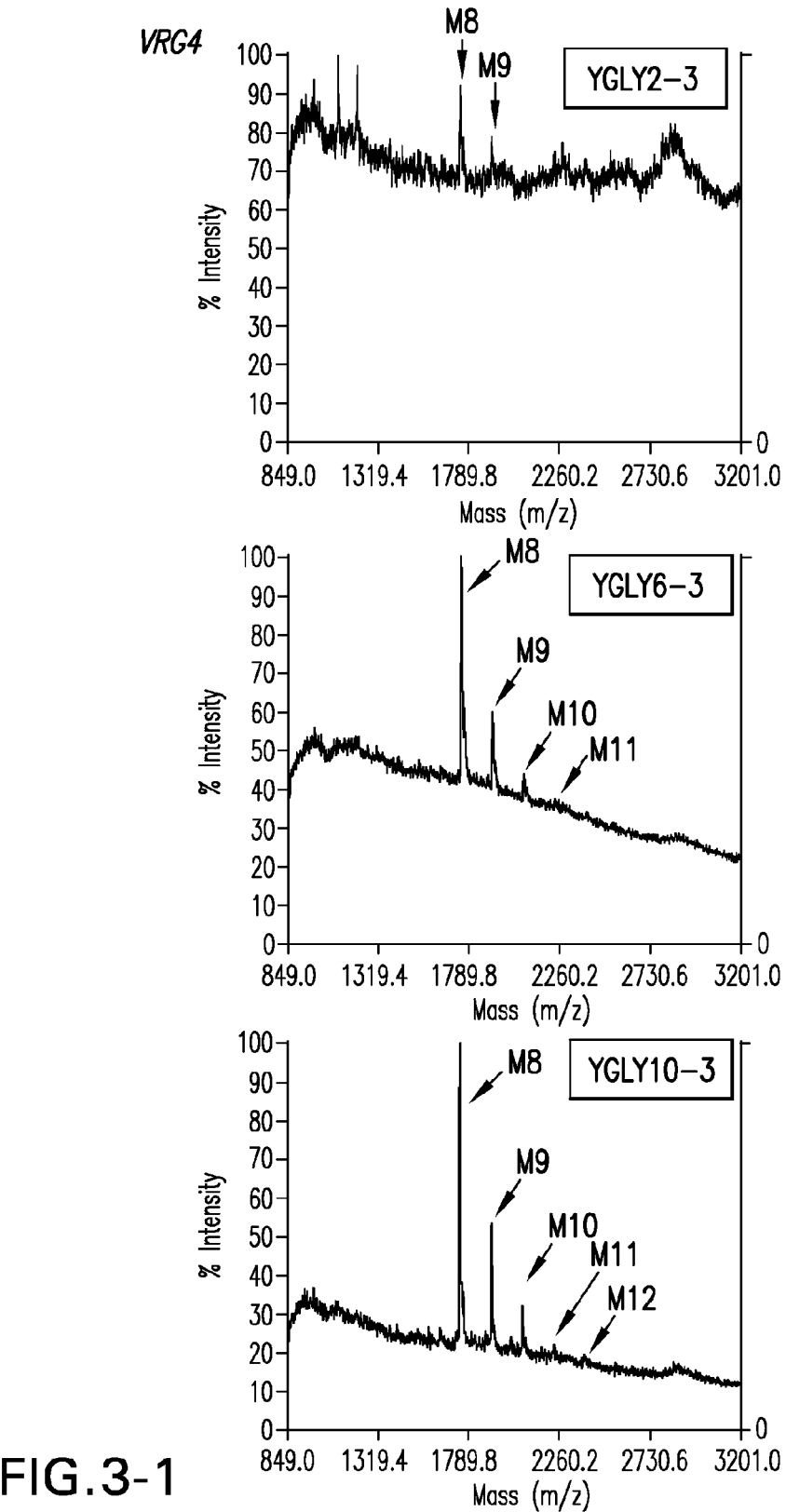
Figures 2, 3:
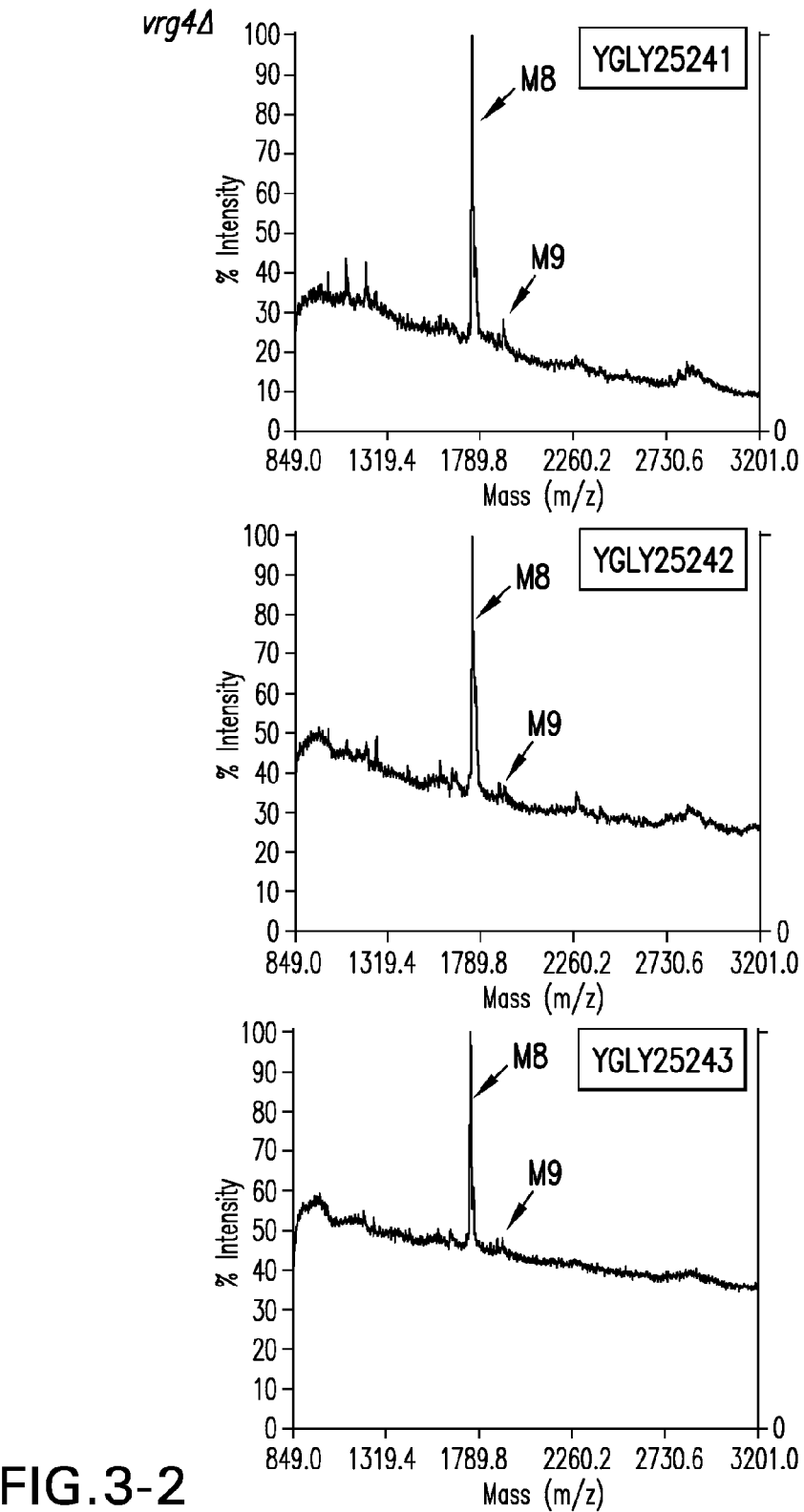

As shown in FIGS. 2-1 and 2-2, vrg4 knock-out (KO) or deletion (vrg4Δ) mutants were obtained from strains YGLY2-3, YGLY6-3, YGLY10-3, YGLY14-3, YGLY3853, and YGLY4754 when transformed with pGLY8655 to delete the VRG4 gene. The vrg4Δ KO mutant obtained from YGLY2-3 was YGLY25241, the vrg4Δ deletion mutant obtained from YGLY6-3 was YGLY25242, the vrg4Δ KO mutant obtained from YGLY10-3 was YGLY25243, the vrg4Δ KO mutant obtained from YGLY3853 was YGLY25245, and the vrg4Δ deletion mutant obtained from YGLY4754 was YGLY25736.

Figures 1, 4:
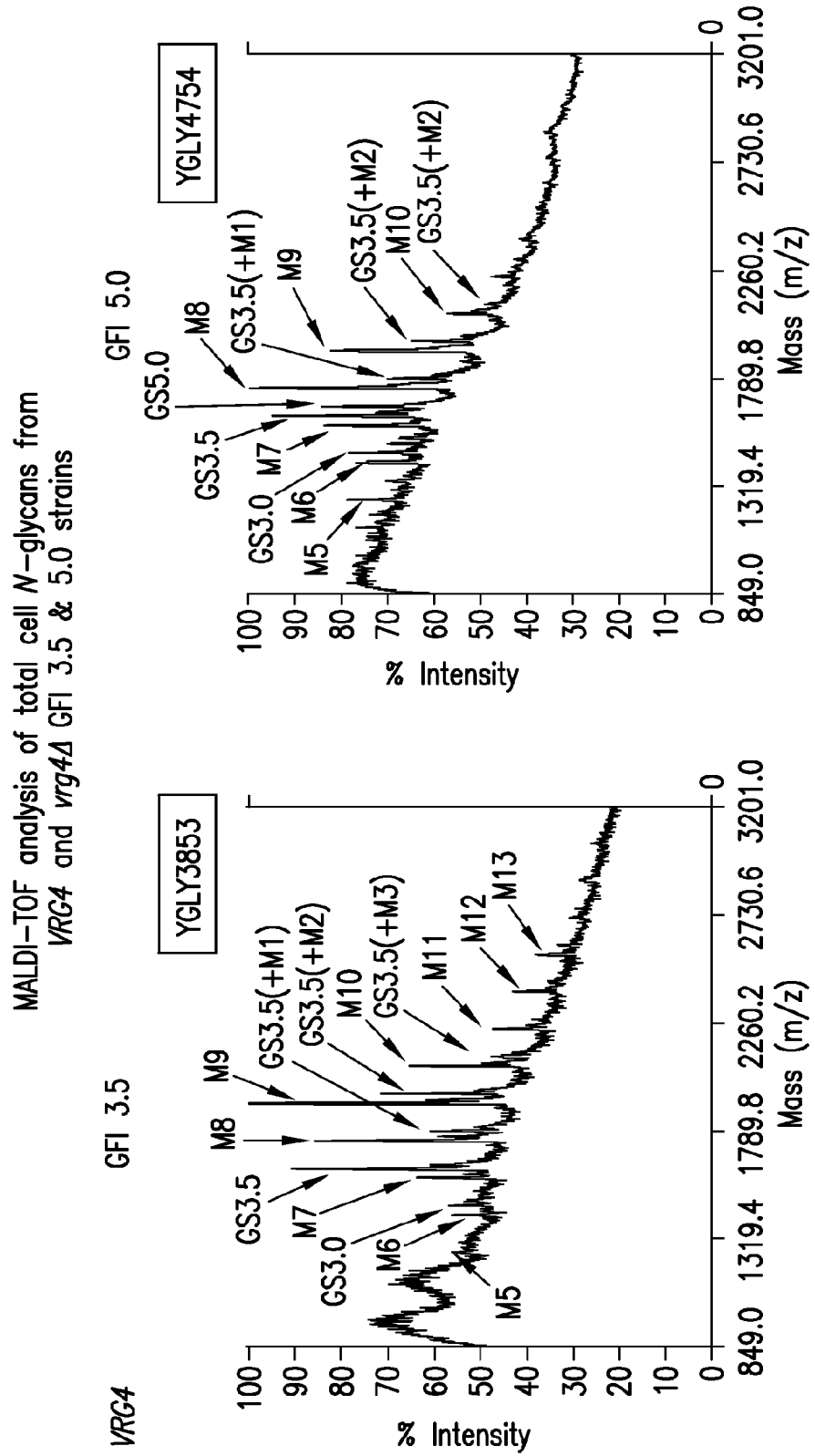
Figures 2, 4:
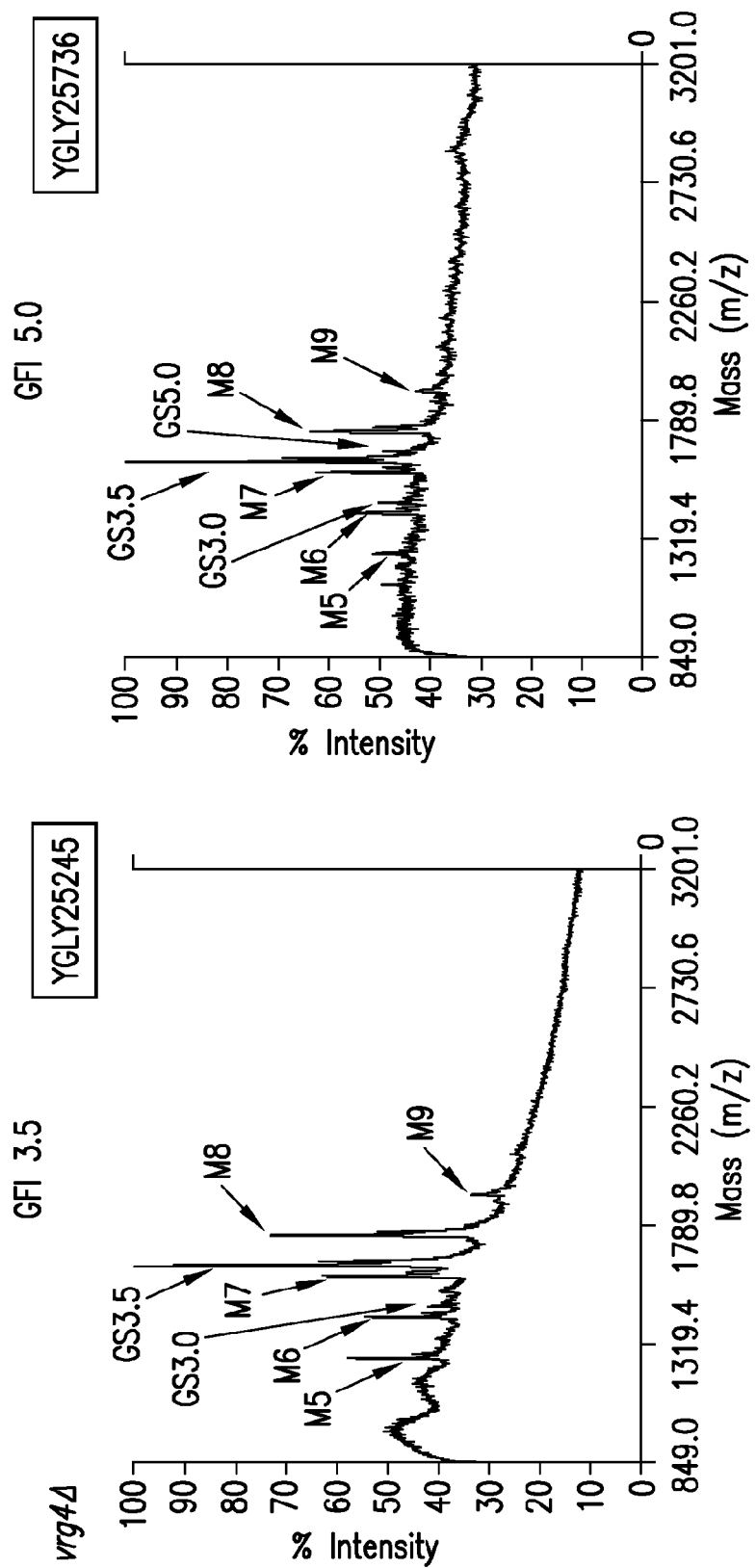

For N-glycan analysis, cell pellets were resuspended and washed twice in 125 μL de-ionized H$_2$O with centrifugation at 2800 RPM for 5 minutes after each wash. 125 μL at of RCM buffer (8M Urea, 360 mM Tris and 3.2 mM EDTA, pH 8.6) and 50 μL of 0.5 mm glass beads were added to the washed cell pellets, followed by vigorous vortexing for two minutes. The sample was boiled for 10 minutes and then allowed to cool prior to centrifugation for 5 minutes at 2800 RPM. The supernatant fraction containing total cell glycoproteins was transferred to a fresh vial, re-centrifuged as before and the supernatant fraction once again transferred to a clean vial. N-glycans were then released from the glycoproteins using N-glycosidase F to release the N-glycans, which were analyzed by positive MALDI-TOF as described in Hamilton et al. Science 301: 1244-1246 (2003). FIGS. 3-1 and 3-2 shows that the N-glycans compositions from vrg4 knock-out (vrg4Δ) mutant strains did not contain detectable amounts of high mannose N-glycans having more than nine mannose (M9) residues, e.g., M10, M11, and M12. Since these strains lack a mammalian α1,2-mannosidase, the predominant N-glycans are those with eight mannose residues (M8) or nine mannose residue (M9). FIGS. 4-1 and 4-2 shows that the N-glycans from vrg4Δ knock-out (KO) mutant strains genetically engineered to produce galactose-terminated hybrid N-glycans (YGLY3853) or galactose terminated complex N-glycans (YGLY4754) also did not contain detectable high mannose N-glycans having more than nine mannose (M9) residues, e.g., M10, M11, and M12. These results show that transforming YGLY2-3 or strains descended from YGLY2-3 with a plasmid vector designed to disrupt expression of the VRG4 gene produced strains that did not produce detectable amounts of high mannose N-glycans and the cells were viable. Furthermore, parallel lineages from NRRL-Y11430 showed similar phenotypes on knock-out of VRG4, thus confirming that the ability to knock-out this gene was not specific to the YGLY2-3 lineage.

During the sequencing of the 3' flanking region (SEQ ID NO: 2) of VRG4 in the vector pGLY8655, it was determined that a point mutation had been generated during this amplification of this fragment from genomic DNA. The mutation was a single nucleotide change from thymidine residue at position 1892 in the genome sequence shown in SEQ ID NO:3 to cytidine. This corresponds to the cytidine residue at position 84 in the amplified 3' flanking region in vector pGLY8655 shown in SEQ ID NO:2. As such when pGLY8655 was used to knock-out VRG4 it introduced this mutation into the genome, as confirmed by deep sequencing of the VRG4 knock-out strains. The location of this mutation in the genome did not indicate that this would have any effect on strain phenotype. However, to confirm that this mutation had no influence on the ability to knock-out VRG4, or the resultant phenotype of knock-out strains, this cytidine residue at position 84 in pGLY8655 was mutated to the native thymidine and the new vector designated pGLY11989. Subsequent VRG4 knock-out was confirmed using this latter vector and the resultant VRG4 knock-out strains had similar phenotypes to the strains that had been made using pGLY8655.

Example 3

In this example, recombinant strains were constructed that expressed a TNFRII-Fc fusion protein with predominantly particular N-glycan structures. The N-glycan composition of glycoprotein compositions obtained from cultures of these strains were compared to the N-glycan composition from these strains after expression of the VRG4 gene in the strains had been disrupted.

Figure 5:
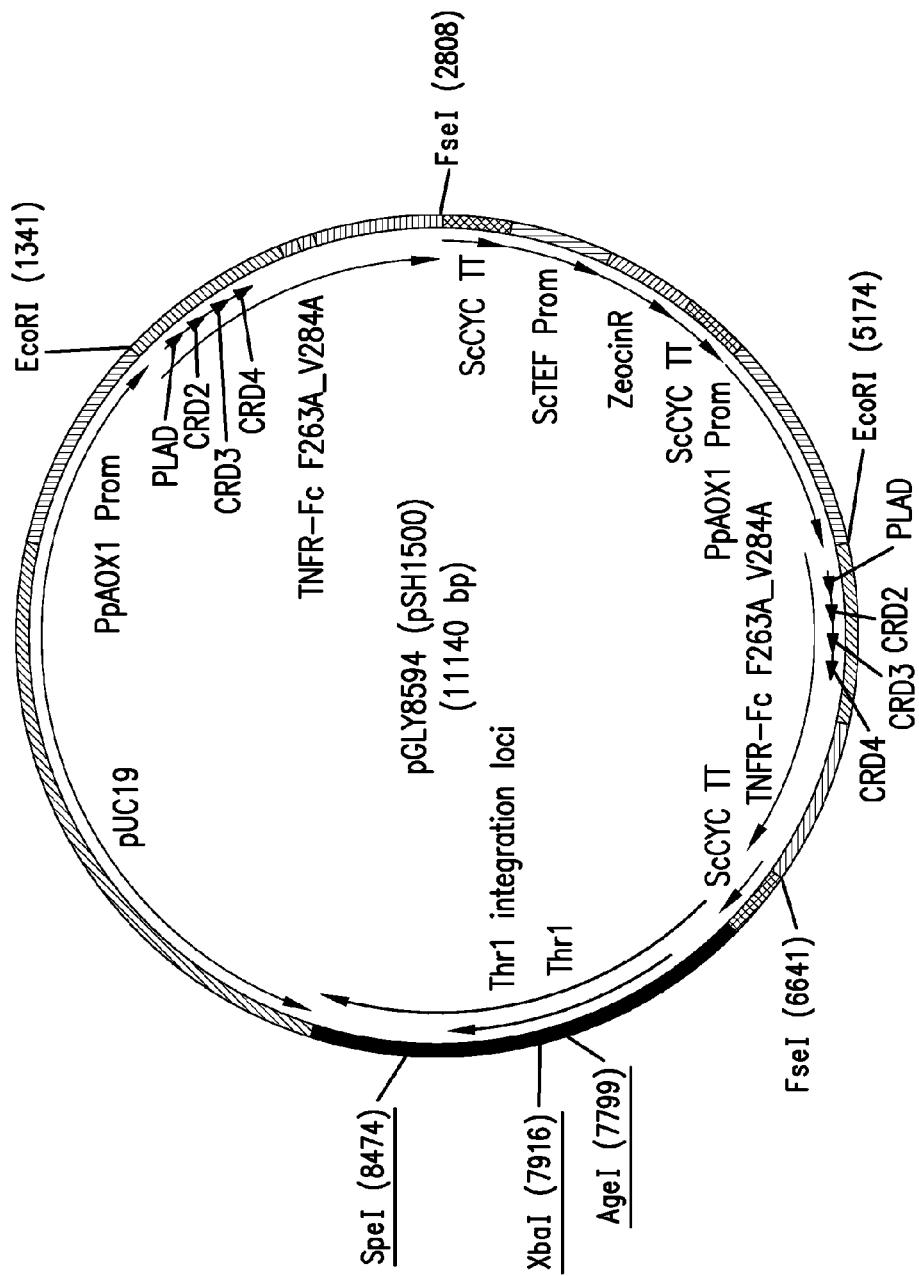
FIG. 5 shows a map of plasmid pGLY8594, an integration vector that targets the THR1 locus and comprises two expression cassettes encoding a TNFRII-Fc fusion protein operably linked to the *P. pastoris* AOX1 promoter. The vector further includes an expression cassette encoding the selectable marker encoding Zeocin (Sh bl) resistance.

Plasmid pGLY8594 (FIG. 5) is a roll-in integration vector that targets the THR1 locus and contains duplicate expression cassettes encoding the TNFRII-Fc fusion protein modified in the CH2 region of the Fc to incorporate mutations equivalent to those corresponding to F263A and V284A of IgG1. Each expression cassette comprises a nucleic acid molecule encoding a fusion protein comprising human serum albumin signal peptide fused to the N-terminus of the TNFRII-Fc fusion protein (SEQ ID NO:4) encoded by a nucleic acid molecule having the nucleotide sequence of SEQ ID NO:5 (codon-optimized for expression in *P. pastoris*). The expression cassettes are operably linked at the 5' end to a nucleic acid molecule comprising the *P. pastoris* AOX1 promoter (SEQ ID NO:61) and at the 3' end to a nucleic acid molecule comprising the *S. cerevisiae* CYC transcription termination sequence (SEQ ID NO:21). The plasmid also includes a Zeocin$^R$ expression cassette comprising a nucleic acid molecule encoding the Sh ble ORF (SEQ ID NO:62) operably linked at the 5' end to the *S. cerevisiae* TEF1 promoter (SEQ ID NO:63) and at the 3' end to the *S. cerevisiae* CYC termination sequence (SEQ ID NO:21). The plasmid further includes a nucleic acid molecule that targets the THR1 locus (SEQ ID NO:64). Plasmid pGLY8594 was transformed into the desired prototrophic host strains by digesting 10 µg of vector with XbaI. Transformed strains were plated on YSD plates containing 0.125×, 1× or 3× Zeocin and incubated at 24° C. Individual clones expressing TNFR-Fc were isolated and analyzed. Strain YGLY27018 is strain YGLY2-3 transformed with pGLY8594, strain YGLY27020 is strain YGLY6-3 transformed with pGLY8594, and strain YGLY27026 is strain YGLY4754 transformed with pGLY8594. These strains are all VRG4. Strain YGLY27028 is strain YGLY25241 transformed with pGLY8594, strain YGLY27031 is strain YGLY25242 transformed with pGLY8594, and strain YGLY27044 is strain YGLY25736 transformed with pGLY8594. These strains are all vrg4 knock-out.

96-well plate growth conditions were as follows. Standard 96 deep-well plates (2.2 mL capacity) are filled with 600 µl BSGY media containing 4% glycerol. Each well is inoculated with a single colony picked from selective media plates. These "seed Plates" are sealed with a breathable film and incubated for 48 hours in an Infors Multitron shaker set to 80% humidity, 24° C., 840 RPM with a 3 mm throw. After the initial growth phase, 100 µL of culture is mixed with 100 µL 50% glycerol and frozen at −80° C. for future use. The remaining 500 µL is transferred by a TECAN Evo liquid handler to a single well of a 24-well plate containing 3 mL BSGY containing 4% glycerol. From a seed plate, four 24-well plates are created. These are sealed with a breathable film and incubated at 80% humidity, 24° C., 650 RPM with a 3 mm throw for 48 hours. Following the second growth phase, the plates are centrifuged at 3000 RPM in a Sorvall Legend XT centrifuge for 5 minutes and the media removed. The wells are filled with 2 mL BSMY induction media containing 2% methanol. These are sealed with a breathable film and incubated at 80% humidity, 24° C., 650 RPM with a 3 mm throw for 48 hours. The plates are then centrifuged at 3000 RPM for eight minutes and the media is harvested into a clean 96-well plate for subsequent recombinant protein purification. If cellular glycans are to be analyzed, the culture is first moved to a 96-well plate by the TECAN liquid handler and then centrifuged as described previously. The media is then discarded and the cell pellets analyzed as described below.

Under shake-flask growth conditions, the yeast strains were grown in 50 mL BSGY for approximately 65 hours at 24° C. Subsequently, the cultures were induced in 5 mL BSMY (BSGY containing 1% MeOH in place of glycerol) and grown for at least another 24 hours. The culture was centrifuged at 2400 rpm for five minutes to pellet the cells. For recombinant protein analysis, the supernatant was removed and the protein purified as described below.

Under DASGIP fermentation: growth conditions, the growth of strains expressing TNFR-Fc was performed in bioreactors using inoculum seed flasks as described below. The inoculum seed flasks were inoculated from yeast patches (isolated from a single colony) on agar plates into 0.1 L of 4% BSGY in a 0.5-L baffled flask. Seed flasks were grown at 180 rpm and 24° C. (Innova 44, New Brunswick Scientific) for 48 hours. Cultivations were done in 1 L (fedbatch-pro, DASGIP BioTools) bioreactors. Vessels were charged with 0.54 L of 0.22 µm filtered 4% BSGY media (with 4 drops/L Sigma 204 antifoam) and autoclaved at 121° C. for 45 minutes. After sterilization and cooling, the aeration, agitation and temperatures were set to 0.7 vvm, 400 rpm and 24° C., respectively. The pH was adjusted to and controlled at 6.5 using 30% ammonium hydroxide. Inoculation of a prepared bioreactor occurred aseptically with 60 mL from a seed flask. Agitation was ramped to maintain 20% dissolved oxygen (DO) saturation. After the initial glycerol charge was consumed, denoted by a sharp increase in the dissolved oxygen, a 50% w/w glycerol solution containing 5 mg/L biotin and 10.8 mg/L PMTi-4, a PMT inhibitor described in Example 4 of U.S. Published Application No. 20110076721 and having the structure

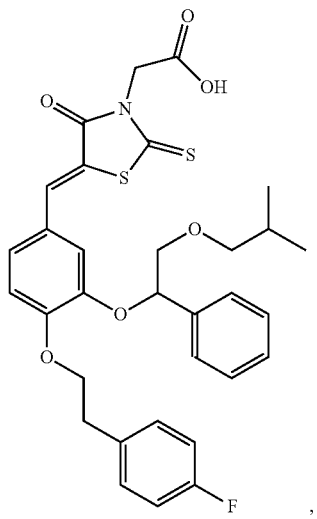 [SMILES: CC(C)COCC(Oc1cc(/C=C2\SC(=S)N(CC(=O)O)C2=O)ccc1OCCc1ccc(F)cc1)c1ccccc1]

was triggered to feed at 3.68 mL/hr for 8 hours. During the glycerol fed-batch phase 0.375 mL of PTM2 salts were injected manually. Completion of the glycerol fed-batch was followed by a 0.5 hour starvation period and initiation of the induction phase. A continuous feed of a 50% v/v methanol solution containing 2.5 mg/L biotin and 6.25 mL/L PTM2 salts was started at a flat rate of 1.5 mL/hr. Injections of 0.5 mL of protease inhibitor solution containing 3.6 mg/mL Pepstatin A and 2.2 mg/mL Chymostatin (in methanol) were added at the start of induction and after each 24 hours of induction time. Additionally, injections of 0.25 mL of 0.6 mg/ml PMTi4 (in methanol) were added each 24 hours of induction. Individual fermentations were harvested within 36-66 hours of induction. The culture broth was clarified by centrifugation (Sorvall Evolution RC, Thermo Scientific) at 8500 rpm for 40 minutes and the resulting supernatant was submitted for purification.

Recombinant TNFR-Fc purification from Shake-flask and 96-well plate material was as follows. Secreted TNFRII-Fc fragment fusion protein is purified from cleared supernatants using protein A chromatography (Li et al. Nat. Biotechnol. 24(2):210-5 (2006)).

Recombinant TNFR-Fc purification from DASGIP material was as follows. The TNFRII-Fc fragment fusion protein was captured by affinity chromatography from the culture medium (supernatant medium) of *P. pastoris* using MABSELECT from GE Healthcare (PolyA-agarose media; Cat. #17-5199-03). The cell free supernatant medium was loaded on to MABSELECT column pre-equilibrated with 3 column volume of 20 mM Tris-HCl pH 7.0. The column was washed with 2 column volumes of 20 mM Tris-HCl pH 7.0 and five column volumes of 20 mM Tris-HCl, 1 M NaCl pH 7.0 to remove the host cell protein contaminants. The TNFRII-Fc fragment fusion protein was eluted with seven column volumes of 50 mM sodium citrate pH 3.0. The eluted fusion protein was neutralized immediately with 1 M Tris-HCl pH 8.0.

N-glycans were released from the recombinant protein using N-glycosidase F and analyzed by MALDI-TOF as described in Hamilton et al. Science 301: 1244-1246 (2003). 2-AB labeling and HPLC (neutral and charged glycans) was used to quantify the relative amount of each glycoform. In general, the N-glycosidase F released glycans were labeled with 2-aminobenzidine (2-AB) and analyzed by HPLC as described in Choi et al., Proc. Natl. Acad. Sci. USA 100: 5022-5027 (2003) except for the following modifications. Fluorescence-labeled oligosaccharide was analyzed by HPLC with Prevail™ Carbohydrate ES columns 4.6×250 mm, 5 μm bead (Alltech, Avondale, Pa.). The flow rate was 1.3 mL/minute for 40 minutes and the column was maintained at 45° C. After eluting isocratically (70% A:30% B) for 3 minutes, a linear solvent gradient (70% A:30% B to 44% A:56% B) was used over 20 minutes to elute the neutral glycans followed by a linear solvent gradient (44% A:56% B to 0% A:100% B) over 15 minutes to elute charged glycanS. Solvent A was acetonitrile and solvent B was an aqueous solution of ammonium formate, 100 mM (pH 4.5). The column was equilibrated with solvent (70% A:30% B) for seven minutes between runs.

O-glycan analysis (Dionex) was as follows. Approximately 0.5 nmole of protein in 100 μL PBS buffer was used for β-elimination (Harvey, Mass Spectrometry Reviews 18: 349-451 (1999), Stadheim et al., Nat. Protoc. 3:1026-31 (2006). The protein sample was treated with 25 μL alkaline borohydride reagent and incubated at 50° C. for 16 hours. Ten μL arabitol was added as an internal standard, followed by the addition of 10 μL glacial acetic acid. The sample was then centrifuged through a Millipore filter plate containing SEPABEADS and washed with water. The samples, including the wash, were transferred to glass autosampler vials and evaporated to dryness in a centrifugal evaporator. 150 μL 1% AcOH/MeOH was added to the samples and the samples evaporated to dryness in a centrifugal evaporator. This last step was repeated five times. 200 μL of water was added and 100 μL of the sample was analyzed by high pH anion-exchange chromatography coupled with pulsed electrochemical detection-HPLC (HPAEC-PAD) according to the manufacturer (Dionex, Sunnyvale, Calif.).

Enzymatic digests were as follows. α-Mannosidase treatment was performed by adding 0.2 μL of enzyme to dried sample resuspended in 50 μL of ammonium acetate pH 5.0 and incubation overnight at 37° C., with subsequent analysis by MALDI-TOF and/or HPLC.

Figures 1, 6:
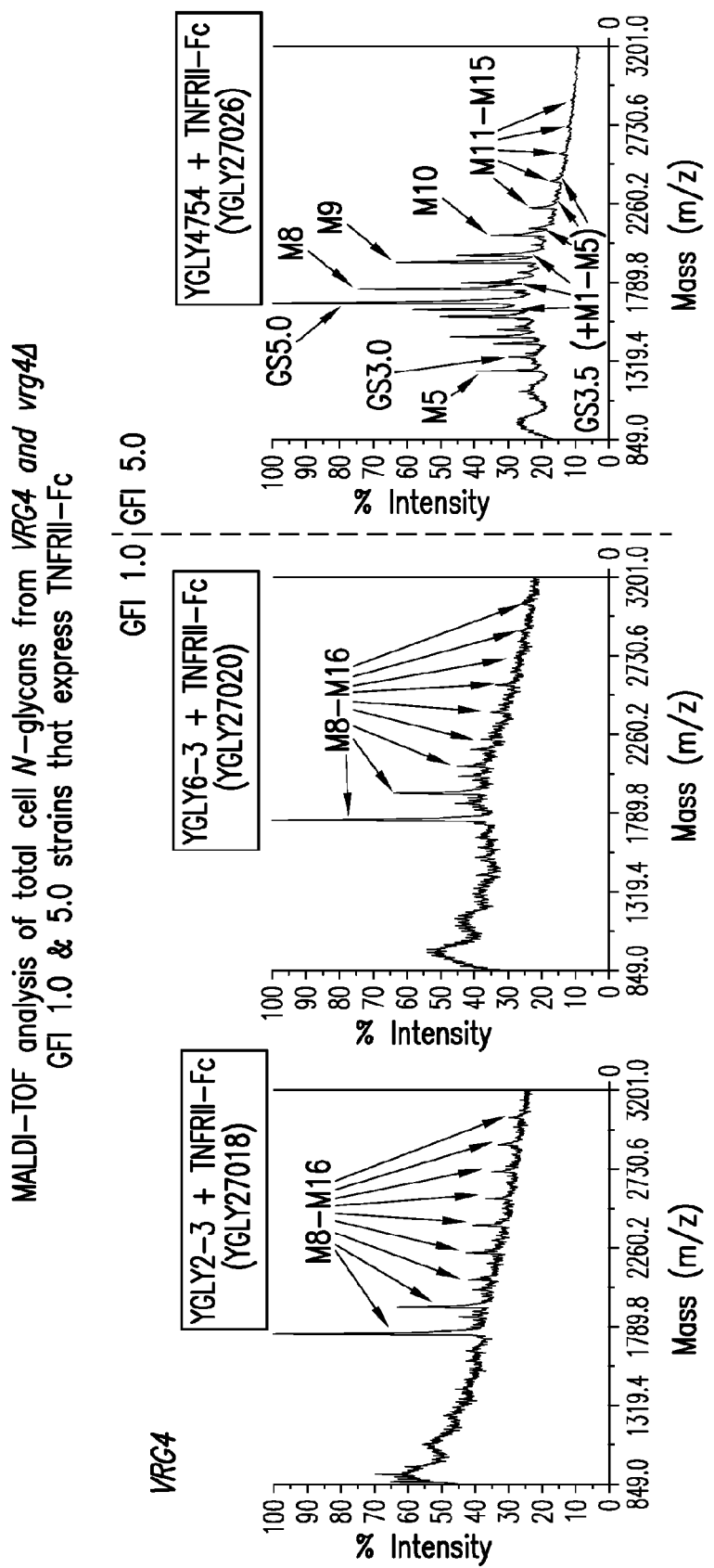
Figures 2, 6:
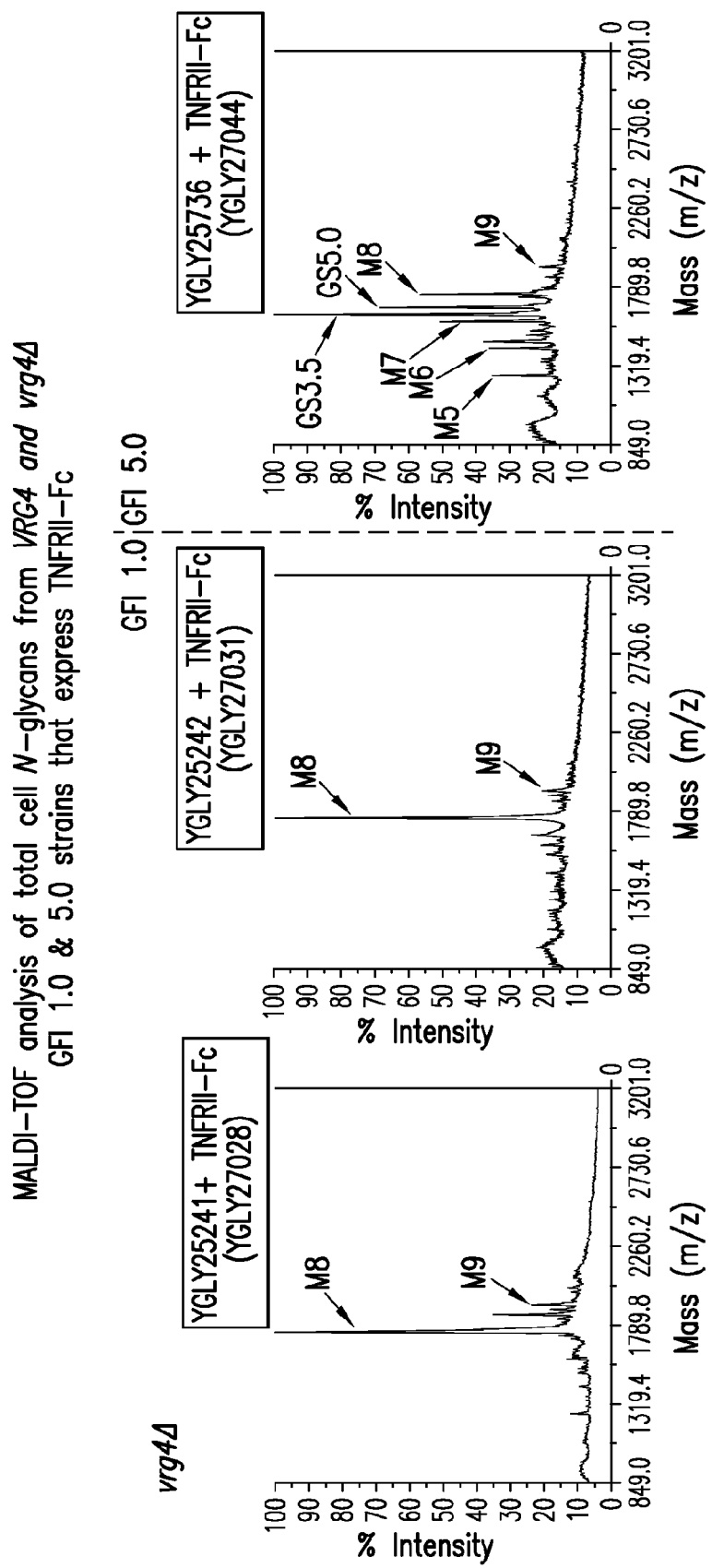

The positive ion MALDI-TOF tracings shown in FIGS. 6-1 and 6-2 show that for each strain expressing recombinant TNFRII-Fc fusion protein in the vrg4 knock-out (vrg4Δ) background there were no detectable amounts of high mannose N-glycans having more than nine mannose (M9) residues, e.g., M10, M11, and M12 in the total cell glycans extracted from the cells.

Figure 7:
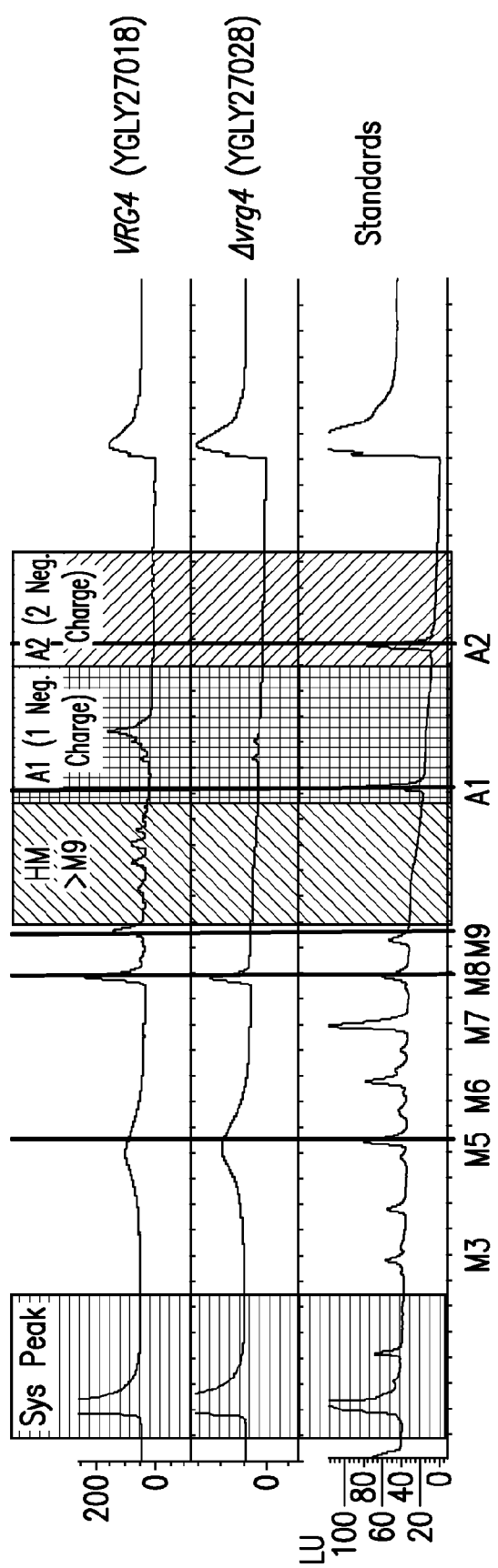
FIG. 7 shows a comparison of N-glycans from total cell mass from VRG4 and vrg4Δ glycoengineered strains from the YGLY2-3 background that further express the TNFRII-Fc.

FIG. 7 shows a comparison of N-glycan content of TNFRII-Fc produced in strain YGLY2-3 in a VRG4 or vrg4 knock-out background (strains YGLY27018 and YGLY27028, respectively). The HPLC tracings show that in the vrg4 knock-out background there was no detectable high mannose N-glycans and phosphorylated N-glycans were greatly reduced compared to the amount present in VRG4 cells.

Figure 8:
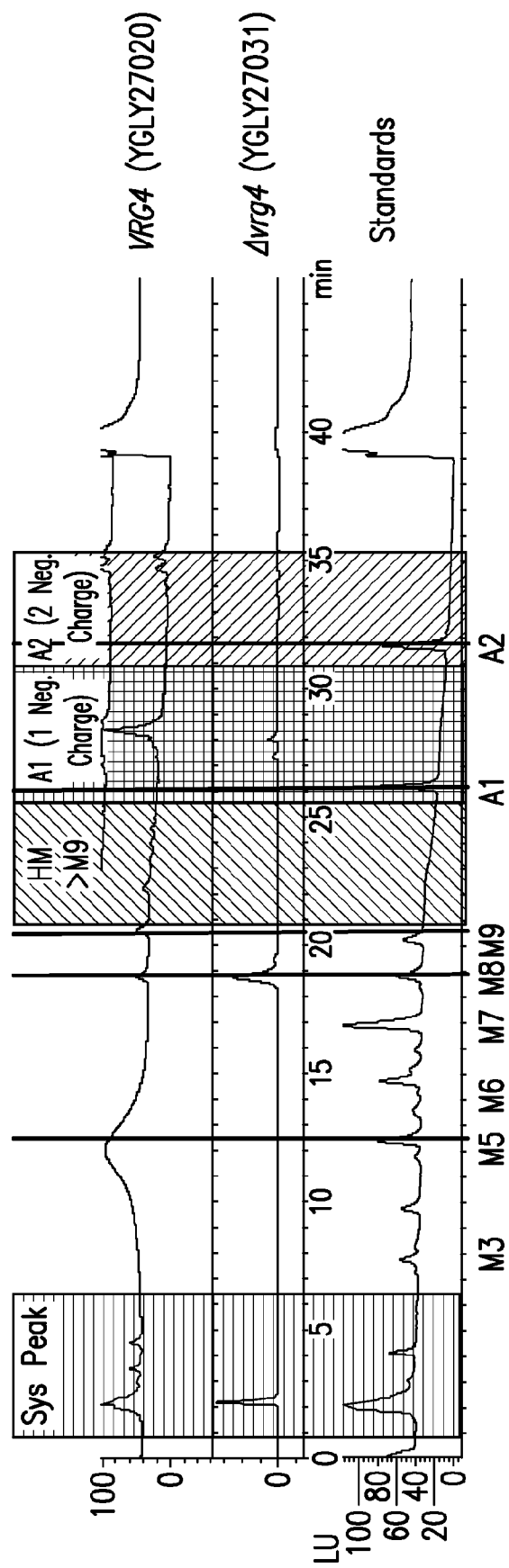
FIG. 8 shows a comparison of N-glycans from total cell mass from VRG4 and vrg4Δ glycoengineered strains from the YGLY6-3 background that further express the TNFRII-Fc.

FIG. 8 shows a comparison of N-glycan content of TNFRII-Fc produced in strain YGLY6-3 in a VRG4 or vrg4 knock-out background (strains YGLY27020 and YGLY27031, respectively). The HPLC tracings show that in the vrg4 knock-out background there was no detectable high mannose N-glycans and phosphorylated N-glycans were greatly reduced compared to the amount present in VRG4 cells. The amount phosphorylated N-glycans appeared to be a little higher in the YGLY6-3 background compared to the YGLY2-3 background.

Figure 9:
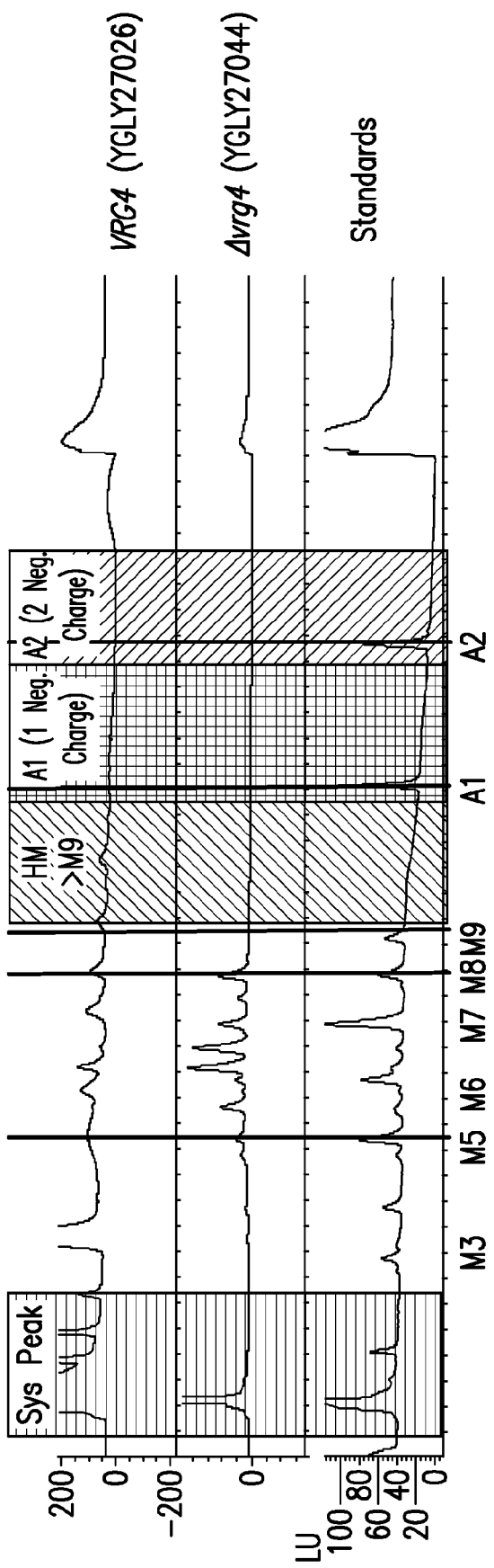
FIG. 9 shows a comparison of N-glycans from total cell mass from VRG4 and vrg4Δ glycoengineered strains from the YGLY4754 background that further express the TNFRII-Fc.

FIG. 9 shows a comparison of N-glycan content of TNFRII-Fc produced in strain YGLY4754 in a VRG4 or vrg4 knock-out background (strains YGLY27026 and YGLY27044, respectively). The HPLC tracings show that in the vrg4 knock-out background there was no detectable high mannose N-glycans compared to the amount present in VRG4 cells. Both strain backgrounds lacked detectable phosphorylated N-glycans because these backgrounds include a deletion of the PNO1, MNN4, and MNN4-L1 genes, which are involved in phosphomannosylation of N-glycans.

Table 1 shows a quantitative analysis of the N-glycans present in TNFRII-Fc compositions obtained from the various VRG4 and vrg4 strains described above. The figure shows that the vrg4 strains produced TNFRII-Fc compositions with no detectable higher mannose (greater than $Man_9GlcNAc_2$) N-glycans. The amount of phosphorylated N-glycans was significantly reduced and the amount of complex N-glycan formation in the vrg4 strain YGLY27044, a strain capable of producing glycoproteins with galactose-terminated complex N-glycans, was increased over that produced in the corresponding VRG4 strain YGLY27026, also capable of producing glycoproteins with GS5.0 glycoform.

TABLE 1

Quantitative HPLC analysis of TNFRII-Fc
N-glycans isolated from VRG4 and vrg4Δ strains in Mol %

| Strain | G0 | G1 | G2 | -1 | -2 | GN-M3 | GN-M5 | GalGN-M5 | HM HB | M5 | M6 |
|---|---|---|---|---|---|---|---|---|---|---|---|
| YGLY27018 |  |  | 32 | 2 |  |  |  |  | 31 |  |  |
| YGLY27028 |  |  | 14 |  |  |  |  |  | 5 |  |  |
| YGLY27020 |  |  | 52 | 20 |  |  |  |  |  |  |  |
| YGLY27031 |  |  | 17 | 1 |  |  |  |  | 6 |  |  |
| YGLY27026 |  | 1 | 13 | 3 |  |  | 17 | 2 | 26 |  |  |
| YGLY27044 | 3 |  | 26 | 1 | 0 | 1 | 1 | 24 | 5 | 5 | 4 |

TABLE 1-continued

Quantitative HPLC analysis of TNFRII-Fc
N-glycans isolated from VRG4 and vrg4Δ strains in Mol %

| Strain | HM | M7 | M8 | M9 | M10 | M11 | M12 | M13 | M14 | Total |
|---|---|---|---|---|---|---|---|---|---|---|
| YGLY27018 | 35 | | | 14 | 0 | 0 | 3 | 6 | 6 | 100 |
| YGLY27028 | 81 | | 81 | | | | | | | 100 |
| YGLY27020 | 28 | | 8 | 8 | 6 | 1 | 2 | 2 | | 100 |
| YGLY27031 | 76 | 0 | 75 | 2 | 0 | | | | | 100 |
| YGLY27026 | 37 | | 15 | 10 | 1 | 10 | 2 | | | 100 |
| YGLY27044 | 29 | 14 | 14 | 1 | | | | | | 100 |

G0 - GlcNAc$_2$Man$_3$GlcNAc$_2$
G1 - GalGlcNAc$_2$Man$_3$GlcNAc$_2$
G2 - Gal$_2$GlcNAc$_2$Man$_3$GlcNAc$_2$
GnM3 - G-1 or GlcNAcMan$_3$GlcNAc$_2$ hybrid
GnM5 - GlcNAcMan$_5$GlcNAc$_2$ hybrid
GalGNM5 - GalGlcNAcMan$_5$GlcNAc$_2$ hybrid
HM HB - High mannose hybrid N-glycan
HM - High mannose
M8 - Man$_8$GlcNAc$_2$
M9 - Man$_9$GlcNAc$_2$
M10 - Man$_{10}$GlcNAc$_2$
M11 - Man$_{11}$GlcNAc$_2$
M12 - Man$_{12}$GlcNAc$_2$
M13 - Man$_{13}$GlcNAc$_2$
M14 - Man$_{14}$GlcNAc$_2$
−1 - N-glycan migrates in position expected for N-glycan with 1 negative charge
−2 - N-glycan migrates in position expected for N-glycan with 2 negative charges Table 2 shows a quantitative analysis of the O-glycans present in TNFRII-Fc compositions obtained from the various VRG4 and vrg4 strains described above. The figure shows that the vrg4 strains produced TNFRII-Fc compositions with significantly reduced O-glycan complexity compared to that produced in the corresponding VRG4 strains. In the vrg4Δ strains capable of producing GS1.0 glycan structures, about greater than 80% of the O-glycans had only one mannose residue. These strains lack expression of a secreted chimeric *T. reesei* mannosidase, which is generally included in production strains for producing heterologous glycoproteins in order to reduce O-glycan chain length (See Published International Application No. WO2007061631).

TABLE 2

Quantitative HPLC analysis of TNFRII-Fc
O-glycans isolated from VRG4 and vrg4Δ strains

| Strain | Genotype | Occupancy (Mol/Mol) | Chain Length | | | |
|---|---|---|---|---|---|---|
| | | | Man1ol | Man2ol | Man3ol | Man4ol |
| YGLY27018 | VRG4 | 26.92 | 16 | 44 | 34 | 6 |
| YGLY27028 | vrg4Δ | 24.69 | 86 | 13 | 1 | 0 |
| YGLY27020 | VRG4 | 21.53 | 37 | 38 | 20 | 4 |
| YGLY27031 | vrg4Δ | 16.87 | 80 | 19 | 1 | 0 |
| YGLY27026 | VRG4 | 40.5 | 14 | 43 | 34 | 9 |
| YGLY27044 | vrg4Δ | 32.22 | 49 | 45 | 6 | 0 |

Man1ol - mannose (one mannose residue)
Man2ol - mannobiose (two mannose residues)
Man3ol - mannotriose (three mannose residues)
Man4ol - mannotetraose (four mannose residues)

Example 4

In this example, recombinant strains were constructed that express a recombinant rat erythropoietin (rEPO) with predominantly particular N-glycan structures. The N-glycan composition of glycoprotein compositions obtained from cultures of these strains were compared to the N-glycan composition from these strains after expression of the VRG4 gene in the strains had been disrupted.

Figure 10:
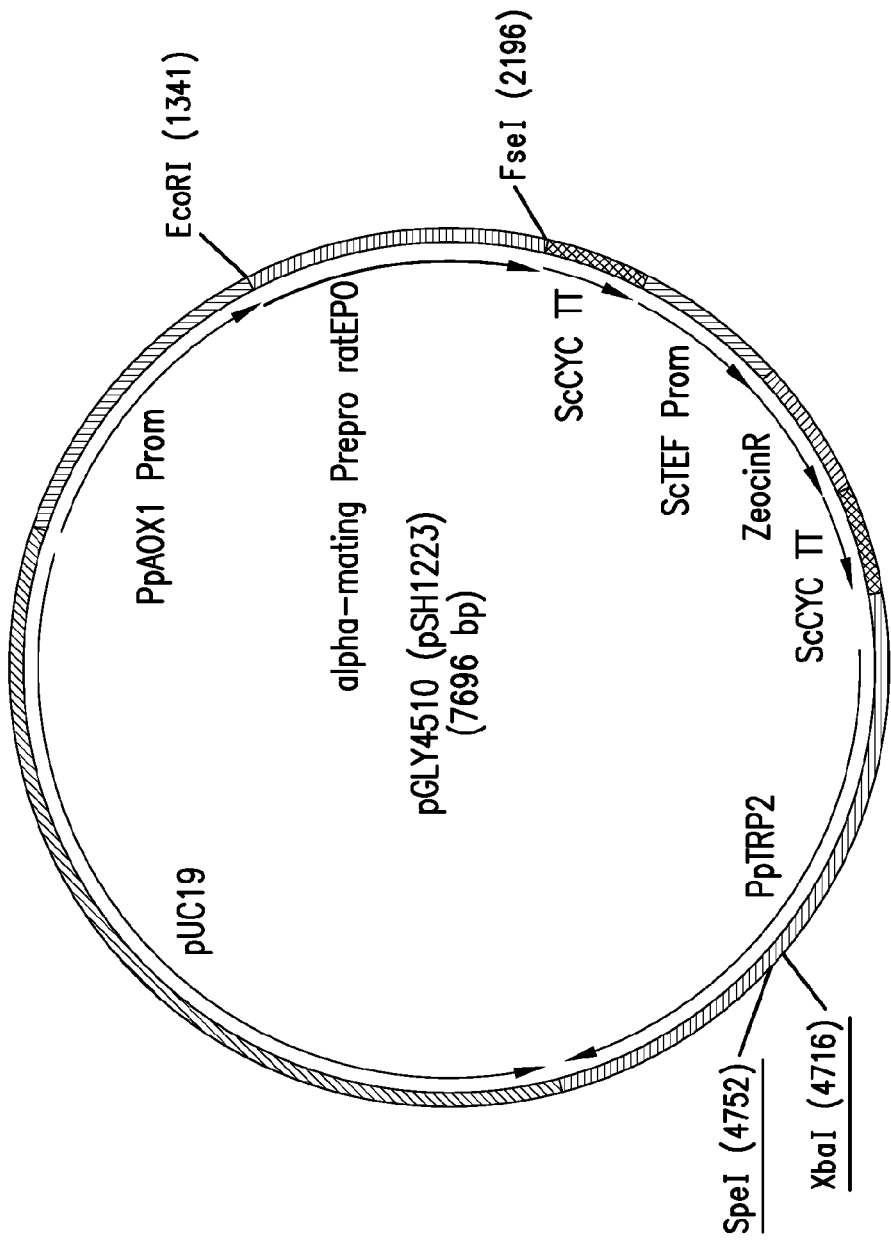
FIG. 10 shows a plasmid map of pGLY4510, an integration vector that targets *P. pastoris* TRP2 locus and comprises two expression cassettes encoding a rat erythropoietin (rEPO or ratEPO) operably linked to the *P. pastoris* AOX1 promoter. The vector further includes an expression cassette encoding the selectable marker encoding Zeocin (Sh bl) resistance.

Plasmid pGLY4510 (FIG. 10) is a roll-in integration vector that targets the TRP2 locus and contains a single expression cassette encoding rat erythropoietin codon-optimized for expression in *P. pastoris* and fused to the α-mating factor pre pro signal sequence at the N-terminus and a six-histidine tag at the C-terminus (amino acid sequence SEQ ID NO:6; encoded by nucleotide sequence SEQ ID NO:7). The expression cassette is operably linked at the 5' end to a nucleic acid molecule comprising the *P. pastoris* AOX1 promoter (SEQ ID NO:61) and at the 3' end to a nucleic acid molecule comprising the *S. cerevisiae* CYC transcription termination sequence (SEQ ID NO:21). The plasmid also includes a Zeocin$^R$ expression cassette comprising a nucleic acid molecule encoding the Sh ble ORF operably linked at the 5' end to the *S. cerevisiae* TEF1 promoter (SEQ ID NO:63) and at the 3' end to the *S. cerevisiae* CYC termination sequence (SEQ ID NO:21). The plasmid further includes a nucleic acid molecule that targets the THR1 locus (SEQ ID NO:64). Plasmid pGLY4510 was transformed into the desired prototrophic host strain by digesting 10 μg of vector with XbaI. Transformed strains were plated on YSD plates containing 0.125×, 1× or 3× Zeocin and incubated at 24° C. Individual clones expressing rat EPO were isolated and analyzed. Strain YGLY27712 is strain YGLY2-3 transformed with pGLY4510, strain YGLY27682 is strain YGLY6-3 transformed with pGLY4510, strain YGLY27685 is strain YGLY10-3 transformed with pGLY4510, and strain YGLY27691 is strain YGLY4754 transformed with pGLY4510: these strains are all VRG4 and express a GDP-mannose transmembrane transporter protein. Strain YGLY27097 is a VRG4 knock-out strain derived YGLY2-3 transformed with pGLY4510, strain YGLY27100 is a VRG4 knock-out strain derived YGLY6-3 transformed with pGLY4510, strain YGLY27103 is a VRG4 knock-out strain derived YGLY10-3 transformed with pGLY4510, and strain YGLY27109 is a VRG4 knock-out strain derived YGLY4754 transformed with pGLY4510: these strains are all vrg4 knock-out and do not express a GDP-mannose transmembrane transporter protein.

The growth of strains expressing rEPO in 96-well plates, Shake-flasks, and DASGIP was performed as described in Example 3 except that in bioreactors no Chymostatin was added and the methanol feed rate was 2.16 mL/hr instead of 1.5 mL/hr. Also, PMTi-4 inhibitor concentration levels were three times higher, at 32.3 mg/L and 1.9 mg/L in the initial and subsequent additions.

Recombinant rat erythropoietin purification from Shake-flask and 96-well plate material was as follows. Secreted rEPO is purified from cleared supernatants using Ni-chelate chromatography, as described for His-tagged Kringle 3 in Choi et al., PNAS USA. 100:5022-5027 (2003) and in Hamilton et al., Science 301: 1244-1246)

Recombinant rat erythropoietin purification from DASGIP material was as follows. His-tagged rat EPO protein was purified through Immobilized Metal Affinity Chromatographic (IMAC) step employing zinc ions. Streamline Chelating medium (GE healthcare Cat.#17-1280-01) was first equilibrated with 50 mM zinc chloride to charge the column with zinc ions followed by 5 column volumes of distilled water to remove unbound zinc ions, and then by 5 column volumes of equilibration buffer (20 mM TRIS-HCl, 200 mM sodium chloride, pH 7.9) to equilibrate the column. The cell free supernatant sample containing the His-tagged rat EPO protein was applied to the zinc charged streamline chelating medium. After loading, the column was washed with 3 column volume of equilibration buffer to remove unbound host cell proteins. The target protein was eluted by applying a linear gradient of 10 column volume from 0 to 500 mM Imidazole in 20 mM TRIS-HCl, 200 mM sodium chloride, pH 7.9. The eluted fractions were analyzed by SDS-polyacrylamide gel electrophoresis (SDS-PAGE) and fractions containing His-tagged rat EPO protein were collected and store at 4° C. until use.

N-glycans were released from the recombinant protein using N-glycosidase F and analyzed by MALDI-TOF as described in Hamilton et al. Science 301: 1244-1246 (2003). 2-AB labeling and HPLC (neutral and charged glycans) was used to quantify the relative amount of each glycoform. In general, the N-glycosidase F released glycans were labeled with 2-aminobenzidine (2-AB) and analyzed by HPLC as described in Choi et al., Proc. Natl. Acad. Sci. USA 100: 5022-5027 (2003) except for the following modifications. Fluorescence-labeled oligosaccharide was analyzed by HPLC with Prevail™ Carbohydrate ES columns 4.6×250 mm, 5 µm bead (Alltech, Avondale, Pa.). The flow rate was 1.3 mL/minute for 40 minutes and the column was maintained at 45° C. After eluting isocratically (70% A:30% B) for 3 minutes, a linear solvent gradient (70% A:30% B to 44% A:56% B) was used over 20 minutes to elute the neutral glycans followed by a linear solvent gradient (44% A:56% B to 0% A:100% B) over 15 minutes to elute charged glycanS. Solvent A was acetonitrile and solvent B was an aqueous solution of ammonium formate, 100 mM (pH 4.5). The column was equilibrated with solvent (70% A:30% B) for seven minutes between runs.

Enzymatic digests were as follows. α-Mannosidase treatment was performed by adding 0.2 µL of enzyme to dried sample resuspended in 50 µL of ammonium acetate pH 5.0 and incubation overnight at 37° C., with subsequent analysis by MALDI-TOF and/or HPLC.

Figures 1, 11:
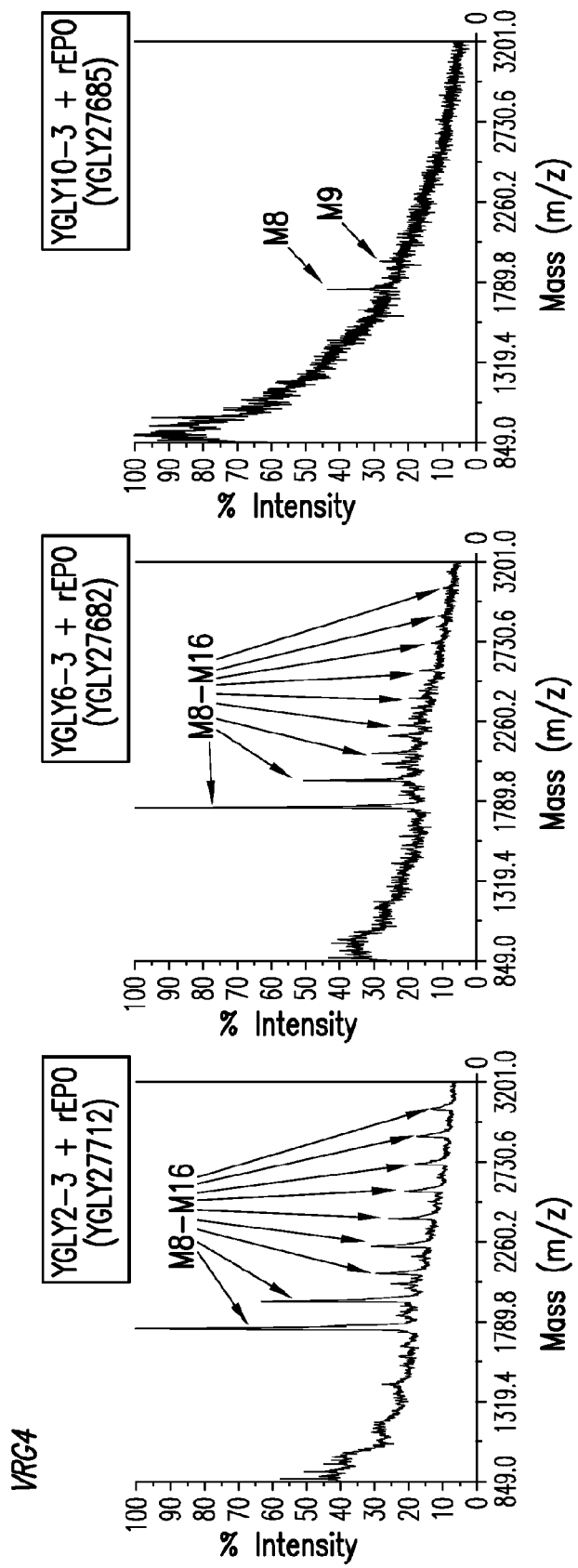
Figures 1, 12:
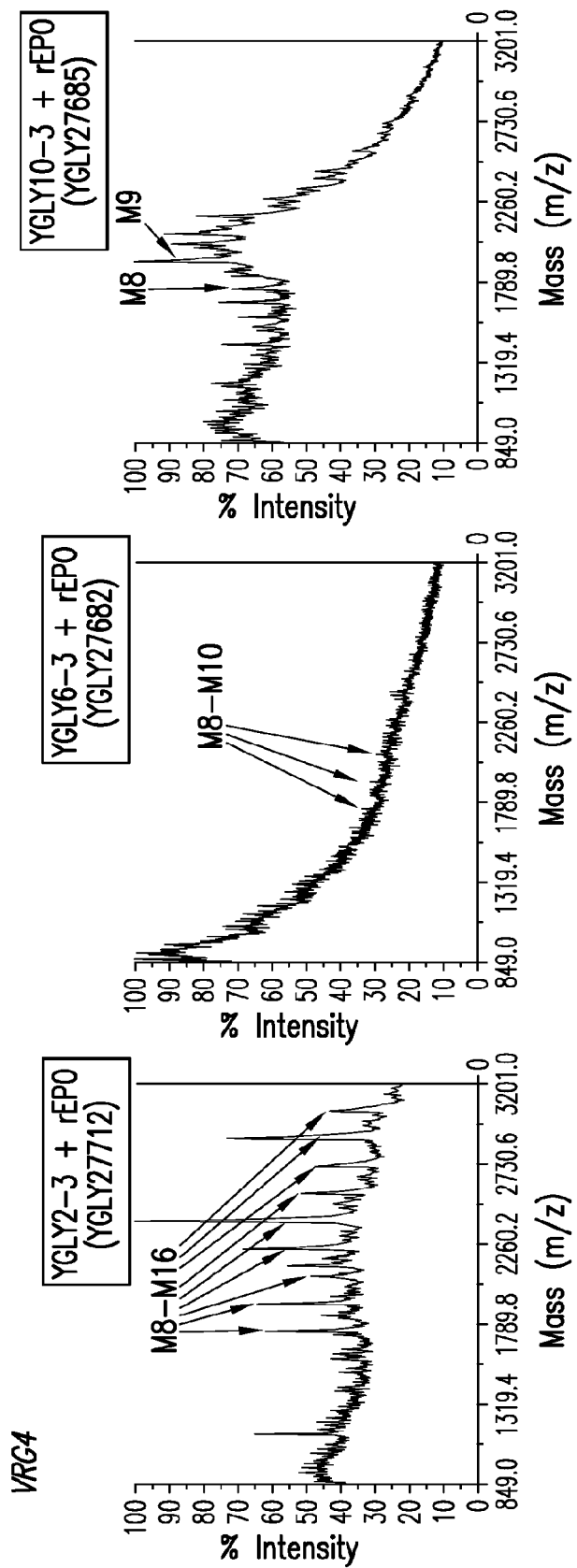
Figures 2, 12:
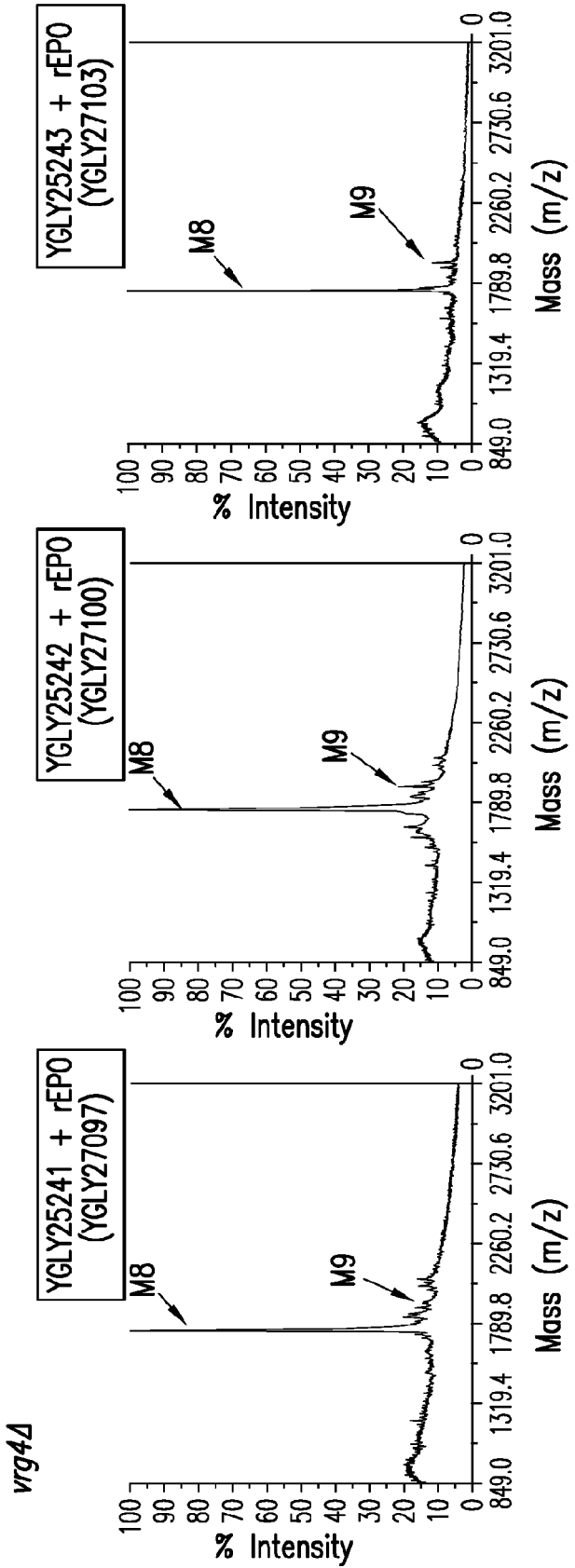
Figure 13:
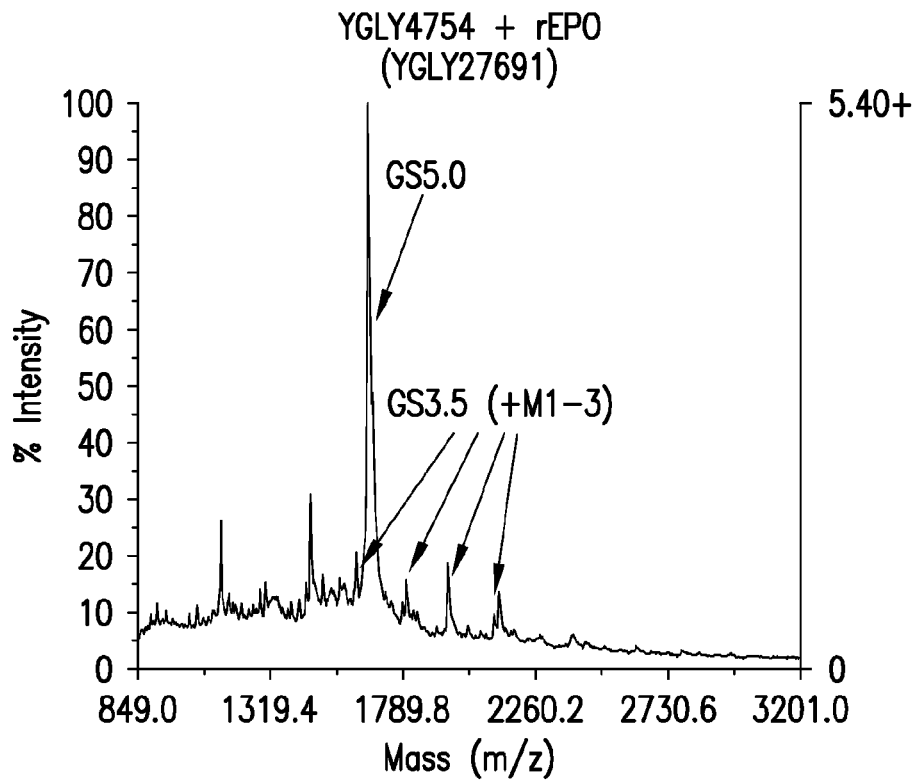
FIG. 13 shows MALDI-TOF analyses of compositions of rEPO N-glycans from compositions of rEPO obtained from VRG4 and vrg4Δ GFI 5.0 glycoengineered strains.
Figure 13:
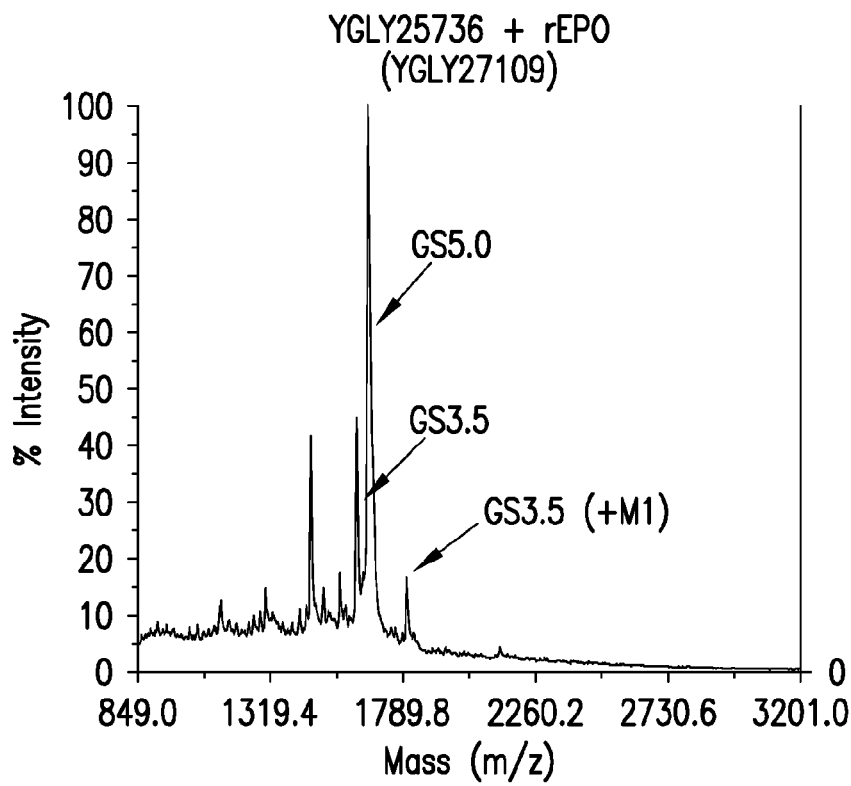

The positive ion MALDI-TOF tracings shown in FIGS. 11-1 and 11-2 shows that for strains expressing recombinant rEPO in the vrg4 knock-out (vrg4Δ) background there were no significant detectable amounts of high mannose N-glycans having more than nine mannose (M9) residues, e.g., M10, M11, and M12, in the composition of total cell N-glycans obtained from the cells.

The positive ion MALDI-TOF tracings shown in FIGS. 12-1 and 12-2 and FIG. 13 show that for each strain expressing recombinant rEPO in the vrg4 knock-out (vrg4Δ) background there were no detectable amounts of high mannose N-glycans having more than nine mannose (M9) residues, e.g., M10, M11, and M12, in the composition of N-glycans obtained from an rEPO composition obtained from the strains.

Table 3 shows a quantitative HPLC analysis of the N-glycans present in rEPO compositions obtained from the various VRG4 and vrg44 strains described above. The table shows that the vrg4 strains produced rEPO compositions with no detectable higher mannose (greater than $Man_9GlcNAc_2$) N-glycans. The amount of phosphorylated N-glycans was significantly reduced in the vrg4 strains capable of producing GS 1.0 glycan structures. Strains in which expression of MNN4L1 was disrupted but which expressed PNO1 and MNN4 produced phosphorylated N-glycans (e.g., strain YGLY27685). However, when the strain further included a disruption of VRG4 produced rEPO compositions the amount of phosphorylated N-glycans was substantially reduced (e.g., strain YGLY27103).

TABLE 3

Quantitative HPLC analysis of rEPO
N-glycans isolated from VRG4 andvrg4Δ strains in mol %

| Strain | Genotype | G1 | G2 | −1 | −2 | GalGN-M5 | HM HB | HM | M8 |
|---|---|---|---|---|---|---|---|---|---|
| YGLY27112 | VRG4 | | | 52 | 4 | | | 44 | 4 |
| YGLY27097 | vrg4Δ | | | 28 | | | | 72 | 70 |
| YGLY27682 | VRG4 | | | 43 | 48 | | | 9 | 0 |
| YGLY27100 | vrg4Δ | | | 8 | | | | 92 | 91 |
| YGLY27685 | VRG4 | | | 35 | 58 | | | 7 | 1 |
| YGLY27103 | vrg4Δ | | | | | | | 100 | 95 |
| YGLY27691 | VRG4 | 10 | 84 | | | | 7 | | |
| YGLY27109 | vrg4Δ | 14 | 72 | | | 14 | | 0 | |

| Strain | Genotype | M9 | M10 | M11 | M12 | M13 | ≥M14 | Total |
|---|---|---|---|---|---|---|---|---|
| YGLY27112 | VRG4 | 3 | 3 | 6 | 11 | 3 | 14 | 100 |
| YGLY27097 | vrg4Δ | 1 | | | | | | 100 |
| YGLY27682 | VRG4 | 1 | 4 | 1 | 1 | 0 | 1 | 100 |
| YGLY27100 | vrg4Δ | 1 | | | | | | 100 |
| YGLY27685 | VRG4 | 2 | 2 | 1 | 1 | 1 | | 100 |
| YGLY27103 | vrg4Δ | 5 | | | | | | 100 |
| YGLY27691 | VRG4 | | | | | | | 100 |
| YGLY27109 | vrg4Δ | | | | | | | 100 |

G1 - $GalGlcNAc_2Man_3GlcNAc_2$
G2 - $Gal2GlcNAc_2Man_3GlcNAc_2$
GalGnM5 - $GalGlcNAcMan_5GlcNAc_2$ hybrid
HM HB - High mannose hybrid N-glycan
HM - High mannose
M8 - $Man_8GlcNAc_2$
M9 - $Man_9GlcNAc_2$
M10 - $Man_{10}GlcNAc_2$
M11 - $Man_{11}GlcNAc_2$
M12 - $Man_{12}GlcNAc_2$
M13 - $Man_{13}GlcNAc_2$
M14 - $Man_{14}GlcNAc_2$
−1 - N-glycan migrates in position expected for N-glycan with 1 negative charge
−2 - N-glycan migrates in position expected for N-glycan with 2 negative charges Example 5

In the aforementioned strains in Examples 2 to 4, the host cells were och1Δ. These strains lack expression of an initiating α1,6-mannosyltranferase and thus, lack outerchain mannosylation. In this example, several of the och1Δ strains from Examples 3 and 4 were transformed with a plasmid vector comprising the OCH1 gene to observe the effect of the VRG4 disruption on N-glycan composition in a host cell that expressed an α1,6-mannosyltranferase and thus capable of outerchain mannosylation.

Figure 14:
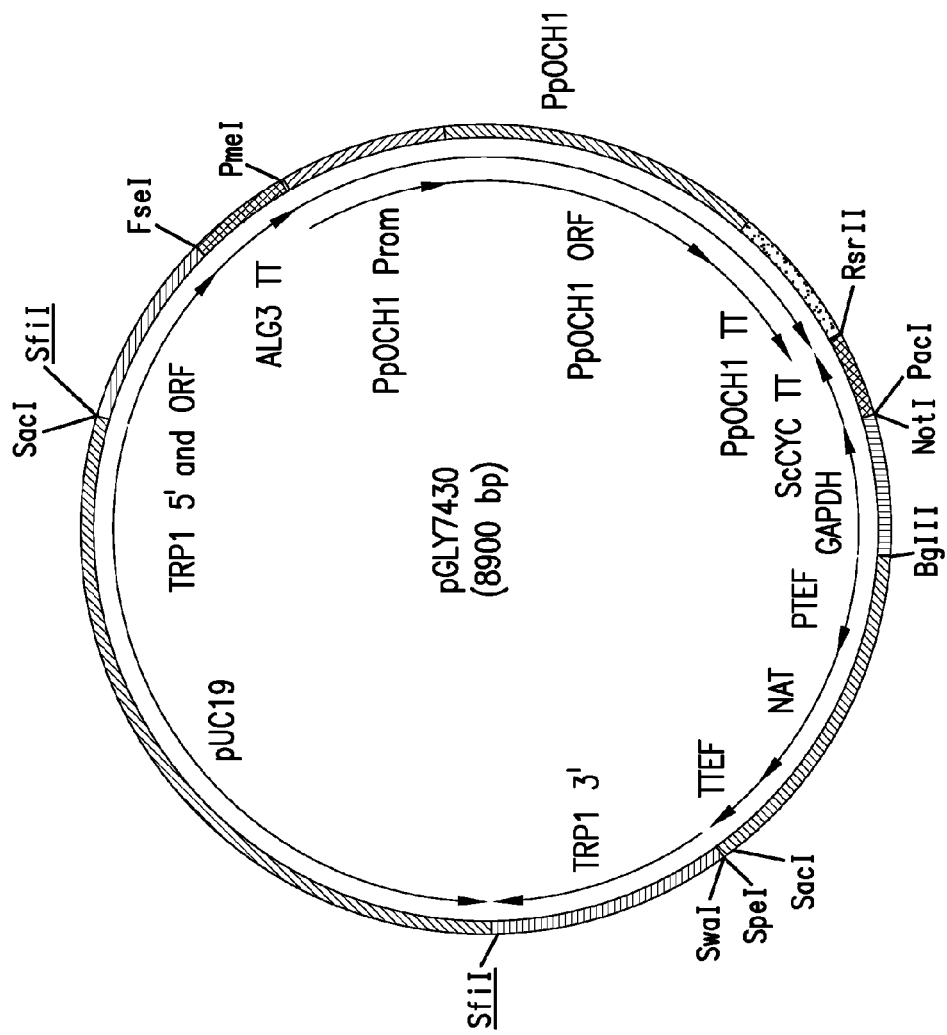
FIG. 14 shows a plasmid map of pGLY7430, a KINKO integration vector that targets the TRP1 locus and which carries the *P. pastoris* OCH1 gene. The vector further includes an expression cassette encoding the selectable marker encoding Nourseothricin ($NAT^R$) resistance.

Re-introduction (knock-in) of the OCH1 into was performed as follows. Plasmid pGLY7430 (FIG. 14) is a KINKO integration vector that comprises the OCH1 gene and targets the TRP1 locus without disrupting expression of the locus. The salient features of the plasmid include the following. The OCH1 gene in the plasmid comprises a nucleic acid molecule comprising a 600 bp nucleic acid fragment containing the OCH1 promoter, a 1143 bp nucleic acid fragment encoding the Och1p, and a 504 bp nucleic acid fragment containing OCH1 terminator sequence and having the nucleotide sequence shown in SEQ ID NO:8. The OCH1 gene is flanked on one side by a nucleic acid molecule comprising the 5' region and complete ORF of the TRP1 gene (SEQ ID NO:65) in which the stop codon is adjacent to a nucleic acid molecule comprising the *P. pastoris* ALG3 termination sequence (SEQ ID NO:33) and on the other side by a nucleic acid molecule comprising the 3' region of the TRP1 gene (SEQ ID NO:66). For selecting transformants, the plasmid comprises an expression cassette encoding the Nourseothricin resistance (NAT$^R$) ORF (originally from pAG25 from EROSCARF, Scientific Research and Development GmbH, Daimlerstrasse 13a, D-61352 Bad Homburg, Germany, See Goldstein et al., Yeast 15: 1541 (1999); GenBank Accession Nos. CAR31387.1 and CAR31383.1) situated between the nucleic acid molecule comprising the 3' region of the TRP1 gene and the nucleic acid molecule comprising the OCH1 gene. The NAT$^R$ expression cassette has the nucleotide sequence shown in SEQ ID NO:67 in which the NAT$^R$ ORF is encoded by nucleotides 494-1066 and is operably linked at the 5' end to *Ashbya gossypii* TEF1 promoter sequence (nucleotides 494-1066) and at the 3' end to a nucleic acid molecule that has the *Ashbya gossypii* TEF1 termination sequence (nucleotides 1067-1313).

Figure 15:
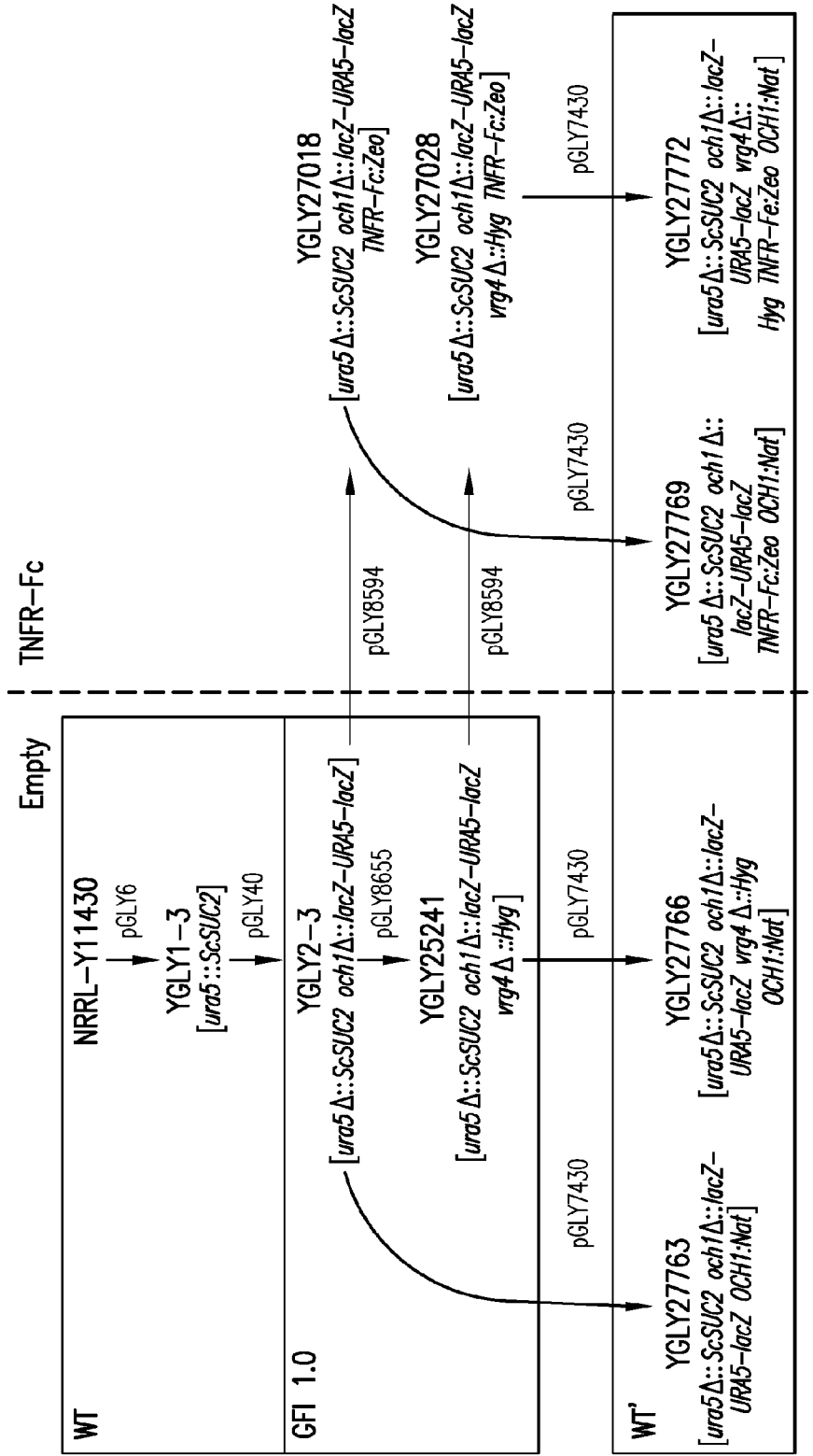
FIG. 15 shows schematically the construction of several VRG4 and vrg4Δ strains in various glycoengineered *Pichia pastoris* cells that in which the OCH1 gene has been re-introduced into the strains and either express as a reporter protein TNFRII-Fc or not.

Prototrophic *Pichia pastoris* host strains YGLY2-3, YGLY2541, YGLY27018, and YGLY27028 were transformed by digesting 10 μg of pGLY7430 with SfiII and transforming as described in Choi et al., Proc. Natl. Acad. Sci. USA. 100: 5022-5027 (2003) and Hamilton et al., Science 301: 1244-1246 (2003) (See FIG. 15). The transformants were plated on YSD plates containing 100 μg/ml nourseothricin to select for incorporation of the transformed vector. Successful knock-in of the OCH1 gene was confirmed by PCR the following primer sets.

PCR primers SH1406-GTTTCGCGTTCTCACTTAGATGGAG (SEQ ID NO:68) and SH1420-CCATTTCTCCGTCAATCCGATTCTCGC (SEQ ID NO:69) for PCR amplifying a 1.3 kbp nucleic acid fragment from the 5' crossover region. PCR primers SH1407-CCACTCGCCAGATCGGAGCTGCAAACACTC (SEQ ID NO:70) and SH1421-CCGCCCTGTACGACGGCACCGCCTC (SEQ ID NO:71) for PCR amplifying a 1.3 kbp fragment from the 3' crossover region. PCR primers SH1417-CGAACCTTTTCCCCAACATATTTGGCAAACG (SEQ ID NO:72) and SH1418-GCAAGGTGATGGTTCAAATCTCCAGCTCCAC (SEQ ID NO:73) for PCR amplifying a 900 bp region from the ORF encoding Och1p. The transformation yielded strains YGLY22763 (VRG4 and OCH1), YGLY22766 (vrg4 and OCH1), YGLY22769 (VRG4 and OCH1 and expresses TNFRII-Fc), and YGLY22772 (vrg4 and OCH1 and expresses TNFRII-Fc).

The strains were grown and purified as described in Example 3.

N-glycans were released from the recombinant protein using N-glycosidase F and analyzed by MALDI-TOF as described in Hamilton et al. Science 301: 1244-1246 (2003). 2-AB labeling and HPLC (neutral and charged glycans) was used to quantify the relative amount of each glycoform. In general, the N-glycosidase F released glycans were labeled with 2-aminobenzidine (2-AB) and analyzed by HPLC as described in Choi et al., Proc. Natl. Acad. Sci. USA 100: 5022-5027 (2003) except for the following modifications. Fluorescence-labeled oligosaccharide was analyzed by HPLC with Prevail™ Carbohydrate ES columns 4.6×250 mm, 5 μm bead (Alltech, Avondale, Pa.). The flow rate was 1.3 mL/minute for 40 minutes and the column was maintained at 45° C. After eluting isocratically (70% A:30% B) for 3 minutes, a linear solvent gradient (70% A:30% B to 44% A:56% B) was used over 20 minutes to elute the neutral glycans followed by a linear solvent gradient (44% A:56% B to 0% A:100% B) over 15 minutes to elute charged glycanS. Solvent A was acetonitrile and solvent B was an aqueous solution of ammonium formate, 100 mM (pH 4.5). The column was equilibrated with solvent (70% A:30% B) for seven minutes between runs.

Figures 1, 16:
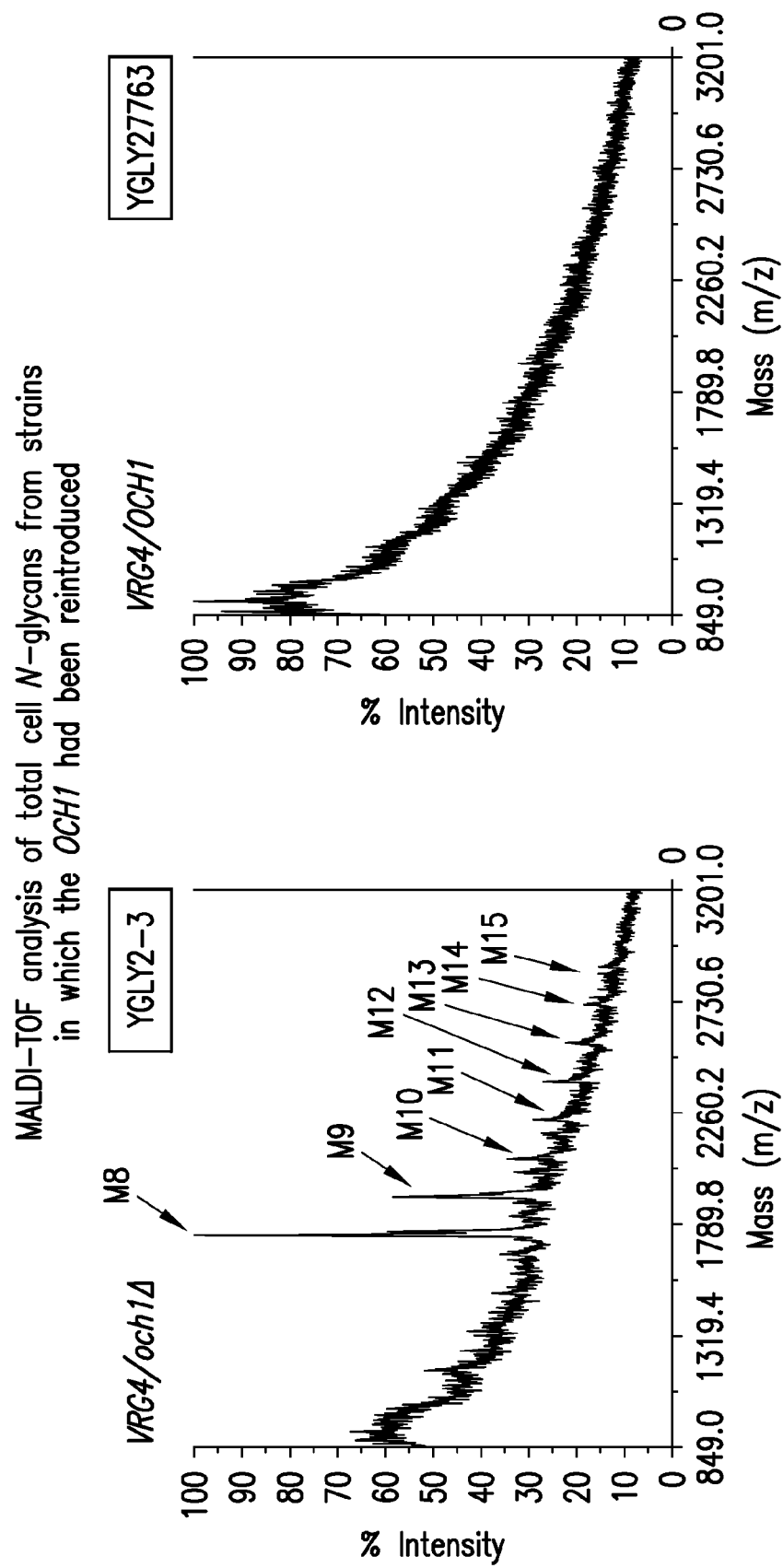
Figures 2, 16:
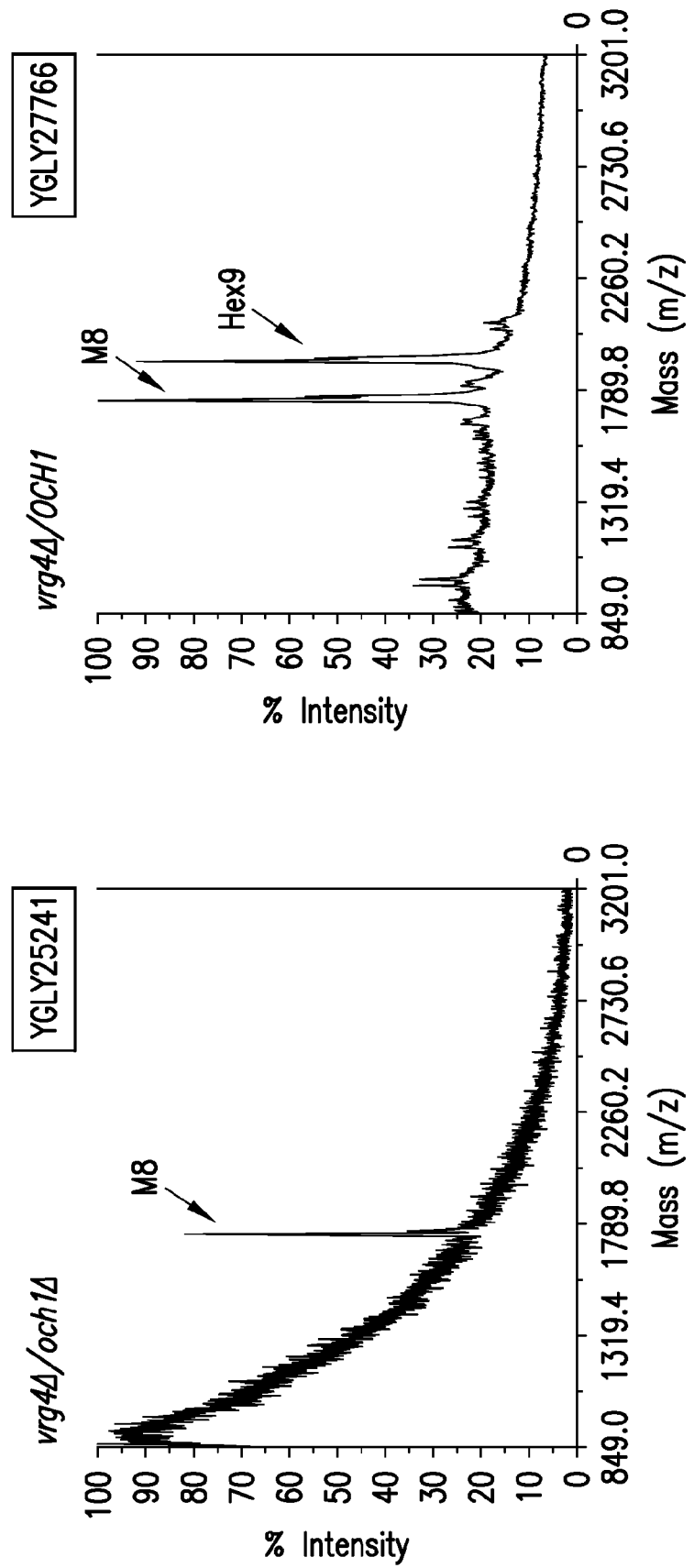

FIGS. 16-1 and 16-2 shows a MALDI-TOF analysis of cell N-glycans extracted from the total cell mass obtained from VRG4 cells and vrg4Δ GFI 1.0 glycoengineered strains in which the OCH1 gene has been re-introduced and thus, OCH1 compared to strains that are och1Δ. The tracings show that the proportion of high mannose N-glycans in compositions of total cell N-glycans obtained from vrg4Δ deletion mutants was significantly reduced even after the OCH1 gene had been reintroduced into the och1Δ cells to render the cells OCH1.

Figures 1, 17:
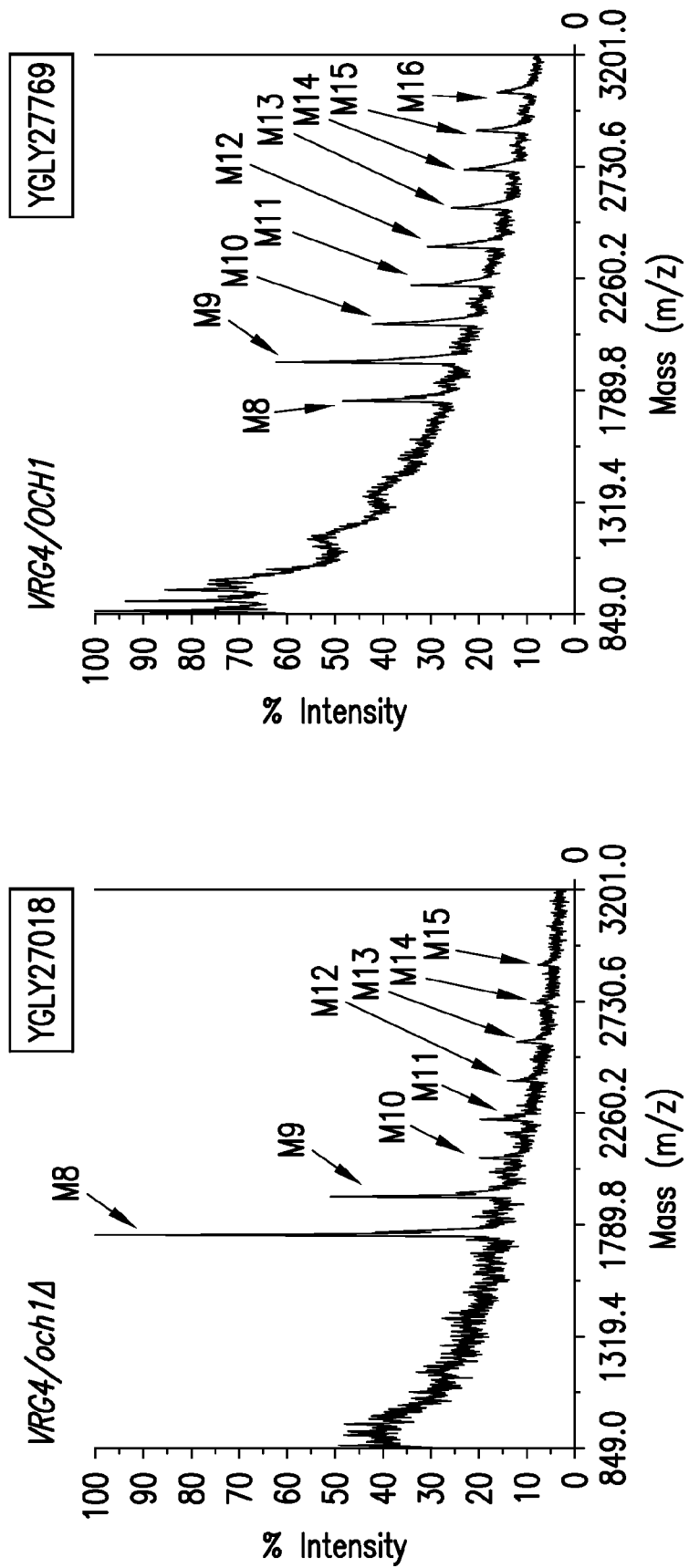
Figures 2, 17:
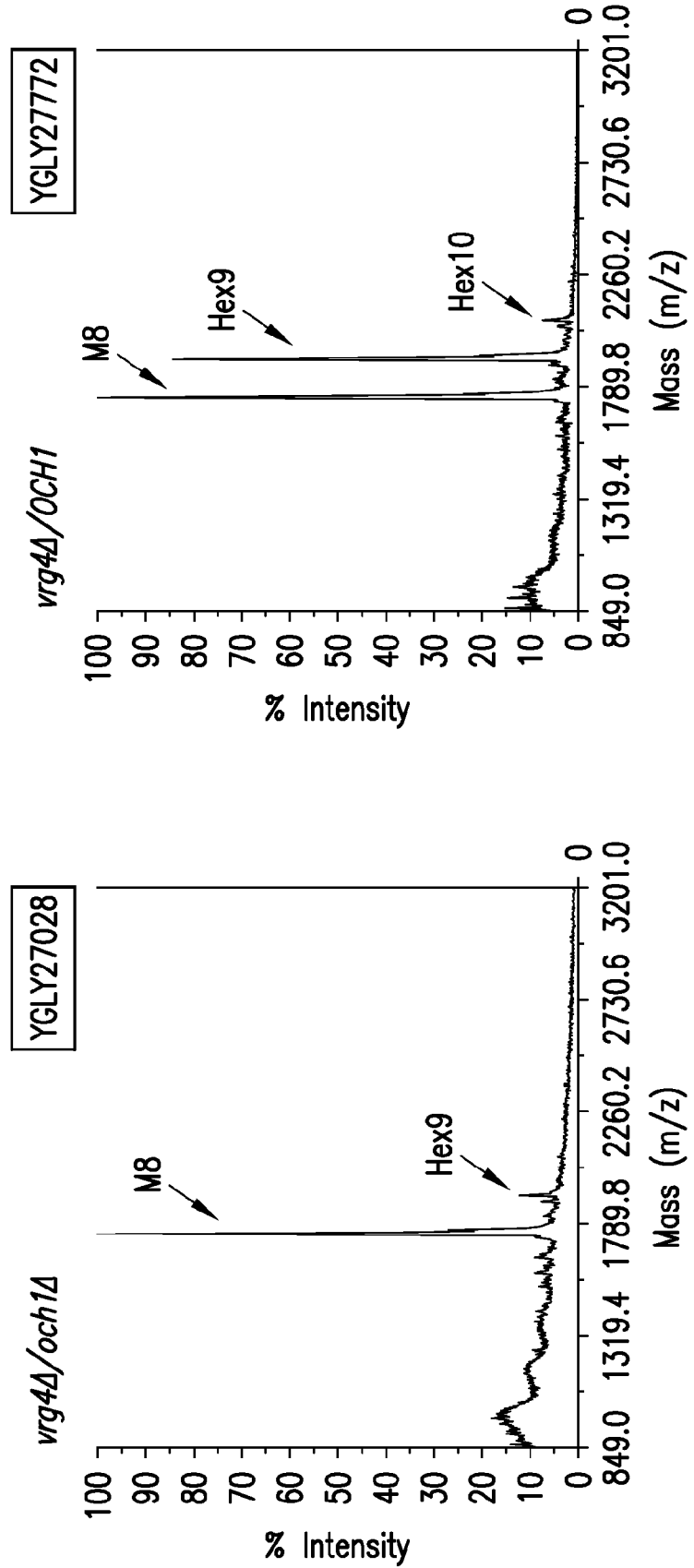

FIGS. 17-1 and 17-2 shows a MALDI-TOF analysis of cell N-glycans extracted from the total cell mass obtained from VRG4 cells and vrg4Δ GFI 1.0 glycoengineered strains in which the OCH1 gene has been re-introduced and thus, OCH1 compared to strains that are och1Δ. The strains further express TNFRII-Fc as a reporter protein. The tracings show that the proportion of high mannose N-glycans to total N-glycans in total cell protein compositions obtained from vrg4Δ deletion mutants that express TNFRII-Fc was significantly reduced even after the OCH1 gene had been reintroduced into the och1Δ cells to render the cells OCH1.

Figures 1, 18:
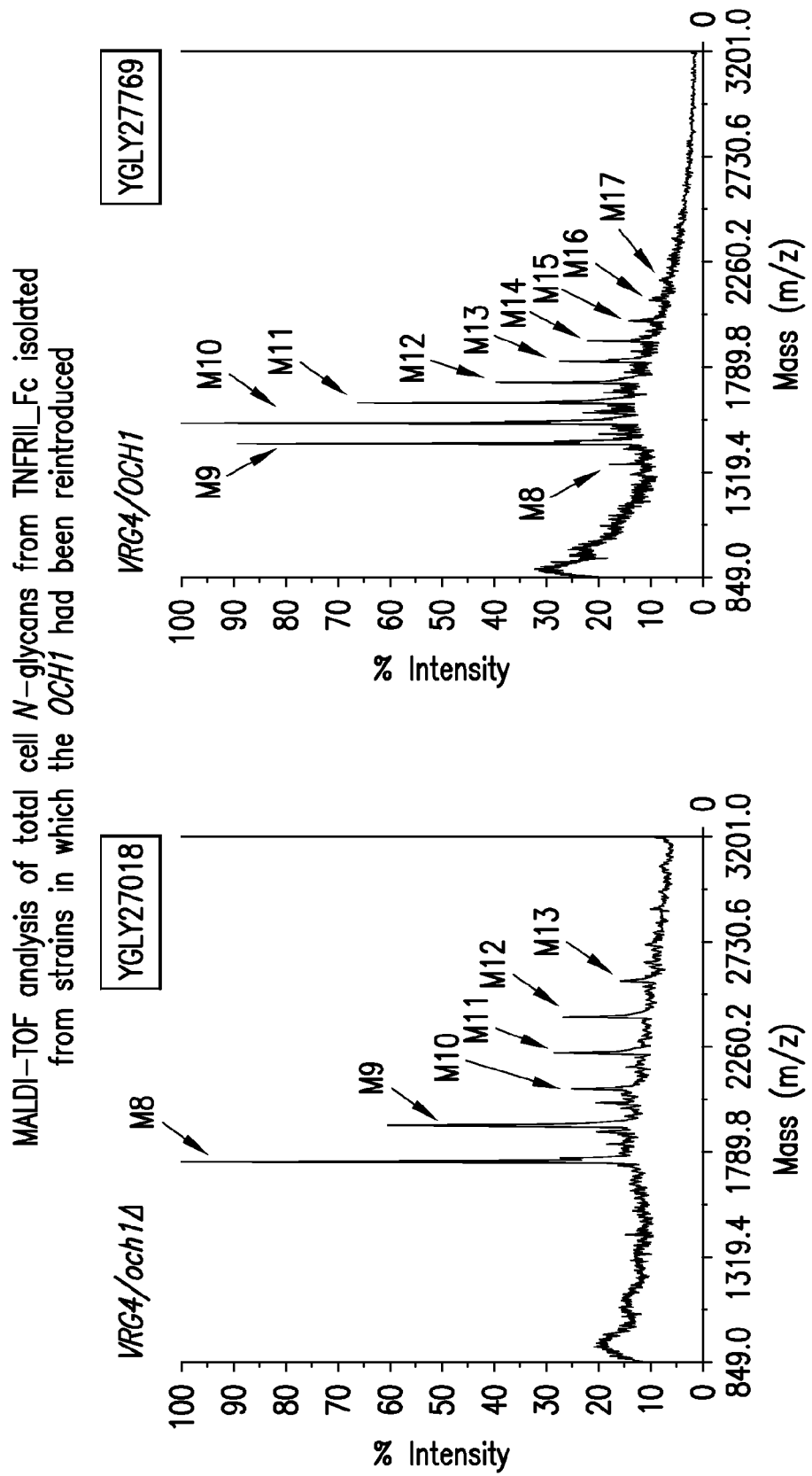
Figures 2, 18:
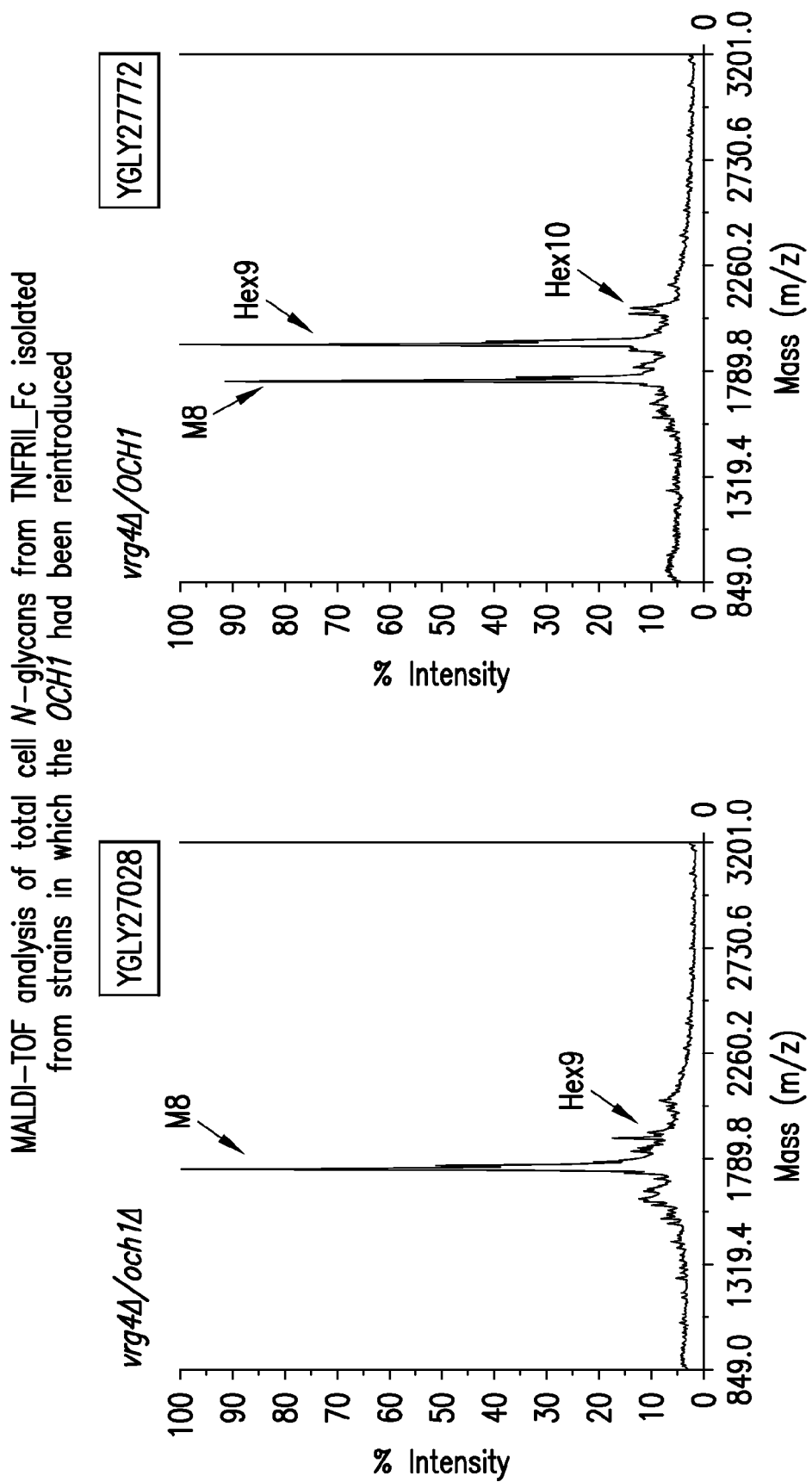

FIGS. 18-1 and 18-2 shows a MALDI-TOF analysis of N-glycans extracted from TNFRII-Fc compositions obtained from VRG4 cells and vrg4Δ GFI 1.0 glycoengineered strains in which the OCH1 gene has been re-introduced compared to strains that are och1Δ. The analyses show that the proportion of high mannose N-glycans to total N-glycans in the TNFRII-Fc compositions obtained from vrg4Δ deletion mutants was significantly reduced even from strains in which the OCH1 gene had been reintroduced.

The N-glycan composition was determined by HPLC as described in Example 3 and the results shown in Table 4. Consistent with the results shown in the previous analyses, the amount of high mannose N-glycans remained significantly reduced even when the OCH1 gene was reintroduced into the vrg4Δ strains. The amount of charged N-glycans with −1 or −2 charge remained reduced as well. However, the reintroduction of the OCH1 gene into the vrg4Δ strain YGLY27772 resulted in about half of the M8 N-glycans being converted to a form with an extra hexose and thus co-migrating in the position expected for M9. In the VRG4 strain there was a more pronounced conversion from Man$_8$GlcNAc$_2$ and higher glycans to Man$_9$GlcNAc$_2$ and higher glycans.

TABLE 4

Quantitative HPLC analysis of total cell N-glycans from VRG4 and vrg4Δ strains that are OCH1 or och1 in mol %

| Strain | Geno-type | M8 | M9 | M10 | M11 | ≥M12 | −1 | −2 | Total |
|---|---|---|---|---|---|---|---|---|---|
| YGLY27018 | och1Δ | 34 | 17 | 3 | 6 | 11 | 22 | 6 | 100 |
| YGLY27769 | och1Δ OCH1 | 2 | 24 | 27 | 12 | 8 | 27 | | 100 |
| YGLY27028 | och1Δ vrg4Δ | 88 | | | | | 12 | | 100 |
| YGLY27772 | och1Δ vrg4Δ OCH1 | 41 | 49 | 1 | | | 9 | | 100 |

M8 - Man$_8$GlcNAc$_2$
M9 - Man$_9$GlcNAc$_2$
M10 - Man$_{10}$GlcNAc$_2$
M11 - Man$_{11}$GlcNAc$_2$
M12 - Man$_{12}$GlcNAc$_2$
−1 - N-glycan migrates in position expected for N-glycan with 1 negative charge
−2 - N-glycan migrates in position expected for N-glycan with 2 negative charges Example 6

As shown in FIGS. 2-1 and 2-2, the attempt to disrupt expression of the VRG4 gene in strain YGLY14-3 using VRG4 knock-out plasmid pGLY8655 appeared to be unsuccessful. While PCR analysis showed that cross-over of the 5' and 3' regions of the VRG4 gene had occurred, PCR analysis using internal PCR primers to the VRG4 gene produced a nucleic acid fragment that suggested YGLY14-3 contained an intact copy of the VRG4 gene that was capable of expressing a functional GDP-mannose transmembrane transporter protein activity. This result suggested that strain YGLY14-3 contained a duplication of the VRG4 gene, which was subsequently lost when strain YGLY3853 was constructed from YGLY14-3, since the VRG4 knock-out was obtainable in strain YGLY3853.

Strain YGLY10-3 is the predecessor to strain YGLY14-3. As shown in FIGS. 2-1 and 2-2 and 3-1 and 3-2, the VRG4 gene could be disrupted in YGLY10-3 and the resulting strain YGLY25243, lacking expression of GDP-mannose transmembrane transporter protein activity, was viable. Strain YGLY14-3 was reconstructed from strain YGLY10-3 as follows.

Figure 20:
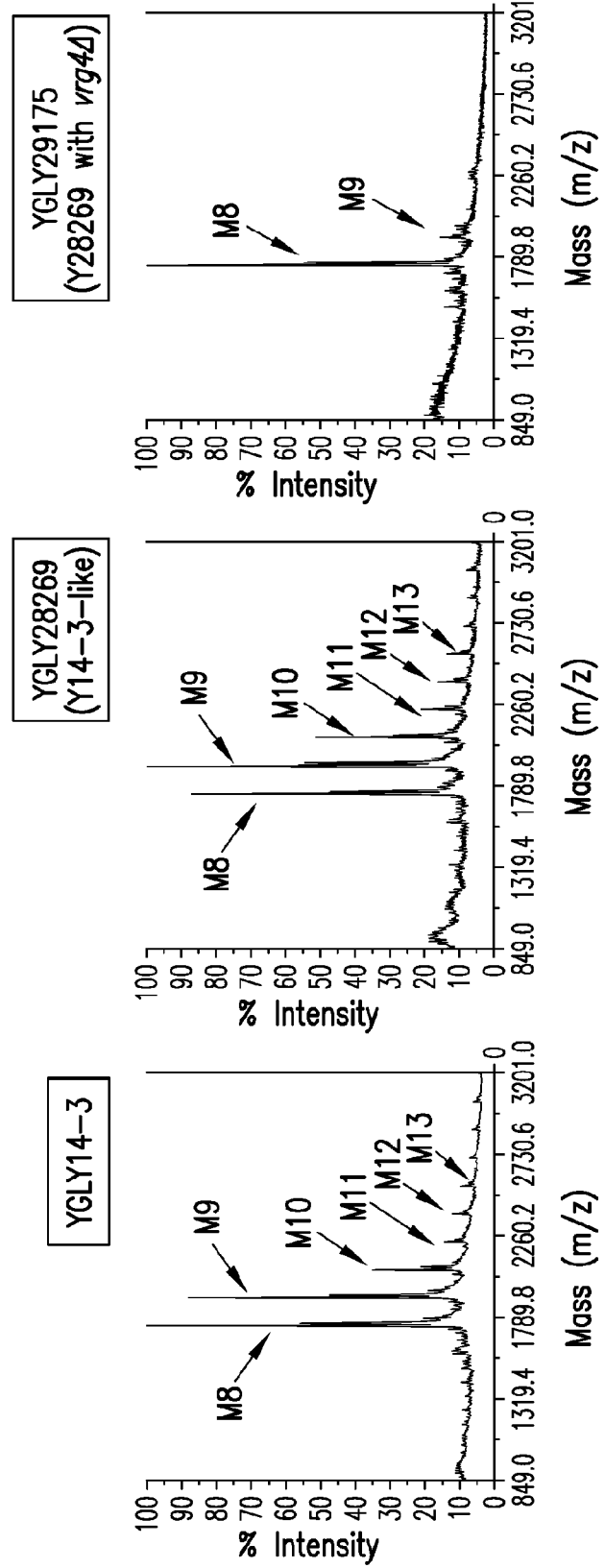
FIG. 20 shows MALDI-TOF analyses of N-glycans extracted from the total cell mass from strain YGLY29175 (vrg4Δ) compared to strain YGLY14-3 and parent strain YGLY28269 (remake of strain YGLY14-3).
Figure 21:
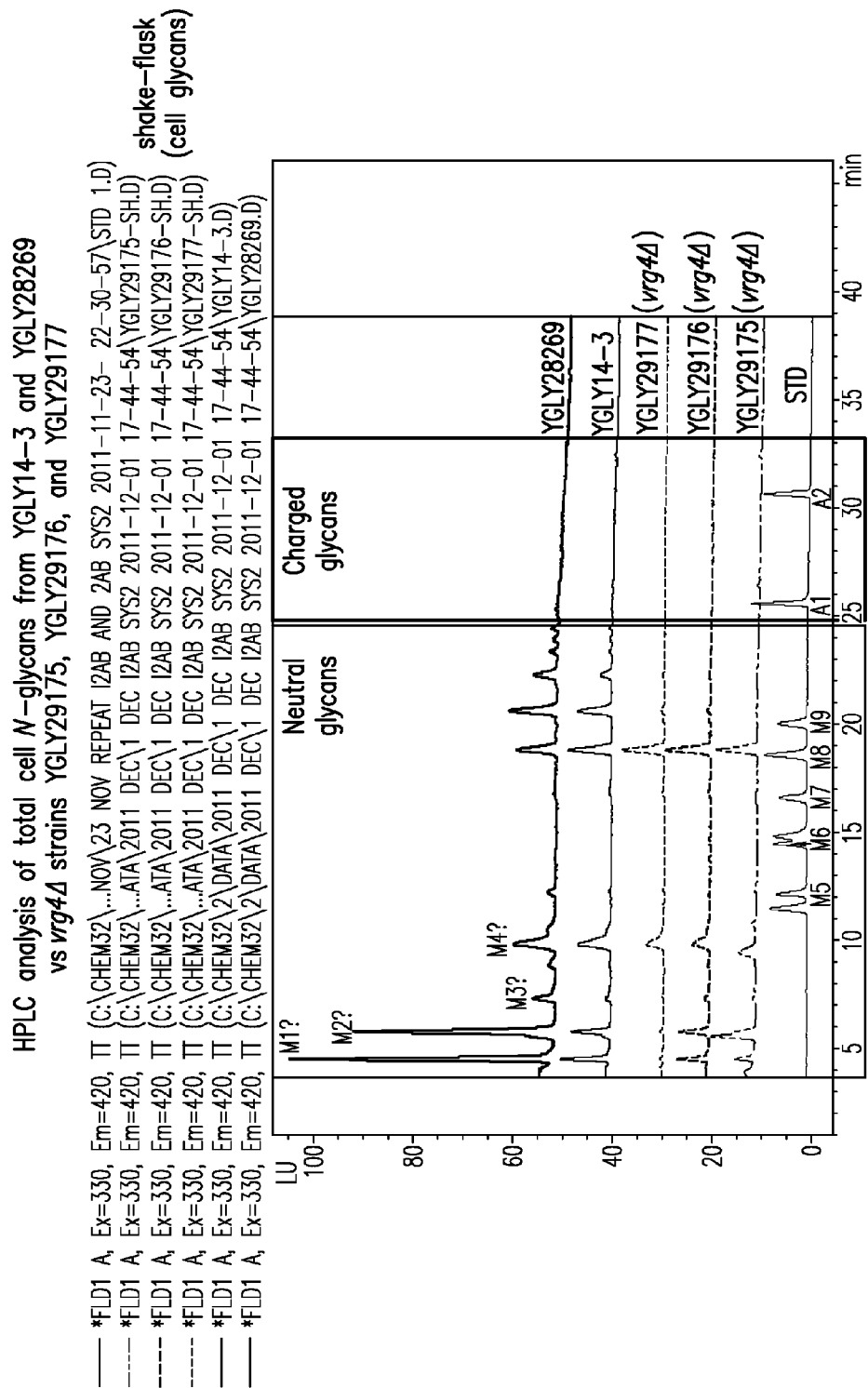
FIG. 21 shows HPLC analyses of N-glycans extracted from the total cell mass from strains YGLY29175, YGLY29176, and YGLY29177 (all vrg4Δ) compared to strain YGLY14-3 and parent strain YGLY28269 (remake of strain YGLY14-3).

Strain YGLY10-3 was counterselected in the presence of 5-fluoroorotic acid (5-FOA) to produce a strain lacking the URA5 marker gene and then transformed with plasmid pGLY45, the same vector that had been used to construct strain YGLY14-3, to delete expression of the PNO1 and MNN4 genes, to produce strain YGLY28269. When this strain was transformed with plasmid pGLY8655 to disrupt expression of the VRG4 gene, knock-out clones (strains YGLY29175, YGLY29176, and YGLY29177) were obtained that were vrg4 (lacking expression of a functional GDP-mannose transmembrane transporter activity) and viable. MALDI-TOF analysis of one of these strains grown in shake-flasks (strain YGLY29175) showed that the total cell glycans isolated from the strain reduced mannosylation, with the prominent N-glycan being Man$_8$GlcNAc$_2$ (FIG. 20). FIG. 21 shows the results of HPLC analyses of the total cell N-glycans isolated from various strains grown in shack-flasks, including the three vrg4 clones (YGLY29175, YGLY29176, and YGLY29177).

Example 7

Previously, it had been difficult to get a vrg4 knock-out in an OCH1 wild-type strain (either NRRL-Y11430 or URA5 complemented YGLY1-3 due to high colony background. In this example, a host strain was constructed by complementing URA5 in YGLY1-3, while knocking-out the ATT1 gene. Transformation of these strains with the VRG4 knock-out plasmid pGLY8655 resulted in a number of vrg4 knock-out strains.

Figures 1, 22:
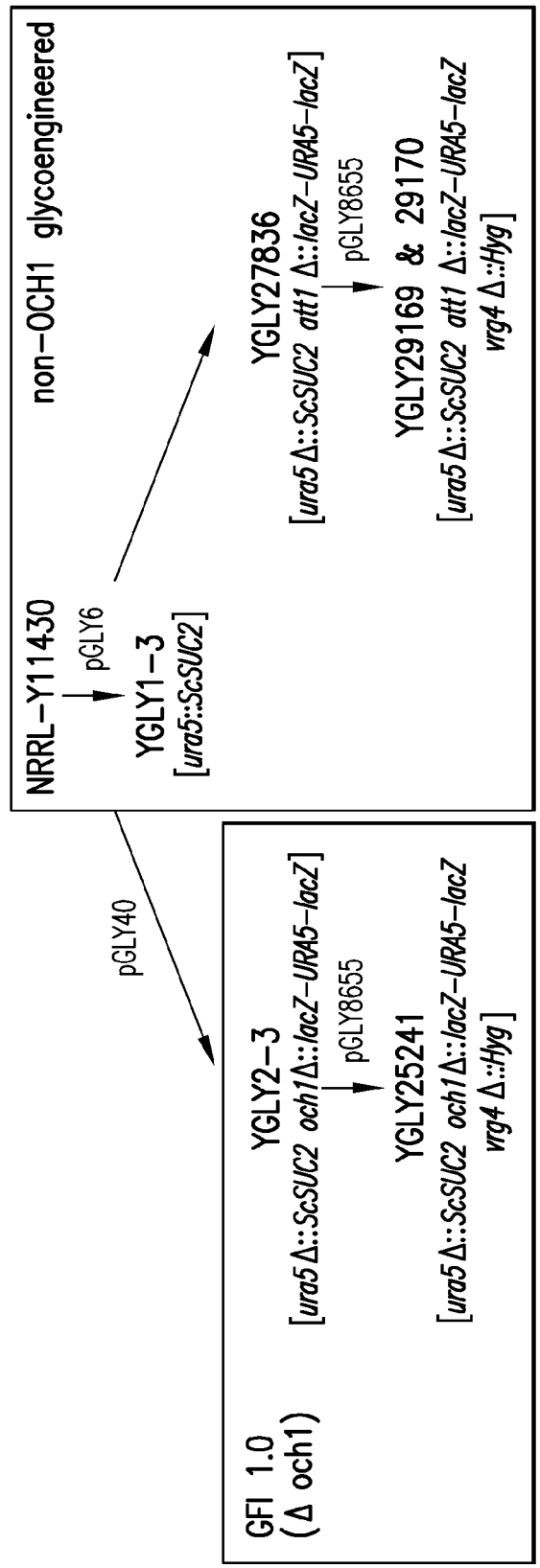
Figures 2, 22:
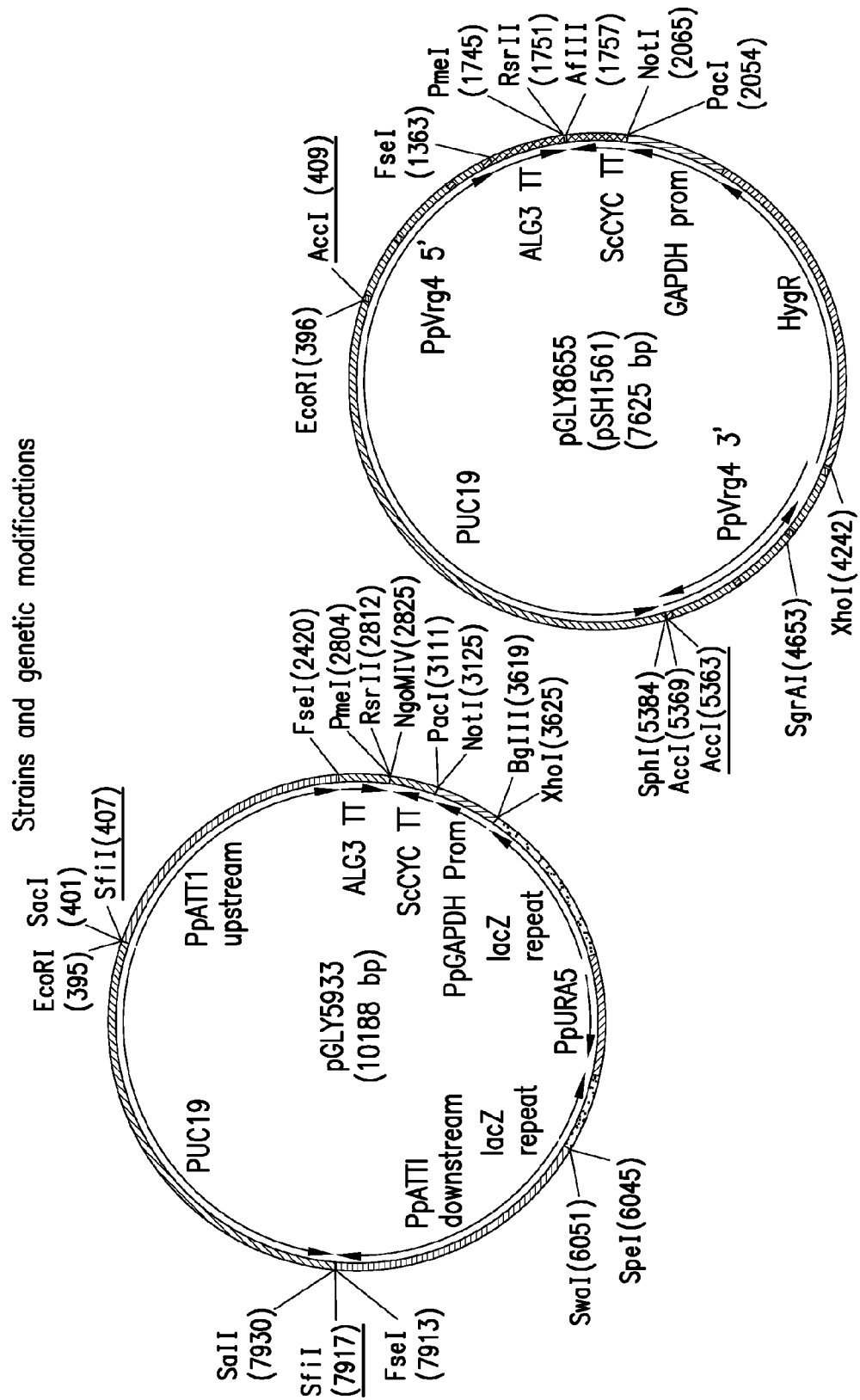

As shown in FIGS. 22-1 and 22-2, strain YGLY1-3 was transformed with plasmid pGLY5933, which disrupts the ATT1 gene. The salient features of the plasmid is that it comprises the URA5 expression cassette described above is flanked on one end with a nucleic acid molecule comprising the 5' or upstream region of the ATT1 gene (SEQ ID NO:74) and the other end with a nucleic acid molecule encoding the 3' or downstream region of the ATT1 gene (SEQ ID NO:75). YGLY1-3 was transformed with plasmid pGLY5933 resulted in a number of strains of which strain YGLY27836 was selected. Strain YGLY27836 was transformed with plasmid pGLY8655 as described in Example 2 to produce strains YGLY29169 and YGLY29170. These strains were att1 and vrg4 knock-outs. Construction of strain YGLY25241, which is an och1 and vrg4 knock-out, is shown in Example 2.

Figures 1, 23:
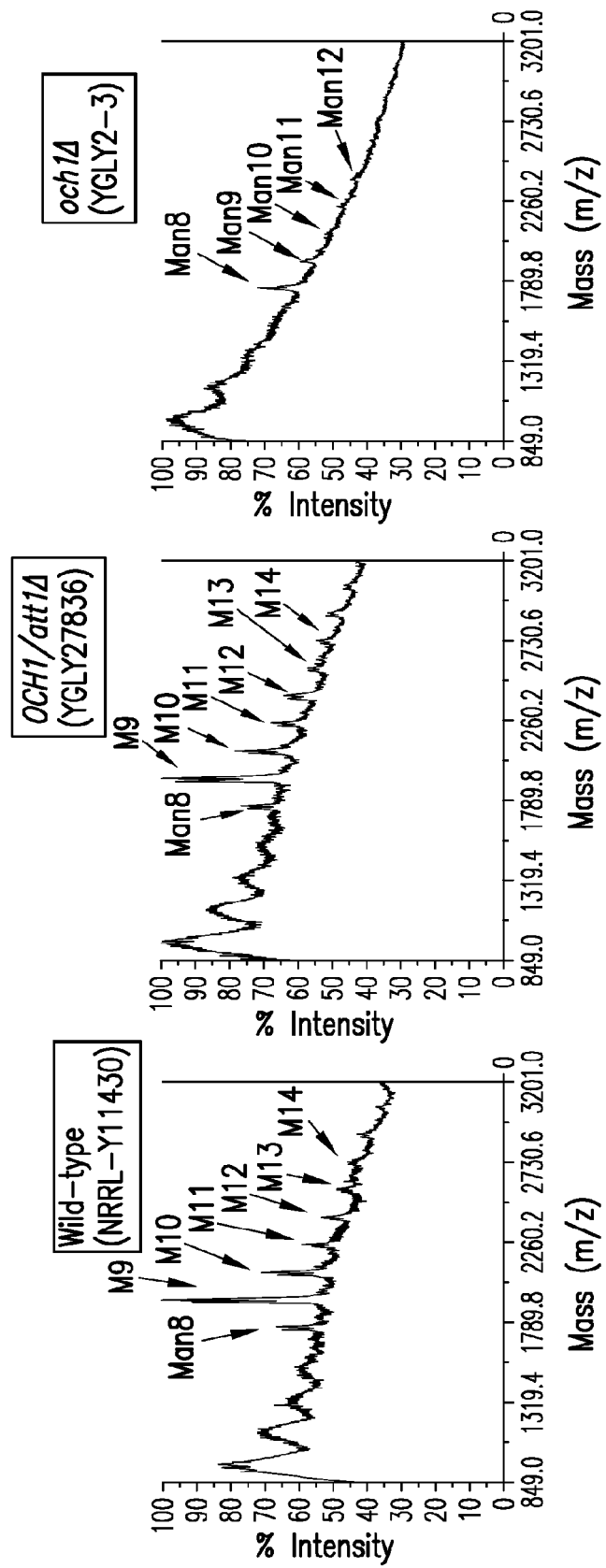
Figures 2, 23:
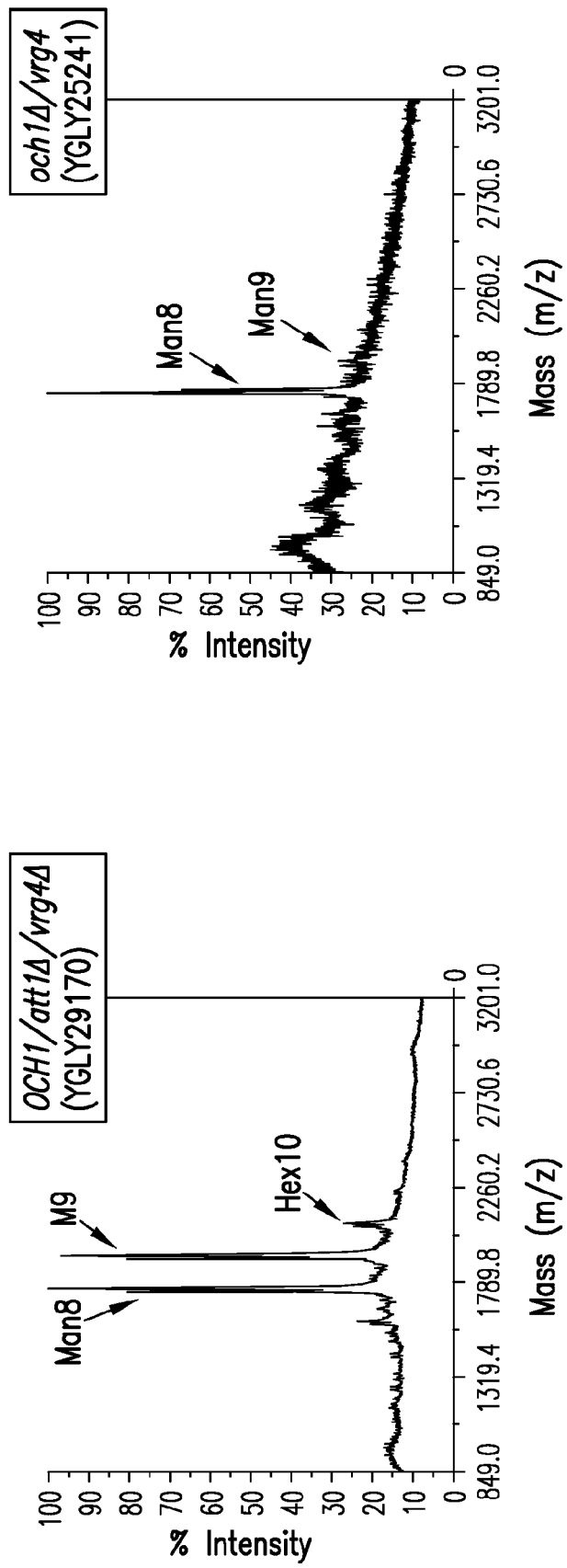

FIGS. 23-1 and 23-2 shows MALDI-TOFs in which the prominent glycans observed in YGLY29170 were Man$_8$GlcNAc$_2$ and Man$_9$GlcNAc$_2$, with no glycans larger than Man$_{10}$GlcNAc$_2$. This is similar to what was observed in strains where the OCH1 gene was reintroduced into the vrg4/och1 strains (See FIGS. 16-1 through 18-2). The results show that expression of the VRG4 gene can be disrupted in a non-glycoengineered strain and that the VRG4 disruption reduced mannosylation as was observed in strains that had been glycoengineered.

Example 8

A VRG4 knock-out vector (pGLY12391) was designed, which when integrated into the *P. pastoris* genome disrupts the endogenous VRG4 ORF while introducing a heterologous VRG4 open reading frame (ORF) operably linked to a heterologous promoter (*S. cerevisiae* DPM1 promoter) and heterologous transcription termination sequence (*S. cerevisiae* DPM1 transcription termination sequence), a Cre recombinase (Cre) gene operably linked to a *P. pastoris* AOX1 promoter and *P. pastoris* AOX1 transcription termination sequences, and a URA5 expression cassette located between two LoxP recombination motifs. Following integration, the growth of the transformed strain in methanol induces expression of the Cre recombinase, which recombines out its own expression cassette along with the URA5 expression cassette and the heterologous VRG4 gene. Successful recombination results in the production of VRG4 knock-out clones. Utilization of this vector to manipulate the non-glycoengineered *P. pastoris* strain YGLY1-3 resulted in VRG4 knock-out clones that when tested displayed reduced mannosyltransferase activity, producing glycoproteins having primarily Man$_8$GlcNAc$_2$ and Man$_9$GlcNAc$_2$ glycoforms.

Table of Sequences

| SEQ ID NO: | Description | Sequence |
|---|---|---|
| 1 | Pichia pastoris (Pp) VRG4 5' knock-out region: (VRG4 flanking region underlined) | GCGAGCTCGTCTACAAACAGTATCACTGTTCGTCAGGAT<br>CCAGAAATCGAACGGGAGATGGAGTTGAAAAGGCAGC<br>AAGAAGAACAGGAAAAGATGGAACTGACTGATATGATC<br>AAGACTGCTCTACGAGACCAGGTAGAGCATATGCCTGC<br>TGCCAAAACGATCGATGTTAACAAAATGACGACAGAAG<br>ATTTGCTAAACTGGCACCTGGGAGATCAGTCCACAAAA<br>AACAGTTCTATCCATCGTGAATTTGATCCATCAGAGCAA<br>GAAGAGTTTAATAGGCTAGCACAAAAGATTGCCAAAGT<br>TAAGATAAAGAACGATCTGAAGGAAAAATTTGGCAAAT<br>CAAAACCGAAACCTTCTGGAAAAGTTCTCCAATTGAAC<br>ACTTCAAATGACGGATCCAAATATCAAAAGGCTCTACA<br>AAAGGAGTTGGCAGATCTTTCCTTCAAGGAGAAATTCA<br>GCGTAGCTACTGAGATCAACGATGATCTGAGTGAGTTA<br>CTCGGCGAGAACATTTTCGTTTCAGACTCTGTTTCAAGA<br>GATGATGCGACCGAAGATATTGACGCGTTGTTGAAGGA<br>CAGCTCAGCTAAAAAGCCCGAAACAATAGAGAGACAA<br>AGCGTTGCGCCGACTTCTCAAAAGCTTAATTCCATCGAT<br>CCCGAGGCCGATAAATTTCTCGATGATCTACTCGGCTAA<br>ATCTCGTACCTATTCTGCTCTTTTCGTGTCGTCTTCCGGT<br>TCACCCCTATCTGCATTCTTATCCATAACTAATTTATTTC<br>ATGTATATTGCCAATTACAATTGCGCGCACCAGCCTCGC<br>GTTTCATTCCACAGCTGTGCAACCATTAGGGAAACGTTT<br>TTCCATCGCGCTTTCCTCCTAATCCTACTGAAAAACTAA<br>AAAAAAACAAGTTGCTTCAGTACTTTTTCTCTTTTGTGG<br>ACGTGTTCTAATACTTATCATCAAAGCAAGACATCGGCC<br>GGCCGC |
| 2 | Pichia pastoris VRG4 3' knock-out region: (VRG4 flanking region underlined and the introduced point mutation at nucleotide 84 is represent by larger text) | CCACTAGTGCTTTGAACAAGCTTCCAATTGCCCTGTCTG<br>GTTTGCTATTTTTCAAGGCTCCTATCAACTTCTATTCTAT<br>CAGCCCTATCTTTATTGGTTTTGCCGCTGGTCTAGTCTA<br>TGCCATTGCCAAGCAGAAGCAAAAGAAGGAAGACGAG<br>TTGCAGTTACCAACTGACAAGAGCTAGATTATAAGGAA<br>AAGAAACACTCTATATATGGTTTATTTATTGATTTTCAG<br>ACTGAAGTCCACTATACCGACTCCCTGATGGATCGAAG<br>AAGTACTATAGATATCAATTTCATTGCACAGATAATCCT<br>TTATATTATCCAAAGTCAAACCTCCACTGCACTCCAAAT<br>AGAATTTCTTGTTTGTGTTAGCCCACTTGTTCTTCAAATT<br>GATGGCTGCGACTTTCAGCCCCTCACCGGTGAAATTGTC<br>CAACATGATAATATCGGCTCCTGCTGCTATGGCCTCATT<br>GGCTTCAGCTTCGTCTTGCACTTCCACCTCAATCTTAGT<br>GCTAAATCCAATCACTTTTTGAGCACTTTCAATGGCCTT<br>GGTGATCGAACCAGTTGACCAGATATGGTTGTCTTTCAG<br>CATAATCATAGAACTTAGATCATAACGGTGACTGTCGC<br>ATCCACCAACGAGCATTGAGTATTTTTCCAACAATCGTA<br>ATCCTGGAGTAGTCTTTCTGGTTCCCGCAATGATTCCTTT<br>GTATCCAGCTTCTCTAGCCCTTTTTATAGTAATATAGCTT<br>TGAGTAGCGACCCCAGAGCATCTTGCTAGAATATTCAG<br>CGATAACCGTTCAGCGAGGAGGATGTTTCGAACAGGGC<br>CCTTAACGAGTGCAACTTTCACTTTACCCTCGTCTCCAC<br>CACAAATGTAATCCCCTTCCTTTAGAAACCACTCGACCT<br>CCAAACCGCATTGTTTGTAAACCTCTTGTGCAAACGGTA<br>CTCCACTAATGACTCCGTTGGACTTTATCCATAGAGTAG<br>CACTCTGCAGGTTTTCACCCACCACATATCCTCCGTAAT<br>CAAAAGAAGGGGTATCCTCGTCTAGCCAGCTGGTGATA<br>TCTTTCTTCCATTTTCCGTCCACAGGTAAAAGATGGGCA<br>AATTCGGGGTTGGGGTTGGAGAAACTCATAGTCGTCTA<br>CGTCGACCC |
| 3 | Pichia pastoris VRG4 gene Codons: nucleotides 1001 to 1990 (The native nucleotide at 1892, represented in larger text, is mutated by vector pGLY8655 with no | AAATATGCCAGAAGGCCGATGATAGATAATTCATACAG<br>ATATGGTTTGGAGTCTACAAACAGTATCACTGTTCGTCA<br>GGATCCAGAAATCGAACGGGAGATGGAGTTGAAAAGG<br>CAGCAAGAAGAACAGGAAAAGATGGAACTGACTGATA<br>TGATCAAGACTGCTCTACGAGACCAGGTAGAGCATATG<br>CCTGCTGCCAAAACGATCGATGTTAACAAAATGACGAC<br>AGAAGATTTGCTAAACTGGCACCTGGGAGATCAGTCCA<br>CAAAAAACAGTTCTATCCATCGTGAATTTGATCCATCAG<br>AGCAAGAAGAGTTTAATAGGCTAGCACAAAAGATTGCC<br>AAAGTTAAGATAAAGAACGATCTGAAGGAAAAATTTGG<br>CAAATCAAAACCGAAACCTTCTGGAAAAGTTCTCCAAT<br>TGAACACTTCAAATGACGGATCCAAATATCAAAAGGCT<br>CTACAAAAGGAGTTGGCAGATCTTTCCTTCAAGGAGAA<br>ATTCAGCGTAGCTACTGAGATCAACGATGATCTGAGTG<br>AGTTACTCGGCGAGAACATTTTCGTTTCAGACTCTGTTT<br>CAAGAGATGATGCGACCGAAGATATTGACGCGTTGTTG<br>AAGGACAGCTCAGCTAAAAAGCCCGAAACAATAGAGA |

Table of Sequences

| SEQ ID NO: | Description | Sequence |
|---|---|---|
| | resulting phenotype) | GACAAAGCGTTGCGCCGACTTCTCAAAAGCTTAATTCCA<br>TCGATCCCGAGGCCGATAAATTTCTCGATGATCTACTCG<br>GCTAAATCTCGTACCTATTCTGCTCTTTTCGTGTCGTCTT<br>CCGGTTCACCCCTATCTGCATTCTTATCCATAACTAATTT<br>ATTTCATGTATATTGCCAATTACAATTGCGCGCACCAGC<br>CTCGCGTTTCATTCCACAGCTGTGCAACCATTAGGGAAA<br>CGTTTTTCCATCGCGCTTTCCTCCTAATCCTACTGAAAA<br>ACTAAAAAAAAACAAGTTGCTTCAGTACTTTTTCTCTTT<br>TGTGGACGTGTTCTAATACTTATCATCAAAGCAAGACAT<br>CATGGCTGACAAAGGATCGGTAGCGGCTAAATCGCTTA<br>CCAACTCTGCACCCTTATCCATCTTTTCTTACTGTGCTGC<br>ATCAATTCTGATGACAGTTACCAATAAGTATGCCGTGTC<br>CGGTGTCGATTTCAACTTTAACTTCTTTTTGCTTGCCGTT<br>CAGGGAATCGTTTGTATTACCTTGATTAGCTCGTTGAAG<br>CAATTGAATGTTATCACCTTTAGAGAGTTCAACAAGGTT<br>GAAGCAAAGAAATGGTTCCCAATCGCCGTGCTGTTAGT<br>TGTCATGATTTATACCTCCTCCAAGGCTCTACAGTATCT<br>GAGCATTCCAATTTACACGATATTCAAAAACTTGACCAT<br>TATCCTTATTGCTTATGGTGAAGTCATCTGGTTCGGAGG<br>CCGTGTGACCAACTTGGCTCTGGGCTCGTTTGTATTGAT<br>GGTGCTCTCCTCTGCAGTGGCTTCTTATGGTGATTCTAA<br>TGTTGACACTGGTAAACTCAATTTTAACATTGGCTATTT<br>CTGGATGTTCACCAACTGTTTCTCCTCTGCCGCATTTGTG<br>TTGTTCATGAGAAAGAGAATAAAGTTGACCAACTTCAA<br>AGACTTTGACACCATGTATTACAACAACCTTCTCTCCAT<br>TCCAATTTTGCTCTTTGCATCTTTGACTACTGAAGACTG<br>GTCCGCTAAAAACATAGCTCAGAACTTCCCTGAAGACA<br>CCAAATACGCTGTCATCGCTTCCATGATTATTTCAGGAA<br>TGTCTGCCGTGGGTATCTCATACACATCTGCATGGTGTG<br>TCCGTGTGACATCTTCCACGACATACTCGATGGTTGGTG<br>CTTTGAACAAGCTTCCAATTGCCCTGTCTGGTTTGCTATT<br>TTTCAAGGCTCCTATCAACTTCTATTCTATCAGCTCTAT<br>CTTTATTGGTTTTGCCGCTGGTCTAGTCTATGCCATTGCC<br>AAGCAGAAGCAAAAGAAGGAAGACGAGTTGCAGTTAC<br>CAACTGACAAGAGCTAGATTATAAGGAAAAGAAACACT<br>CTATATATGGTTTATTTATTGATTTTCAGACTGAAGTCC<br>ACTATACCGACTCCCTGATGGATCGAAGAAGTACTATA<br>GATATCAATTTCATTGCACAGATAATCCTTTATATTATC<br>CAAAGTCAAACCTCCACTGCACTCCAAATAGAATTTCTT<br>GTTTGTGTTAGCCCACTTGTTCTTCAAATTGATGGCTGC<br>GACTTTCAGCCCCTCACCGGTGAAATTGTCCAACATGAT<br>AATATCGGCTCCTGCTGCTATGGCCTCATTGGCTTCAGC<br>TTCGTCTTGCACTTCCACCTCAATCTTAGTGCTAAATCC<br>AATCACTTTTTGAGCACTTTCAATGGCCTTGGTGATCGA<br>ACCAGTTGACCAGATATGGTTGTCTTTCAGCATAATCAT<br>AGAACTTAGATCATAACGGTGACTGTCGCATCCACCAA<br>CGAGCATTGAGTATTTTTCCAACAATCGTAATCCTGGAG<br>TAGTCTTTCTGGTTCCCGCAATGATTCCTTTGTATCCAGC<br>TTCTCTAGCCCTTTTTATAGTAATATAGCTTTGAGTAGC<br>GACCCCAGAGCATCTTGCTAGAATATTCAGCGATAACC<br>GTTCAGCGAGGAGGATGTTTCGAACAGGGCCCTTAACG<br>AGTGCAACTTTCACTTTACCCTCGTCTCCACCACAAATG<br>TAATCCCCTTCCTTTAGAAACCACTCGACCTCCAAACCG<br>CATTGTTTGTAAACCTCTTGTGCAAACGGTACTCCACTA<br>ATGACTCCGTTGGACTTTATCCATAGAGTAGCACTCTGC<br>AGGTTTTCACCCACCACATATCCTCCGTAATCAAAAGAA<br>GGGGTATCCTCGTCTAGCCAGCTGGTGATATCTTTCTTC<br>CATTTTCCGTCCACAGGTAAAAGATGGGCAAATTCGGG<br>GTTGGGGTTGGAGAAACTCATAGTCGTCTACAAATGTG<br>AAGGAAATGGATGATATTGTTAGGCCATTCTCCGCGAG<br>TCATTCCGGG |
| 4 | HSA-<br>TNFR-Fc<br>double<br>mutein ORF | MKWVTFISLLFLFSSAYSLPAQVAFTPYAPEPGSTCRLREY<br>YDQTAQMCCSKCSPGQHAKVFCTKTSDTVCDSCEDSTYT<br>QLWNWVPECLSCGSRCSSDQVETQACTREQNRICTCRPG<br>WYCALSKQEGCRLCAPLRKCRPGFGVARPGTETSDVVCK<br>PCAPGTFSNTTSSTDICRPHQICNVVAIPGNASMDAVCTSTS<br>PTRSMAPGAVHLPQPVSTRSQHTQPTPEPSTAPSTSFLLPM<br>GPSPPAEGSTGDEPKSCDKTHTCPPCPAPELLGGPSVFLAPP<br>KPKDTLMISRTPEVTCVVADVSHEDPEVKFNWYVDGVEV<br>HNAKTKPREEQYNSTYRVVSVLTVLHQDWLNGKEYKCK<br>VSNKALPAPIEKTISKAKGQPREPQVYTLPPSREEMTKNQV<br>SLTCLVKGFYPSDIAVEWESNGQPENNYKTTPPVLDSDGSF |

| SEQ ID NO: | Description | Sequence |
|---|---|---|
| | | FLYSKLTVDKSRWQQGNVFSCSVMHEALHNHYTQKSLSL<br>SPG |
| 5 | DNA sequence encoding HSA-TNFR-Fc double mutein ORF | ATGAAGTGGGTTACCTTTATCTCTTTGTTGTTTCTTTTCT<br>CTTCTGCTTACTCTCTGCCAGCTCAAGTTGCTTTTACTCC<br>ATACGCTCCAGAACCAGGTTCTACTTGTAGATTGAGAG<br>AGTACTACGACCAAACTGCTCAGATGTGTTGTTCCAAGT<br>GTTCTCCAGGTCAACACGCTAAGGTTTTCTGTACTAAGA<br>CTTCCGACACTGTTTGTGACTCTTGTGAGGACTCCACTT<br>ACACTCAATTGTGGAACTGGGTTCCAGAATGTTTGTCCT<br>GTGGTTCCAGATGTTCTTCCGACCAAGTTGAGACTCAGG<br>CTTGTACTAGAGAGCAGAACAGAATCTGTACTTGTAGA<br>CCTGGTTGGTACTGTGCTTTGTCCAAGCAAGAGGGTTGT<br>AGATTGTGTGCTCCATTGAGAAAGTGTAGACCAGGTTTC<br>GGTGTTGCTAGACCAGGTACAGAAACTTCCGACGTTGTT<br>TGTAAGCCATGTGCTCCAGGAACTTTCTCCAACACTACT<br>TCCTCCACTGACATCTGTAGACCACACCAAATCTGTAAC<br>GTTGTTGCTATCCCAGGTAACGCTTCTATGGACGCTGTT<br>TGTACTTCTACTTCCCCAACTAGATCCATGGCTCCAGGT<br>GCTGTTCATTTGCCACAGCCAGTTTCCACTAGATCCCAA<br>CACACTCAACCAACTCCAGAACCATCTACTGCTCCATCC<br>ACTTCCTTTTTGTTGCCAATGGGACCATCTCCACCTGCT<br>GAAGGTTCTACTGGTGACGAGCCAAAGTCCTGTGACAA<br>GACACATACTTGTCCACCATGTCCAGCTCCAGAATTGTT<br>GGGTGGTCCATCCGTTTTCTTGGCCCCACCAAAGCCAAA<br>GGACACTTTGATGATCTCCAGAACTCCAGAGGTTACATG<br>TGTTGTTGCTGACGTTTCTCACGAGGACCCAGAGGTTAA<br>GTTCAACTGGTACGTTGACGGTGTTGAAGTTCACAACGC<br>TAAGACTAAGCCAAGAGAAGAGCAGTACAACTCCACTT<br>ACAGAGTTGTTTCCGTTTTGACTGTTTTGCACCAGGATT<br>GGTTGAACGGTAAAGAATACAAGTGTAAGGTTTCCAAC<br>AAGGCTTTGCCAGCTCCAATCGAAAAGACAATCTCCAA<br>GGCTAAGGGTCAACCAAGAGAGCCACAGGTTTACACTT<br>TGCCACCATCCAGAGAAGAGATGACTAAGAACCAGGTT<br>TCCTTGACTTGTTTGGTTAAAGGATTCTACCCATCCGAC<br>ATTGCTGTTGAATGGGAATCTAACGGTCAACCAGAGAA<br>CAACTACAAGACTACTCCACCAGTTTTGGATTCTGACGG<br>TTCCTTCTTCTTGTACTCCAAGTTGACTGTTGACAAGTCC<br>AGATGGCAACAGGGTAACGTTTTCTCCTGTTCCGTTATG<br>CATGAGGCTTTGCACAACCACTACACTCAAAAGTCCTTG<br>TCTTTGTCCCCAGGTTAG |
| 6 | α-mating factor prepro EPO ORF | MRFPSIFTAVLFAASSALAAPVNTTTEDETAQIPAEAVIGYS<br>DLEGDFDVAVLPFSNSTNNGLLFINTTIASIAAKEEGVSLEK<br>REAEAEFAPPRLICDSRVLERYILEAKEAENVTMGCAEGPR<br>LSENITVPDTKVNFYAWKRMKVEEQAVEVWQGLSLLSEA<br>ILQAQALQANSSQPPESLQLHIDKAISGLRSLTSLLRVLGAQ<br>KELMSPPDATQAAPLRTLTADTFCKLFRVYSNFLRGKLKL<br>YTGEACRRGDRGLEQKLISEEDLNSAVDHHHHHH |
| 7 | DNA sequence encoding α-mating factor prepro EPO ORF | ATGAGATTTCCTTCAATTTTTACTGCTGTTTTATTCGCAG<br>CATCCTCCGCATTAGCTGCTCCAGTCAACACTACAACAG<br>AAGATGAAACGGCACAAATTCCGGCTGAAGCTGTCATC<br>GGTTACTCAGATTTAGAAGGGGATTTCGATGTTGCTGTT<br>TTGCCATTTTCCAACAGCACAAATAACGGGTTATTGTTT<br>ATAAATACTACTATTGCCAGCATTGCTGCTAAAGAAGA<br>AGGGGTATCTCTGGAGAAAAGAGAGGCTGAAGCTGAGT<br>TCGCTCCCCCACGCCTCATTTGCGACAGTCGCGTTCTGG<br>AGAGGTACATCTTGGAGGCCAAGGAGGCAGAAAATGTC<br>ACAATGGGCTGTGCAGAAGGTCCCAGACTGAGTGAGAA<br>TATTACCGTCCCAGATACCAAAGTCAACTTCTACGCTTG<br>GAAAAGAATGAAGGTGGAAGAACAGGCTGTAGAAGTTT<br>GGCAAGGCCTGTCTCTGCTCTCAGAAGCCATCCTGCAGG<br>CCCAGGCTCTGCAGGCCAATTCCTCCCAGCCACCAGAG<br>AGTCTTCAGCTTCATATAGACAAAGCCATCAGTGGGCTA<br>CGTAGCCTCACTTCACTGCTTCGGGTGCTGGGAGCTCAG<br>AAGGAATTGATGTCGCCTCCAGACGCCACCCAAGCCGC<br>TCCACTCCGAACACTCACAGCGGATACTTTCTGCAAGCT<br>CTTCCGGGTCTACTCCAACTTCCTCCGGGGGAAACTGAA<br>GCTGTACACGGGGGAGGCCTGCAGGAGAGGGGACAGG<br>GTCTGGAACAAAAACTCATCTCAGAAGAGGATCTGAA<br>TAGCGCCGTCGACCATCATCATCATCATCATTGA |

| SEQ ID NO: | Description | Sequence |
|---|---|---|
| 8 | OCH1 Codons underlined | CAATACAAGGTTGTCTTGGAGTTTACATTGACCAGATGA<br>TTTGGCTTTTTCTCTGTTCAATTCACATTTTTCAGCGAGA<br>ATCGGATTGACGGAGAAATGGCGGGGTGTGGGGTGGAT<br>AGATGGCAGAAATGCTCGCAATCACCGCGAAAGAAAGA<br>CTTTATGGAATAGAACTACTGGGTGGTGTAAGGATTAC<br>ATAGCTAGTCCAATGGAGTCCGTTGGAAAGGTAAGAAG<br>AAGCTAAAACCGGCTAAGTAACTAGGGAAGAATGATCA<br>GACTTTGATTTGATGAGGTCTGAAAATACTCTGCTGCTT<br>TTTCAGTTGCTTTTTCCCTGCAACCTATCATTTTCCTTTT<br>CATAAGCCTGCCTTTTCTGTTTTCACTTATATGAGTTCCG<br>CCGAGACTTCCCCAAATTCTCTCCTGGAACATTCTCTAT<br>CGCTCTCCTTCCAAGTTGCGCCCCCTGGCACTGCCTAGT<br>AATATTACCACGCGACTTATATTCAGTTCCACAATTTCC<br>AGTGTTCGTAGCAAATATCATCAGCCATGGCGAAGGCA<br>GATGGCAGTTTGCTCTACTATAATCCTCACAATCCACCC<br>AGAAGGTATTACTTCTACATGGCTATATTCGCCGTTTCT<br>GTCATTTGCGTTTTGTACGGACCCTCACAACAATTATCA<br>TCTCCAAAAATAGACTATGATCCATTGACGCTCCGATCA<br>CTTGATTTGAAGACTTTGGAAGCTCCTTCACAGTTGAGT<br>CCAGGCACCGTAGAAGATAATCTTCGAAGACAATTGGA<br>GTTTCATTTTCCTTACCGCAGTTACGAACCTTTTCCCCAA<br>CATATTTGGCAAACGTGGAAAGTTTCTCCCTCTGATAGT<br>TCCTTTCCGAAAAACTTCAAAGACTTAGGTGAAAGTTGG<br>CTGCAAAGGTCCCCAAATTATGATCATTTTGTGATACCC<br>GATGATGCAGCATGGGAACTTATTCACCATGAATACGA<br>ACGTGTACCAGAAGTCTTGGAAGCTTTCCACCTGCTACC<br>AGAGCCCATTCTAAAGGCCGATTTTTTCAGGTATTTGAT<br>TCTTTTTGCCCGTGGAGGACTGTATGCTGACATGGACAC<br>TATGTTATTAAAACCAATAGAATCGTGGCTGACTTTCAA<br>TGAAACTATTGGTGGAGTAAAAAACAATGCTGGGTTGG<br>TCATTGGTATTGAGGCTGATCCTGATAGACCTGATTGGC<br>ACGACTGGTATGCTAGAAGGATACAATTTTGCCAATGG<br>GCAATTCAGTCCAAACGAGGACACCCAGCACTGCGTGA<br>ACTGATTGTAAGAGTTGTCAGCACGACTTTACGGAAAG<br>AGAAAAGCGGTTACTTGAACATGGTGGAAGGAAAGGAT<br>CGTGGAAGTGATGTGATGGACTGGACGGGTCCAGGAAT<br>ATTTACAGACACTCTATTTGATTATATGACTAATGTCAA<br>TACAACAGGCCACTCAGGCCAAGGAATTGGAGCTGGCT<br>CAGCGTATTACAATGCCTTATCGTTGGAAGAACGTGATG<br>CCCTCTCTGCCCGCCCGAACGGAGAGATGTTAAAAGAG<br>AAAGTCCCAGGTAAATATGCACAGCAGGTTGTTTTATG<br>GGAACAATTTACCAACCTGCGCTCCCCCAAATTAATCGA<br>CGATATTCTTATTCTTCCGATCACCAGCTTCAGTCCAGG<br>GATTGGCCACAGTGGAGCTGGAGATTTGAACCATCACC<br>TTGCATATATTAGGCATACATTTGAAGGAAGTTGGAAG<br>GACTAAAGAAAGCTAGAGTAAAATAGATATAGCGAGAT<br>TAGAGAATGAATACCTTCTTCTAAGCGATCGTCCGTCAT<br>CATAGAATATCATGGACTGTATAGTTTTTTTTTTGTACAT<br>ATAATGATTAAACGGTCATCCAACATCTCGTTGACAGAT<br>CTCTCAGTACGCGAAATCCCTGACTATCAAAGCAAGAA<br>CCGATGAAGAAAAAACAACAGTAACCCAAACACCAC<br>AACAAACACTTTATCTTCTCCCCCCCAACACCAATCATC<br>AAAGAGATGTCGGAACCAAACACCAAGAAGCAAAAAC<br>TAACCCCATATAAAAACATCCTGGTAGATAATGCTGGT<br>AACCCGCTCTCCTTCCATATTCTGGGCTACTTCACGAAG<br>TCTGACCGGTCTCAGTTGATCAACATGATCCTCGAAATG<br>GGTGGCAAGATCGTTCCAGACCTGCCTCCTCTGGTAGAT<br>GGAGTGTTGTTTTTGACAGGGGATTACAAGTCTATTGAT<br>GAAGATACC |
| 9 | S. cerevisiae invertase gene (ScSUC2) ORF underlined | AGGCCTCGCAACAACCTATAATTGAGTTAAGTGCCTTTC<br>CAAGCTAAAAAGTTTGAGGTTATAGGGGCTTAGCATCC<br>ACACGTCACAATCTCGGGTATCGAGTATAGTATGTAGA<br>ATTACGGCAGGAGGTTTCCCAATGAACAAAGGACAGGG<br>GCACGGTGAGCTGTCGAAGGTATCCATTTTATCATGTTT<br>CGTTTGTACAAGCACGACATACTAAGACATTTACCGTAT<br>GGGAGTTGTTGTCCTAGCGTAGTTCTCGCTCCCCCAGCA<br>AAGCTCAAAAAGTACGTCATTTAGAATAGTTTGTGAG<br>CAAATTACCAGTCGGTATGCTACGTTAGAAAGGCCCAC<br>AGTATTCTTCTACCAAAGGCGTGCCTTTGTTGAACTCGA<br>TCCATTATGAGGGCTTCCATTATTCCCCGCATTTTTATTA<br>CTCTGAACAGGAATAAAAGAGAAAAACCCAGTTTAGGA<br>AATTATCCGGGGGCGAAGAAATACGCGTAGCGTTAATC |

| SEQ ID NO: | Description | Sequence |
|---|---|---|
| | | GACCCCACGTCCAGGGTTTTTCCATGGAGGTTTCTGGAA
AAACTGACGAGGAATGTGATTATAAATCCCTTTATGTGA
TGTCTAAGACTTTTAAGGTACGCCCGATGTTTGCCTATT
ACCATCATAGAGACGTTTCTTTTCGAGGAATGCTTAAAC
GACTTTGTTTGACAAAAATGTTGCCTAAGGGCTCTATAG
TAAACCATTTGGAAGAAAGATTTGACGACTTTTTTTTTT
TGGATTTCGATCCTATAATCCTTCCTCCTGAAAAGAAAC
ATATAAATAGATATGTATTATTCTTCAAAACATTCTCTT
GTTCTTGTGCTTTTTTTTTACCATATATCTTACTTTTTTTT
TTCTCTCAGAGAAACAAGCAAAACAAAAAGCTTTTCTTT
TCACTAACGTATATGATGCTTTTGCAAGCTTTCCTTTTCC
TTTTGGCTGGTTTTGCAGCCAAAATATCTGCATCAATGA
CAAACGAAACTAGCGATAGACCTTTGGTCCACTTCACA
CCCAACAAGGGCTGGATGAATGACCCAAATGGGTTGTG
GTACGATGAAAAGATGCCAAATGGCATCTGTACTTTC
AATACAACCCAAATGACACCGTATGGGGTACGCCATTG
TTTTGGGGCCATGCTACTTCCGATGATTTGACTAATTGG
GAAGATCAACCCATTGCTATCGCTCCCAAGCGTAACGA
TTCAGGTGCTTTCTCTGGCTCCATGGTGGTTGATTACAA
CAACACGAGTGGGTTTTTCAATGATACTATTGATCCAAG
ACAAAGATGCGTTGCGATTTGGACTTATAACACTCCTGA
AAGTGAAGAGCAATACATTAGCTATTCTCTTGATGGTGG
TTACACTTTTACTGAATACCAAAAGAACCCTGTTTTAGC
TGCCAACTCCACTCAATTCAGAGATCCAAAGGTGTTCTG
GTATGAACCTTCTCAAAAATGGATTATGACGGCTGCCA
AATCACAAGACTACAAAATTGAAATTTACTCCTCTGATG
ACTTGAAGTCCTGGAAGCTAGAATCTGCATTTGCCAATG
AAGGTTTCTTAGGCTACCAATACGAATGTCCAGGTTTGA
TTGAAGTCCCAACTGAGCAAGATCCTTCCAAATCTTATT
GGGTCATGTTTATTTCTATCAACCCAGGTGCACCTGCTG
GCGGTTCCTTCAACCAATATTTTGTTGGATCCTTCAATG
GTACTCATTTTGAAGCGTTTGACAATCAATCTAGAGTGG
TAGATTTTGGTAAGGACTACTATGCCTTGCAAACTTTCT
TCAACACTGACCCAACCTACGGTTCAGCATTAGGTATTG
CCTGGGCTTCAAACTGGGAGTACAGTGCCTTTGTCCCAA
CTAACCCATGGAGATCATCCATGTCTTTGGTCCGCAAGT
TTTCTTTGAACACTGAATATCAAGCTAATCCAGAGACTG
AATTGATCAATTTGAAAGCCGAACCAATATTGAACATT
AGTAATGCTGGTCCCTGGTCTCGTTTTGCTACTAACACA
ACTCTAACTAAGGCCAATTCTTACAATGTCGATTTGAGC
AACTCGACTGGTACCCTAGAGTTTGAGTTGGTTTACGCT
GTTAACACCACACAAACCATATCCAAATCCGTCTTTGCC
GACTTATCACTTTGGTTCAAGGGTTTAGAAGATCCTGAA
GAATATTTGAGAATGGGTTTTGAAGTCAGTGCTTCTTCC
TTCTTTTTGGACCGTGGTAACTCTAAGGTCAAGTTTGTC
AAGGAGAACCCATATTTCACAAACAGAATGTCTGTCAA
CAACCAACCATTCAAGTCTGAGAACGACCTAAGTTACT
ATAAAGTGTACGGCCTACTGGATCAAAACATCTTGGAA
TTGTACTTCAACGATGGAGATGTGGTTTCTACAAATACC
TACTTCATGACCACCGGTAACGCTCTAGGATCTGTGAAC
ATGACCACTGGTGTCGATAATTTGTTCTACATTGACAAG
TTCCAAGTAAGGGAAGTAAAATAGAGGTTATAAAACTT
ATTGTCTTTTTATTTTTTTCAAAAGCCATTCTAAAGGGC
TTTAGCTAACGAGTGACGAATGTAAAACTTTATGATTTC
AAAGAATACCTCCAAACCATTGAAAATGTATTTTTATTT
TTATTTTCTCCCGACCCCAGTTACCTGGAATTTGTTCTTT
ATGTACTTTATATAAGTATAATTCTCTTAAAAATTTTTAC
TACTTTGCAATAGACATCATTTTTTCACGTAATAAACCC
ACAATCGTAATGTAGTTGCCTTACACTACTAGGATGGAC
CTTTTTGCCTTTATCTGTTTTGTTACTGACACAATGAAAC
CGGGTAAAGTATTAGTTATGTGAAAATTTAAAAGCATT
AAGTAGAAGTATACCATATTGTAAAAAAAAAAGCGTT
GTCTTCTACGTAAAAGTGTTCTCAAAAAGAAGTAGTGA
GGGAAATGGATACCAAGCTATCTGTAACAGGAGCTAAA
AAATCTCAGGGAAAAGCTTCTGGTTTGGGAAACGGTCG
AC |
| 10 | Sequence of the 5'-Region used for knock out of PpURA5: | ATCGGCCTTTGTTGATGCAAGTTTTACGTGGATCATGGA
CTAAGGAGTTTTATTTGGACCAAGTTCATCGTCCTAGAC
ATTACGGAAAGGGTTCTGCTCCTCTTTTTGGAAACTTTT
TGGAACCTCTGAGTATGACAGCTTGGTGGATTGTACCCA
TGGTATGGCTTCCTGTGAATTTCTATTTTTTCTACATTGG
ATTCACCAATCAAAACAAATTAGTCGCCATGGCTTTTTG
GCTTTTGGGTCTATTTGTTTGGACCTTCTTGGAATATGCT |

| SEQ ID NO: | Description | Sequence |
|---|---|---|
| | | TTGCATAGATTTTGTTCCACTTGGACTACTATCTTCCAG<br>AGAATCAAATTGCATTTACCATTCATTTCTTATTGCATG<br>GGATACACCACTATTTACCAATGGATAAATACAGATTG<br>GTGATGCCACCTACACTTTTCATTGTACTTTGCTACCCA<br>ATCAAGACGCTCGTCTTTTCTGTTCTACCATATTACATG<br>GCTTGTTCTGGATTTGCAGGTGGATTCCTGGGCTATATC<br>ATGTATGATGTCACTCATTACGTTCTGCATCACTCCAAG<br>CTGCCTCGTTATTTCCAAGAGTTGAAGAAATATCATTTG<br>GAACATCACTACAAGAATTACGAGTTAGGCTTTGGTGTC<br>ACTTCCAAATTCTGGGACAAAGTCTTTGGGACTTATCTG<br>GGTCCAGACGATGTGTATCAAAAGACAAATTAGAGTAT<br>TTATAAAGTTATGTAAGCAAATAGGGGCTAATAGGGAA<br>AGAAAAATTTTGGTTCTTTATCAGAGCTGGCTCGCGCGC<br>AGTGTTTTTCGTGCTCCTTTGTAATAGTCATTTTTGACTA<br>CTGTTCAGATTGAAATCACATTGAAGATGTCACTCGAGG<br>GGTACCAAAAAAGGTTTTTGGATGCTGCAGTGGCTTCGC |
| 11 | Sequence of the 3'-Region used for knock out of PpURA5: | GGTCTTTTCAACAAAGCTCCATTAGTGAGTCAGCTGGCT<br>GAATCTTATGCACAGGCCATCATTAACAGCAACCTGGA<br>GATAGACGTTGTATTTGGACCAGCTTATAAAGGTATTCC<br>TTTGGCTGCTATTACCGTGTTGAAGTTGTACGAGCTCGG<br>CGGCAAAAAATACGAAAATGTCGGATATGCGTTCAATA<br>GAAAAGAAAAGAAAGACCACGGAGAAGGTGGAAGCAT<br>CGTTGGAGAAAGTCTAAAGAATAAAAGAGTACTGATTA<br>TCGATGATGTGATGACTGCAGGTACTGCTATCAACGAA<br>GCATTTGCTATAATTGGAGCTGAAGGTGGGAGAGTTGA<br>AGGTAGTATTATTGCCCTAGATAGAATGGAGACTACAG<br>GAGATGACTCAAATACCAGTGCTACCCAGGCTGTTAGT<br>CAGAGATATGGTACCCCTGTCTTGAGTATAGTGACATTG<br>GACCATATTGTGGCCCATTTGGGCGAAACTTTCACAGCA<br>GACGAGAAATCTCAAATGGAAACGTATAGAAAAAAGTA<br>TTTGCCCAAATAAGTATGAATCTGCTTCGAATGAATGAA<br>TTAATCCAATTATCTTCTCACCATTATTTTCTTCTGTTTC<br>GGAGCTTTGGGCACGGCGGCGGGTGGTGCGGGCTCAGG<br>TTCCCTTTCATAAACAGATTTAGTACTTGGATGCTTAAT<br>AGTGAATGGCGAATGCAAAGGAACAATTTCGTTCATCT<br>TTAACCCTTTCACTCGGGGTACACGTTCTGGAATGTACC<br>CGCCCTGTTGCAACTCAGGTGGACCGGGCAATTCTTGAA<br>CTTTCTGTAACGTTGTTGGATGTTCAACCAGAAATTGTC<br>CTACCAACTGTATTAGTTTCCTTTTGGTCTTATATTGTTC<br>ATCGAGATACTTCCCACTCTCCTTGATAGCCACTCTCAC<br>TCTTCCTGGATTACCAAAATCTTGAGGATGAGTCTTTTC<br>AGGCTCCAGGATGCAAGGTATATCCAAGTACCTGCAAG<br>CATCTAATATTGTCTTTGCCAGGGGGTTCTCCACACCAT<br>ACTCCTTTTGGCGCATGC |
| 12 | Sequence of the PpURA5 auxotrophic marker: | TCTAGAGGGACTTATCTGGGTCCAGACGATGTGTATCAA<br>AAGACAAATTAGAGTATTTATAAAGTTATGTAAGCAAA<br>TAGGGGCTAATAGGGAAAGAAAAATTTTGGTTCTTTATC<br>AGAGCTGGCTCGCGCGCAGTGTTTTTCGTGCTCCTTTGT<br>AATAGTCATTTTTGACTACTGTTCAGATTGAAATCACAT<br>TGAAGATGTCACTGGAGGGGTACCAAAAAAGGTTTTTG<br>GATGCTGCAGTGGCTTCGCAGGCCTTGAAGTTTGGAACT<br>TTCACCTTGAAAAGTGGAAGACAGTCTCCATACTTCTTT<br>AACATGGGTCTTTTCAACAAAGCTCCATTAGTGAGTCAG<br>CTGGCTGAATCTTATGCTCAGGCCATCATTAACAGCAAC<br>CTGGAGATAGACGTTGTATTTGGACCAGCTTATAAAGGT<br>ATTCCTTTGGCTGCTATTACCGTGTTGAAGTTGTACGAG<br>CTGGGCGGCAAAAAATACGAAAATGTCGGATATGCGTT<br>CAATAGAAAAGAAAAGAAAGACCACGGAGAAGGTGGA<br>AGCATCGTTGGAGAAAGTCTAAAGAATAAAAGAGTACT<br>GATTATCGATGATGTGATGACTGCAGGTACTGCTATCAA<br>CGAAGCATTTGCTATAATTGGAGCTGAAGGTGGGAGAG<br>TTGAAGGTTGTATTATTGCCCTAGATAGAATGGAGACTA<br>CAGGAGATGACTCAAATACCAGTGCTACCCAGGCTGTT<br>AGTCAGAGATATGGTACCCCTGTCTTGAGTATAGTGACA<br>TTGGACCATATTGTGGCCCATTTGGGCGAAACTTTCACA<br>GCAGACGAGAAATCTCAAATGGAAACGTATAGAAAAA<br>AGTATTTGCCCAAATAAGTATGAATCTGCTTCGAATGAA<br>TGAATTAATCCAATTATCTTCTCACCATTATTTTCTTCTG<br>TTTCGGAGCTTTGGGCACGGCGGCGGATCC |
| 13 | Sequence of the part of | CCTGCACTGGATGGTGGCGCTGGATGGTAAGCCGCTGG<br>CAAGCGGTGAAGTGCCTCTGGATGTCGCTCCACACAAGGT |

| SEQ ID NO: | Description | Sequence |
|---|---|---|
|  | the Ec lacZ gene that was used to construct the PpURA5 blaster (recyclable auxotrophic marker) | AAACAGTTGATTGAACTGCCTGAACTACCGCAGCCGGA GAGCGCCGGGCAACTCTGGCTCACAGTACGCGTAGTGC AACCGAACGCGACCGCATGGTCAGAAGCCGGGCACATC AGCGCCTGGCAGCAGTGGCGTCTGGCGGAAAACCTCAG TGTGACGCTCCCCGCCGCGTCCCACGCCATCCCGCATCT GACCACCAGCGAAATGGATTTTTGCATCGAGCTGGGTA ATAAGCGTTGGCAATTTAACCGCCAGTCAGGCTTTCTTT CACAGATGTGGATTGGCGATAAAAAACAACTGCTGACG CCGCTGCGCGATCAGTTCACCCGTGCACCGCTGGATAAC GACATTGGCGTAAGTGAAGCGACCCGCATTGACCCTAA CGCCTGGGTCGAACGCTGGAAGGCGGCGGGCCATTACC AGGCCGAAGCAGCGTTGTTGCAGTGCACGGCAGATACA CTTGCTGATGCGGTGCTGATTACGACCGCTCACGCGTGG CAGCATCAGGGGAAAACCTTATTTATCAGCCGGAAAAC CTACCGGATTGATGGTAGTGGTCAAATGGCGATTACCGT TGATGTTGAAGTGGCGAGCGATACACCGCATCCGGCGC GGATTGGCCTGAACTGCCAG |
| 14 | Sequence of the 5'-Region used for knock out of PpOCH1: | AAAACCTTTTTTCCTATTCAAACACAAGGCATTGCTTCA ACACGTGTGCGTATCCTTAACACAGATACTCCATACTTC TAATAATGTGATAGACGAATACAAAGATGTTCACTCTGT GTTGTGTCTACAAGCATTTCTTATTCTGATTGGGGATAT TCTAGTTACAGCACTAAACAACTGGCGATACAAACTTA AATTAAATAATCCGAATCTAGAAAATGAACTTTTGGAT GGTCCGCCTGTTGGTTGGATAAATCAATACCGATTAAAT GGATTCTATTCCAATGAGAGAGTAATCCAAGACACTCT GATGTCAATAATCATTTGCTTGCAACAACAAACCCGTCA TCTAATCAAAGGGTTTGATGAGGCTTACCTTCAATTGCA GATAAACTCATTGCTGTCCACTGCTGTATTATGTGAGAA TATGGGTGATGAATCTGGTCTTCTCCACTCAGCTAACAT GGCTGTTTGGGCAAAGGTGGTACAATTATACGGAGATC AGGCAATAGTGAAATTGTTGAATATGGCTACTGGACGA TGCTTCAAGGATGTACGTCTAGTAGGAGCCGTGGGAAG ATTGCTGGCAGAACCAGTTGGCACGTCGCAACAATCCC CAAGAAATGAAATAAGTGAAAACGTAACGTCAAAGAC AGCAATGGAGTCAATATTGATAACACCACTGGCAGAGC GGTTCGTACGTCGTTTTGGAGCCGATATGAGGCTCAGCG TGCTAACAGCACGATTGACAAGAAGACTCTCGAGTGAC AGTAGGTTGAGTAAAGTATTCGCTTAGATTCCCAACCTT CGTTTTATTCTTTCGTAGACAAAGAAGCTGCATGCGAAC ATAGGGACAACTTTTATAAATCCAATTGTCAAACCAAC GTAAAACCCTCTGGCACCATTTTCAACATATATTTGTGA AGCAGTACGCAATATCGATAAATACTCACCGTTGTTTGT AACAGCCCCAACTTGCATACGCCTTCTAATGACCTCAAA TGGATAAGCCGCAGCTTGTGCTAACATACCAGCAGCAC CGCCCGCGGTCAGCTGCGCCCACACATATAAAGGCAAT CTACGATCATGGGAGGAATTAGTTTTGACCGTCAGGTCT TCAAGAGTTTTGAACTCTTCTTCTTGAACTGTGTAACCTT TTAAATGACGGGATCTAAATACGTCATGGATGAGATCA TGTGTGTAAAAACTGACTCCAGCATATGGAATCATTCCA AAGATTGTAGGAGCGAACCCACGATAAAAGTTTCCCAA CCTTGCCAAAGTGTCTAATGCTGTGACTTGAAATCTGGG TTCCTCGTTGAAGACCCTGCGTACTATGCCCAAAAACTT TCCTCCACGAGCCCTATTAACTTCTCTATGAGTTTCAAA TGCCAAACGGACACGGATTAGGTCCAATGGGTAAGTGA AAAACACAGAGCAAACCCCAGCTAATGAGCCGGCCAGT AACCGTCTTGGAGCTGTTTCATAAGAGTCATTAGGGATC AATAACGTTCTAATCTGTTCATAACATACAAATTTTATG GCTGCATAGGGAAAAATTCTCAACAGGGTAGCCGAATG ACCCTGATATAGACCTGCGACACCATCATACCCATAGAT CTGCCTGACAGCCTTAAAGAGCCCGCTAAAAGACCCGG AAAACCGAGAGAACTCTGGATTAGCAGTCTGAAAAAGA ATCTTCACTCTGTCTAGTGGAGCAATTAATGTCTTAGCG GCACTTCCTGCTACTCCGCCAGCTACTCCTGAATAGATC ACATACTGCAAAGACTGCTTGTCGATGACCTTGGGGTTA TTTAGCTTCAAGGGCAATTTTTGGGACATTTTGGACACA GGAGACTCAGAAACAGACACAGAGCGTTCTGAGTCCTG GTGCTCCTGACGTAGGCCTAGAACAGGAATTATTGGCTT TATTTGTTTGTCCATTTCATAGGCTTGGGGTAATAGATA GATGACAGAGAAATAGAGAAGACCTAATATTTTTTGTT CATGGCAAATCGCGGGTTCGCGGTCGGGTCACACACGG AGAAGTAATGAGAAGAGCTGGTAATCTGGGGTAAAAGG GTTCAAAAGAAGGTCGCCTGGTAGGGATGCAATACAAG GTTGTCTTGGAGTTTACATTGACCAGATGATTTGGCTTT |

| SEQ ID NO: | Description | Sequence |
|---|---|---|
| | | TTCTCTGTTCAATTCACATTTTTCAGCGAGAATCGGATT<br>GACGGAGAAATGGCGGGGTGTGGGGTGGATAGATGGC<br>AGAAATGCTCGCAATCACCGCGAAAGAAAGACTTTATG<br>GAATAGAACTACTGGGTGGTGTAAGGATTACATAGCTA<br>GTCCAATGGAGTCCGTTGGAAAGGTAAGAAGAAGCTAA<br>AACCGGCTAAGTAACTAGGGAAGAATGATCAGACTTTG<br>ATTTGATGAGGTCTGAAAATACTCTGCTGCTTTTTCAGT<br>TGCTTTTTCCCTGCAACCTATCATTTTCCTTTTCATAAGC<br>CTGCCTTTTCTGTTTTCACTTATATGAGTTCCGCCGAGAC<br>TTCCCCAAATTCTCTCCTGGAACATTCTCTATCGCTCTCC<br>TTCCAAGTTGCGCCCCCTGGCACTGCCTAGTAATATTAC<br>CACGCGACTTATATTCAGTTCCACAATTTCCAGTGTTCG<br>TAGCAAATATCATCAGCCATGGCGAAGGCAGATGGCAG<br>TTTGCTCTACTATAATCCTCACAATCCACCCAGAAGGTA<br>TTACTTCTACATGGCTATATTCGCCGTTTCTGTCATTTGC<br>GTTTTGTACGGACCCTCACAACAATTATCATCTCCAAAA<br>ATAGACTATGATCCATTGACGCTCCGATCACTTGATTTG<br>AAGACTTTGGAAGCTCCTTCACAGTTGAGTCCAGGCACC<br>GTAGAAGATAATCTTCG |
| 15 | Sequence of the 3'-Region used for knock out of PpOCH1: | AAAGCTAGAGTAAAATAGATATAGCGAGATTAGAGAAT<br>GAATACCTTCTTCTAAGCGATCGTCCGTCATCATAGAAT<br>ATCATGGACTGTATAGTTTTTTTTTGTACATATAATGAT<br>TAAACGGTCATCCAACATCTCGTTGACAGATCTCTCAGT<br>ACGCGAAATCCCTGACTATCAAAGCAAGAACCGATGAA<br>GAAAAAAACAACAGTAACCCAAACACCACAACAAACA<br>CTTTATCTTCTCCCCCCCAACACCAATCATCAAAGAGAT<br>GTCGGAACCAAACACCAAGAAGCAAAAACTAACCCCAT<br>ATAAAAACATCCTGGTAGATAATGCTGGTAACCCGCTCT<br>CCTTCCATATTCTGGGCTACTTCACGAAGTCTGACCGGT<br>CTCAGTTGATCAACATGATCCTCGAAATGGGTGGCAAG<br>ATCGTTCCAGACCTGCCTCCTCTGGTAGATGGAGTGTTG<br>TTTTTGACAGGGGATTACAAGTCTATTGATGAAGATACC<br>CTAAAGCAACTGGGGGACGTTCCAATATACAGAGACTC<br>CTTCATCTACCAGTGTTTTGTGCACAAGACATCTCTTCC<br>CATTGACACTTTCCGAATTGACAAGAACGTCGACTTGGC<br>TCAAGATTTGATCAATAGGGCCCTTCAAGAGTCTGTGGA<br>TCATGTCACTTCTGCCAGCACAGCTGCAGCTGCTGCTGT<br>TGTTGTCGCTACCAACGGCCTGTCTTCTAAACCAGACGC<br>TCGTACTAGCAAAATACAGTTCACTCCCGAAGAAGATC<br>GTTTTATTCTTGACTTTGTTAGGAGAAATCCTAAACGAA<br>GAAACACACATCAACTGTACACTGAGCTCGCTCAGCAC<br>ATGAAAAACCATACGAATCATTCTATCCGCCACAGATTT<br>CGTCGTAATCTTTCCGCTCAACTTGATTGGGTTTATGAT<br>ATCGATCCATTGACCAACCAACCTCGAAAAGATGAAAA<br>CGGGAACTACATCAAGGTACAAGGCCTTCCA |
| 16 | *K. lactis* UDP-GlcNAc transporter gene (KIMNN2-2) ORF underlined | AAACGTAACGCCTGGCACTCTATTTTCTCAAACTTCTGG<br>GACGGAAGAGCTAAATATTGTGTTGCTTGAACAAACCC<br>AAAAAAACAAAAAATGAACAAACTAAAACTACACCT<br>AAATAAACCGTGTGTAAAACGTAGTACCATATTACTAG<br>AAAAGATCACAAGTGTATCACACATGTGCATCTCATATT<br>ACATCTTTTATCCAATCCATTCTCTCTATCCCGTCTGTTC<br>CTGTCAGATTCTTTTTCCATAAAAAGAAGAAGACCCCGA<br>ATCTCACCGGTACAATGCAAAACTGCTGAAAAAAAAAG<br>AAAGTTCACTGGATACGGGAACAGTGCCAGTAGGCTTC<br>ACCACATGGACAAAACAATTGACGATAAAATAAGCAGG<br>TGAGCTTCTTTTTCAAGTCACGATCCCTTTATGTCTCAGA<br>AACAATATATACAAGCTAAACCCTTTTGAACCAGTTCTC<br>TCTTCATAGTTATGTTCACATAAATTGCGGGAACAAGAC<br>TCCGCTGGCTGTCAGGTACACGTTGTAACGTTTTCGTCC<br>GCCCAATTATTAGCACAACATTGGCAAAAAGAAAAACT<br>GCTCGTTTTCTCTACAGGTAAATTACAATTTTTTTCAGTA<br>ATTTTCGCTGAAAAATTTAAAGGGCAGGAAAAAAAAGAC<br>GATCTCGACTTTGCATAGATGCAAGAACTGTGGTCAAA<br>ACTTGAAATAGTAATTTTGCTGTGCGTGAACTAATAAAT<br>ATATATATATATATATATATATATTTGTGTATTTTGTATA<br>TGTAATTGTGCACGTCTTGGCTATTGGATATAAGATTTT<br>CGCGGGTTGATGACATAGAGCGTGTACTACTGTAATAG<br>TTGTATATTCAAAAGCTGCTGCGTGGAGAAAGACTAAA<br>ATAGATAAAAAGCACACATTTTGACTTCGGTACCGTCA<br>ACTTAGTGGGACAGTCTTTTATATTTGGTGTAAGCTCAT<br>TTCTGGTACTATTCGAAACAGAACAGTGTTTTCTGTATT<br>ACCGTCCAATCGTTTGTCATGAGTTTTGTATTGATTTTGT |

Table of Sequences

| SEQ ID NO: | Description | Sequence |
|---|---|---|
| | | CGTTAGTGTTCGGAGGATGTTGTTCCAATGTGATTAGTT<br>TCGAGCACATGGTGCAAGGCAGCAATATAAATTTGGGA<br>AATATTGTTACATTCACTCAATTCGTGTCTGTGACGCTA<br>ATTCAGTTGCCCAATGCTTTGGACTTCTCTCACTTTCCGT<br>TTAGGTTGCGACCTAGACACATTCCTCTTAAGATCCATA<br>TGTTAGCTGTGTTTTTGTTCTTTACCAGTTCAGTCGCCAA<br>TAACAGTGTGTTTAAATTTGACATTTCCGTTCCGATTCA<br>TATTATCATTAGATTTTCAGGTACCACTTTGACGATGAT<br>AATAGGTTGGGCTGTTTGTAATAAGAGGTACTCCAAACT<br>TCAGGTGCAATCTGCCATCATTATGACGCTTGGTGCGAT<br>TGTCGCATCATTATACCGTGACAAAGAATTTTCAATGGA<br>CAGTTTAAAGTTGAATACGGATTCAGTGGGTATGACCC<br>AAAAATCTATGTTTGGTATCTTTGTTGTGCTAGTGGCCA<br>CTGCCTTGATGTCATTGTTGTCGTTGCTCAACGAATGGA<br>CGTATAACAAGTACGGGAAACATTGGAAAGAAACTTTG<br>TTCTATTCGCATTTCTTGGCTCTACCGTTGTTTATGTTGG<br>GGTACACAAGGCTCAGAGACGAATTCAGAGACCTCTTA<br>ATTTCCTCAGACTCAATGGATATTCCTATTGTTAAATTA<br>CCAATTGCTACGAAACTTTTCATGCTAATAGCAAATAAC<br>GTGACCCAGTTCATTTGTATCAAAGGTGTTAACATGCTA<br>GCTAGTAACACGGATGCTTTGACACTTTCTGTCGTGCTT<br>CTAGTGCGTAAATTTGTTAGTCTTTTACTCAGTGTCTAC<br>ATCTACAAGAACGTCCTATCCGTGACTGCATACCTAGGG<br>ACCATCACCGTGTTCCTGGGAGCTGGTTTGTATTCATAT<br>GGTTCGGTCAAAACTGCACTGCCTCGCTGAAACAATCC<br>ACGTCTGTATGATACTCGTTTCAGAATTTTTTTGATTTTC<br>TGCCGGATATGGTTTCTCATCTTTACAATCGCATTCTTA<br>ATTATACCAGAACGTAATTCAATGATCCCAGTGACTCGT<br>AACTCTTATATGTCAATTTAAGC |
| 17 | Sequence of the 5'-Region used for knock out of PpBMT2: | GGCCGAGCGGGCCTAGATTTTCACTACAAATTTCAAAA<br>CTACGCGGATTTATTGTCTCAGAGAGCAATTTGGCATTT<br>CTGAGCGTAGCAGGAGGCTTCATAAGATTGTATAGGAC<br>CGTACCAACAAATTGCCGAGGCACAACACGGTATGCTG<br>TGCACTTATGTGGCTACTTCCCTACAACGGAATGAAACC<br>TTCCTCTTTCCGCTTAAACGAGAAAGTGTGTCGCAATTG<br>AATGCAGGTGCCTGTGCGCCTTGGTGTATTGTTTTTGAG<br>GGCCCAATTTATCAGGCGCCTTTTTTCTTGGTTGTTTTCC<br>CTTAGCCTCAAGCAAGGTTGGTCTATTTCATCTCCGCTT<br>CTATACCGTGCCTGATACTGTTGGATGAGAACACGACTC<br>AACTTCCTGCTGCTCTGTATTGCCAGTGTTTTGTCTGTGA<br>TTTGGATCGGAGTCCTCCTTACTTGGAATGATAATAATC<br>TTGGCGGAATCTCCCTAAACGGAGGCAAGGATTCTGCC<br>TATGATGATCTGCTATCATTGGGAAGCTTCAACGACATG<br>GAGGTCGACTCCTATGTCACCAACATCTACGACAATGCT<br>CCAGTGCTAGGATGTACGGATTTGTCTTATCATGGATTG<br>TTGAAAGTCACCCCAAAGCATGACTTAGCTTGCGATTTG<br>GAGTTCATAAGAGCTCAGATTTTGGACATTGACGTTTAC<br>TCCGCCATAAAAGACTTAGAAGATAAAGCCTTGACTGT<br>AAAACAAAAGGTTGAAAAACACTGGTTTACGTTTTATG<br>GTAGTTCAGTCTTTCTGCCCGAACACGATGTGCATTACC<br>TGGTTAGACGAGTCATCTTTTCGGCTGAAGGAAAGGCG<br>AACTCTCCAGTAACATC |
| 18 | Sequence of the 3'-Region used for knock out of PpBMT2: | CCATATGATGGGTGTTTGCTCACTCGTATGGATCAAAAT<br>TCCATGGTTTCTTCTGTACAACTTGTACACTTATTTGGAC<br>TTTTCTAACGGTTTTTCTGGTGATTTGAGAAGTCCTTATT<br>TTGGTGTTCGCAGCTTATCCGTGATTGAACCATCAGAAA<br>TACTGCAGCTCGTTATCTAGTTTCAGAATGTGTTGTAGA<br>ATACAATCAATTCTGAGTCTAGTTTGGGTGGGTCTTGGC<br>GACGGGACCGTTATATGCATCTATGCAGTGTTAAGGTAC<br>ATAGAATGAAAATGTAGGGGTTAATCGAAAGCATCGTT<br>AATTTCAGTAGAACGTAGTTCTATTCCCTACCCAAATAA<br>TTTGCCAAGAATGCTTCGTATCCACATACGCAGTGGACG<br>TAGCAAATTTCACTTTGGACTGTGACCTCAAGTCGTTAT<br>CTTCTACTTGGACATTGATGGTCATTACGTAATCCACAA<br>AGAATTGGATAGCCTCTCGTTTTATCTAGTGCACAGCCT<br>AATAGCACTTAAGTAAGAGCAATGGACAAATTTGCATA<br>GACATTGAGCTAGATACGTAACTCAGATCTTGTTCACTC<br>ATGGTGTACTCGAAGTACTGCTGGAACCGTTACCTCTTA<br>TCATTTCGCTACTGGCTCGTGAAACTACTGGATGAAAAA<br>AAAAAAGAGCTGAAAGCGAGATCATCCCATTTTGTCA<br>TCATACAAATTCACGCTTGCAGTTTTGCTTCGTTAACAA<br>GACAAGATGTCTTTATCAAAGACCCGTTTTTTCTTCTTG |

| SEQ ID NO: | Description | Sequence |
|---|---|---|
|  |  | AAGAATACTTCCCTGTTGAGCACATGCAAACCATATTTA TCTCAGATTTCACTCAACTTGGGTGCTTCCAAGAGAAGT AAAATTCTTCCCACTGCATCAACTTCCAAGAAACCCGTA GACCAGTTTCTCTTCAGCCAAAAGAAGTTGCTCGCCGAT CACCGCGGTAACAGAGGAGTCAGAAGGTTTCACACCCT TCCATCCCGATTTCAAAGTCAAAGTGCTGCGTTGAACCA AGGTTTTCAGGTTGCCAAAGCCCAGTCTGCAAAAACTA GTTCCAAATGGCCTATTAATTCCCATAAAAGTGTTGGCT ACGTATGTATCGGTACCTCCATTCTGGTATTTGCTATTGT TGTCGTTGGTGGGTTGACTAGACTGACCGAATCCGGTCT TTCCATAACGGAGTGGAAACCTATCACTGGTTCGGTTCC CCCACTGACTGAGGAAGACTGGAAGTTGGAATTTGAAA AATACAAACAAAGCCCTGAGTTTCAGGAACTAAATTCT CACATAACATTGGAAGAGTTCAAGTTTATATTTTCCATG GAATGGGGACATAGATTGTTGGGAAGGGTCATCGGCCT GTCGTTTGTTCTTCCCACGTTTTACTTCATTGCCCGTCGA AAGTGTTCCAAAGATGTTGCATTGAAACTGCTTGCAATA TGCTCTATGATAGGATTCCAAGGTTTCATCGGCTGGTGG ATGGTGTATTCCGGATTGGACAAACAGCAATTGGCTGA ACGTAACTCCAAACCAACTGTGTCTCCATATCGCTTAAC TACCCATCTTGGAACTGCATTTGTTATTTACTGTTACATG ATTTACACAGGGCTTCAAGTTTTGAAGAACTATAAGATC ATGAAACAGCCTGAAGCGTATGTTCAAATTTTCAAGCA AATTGCGTCTCCAAAATTGAAAACTTTCAAGAGACTCTC TTCAGTTCTATTAGGCCTGGTG |
| 19 | DNA encodes MmSLC35 A3 UDP-GlcNAc transporter | ATGTCTGCCAACCTAAAATATCTTTCCTTGGGAATTTTG GTGTTTCAGACTACCAGTCTGGTTCTAACGATGCGGTAT TCTAGGACTTTAAAAGAGGAGGGGCCTCGTTATCTGTCT TCTACAGCAGTGGTTGTGGCTGAATTTTTGAAGATAATG GCCTGCATCTTTTTAGTCTACAAAGACAGTAAGTGTAGT GTGAGAGCACTGAATAGAGTACTGCATGATGAAATTCT TAATAAGCCCATGGAAACCCTGAAGCTCGCTATCCCGTC AGGGATATATACTCTTCAGAACAACTTACTCTATGTGGC ACTGTCAAACCTAGATGCAGCCACTTACCAGGTTACATA TCAGTTGAAAATACTTACAACAGCATTATTTTCTGTGTC TATGCTTGGTAAAAAATTAGGTGTGTACCAGTGGCTCTC CCTAGTAATTCTGATGGCAGGAGTTGCTTTTGTACAGTG GCCTTCAGATTCTCAAGAGCTGAACTCTAAGGACCTTTC AACAGGCTCACAGTTTGTAGGCCTCATGGCAGTTCTCAC AGCCTGTTTTTCAAGTGGCTTTGCTGGAGTTTATTTTGA GAAAATCTTAAAAGAAACAAAACAGTCAGTATGGATAA GGAACATTCAACTTGGTTTCTTTGGAAGTATATTTGGAT TAATGGGTGTATACGTTTATGATGGAGAATTGGTCTCAA AGAATGGATTTTTTCAGGGATATAATCAACTGACGTGG ATAGTTGTTGCTCTGCAGGCACTTGGAGGCCTTGTAATA GCTGCTGTCATCAAATATGCAGATAACATTTTAAAAGG ATTTGCGACCTCCTTATCCATAATATTGTCAACAATAAT ATCTTATTTTTGGTTGCAAGATTTTGTGCCAACCAGTGT CTTTTTCCTTGGAGCCATCCTTGTAATAGCAGCTACTTTC TTGTATGGTTACGATCCCAAACCTGCAGGAAATCCCACT AAAGCATAG |
| 20 | PpGAPDH promoter | TTTTTGTAGAAATGTCTTGGTGTCCTCGTCCAATCAGGT AGCCATCTCTGAAATATCTGGCTCCGTTGCAACTCCGAA CGACCTGCTGGCAACGTAAAATTCTCCGGGGTAAAACT TAAATGTGGAGTAATGGAACCAGAAACGTCTCTTCCCTT CTCTCTCCTTCCACCGCCCGTTACCGTCCCTAGGAAATT TTACTCTGCTGGAGAGCTTCTTCTACGGCCCCCTTGCAG CAATGCTCTTCCCAGCATTACGTTGCGGGTAAAACGGA GGTCGTGTACCCGACCTAGCAGCCCAGGGATGGAAAAG TCCCGGCCGTCGCTGGCAATAATAGCGGGCGGACGCAT GTCATGAGATTATTGGAAACCACCAGAATCGAATATAA AAGGCGAACACCTTTCCCAATTTTGGTTTCTCCTGACCC AAAGACTTTAAATTTAATTTATTTGTCCCTATTTCAATCA ATTGAACAACTATCAAAACACA |
| 21 | ScCYC TT | ACAGGCCCCTTTTCCTTTGTCGATATCATGTAATTAGTT ATGTCACGCTTACATTCACGCCCTCCTCCCACATCCGCT CTAACCGAAAGGAAGGAGTTAGACAACCTGAAGTCTA GGTCCCTATTTATTTTTTTTAAGTAGTTATGTTAGTATTAA GAACGTTATTTATATTTCAAATTTTCTTTTTTTTCTGTA CAAACGCGTGTACGCATGTAACATTATACTGAAAACCTT |

Table of Sequences

| SEQ ID NO: | Description | Sequence |
|---|---|---|
| | | GCTTGAGAAGGTTTTGGGACGCTCGAAGGCTTTAATTTG<br>CAAGCTGCCGGCTCTTAAG |
| 22 | Sequence of the 5'-Region used for knock out of PpMNN4L1: | GATCTGGCCATTGTGAAACTTGACACTAAAGACAAAAC<br>TCTTAGAGTTTCCAATCACTTAGGAGACGATGTTTCCTA<br>CAACGAGTACGATCCCTCATTGATCATGAGCAATTTGTA<br>TGTGAAAAAAGTCATCGACCTTGACACCTTGGATAAAA<br>GGGCTGGAGGAGGTGGAACCACCTGTGCAGGCGGTCTG<br>AAAGTGTTCAAGTACGGATCTACTACCAAATATACATCT<br>GGTAACCTGAACGGCGTCAGGTTAGTATACTGGAACGA<br>AGGAAAGTTGCAAAGCTCCAAATTTGTGGTTCGATCCTC<br>TAATTACTCTCAAAAGCTTGGAGGAAACAGCAACGCCG<br>AATCAATTGACAACAATGGTGTGGGTTTTGCCTCAGCTG<br>GAGACTCAGGCGCATGGATTCTTTCCAAGCTACAAGAT<br>GTTAGGGAGTACCAGTCATTCACTGAAAAGCTAGGTGA<br>AGCTACGATGAGCATTTTCGATTTCCACGGTCTTAAACA<br>GGAGACTTCTACTACAGGGCTTGGGGTAGTTGGTATGAT<br>TCATTCTTACGACGGTGAGTTCAAACAGTTTGGTTTGTT<br>CACTCCAATGACATCTATTCTACAAAGACTTCAACGAGT<br>GACCAATGTAGAATGGTGTGTAGCGGGTTGCGAAGATG<br>GGGATGTGGACACTGAAGGAGAACACGAATTGAGTGAT<br>TTGGAACAACTGCATATGCATAGTGATTCCGACTAGTCA<br>GGCAAGAGAGAGCCCTCAAATTTACCTCTCTGCCCCTCC<br>TCACTCCTTTTGGTACGCATAATTGCAGTATAAAGAACT<br>TGCTGCCAGCCAGTAATCTTATTTCATACGCAGTTCTAT<br>ATAGCACATAATCTTGCTTGTATGTATGAAATTTACCGC<br>GTTTTAGTTGAAATTGTTTATGTTGTGTGCCTTGCATGA<br>AATCTCTCGTTAGCCCTATCCTTACATTTAACTGGTCTCA<br>AAACCTCTACCAATTCCATTGCTGTACAACAATATGAGG<br>CGGCATTACTGTAGGGTTGGAAAAAAAATTGTCATTCCA<br>GCTAGAGATCACACGACTTCATCACGCTTATTGCTCCTC<br>ATTGCTAAATCATTTACTCTTGACTTCGACCCAGAAAAG<br>TTCGCC |
| 23 | Sequence of the 3'-Region used for knock out of PpMNN4L1: | GCATGTCAAACTTGAACACAACGACTAGATAGTTGTTTT<br>TTCTATATAAAACGAAACGTTATCATCTTTAATAATCAT<br>TGAGGTTTACCCTTATAGTTCCGTATTTTCGTTTCCAAAC<br>TTAGTAATCTTTTGGAAATATCATCAAAGCTGGTGCCAA<br>TCTTCTTGTTTGAAGTTTCAAACTGCTCCACCAAGCTAC<br>TTAGAGACTGTTCTAGGTCTGAAGCAACTTCGAACACA<br>GAGACAGCTGCCGCCGATTGTTCTTTTTTGTGTTTTTCTT<br>CTGGAAGAGGGGCATCATCTTGTATGTCCAATGCCCGTA<br>TCCTTTCTGAGTTGTCCGACACATTGTCCTTCGAAGAGT<br>TTCCTGACATTGGGCTTCTTCTATCCGTGTATTAATTTTG<br>GGTTAAGTTCCTCGTTTGCATAGCAGTGGATACCTCGAT<br>TTTTTTGGCTCCTATTTACCTGACATAATATTCTACTATA<br>ATCCAACTTGGACGCGTCATCTATGATAACTAGGCTCTC<br>CTTTGTTCAAAGGGGACGTCTTCATAATCCACTGGCACG<br>AAGTAAGTCTGCAACGAGGCGGCTTTTGCAACAGAACG<br>ATAGTGTCGTTTCGTACTTGGACTATGCTAAACAAAAGG<br>ATCTGTCAAACATTTCAACCGTGTTTCAAGGCACTCTTT<br>ACGAATTATCGACCAAGACCTTCCTAGACGAACATTTCA<br>ACATATCCAGGCTACTGCTTCAAGGTGGTGCAAATGAT<br>AAAGGTATAGATATTAGATGTGTTTGGGACCTAAAACA<br>GTTCTTGCCTGAAGATTCCCTTGAGCAACAGGCTTCAAT<br>AGCCAAGTTAGAGAAGCAGTACCAAATCGGTAACAAAA<br>GGGGGAAGCATATAAAACCTTTACTATTGCGACAAAAT<br>CCATCCTTGAAAGTAAAGCTGTTTGTTCAATGTAAAGCA<br>TACGAAACGAAGGAGGTAGATCCTAAGATGGTTAGAGA<br>ACTTAACGGGACATACTCCAGCTGCATCCCATATTACGA<br>TCGCTGGAAGACTTTTTTCATGTACGTATCGCCCACCAA<br>CCTTTCAAAGCAAGCTAGGTATGATTTTGACAGTTCTCA<br>CAATCCATTGGTTTTCATGCAACTTGAAAAAACCCAACT<br>CAAACTTCATGGGGATCCATACAATGTAAATCATTACG<br>AGAGGGCGAGGTTGAAAAGTTTCCATTGCAATCACGTC<br>GCATCATGGCTACTGAAAGGCCTTAAC |
| 24 | Sequence of the 5'-Region used for knock out of PpPNO1 | TCATTCTATATGTTCAAGAAAAGGGTAGTGAAAGGAAA<br>GAAAAGGCATATAGGCGAGGGAGAGTTAGCTAGCATAC<br>AAGATAATGAAGGATCAATAGCGGTAGTTAAAGTGCAC<br>AAGAAAAGAGCACCTGTTGAGGCTGATGATAAAGCTCC<br>AATTACATTGCCACAGAGAAACACAGTAACAGAAATAG<br>GAGGGGATGCACCACGAGAAGAGCATTCAGTGAACAAC |

| SEQ ID NO: | Description | Sequence |
|---|---|---|
| | and PpMNN4: | TTTGCCAAATTCATAACCCCAAGCGCTAATAAGCCAATG TCAAAGTCGGCTACTAACATTAATAGTACAACAACTATC GATTTTCAACCAGATGTTTGCAAGGACTACAAACAGAC AGGTTACTGCGGATATGGTGACACTTGTAAGTTTTTGCA CCTGAGGGATGATTTCAAACAGGGATGGAAATTAGATA GGGAGTGGGAAAATGTCCAAAAGAAGAAGCATAATACT CTCAAAGGGGTTAAGGAGATCCAAATGTTTAATGAAGA TGAGCTCAAAGATATCCCGTTTAAATGCATTATATGCAA AGGAGATTACAAATCACCCGTGAAAACTTCTTGCAATC ATTATTTTTGCGAACAATGTTTCCTGCAACGGTCAAGAA GAAAACCAAATTGTATTATATGTGGCAGAGACACTTTA GGAGTTGCTTTACCAGCAAAGAAGTTGTCCCAATTTCTG GCTAAGATACATAATAATGAAAGTAATAAAGTTTAGTA ATTGCATTGCGTTGACTATTGATTGCATTGATGTCGTGT GATACTTTCACCGAAAAAAAACACGAAGCGCAATAGGA GCGGTTGCATATTAGTCCCCAAAGCTATTTAATTGTGCC TGAAACTGTTTTTTAAGCTCATCAAGCATAATTGTATGC ATTGCGACGTAACCAACGTTTAGGCGCAGTTTAATCATA GCCCACTGCTAAGCC |
| 25 | Sequence of the 3'- Region used for knock out of PpPNO1 and PpMNN4: | CGGAGGAATGCAAATAATAATCTCCTTAATTACCCACTG ATAAGCTCAAGAGACGCGGTTTGAAAACGATATAATGA ATCATTTGGATTTTATAATAAACCCTGACAGTTTTTCCA CTGTATTGTTTTAACACTCATTGGAAGCTGTATTGATTCT AAGAAGCTAGAAATCAATACGGCCATACAAAAGATGAC ATTGAATAAGCACCGGCTTTTTTGATTAGCATATACCTT AAAGCATGCATTCATGGCTACATAGTTGTTAAAGGGCTT CTTCCATTATCAGTATAATGAATTACATAATCATGCACT TATATTTGCCCATCTCTGTTCTCTCACTCTTGCCTGGGTA TATTCTATGAAATTGCGTATAGCGTGTCTCCAGTTGAAC CCCAAGCTTGGCGAGTTTGAAGAGAATGCTAACCTTGC GTATTCCTTGCTTCAGGAAACATTCAAGGAGAAACAGG TCAAGAAGCCAAACATTTTGATCCTTCCCGAGTTAGCAT TGACTGGCTACAATTTTCAAAGCCAGCAGCGGATAGAG CCTTTTTTGGAGGAAACAACCAAGGGAGCTAGTACCCA ATGGGCTCAAAAAGTATCCAAGACGTGGGATTGCTTTA CTTTAATAGGATACCCAGAAAAAAGTTTAGAGAGCCCT CCCCGTATTTACAACAGTGCGGTACTTGTATCGCCTCAG GGAAAAGTAATGAACAACTACAGAAAGTCCTTCTTGTA TGAAGCTGATGAACATTGGGGATGTTCGGAATCTTCTGA TGGGTTTCAAACAGTAGATTATTAATTGAAGGAAAGA CTGTAAAGACATCATTTGGAATTTGCATGGATTTGAATC CTTATAAATTTGAAGCTCCATTCACAGACTTCGAGTTCA GTGGCCATTGCTTGAAAACCGGTACAAGACTCATTTTGT GCCCAATGGCCTGGTTGTCCCCTCTATCGCCTTCCATTA AAAAGGATCTTAGTGATATAGAGAAAAGCAGACTTCAA AAGTTCTACCTTGAAAAAATAGATACCCCGGAATTTGA CGTTAATTACGAATTGAAAAAAGATGAAGTATTGCCCA CCCGTATGAATGAAACGTTGGAAACAATTGACTTTGAG CCTTCAAAACCGGACTACTCTAATATAAATTATTGGATA CTAAGGTTTTTTCCCTTTCTGACTCATGTCTATAAACGA GATGTGCTCAAAGAGAATGCAGTTGCAGTCTTATGCAA CCGAGTTGGCATTGAGAGTGATGTCTTGTACGGAGGAT CAACCACGATTCTAAACTTCAATGGTAAGTTAGCATCGA CACAAGAGGAGCTGGAGTTGTACGGGCAGACTAATAGT CTCAACCCCAGTGTGGAAGTATTGGGGGCCCTTGGCAT GGGTCAACAGGGAATTCTAGTACGAGACATTGAATTAA CATAATATACAATATACAATAAACACAAATAAGAATA CAAGCCTGACAAAAATTCACAAATTATTGCCTAGACTTG TCGTTATCAGCAGCGACCTTTTTCCAATGCTCAATTTCA CGATATGCCTTTTCTAGCTCTGCTTTAAGCTTCTCATTGG AATTGGCTAACTCGTTGACTGCTTGGTCAGTGATGAGTT TCTCCAAGGTCCATTTCTCGATGTTGTTGTTTTCGTTTTC CTTTAATCTCTTGATATAATCAACAGCCTTCTTTAATATC TGAGCCTTGTTCGAGTCCCCTGTTGGCAACAGAGCGGCC AGTTCCTTTATTCCGTGGTTTATATTTTCTCTTCTACGCC TTTCTACTTCTTTTGTGATTCTCTTTACGCATCTTATGCCA TTCTTCAGAACCAGTGGCTGGCTTAACCGAATAGCCAG AGCCTGAAGAAGCCGCACTAGAAGAAGCAGTGGCATTG TTGACTATGG |
| 26 | DNA encodes human | TCAGTCAGTGCTCTTGATGGTGACCCAGCAAGTTTGACC AGAGAAGTGATTAGATTGGCCCAAGACGCAGAGGTGGA GTTGGAGAGACAACGTGGACTGCTGCAGCAAATCGGAG |

| SEQ ID NO: | Description | Sequence |
|---|---|---|
|  | GnTI catalytic domain (NA) Codon-optimized | ATGCATTGTCTAGTCAAAGAGGTAGGGTGCCTACCGCA GCTCCTCCAGCACAGCCTAGAGTGCATGTGACCCCTGCA CCAGCTGTGATTCCTATCTTGGTCATCGCCTGTGACAGA TCTACTGTTAGAAGATGTCTGGACAAGCTGTTGCATTAC AGACCATCTGCTGAGTTGTTCCCTATCATCGTTAGTCAA GACTGTGGTCACGAGGAGACTGCCCAAGCCATCGCCTC CTACGGATCTGCTGTCACTCACATCAGACAGCCTGACCT GTCATCTATTGCTGTGCCACCAGACCACAGAAAGTTCCA AGGTTACTACAAGATCGCTAGACACTACAGATGGGCAT TGGGTCAAGTCTTCAGACAGTTTAGATTCCCTGCTGCTG TGGTGGTGGAGGATGACTTGGAGGTGGCTCCTGACTTCT TTGAGTACTTTAGAGCAACCTATCCATTGCTGAAGGCAG ACCCCATCCCTGTGGTGTCTCTGCCTGGAATGACAACG GTAAGGAGCAAATGGTGGACGCTTCTAGGCCTGAGCTG TTGTACAGAACCGACTTCTTTCCTGGTCTGGGATGGTTG CTGTTGGCTGAGTTGTGGGCTGAGTTGGAGCCTAAGTGG CCAAAGGCATTCTGGGACGACTGGATGAGAAGACCTGA GCAAAGACAGGGTAGAGCCTGTATCAGACCTGAGATCT CAAGAACCATGACCTTTGGTAGAAAGGGAGTGTCTCAC GGTCAATTCTTTGACCAACACTTGAAGTTTATCAAGCTG AACCAGCAATTTGTGCACTTCACCCAACTGGACCTGTCT TACTTGCAGAGAGAGGCCTATGACAGAGATTTCCTAGC TAGAGTCTACGGAGCTCCTCAACTGCAAGTGGAGAAAG TGAGGACCAATGACAGAAAGGAGTTGGGAGAGGTGAG AGTGCAGTACACTGGTAGGGACTCCTTTAAGGCTTTCGC TAAGGCTCTGGGTGTCATGGATGACCTTAAGTCTGGAGT TCCTAGAGCTGGTTACAGAGGTATTGTCACCTTTCAATT CAGAGGTAGAAGAGTCCACTTGGCTCCTCACCTACTTG GGAGGGTTATGATCCTTCTTGGAATTAG |
| 27 | DNA encodes Pp SEC12 (10) The last 9 nucleotides are the linker containing the AscI restriction site used for fusion to proteins of interest. | ATGCCCAGAAAAATATTTAACTACTTCATTTTGACTGTA TTCATGGCAATTCTTGCTATTGTTTTACAATGGTCTATAG AGAATGGACATGGGCGCGCC |
| 28 | Sequence of the PpSEC4 promoter: | GAAGTAAAGTTGGCGAAACTTTGGGAACCTTTGGTTAA AACTTTGTAATTTTTGTCGCTACCCATTAGGCAGAATCT GCATCTTGGGAGGGGGATGTGGTGGCGTTCTGAGATGT ACGCGAAGAATGAAGAGCCAGTGGTAACAACAGGCCTA GAGAGATACGGGCATAATGGGTATAACCTACAAGTTAA GAATGTAGCAGCCCTGGAAACCAGATTGAAACGAAAAA CGAAATCATTTAAACTGTAGGATGTTTTGGCTCATTGTC TGGAAGGCTGGCTGTTTATTGCCCTGTTCTTTGCATGGG AATAAGCTATTATATCCCTCACATAATCCCAGAAAATAG ATTGAAGCAACGCGAAATCCTTACGTATCGAAGTAGCC TTCTTACACATTCACGTTGTACGGATAAGAAAACTACTC AAACGAACAATC |
| 29 | Sequence of the PpOCH1 terminator: | AATAGATATAGCGAGATTAGAGAATGAATACCTTCTTCT AAGCGATCGTCCGTCATCATAGAATATCATGGACTGTAT AGTTTTTTTTTTGTACATATAATGATTAAACGGTCATCC AACATCTCGTTGACAGATCTCTCAGTACGCGAAATCCCT GACTATCAAAGCAAGAACCGATGAAGAAAAAAACAAC AGTAACCCAAACACCACAACAAACACTTTATCTTCTCCC CCCCAACACCAATCATCAAAGAGATGTCGGAACACAAA CACCAAGAAGCAAAAACTAACCCCATATAAAAACATCC TGGTAGATAATGCTGGTAACCCGCTCTCCTTCCATATTC TGGGCTACTTCACGAAGTCTGACCGGTCTCAGTTGATCA ACATGATCCTCGAAATGG |
| 30 | DNA encodes Mm ManI catalytic | GAGCCCGCTGACGCCACCATCCGTGAGAAGAGGGCAAA GATCAAAGAGATGATGACCCATGCTTGGAATAATTATA AACGCTATGCGTGGGGCTTGAACGAACTGAAACCTATA TCAAAAGAAGGCCATTCAAGCAGTTTGTTTGGCAACAT |

Table of Sequences

| SEQ ID NO: | Description | Sequence |
|---|---|---|
| | domain (FB) | CAAAGGAGCTACAATAGTAGATGCCCTGGATACCCTTTT<br>CATTATGGGCATGAAGACTGAATTTCAAGAAGCTAAAT<br>CGTGGATTAAAAAATATTTAGATTTTAATGTGAATGCTG<br>AAGTTTCTGTTTTTGAAGTCAACATACGCTTCGTCGGTG<br>GACTGCTGTCAGCCTACTATTTGTCCGGAGAGGAGATAT<br>TTCGAAAGAAAGCAGTGGAACTTGGGGTAAAATTGCTA<br>CCTGCATTTCATACTCCCTCTGGAATACCTTGGGCATTG<br>CTGAATATGAAAAGTGGGATCGGGCGGAACTGGCCCTG<br>GGCCTCTGGAGGCAGCAGTATCCTGGCCGAATTTGGAA<br>CTCTGCATTTAGAGTTTATGCACTTGTCCCACTTATCAG<br>GAGACCCAGTCTTTGCCGAAAAGGTTATGAAAATTCGA<br>ACAGTGTTGAACAAACTGGACAAACCAGAAGGCCTTTA<br>TCCTAACTATCTGAACCCCAGTAGTGGACAGTGGGGTC<br>AACATCATGTGTCGGTTGGAGGACTTGGAGACAGCTTTT<br>ATGAATATTTGCTTAAGGCGTGGTTAATGTCTGACAAGA<br>CAGATCTCGAAGCCAAGAAGATGTATTTTGATGCTGTTC<br>AGGCCATCGAGACTCACTTGATCCGCAAGTCAAGTGGG<br>GGACTAACGTACATCGCAGAGTGGAAGGGGGGCCTCCT<br>GGAACACAAGATGGGCCACCTGACGTGCTTTGCAGGAG<br>GCATGTTTGCACTTGGGGCAGATGGAGCTCCGGAAGCC<br>CGGGCCCAACACTACCTTGAACTCGGAGCTGAAATTGC<br>CCGCACTTGTCATGAATCTTATAATCGTACATATGTGAA<br>GTTGGGACCGGAAGCGTTTCGATTTGATGGCGGTGTGG<br>AAGCTATTGCCACGAGGCAAAATGAAAAGTATTACATC<br>TTACGGCCCGAGGTCATCGAGACATACATGTACATGTG<br>GCGACTGACTCACGACCCCAAGTACAGGACCTGGGCCT<br>GGGAAGCCGTGGAGGCTCTAGAAAGTCACTGCAGAGTG<br>AACGGAGGCTACTCAGGCTTACGGGATGTTTACATTGCC<br>CGTGAGAGTTATGACGATGTCCAGCAAAGTTTCTTCCTG<br>GCAGAGACACTGAAGTATTTGTACTTGATATTTTCCGAT<br>GATGACCTTCTTCCACTAGAACACTGGATCTTCAACACC<br>GAGGCTCATCCTTTCCCTATACTCCGTGAACAGAAGAAG<br>GAAATTGATGGCAAAGAGAAATGA |
| 31 | DNA encodes ScSEC12 (8) The last 9 nucleotides are the linker containing the AscI restriction site used for fusion to proteins of interest | ATGAACACTATCCACATAATAAAATTACCGCTTAACTAC<br>GCCAACTACACCTCAATGAAACAAAAAATCTCTAAATT<br>TTTCACCAACTTCATCCTTATTGTGCTGCTTTCTTACATT<br>TTACAGTTCTCCTATAAGCACAATTTGCATTCCATGCTTT<br>TCAATTACGCGAAGGACAATTTTCTAACGAAAAGAGAC<br>ACCATCTCTTCGCCCTACGTAGTTGATGAAGACTTACAT<br>CAAACAACTTTGTTTGGCAACCACGGTACAAAAACATC<br>TGTACCTAGCGTAGATTCCATAAAAGTGCATGGCGTGG<br>GGCGCGCC |
| 32 | Sequence of the 5'-region that was used to knock into the PpADE1 locus: | GAGTCGGCCAAGAGATGATAACTGTTACTAAGCTTCTCC<br>GTAATTAGTGGTATTTTGTAACTTTTACCAATAATCGTTT<br>ATGAATACGGATATTTTTCGACCTTATCCAGTGCCAAAT<br>CACGTAACTTAATCATGGTTTAAATACTCCACTTGAACG<br>ATTCATTATTCAGAAAAAAGTCAGGTTGGCAGAAACAC<br>TTGGGCGCTTTGAAGAGTATAAGAGTATTAAGCATTAA<br>ACATCTGAACTTTCACCGCCCCAATATACTACTCTAGGA<br>AACTCGAAAAATTCCTTTCCATGTGTCATCGCTTCCAAC<br>ACACTTTGCTGTATCCTTCCAAGTATGTCCATTGTGAAC<br>ACTGATCTGGACGGAATCCTACCTTTAATCGCCAAAGG<br>AAAGGTTAGAGACATTTATGCAGTCGATGAGAACAACT<br>TGCTGTTCGTCGCAACTGACCGTATCTCCGCTTACGATG<br>TGATTATGACAAACGGTATTCCTGATAAGGGAAAGATT<br>TTGACTCAGCTCTCAGTTTTCTGGTTTGATTTTTTGGCAC<br>CCTACATAAAGAATCATTTGGTTGCTTCTAATGACAAGG<br>AAGTCTTTGCTTTACTACCATCAAAACTGTCTGAAGAAA<br>AaTACAAATCTCAATTAGAGGGACGATCCTTGATAGTAA<br>AAAAGCACAGACTGATACCTTTGGAAGCCATTGTCAGA<br>GGTTACATCACTGGAAGTGCATGGAAAGAGTACAAGAA<br>CTCAAAAACTGTCCATGGAGTCAAGGTTGAAAACGAGA<br>ACCTTCAAGAGAGCGACGCCTTTCCAACTCCGATTTTCA<br>CACCTTCAACGAAAGCTGAACAGGGTGAACACGATGAA<br>AACATCTCTATTGAACAAGCTGCTGAGATTGTAGGTAA<br>AGACATTTGTGAGAAGGTCGCTGTCAAGGCGGTCGAGT |

Table of Sequences

| SEQ ID NO: | Description | Sequence |
|---|---|---|
| | | TGTATTCTGCTGCAAAAAACCTCGCCCTTTTGAAGGGGA TCATTATTGCTGATACGAAATTCGAATTTGGACTGGACG AAAACAATGAATTGGTACTAGTAGATGAAGTTTTAACT CCAGATTCTTCTAGATTTTGGAATCAAAAGACTTACCAA GTGGGTAAATCGCAAGAGAGTTACGATAAGCAGTTTCT CAGAGATTGGTTGACGGCCAACGGATTGAATGGCAAAG AGGGCGTAGCCATGGATGCAGAAATTGCTATCAAGAGT AAAGAAAAGTATATTGAAGCTTATGAAGCAATTACTGG CAAGAAATGGGCTTGA |
| 33 | PpALG3 TT | ATTTACAATTAGTAATATTAAGGTGGTAAAAACATTCGT AGAATTGAAATGAATTAATATAGTATGACAATGGTTCA TGTCTATAAATCTCCGGCTTCGGTACCTTCTCCCCAATT GAATACATTGTCAAATGAATGGTTGAACTATTAGGTTC GCCAGTTTCGTTATTAAGAAAACTGTTAAAATCAAATTC CATATCATCGGTTCCAGTGGGAGGACCAGTTCCATCGCC AAAATCCTGTAAGAATCCATTGTCAGAACCTGTAAAGT CAGTTTGAGATGAAATTTTTCCGGTCTTTGTTGACTTGG AAGCTTCGTTAAGGTTAGGTGAAACAGTTTGATCAACC AGCGGCTCCCGTTTTCGTCGCTTAGTAG |
| 34 | Sequence of the 3'-region that was used to knock into the PpADE1 locus: | ATGATTAGTACCCTCCTCGCCTTTTTCAGACATCTGAAA TTTCCCTTATTCTTCCAATTCCATATAAAATCCTATTTAG GTAATTAGTAAACAATGATCATAAAGTGAAATCATTCA AGTAACCATTCCGTTTATCGTTGATTTAAAATCAATAAC GAATGAATGTCGGTCTGAGTAGTCAATTTGTTGCCTTGG AGCTCATTGGCAGGGGGTCTTTTGGCTCAGTATGGAAG GTTGAAAGGAAAACAGATGGAAAGTGGTTCGTCAGAAA AGAGGTATCCTACATGAAGATGAATGCCAAAGAGATAT CTCAAGTGATAGCTGAGTTCAGAATTCTTAGTGAGTTAA GCCATCCCAACATTGTGAAGTACCTTCATCACGAACATA TTTCTGAGAATAAAACTGTCAATTTATACATGGAATACT GTGATGGTGGAGATCTCTCCAAGCTGATTCGAACACAT AGAAGGAACAAAGAGTACATTTCAGAAGAAAAAATAT GGAGTATTTTTACGCAGGTTTTATTAGCATTGTATCGTT GTCATTATGGAACTGATTTCACGGCTTCAAAGGAGTTTG AATCGCTCAATAAAGGTAATAGACGAACCCAGAATCCT TCGTGGGTAGACTCGACAAGAGTTATTATTCACAGGGA TATAAAACCCGACAACATCTTTCTGATGAACAATTCAAA CCTTGTCAAACTGGGAGATTTTGGATTAGCAAAAATTCT GGACCAAGAAAACGATTTTGCCAAAACATACGTCGGTA CGCCGTATTACATGTCTCCTGAAGTGCTGTTGGACCAAC CCTACTCACCATTATGTGATATATGGTCTCTTGGGTGCG TCATGTATGAGCTATGTGCATTGAGGCCTCCTT |
| 35 | DNA encodes ScGAL10 | ATGACAGCTCAGTTACAAAGTGAAAGTACTTCTAAAAT TGTTTTTGGTTACAGGTGGTGCTGGATACATTGGTTCACA CACTGTGGTAGAGCTAATTGAGAATGGATATGACTGTG TTGTTGCTGATAACCTGTCGAATTCAACTTATGATTCTG TAGCCAGGTTAGAGGTCTTGACCAAGCATCACATTCCCT TCTATGAGGTTGATTTGTGTGACCGAAAAGGTCTGGAA AAGGTTTTCAAAGAATATAAAATTGATTCGGTAATTCAC TTTGCTGGTTTAAAGGCTGTAGGTGAATCTACACAAATC CCGCTGAGATACTATCACAATAACATTTTGGGAACTGTC GTTTTATTAGAGTTAATGCAACAATACAACGTTTCCAAA TTTGTTTTTTCATCTTCTGCTACTGTCTATGGTGATGCTA CGAGATTCCCAAATATGATTCCTATCCCAGAAGAATGTC CCTTAGGGCCTACTAATCCGTATGGTCATACGAAATACG CCATTGAGAATATCTTGAATGATCTTTACAATAGCGACA AAAAAGTTGGAAGTTTGCTATCTTGCGTTATTTTAACC CAATTGGCGCACATCCCTCTGGATTAATCGGAGAAGAT CCGCTAGGTATACCAAACAATTTGTTGCCATATATGGCT CAAGTAGCTGTTGGTAGGCGCGAGAAGCTTTACATCTTC GGAGACGATTATGATTCCAGAGATGGTACCCCGATCAG GGATTATATCCACGTAGTTGATCTAGCAAAAGGTCATAT TGCAGCCCTGCAATACCTAGAGGCCTACAATGAAAATG AAGGTTTGTGTCGTGAGTGGAACTTGGGTTCCGGTAAA GGTTCTACAGTTTTTGAAGTTTATCATGCATTCTGCAAA GCTTCTGGTATTGATCTTCCATACAAAGTTACGGGCAGA AGAGCAGGTGATGTTTGAACTTGACGGCTAAACCAGA TAGGGCCAAACGCGAACTGAAATGGCAGACCGAGTTGC AGGTTGAAGACTCCTGCAAGGATTTATGGAAATGGACT ACTGAGAATCCTTTTGGTTACCAGTTAAGGGGTGTCGAG GCCAGATTTTCCGCTGAAGATATGCGTTATGACGCAAG |

Table of Sequences

| SEQ ID NO: | Description | Sequence |
|---|---|---|
| | | ATTTGTGACTATTGGTGCCGGCACCAGATTTCAAGCCAC<br>GTTTGCCAATTTGGGCGCCAGCATTGTTGACCTGAAAGT<br>GAACGGACAATCAGTTGTTCTTGGCTATGAAAATGAGG<br>AAGGGTATTTGAATCCTGATAGTGCTTATATAGGCGCCA<br>CGATCGGCAGGTATGCTAATCGTATTTCGAAGGGTAAG<br>TTTAGTTTATGCAACAAAGACTATCAGTTAACCGTTAAT<br>AACGGCGTTAATGCGAATCATAGTAGTATCGGTTCTTTC<br>CACAGAAAAAGATTTTTGGGACCCATCATTCAAAATCCT<br>TCAAAGGATGTTTTTACCGCCGAGTACATGCTGATAGAT<br>AATGAGAAGGACACCGAATTTCCAGGTGATCTATTGGT<br>AACCATACAGTATACTGTGAACGTTGCCCAAAAAAGTT<br>TGGAAATGGTATATAAAGGTAAATTGACTGCTGGTGAA<br>GCGACGCCAATAAATTTAACAAATCATAGTTATTTCAAT<br>CTGAACAAGCCATATGGAGACACTATTGAGGGTACGGA<br>GATTATGGTGCGTTCAAAAAAATCTGTTGATGTCGACAA<br>AAACATGATTCCTACGGGTAATATCGTCGATAGAGAAA<br>TTGCTACCTTTAACTCTACAAAGCCAACGGTCTTAGGCC<br>CCAAAAATCCCCAGTTTGATTGTTGTTTTGTGGTGGATG<br>AAAATGCTAAGCCAAGTCAAATCAATACTCTAAACAAT<br>GAATTGACGCTTATTGTCAAGGCTTTTCATCCCGATTCC<br>AATATTACATTAGAAGTTTTAAGTACAGAGCCAACTTAT<br>CAATTTTATACCGGTGATTTCTTGTCTGCTGGTTACGAA<br>GCAAGACAAGGTTTTGCAATTGAGCCTGGTAGATACAT<br>TGATGCTATCAATCAAGAGAACTGGAAAGATTGTGTAA<br>CCTTGAAAAACGGTGAAACTTACGGGTCCAAGATTGTC<br>TACAGATTTTCCTGA |
| 36 | Sequence of the PpPMA1 promoter: | AAATGCGTACCTCTTCTACGAGATTCAAGCGAATGAGA<br>ATAATGTAATATGCAAGATCAGAAAGAATGAAAGGAGT<br>TGAAAAAAAAACCGTTGCGTTTTGACCTTGAATGGGG<br>TGGAGGTTTCCATTCAAAGTAAAGCCTGTGTCTTGGTAT<br>TTTCGGCGGCACAAGAAATCGTAATTTTCATCTTCTAAA<br>CGATGAAGATCGCAGCCCAACCTGTATGTAGTTAACCG<br>GTCGGAATTATAAGAAAGATTTTCGATCAACAAACCCT<br>AGCAAATAGAAAGCAGGGTTACAACTTTAAACCGAAGT<br>CACAAACGATAAACCACTCAGCTCCCACCCAAATTCATT<br>CCCACTAGCAGAAAGGAATTATTTAATCCCTCAGGAAA<br>CCTCGATGATTCTCCCGTTCTTCCATGGGCGGGTATCGC<br>AAAATGAGGAATTTTTCAAATTTCTCTATTGTCAAGACT<br>GTTTATTATCTAAGAAATAGCCCAATCCGAAGCTCAGTT<br>TTGAAAAAATCACTTCCGCGTTTCTTTTTTACAGCCCGA<br>TGAATATCCAAATTTGGAATATGGATTACTCTATCGGGA<br>CTGCAGATAATATGACAACAACGCAGATTACATTTTAG<br>GTAAGGCATAAACACCAGCCAGAAATGAAACGCCCACT<br>AGCCATGGTCGAATAGTCCAATGAATTCAGATAGCTAT<br>GGTCTAAAAGCTGATGTTTTTTATTGGGTAATGGCGAAG<br>AGTCCAGTACGACTTCCAGCAGAGCTGAGATGGCCATT<br>TTTGGGGGTATTAGTAACTTTTTGAGCTCTTTTCACTTCG<br>ATGAAGTGTCCCATTCGGGATATAATCGGATCGCGTCGT<br>TTTCTCGAAAATACAGCTTAGCGTCGTCCGCTTGTTGTA<br>AAAGCAGCACCACATTCCTAATCTCTTATATAAACAAA<br>ACAACCCAAATTATCAGTGCTGTTTTCCCACCAGATATA<br>AGTTTCTTTTCTCTTCCGCTTTTTGATTTTTTATCTCTTTC<br>CTTTAAAAACTTCTTTACCTTAAAGGGCGGCC |
| 37 | Sequence of the PpPMA1 terminator: | TAAGCTTCACGATTTGTGTTCCAGTTTATCCCCCCTTTAT<br>ATACCGTTAACCCTTTCCCTGTTGAGCTGACTGTTGTTGT<br>ATTACCGCAATTTTTCCAAGTTTGCCATGCTTTTCGTGTT<br>ATTTGACCGATGTCTTTTTTCCCAAATCAAACTATATTTG<br>TTACCATTTAAACCAAGTTATCTTTTGTATTAAGAGTCT<br>AAGTTTGTTCCCAGGCTTCATGTGAGAGTGATAACCATC<br>CAGACTATGATTCTTGTTTTTTATTGGGTTTGTTTGTGTG<br>ATACATCTGAGTTGTGATTCGTAAAGTATGTCAGTCTAT<br>CTAGATTTTTAATAGTTAATTGGTAATCAATGACTTGTT<br>TGTTTTAACTTTTAAATTGTGGGTCGTATCCACGCGTTTA<br>GTATAGCTGTTCATGGCTGTTAGAGGAGGGCGATGTTTA<br>TATACAGAGGACAAGAATGAGGAGGCGGCGTGTATTTT<br>TAAAATGGAGACGCGACTCCTGTACACCTTATCGGTTGG |
| 38 | hGalT codon optimized (XB) | GGTAGAGATTTGTCTAGATTGCCACAGTTGGTTGGTGTT<br>TCCACTCCATTGCAAGGAGGTTCTAACTCTGCTGCTGCT<br>ATTGGTCAATCTTCCGGTGAGTTGAGAACTGGTGGAGCT<br>AGACCACCTCCACCATTGGGAGCTTCCTCTCAACCAAGA<br>CCAGGTGGTGATTCTTCTCCAGTTGTTGACTCTGGTCCA |

Table of Sequences

| SEQ ID NO: | Description | Sequence |
|---|---|---|
| | | GGTCCAGCTTCTAACTTGACTTCCGTTCCAGTTCCACAC<br>ACTACTGCTTTGTCCTTGCCAGCTTGTCCAGAAGAATCC<br>CCATTGTTGGTTGGTCCAATGTTGATCGAGTTCAACATG<br>CCAGTTGACTTGGAGTTGGTTGCTAAGCAGAACCCAAA<br>CGTTAAGATGGGTGGTAGATACGCTCCAAGAGACTGTG<br>TTTCCCCACACAAAGTTGCTATCATCATCCCATTCAGAA<br>ACAGACAGGAGCACTTGAAGTACTGGTTGTACTACTTG<br>CACCCAGTTTTGCAAAGACAGCAGTTGGACTACGGTAT<br>CTACGTTATCAACCAGGCTGGTGACACTATTTTCAACAG<br>AGCTAAGTTGTTGAATGTTGGTTTCCAGGAGGCTTTGAA<br>GGATTACGACTACACTTGTTTCGTTTTCTCCGACGTTGA<br>CTTGATTCCAATGAACGACCACAACGCTTACAGATGTTT<br>CTCCCAGCCAAGACACATTTCTGTTGCTATGGACAAGTT<br>CGGTTTCTCCTTGCCATACGTTCAATACTTCGGTGGTGTT<br>TCCGCTTTGTCCAAGCAGCAGTTCTTGACTATCAACGGT<br>TTCCCAAACAATTACTGGGGATGGGGTGGTGAAGATGA<br>CGACATCTTTAACAGATTGGTTTTCAGAGGAATGTCCAT<br>CTCTAGACCAAACGCTGTTGTTGGTAGATGTAGAATGAT<br>CAGACACTCCAGAGACAAGAAGAACGAGCCAAACCCA<br>CAAAGATTCGACAGAATCGCTCACACTAAGGAAACTAT<br>GTTGTCCGACGGATTGAACTCCTTGACTTACCAGGTTTT<br>GGACGTTCAGAGATACCCATTGTACACTCAGATCACTGT<br>TGACATCGGTACTCCATCCTAG |
| 39 | DNA encodes ScMnt1 (Kre2) (33) | ATGGCCCTCTTTCTCAGTAAGAGACTGTTGAGATTTACC<br>GTCATTGCAGGTGCGGTTATTGTTCTCCTCCTAACATTG<br>AATTCCAACAGTAGAACTCAGCAATATATTCCGAGTTCC<br>ATCTCCGCTGCATTTGATTTTACCTCAGGATCTATATCCC<br>CTGAACAACAAGTCATCGGGCGCGCC |
| 40 | DNA encodes DmUGT | ATGAATAGCATACACATGAACGCCAATACGCTGAAGTA<br>CATCAGCCTGCTGACGCTGACCCTGCAGAATGCCATCCT<br>GGGCCTCAGCATGCGCTACGCCCGCACCCGGCCAGGCG<br>ACATCTTCCTCAGCTCCACGGCCGTACTCATGGCAGAGT<br>TCGCCAAACTGATCACGTGCCTGTTCCTGGTCTTCAACG<br>AGGAGGGCAAGGATGCCCAGAAGTTTGTACGCTCGCTG<br>CACAAGACCATCATTGCGAATCCCATGGACACGCTGAA<br>GGTGTGCGTCCCCTCGCTGGTCTATATCGTTCAAAACAA<br>TCTGCTGTACGTCTCTGCCTCCCATTTGGATGCGGCCAC<br>CTACCAGGTGACGTACCAGCTGAAGATTCTCACCACGG<br>CCATGTTCGCGGTTGTCATTCTGCGCCGCAAGCTGCTGA<br>ACACGCAGTGGGTGCGCTGCTGCTCCTGGTGATGGGC<br>ATCGTCCTGGTGCAGTTGGCCCAAACGGAGGGTCCGAC<br>GAGTGGCTCAGCCGGTGGTGCCGCAGCTGCAGCCACGG<br>CCGCCTCCTCTGGCGGTGCTCCCGAGCAGAACAGGATG<br>CTCGGACTGTGGGCCGCACTGGGCGCCTGCTTCCTCTCC<br>GGATTCGCGGGCATCTACTTTGAGAAGATCCTCAAGGG<br>TGCCGAGATCTCCGTGTGGATGCGGAATGTGCAGTTGA<br>GTCTGCTCAGCATTCCCTTCGGCCTGCTCACCTGTTTCGT<br>TAACGACGGCAGTAGGATCTTCGACCAGGGATTCTTCA<br>AGGGCTACGATCTGTTTGTCTGGTACCTGGTCCTGCTGC<br>AGGCCGGCGGTGGATTGATCGTTGCCGTGGTGGTCAAG<br>TACGCGGATAACATTCTCAAGGGCTTCGCCACCTCGCTG<br>GCCATCATCATCTCGTGCGTGGCCTCCATATACATCTTC<br>GACTTCAATCTCACGCTGCAGTTCAGCTTCGGAGCTGGC<br>CTGGTCATCGCCTCCATATTTCTCTACGGCTACGATCCG<br>GCCAGGTCGGCGCCGAAGCCAACTATGCATGGTCCTGG<br>CGGCGATGAGGAGAAGCTGCTGCCGCGCGTCTAG |
| 41 | Sequence of the PpOCH1 promoter: | TGGACACAGGAGACTCAGAAACAGACACAGAGCGTTCT<br>GAGTCCTGGTGCTCCTGACGTAGGCCTAGAACAGGAAT<br>TATTGGCTTTATTTGTTTGTCCATTTCATAGGCTTGGGGT<br>AATAGATAGATGACAGAGAAATAGAGAAGACCTAATAT<br>TTTTTGTTCATGGCAAATCGCGGGTTCGCGGTCGGGTCA<br>CACACGGAGAAGTAATGAGAAGAGCTGGTAATCTGGGG<br>TAAAAGGGTTCAAAAGAAGGTCGCCTGGTAGGGATGCA<br>ATACAAGGTTGTCTTGGAGTTTACATTGACCAGATGATT<br>TGGCTTTTTCTCTGTTCAATTCACATTTTTCAGCGAGAAT<br>CGGATTGACGGAGAAATGGCGGGGTGTGGGGTGGATAG<br>ATGGCAGAAATGCTCGCAATCACCGCGAAAGAAAGACT<br>TTATGGAATAGAACTACTGGGTGGTGTAAGGATTACAT<br>AGCTAGTCCAATGGAGTCCGTTGGAAAGGTAAGAAGAA<br>GCTAAAACCGGCTAAGTAACTAGGGAAGAATGATCAGA<br>CTTTGATTTGATGAGGTCTGAAAATACTCTGCTGCTTTTT |

Table of Sequences

| SEQ ID NO: | Description | Sequence |
|---|---|---|
| | | CAGTTGCTTTTCCCTGCAACCTATCATTTTCCTTTTCAT AAGCCTGCCTTTTCTGTTTTCACTTATATGAGTTCCGCCG AGACTTCCCCAAATTCTCTCCTGGAACATTCTCTATCGC TCTCCTTCCAAGTTGCGCCCCCTGGCACTGCCTAGTAAT ATTACCACGCGACTTATATTCAGTTCCACAATTTCCAGT GTTCGTAGCAAATATCATCAGCC |
| 42 | Sequence of the PpALG12 terminator: | AATATATACCTCATTTGTTCAATTTGGTGTAAAGAGTGT GGCGGATAGACTTCTTGTAAATCAGGAAAGCTACAATT CCAATTGCTGCAAAAAATACCAATGCCCATAAACCAGT ATGAGCGGTGCCTTCGACGGATTGCTTACTTTCCGACCC TTTGTCGTTTGATTCTTCTGCCTTTGGTGAGTCAGTTTGT TTCGACTTTATATCTGACTCATCAACTTCCTTTACGGTTG CGTTTTTAATCATAATTTTAGCCGTTGGCTTATTATCCCT TGAGTTGGTAGGAGTTTTGATGATGCTG |
| 43 | Sequence of the 5'-Region used for knock out of PpHIS1: | TAACTGGCCCTTTGACGTTTCTGACAATAGTTCTAGAGG AGTCGTCCAAAAACTCAACTCTGACTTGGGTGACACCA CCACGGGATCCGGTTCTTCCGAGGACCTTGATGACCTTG GCTAATGTAACTGGAGTTTTAGTATCCATTTTAAGATGT GTGTTTCTGTAGGTTCTGGGTTGGAAAAAAATTTTAGAC ACCAGAAGAGAGGAGTGAACTGGTTTGCGTGGGTTTAG ACTGTGTAAGGCACTACTCTGTCGAAGTTTTAGATAGGG GTTACCCGCTCCGATGCATGGGAAGCGATTAGCCCGGC TGTTGCCCGTTTGGTTTTTGAAGGGTAATTTTCAATATCT CTGTTTGAGTCATCAATTTCATATTCAAAGATTCAAAAA CAAAATCTGGTCCAAGGAGCGCATTTAGGATTATGGAG TTGGCGAATCACTTGAACGATAGACTATTATTTGC |
| 44 | Sequence of the 3'-Region used for knock out of PpHIS1: | GTGACATTCTTGTCTTTGAGATCAGTAATTGTAGAGCAT AGATAGAATAATATTCAAGACCAACGGCTTCTCTTCGG AAGCTCCAAGTAGCTTATAGTGATGAGTACCGGCATAT ATTTATAGGCTTAAAATTTCGAGGGTTCACTATATTCGT TTAGTGGGAAGAGTTCCTTTCACTCTTGTTATCTATATTG TCAGCGTGGACTGTTTATAACTGTACCAACTTAGTTTCT TTCAACTCCAGGTTAAGAGACATAAATGTCCTTTGATGC TGACAATAATCAGTGGAATTCAAGGAAGGACAATCCCG ACCTCAATCTGTTCATTAATGAAGAGTTCGAATCGTCCT TAAATCAAGCGCTAGACTCAATTGTCAATGAGAACCCTT TCTTTGACCAAGAAACTATAAATAGATCGAATGACAAA GTTGGAAATGAGTCCATTAGCTTACATGATATTGAGCAG GCAGACCAAAATAAACCGTCCTTTGAGAGCGATATTGA TGGTTCGGCGCCGTTGATAAGAGACGACAAATTGCCAA AGAAACAAAGCTGGGGGCTGAGCAATTTTTTTTCAAGA AGAAATAGCATATGTTTACCACTACATGAAAATGATTC AAGTGTTGTTAAGACCGAAAGATCTATTGCAGTGGGAA CACCCCATCTTCAATACTGCTTCAATGGAATCTCCAATG CCAAGTACAATGCATTTACCTTTTTCCCAGTCATCCTAT ACGAGCAATTCAAATTTTTTTTCAATTTATACTTTACTTT AGTGGCTCTCTCTCAAGCGATACCGCAACTTCGCATTGG ATATCTTTCTTCGTATGTCGTCCCACTTTTGTTTGTACTC ATAGTGACCATGTCAAAAGAGGCGATGGATGATATTCA ACGCCGAAGAAGGGATAGAGAACAGAACAATGAACCA TATGAGGTTCTGTCCAGCCCATCACCAGTTTTGTCCAAA AACTTAAAATGTGGTCACTTGGTTCGATTGCATAAGGGA ATGAGAGTGCCCGCAGATATGGTTCTTGTCCAGTCAAGC GAATCCACCGGAGAGTCATTTATCAAGACAGATCAGCT GGATGGTGAGACTGATTGGAAGCTTCGGATTGTTTCTCC AGTTACACAATCGTTACCAATGACTGAACTTCAAAATGT CGCCATCACTGCAAGCGCACCCTCAAAATCAATTCACTC CTTTCTTGGAAGATTGACCTACAATGGGCAATCATATGG TCTTACGATAGACAACACAATGTGGTGTAATACTGTATT AGCTTCTGGTTCAGCAATTGGTTGTATAATTTACACAGG TAAAGATACTCGACAATCGATGAACACAACTCAGCCCA AACTGAAAACGGGCTTGTTAGAACTGGAAATCAATAGT TTGTCCAAGATCTTATGTGTTTGTGTGTTTGCATTATCTG TCATCTTAGTGCTATTCCAAGGAATAGCTGATGATTGGT ACGTCGATATCATGCGGTTTCTCATTCTATTCTCCACTAT TATCCCAGTGTCTCTGAGAGTTAACCTTGATCTTGGAAA GTCAGTCCATGCTCATCAAATAGAAACTGATAGCTCAAT ACCTGAAACCGTTGTTAGAACTAGTACAATACCGGAAG ACCTGGGAAGAATTGAATACCTATTAAGTGACAAAACT GGAACTCTTACTCAAAATGATATGGAAATGAAAAAACT ACACCTAGGAACAGTCTCTTATGCTGGTGATACCATGGA |

| SEQ ID NO: | Description | Sequence |
|---|---|---|
| | | TATTATTTCTGATCATGTTAAAGGTCTTAATAACGCTAA<br>AACATCGAGGAAAGATCTTGGTATGAGAATAAGAGATT<br>TGGTTACAACTCTGGCCATCTG |
| 45 | DNA encodes *Drosophila melanogaster* ManII codon-optimized (KD) | AGAGACGATCCAATTAGACCTCCATTGAAGGTTGCTAG<br>ATCCCCAAGACCAGGTCAATGTCAAGATGTTGTTCAGG<br>ACGTCCCAAACGTTGATGTCCAGATGTTGGAGTTGTACG<br>ATAGAATGTCCTTCAAGGACATTGATGGTGGTGTTTGGA<br>AGCAGGGTTGGAACATTAAGTACGATCCATTGAAGTAC<br>AACGCTCATCACAAGTTGAAGGTCTTCGTTGTCCCACAC<br>TCCCACAACGATCCTGGTTGGATTCAGACCTTCGAGGAA<br>TACTACCAGCACGACACCAAGCACATCTTGTCCAACGCT<br>TTGAGACATTTGCACGACAACCCAGAGATGAAGTTCAT<br>CTGGGCTGAAATCTCCTACTTCGCTAGATTCTACCACGA<br>TTTGGGTGAGAACAAGAAGTTGCAGATGAAGTCCATCG<br>TCAAGAACGGTCAGTTGGAATTCGTCACTGGTGGATGG<br>GTCATGCCAGACGAGGCTAACTCCCACTGGAGAAACGT<br>TTTGTTGCAGTTGACCGAAGGTCAAACTTGGTTGAAGCA<br>ATTCATGAACGTCACTCCAACTGCTTCCTGGGCTATCGA<br>TCCATTCGGACACTCTCCAACTATGCCATACATTTTGCA<br>GAAGTCTGGTTTCAAGAATATGTTGATCCAGAGAACCC<br>ACTACTCCGTTAAGAAGGAGTTGGCTCAACAGAGACAG<br>TTGGAGTTCTTGTGGAGACAGATCTGGGACAACAAAGG<br>TGACACTGCTTTGTTCACCCACATGATGCCATTCTACTC<br>TTACGACATTCCTCATACCTGTGGTCCAGATCCAAAGGT<br>TTGTTGTCAGTTCGATTTCAAAAGAATGGGTTCCTTCGG<br>TTTGTCTTGTCCATGGAAGGTTCCACCTAGAACTATCTC<br>TGATCAAAATGTTGCTGCTAGATCCGATTTGTTGGTTGA<br>TCAGTGGAAGAAGAAGGCTGAGTTGTACAGAACCAACG<br>TCTTGTTGATTCCATTGGGTGACGACTTCAGATTCAAGC<br>AGAACACCGAGTGGGATGTTCAGAGAGTCAACTACGAA<br>AGATTGTTCGAACACATCAACTCTCAGGCTCACTTCAAT<br>GTCCAGGCTCAGTTCGGTACTTTGCAGGAATACTTCGAT<br>GCTGTTCACCAGGCTGAAAGAGCTGGACAAGCTGAGTT<br>CCCAACCTTGTCTGGTGACTTCTTCACTTACGCTGATAG<br>ATCTGATAACTACTGGTCTGGTTACTACACTTCCAGACC<br>ATACCATAAGAGAATGGACAGAGTCTTGATGCACTACG<br>TTAGAGCTGCTGAAATGTTGTCCGCTTGGCACTCCTGGG<br>ACGGTATGGCTAGAATCGAGGAAAGATTGGAGCAGGCT<br>AGAAGAGAGTTGTCCTTGTTCCAGCACCACGACGGTATT<br>ACTGGTACTGCTAAAACTCACGTTGTCGTCGACTACGAG<br>CAAAGAATGCAGGAAGCTTTGAAAGCTTGTCAAATGGT<br>CATGCAACAGTCTGTCTACAGATTGTTGACTAAGCCATC<br>CATCTACTCTCCAGACTTCTCCTTCTCCTACTTCACTTTG<br>GACGACTCCAGATGGCCAGGTTCTGGTGTTGAGGACTCT<br>AGAACTACCATCATCTTGGGTGAGGATATCTTGCCATCC<br>AAGCATGTTGTCATGCACAACACCTTGCCACACTGGAG<br>AGAGCAGTTGGTTGACTTCTACGTCTCCTCTCCATTCGT<br>TTCTGTTACCGACTTGGCTAACAATCCAGTTGAGGCTCA<br>GGTTTCTCCAGTTTGGTCTTGGCACCACGACACTTTGAC<br>TAAGACTATCCACCCACAAGGTTCCACCACCAAGTACA<br>GAATCATCTTCAAGGCTAGAGTTCCACCAATGGGTTTGG<br>CTACCTACGTTTTGACCATCTCCGATTCCAAGCCAGAGC<br>ACACCTCCTACGCTTCCAATTTGTTGCTTAGAAAGAACC<br>CAACTTCCTTGCCATTGGGTCAATACCCAGAGGATGTCA<br>AGTTCGGTGATCCAAGAGAGATCTCCTTGAGAGTTGGT<br>AACGGTCCAACCTTGGCTTTCTCTGAGCAGGGTTTGTTG<br>AAGTCCATTCAGTTGACTCAGGATTCTCCACATGTTCCA<br>GTTCACTTCAAGTTCTTGAAGTACGGTGTTAGATCTCAT<br>GGTGATAGATCTGGTGCTTACTTGTTCTTGCCAAATGGT<br>CCAGCTTCTCCAGTCGAGTTGGGTCAGCCAGTTGTCTTG<br>GTCACTAAGGGTAAATTGGAGTCTTCCGTTTCTGTTGGT<br>TTGCCATCTGTCGTTCACCAGACCATCATGAGAGGTGGT<br>GCTCCAGAGATTAGAAATTTGGTCGATATTGGTTCTTTG<br>GACAACACTGAGATCGTCATGAGATTGGAGACTCATAT<br>CGACTCTGGTGATATCTTCTACACTGATTTGAATGGATT<br>GCAATTCATCAAGAGGAGAAGATTGGACAAGTTGCCAT<br>TGCAGGCTAACTACTACCCAATTCCATCTGGTATGTTCA<br>TTGAGGATGCTAATACCAGATTGACTTTGTTGACCGGTC<br>AACCATTGGGTGGATCTTCTTTGGCTTCTGGTGAGTTGG<br>AGATTATGCAAGATAGAAGATTGGCTTCTGATGATGAA<br>AGAGGTTTGGGTCAGGGTGTTTTGGACAACAAGCCAGT<br>TTTGCATATTTACAGATTGGTCTTGGAGAAGGTTAACAA<br>CTGTGTCAGACCATCTAAGTTGCATCCAGCTGGTTACTT |

Table of Sequences

| SEQ ID NO: | Description | Sequence |
|---|---|---|
| | | GACTTCTGCTGCTCACAAAGCTTCTCAGTCTTTGTTGGA<br>TCCATTGGACAAGTTCATCTTCGCTGAAAATGAGTGGAT<br>CGGTGCTCAGGGTCAATTCGGTGGTGATCATCCATCTGC<br>TAGAGAGGATTTGGATGTCTCTGTCATGAGAAGATTGA<br>CCAAGTCTTCTGCTAAAACCCAGAGAGTTGGTTACGTTT<br>TGCACAGAACCAATTTGATGCAATGTGGTACTCCAGAG<br>GAGCATACTCAGAAGTTGGATGTCTGTCACTTGTTGCCA<br>AATGTTGCTAGATGTGAGAGAACTACCTTGACTTTCTTG<br>CAGAATTTGGAGCACTTGGATGGTATGGTTGCTCCAGA<br>AGTTTGTCCAATGGAAACCGCTGCTTACGTCTCTTCTCA<br>CTCTTCTTGA |
| 46 | DNA encodes Mnn2 leader (53) | ATGCTGCTTACCAAAAGGTTTTCAAAGCTGTTCAAGCTG<br>ACGTTCATAGTTTTGATATTGTGCGGGCTGTTCGTCATT<br>ACAAACAAATACATGGATGAGAACACGTCG |
| 47 | Sequence of the PpHIS1 auxotrophic marker: | CAAGTTGCGTCCGGTATACGTAACGTCTCACGATGATCA<br>AAGATAATACTTAATCTTCATGGTCTACTGAATAACTCA<br>TTTAAACAATTGACTAATTGTACATTATATTGAACTTAT<br>GCATCCTATTAACGTAATCTTCTGGCTTCTCTCTCAGACT<br>CCATCAGACACAGAATATCGTTCTCTCTAACTGGTCCTT<br>TGACGTTTCTGACAATAGTTCTAGAGGAGTCGTCCAAAA<br>ACTCAACTCTGACTTGGGTGACACCACCACGGGATCCG<br>GTTCTTCCGAGGACCTTGATGACCTTGGCTAATGTAACT<br>GGAGTTTTAGTATCCATTTTAAGATGTGTGTTTCTGTAG<br>GTTCTGGGTTGGAAAAAAATTTTAGACACCAGAAGAGA<br>GGGAGTGAACTGGTTTGCGTGGGTTTAGACTGTGTAAGG<br>CACTACTCTGTCGAAGTTTTAGATAGGGGTTACCCGCTC<br>CGATGCATGGGAAGCGATTAGCCCGGCTGTTGCCCGTTT<br>GGTTTTTGAAGGGTAATTTTCAATATCTCTGTTTGAGTC<br>ATCAATTTCATATTCAAAGATTCAAAAACAAAATCTGGT<br>CCAAGGAGCGCATTTAGGATTATGGAGTTGGCGAATCA<br>CTTGAACGATAGACTATTATTTGCTGTTCCTAAAGAGGG<br>CAGATTGTATGAGAAATGCGTTGAATTACTTAGGGGAT<br>CAGATATTCAGTTTCGAAGATCCAGTAGATTGGATATAG<br>CTTTGTGCACTAACCTGCCCCTGGCATTGGTTTTCCTTCC<br>AGCTGCTGACATTCCCACGTTTGTAGGAGAGGGTAAAT<br>GTGATTTGGGTATAACTGGTATTGACCAGGTTCAGGAA<br>AGTGACGTAGATGTCATACCTTTATTAGACTTGAATTTC<br>GGTAAGTGCAAGTTGCAGATTCAAGTTCCCGAGAATGG<br>TGACTTGAAAGAACCTAAACAGCTAATTGGTAAAGAAA<br>TTGTTTCCTCCTTTACTAGCTTAACCACCAGGTACTTTGA<br>ACAACTGGAAGGAGTTAAGCCTGGTGAGCCACTAAAGA<br>CAAAAATCAAATATGTTGGAGGGTCTGTTGAGGCCTCTT<br>GTGCCCTAGGAGTTGCCGATGCTATTGTGGATCTTGTTG<br>AGAGTGGAGAAACCATGAAAGCGGCAGGGCTGATCGAT<br>ATTGAAACTGTTCTTTCTACTTCCGCTTACCTGATCTCTT<br>CGAAGCATCCTCAACACCCAGAACTGATGGATACTATC<br>AAGGAGAGAATTGAAGGTGTACTGACTGCTCAGAAGTA<br>TGTCTTGTGTAATTACAACGCACCTAGAGGTAACCTTCC<br>TCAGCTGCTAAAACTGACTCCAGGCAAGAGAGCTGCTA<br>CCGTTTCTCCATTAGATGAAGAAGATTGGGTGGGAGTGT<br>CCTCGATGGTAGAGAAGAAAGATGTTGGAAGAATCATG<br>GACGAATTAAAGAAACAAGGTGCCAGTGACATTCTTGT<br>CTTTGAGATCAGTAATTGTAGAGCATAGATAGAATAAT<br>ATTCAAGACCAACGGCTTCTCTTCGGAAGCTCCAAGTAG<br>CTTATAGTGATGAGTACCGGCATATATTTATAGGCTTAA<br>AATTTCGAGGGTTCACTATATTCGTTTAGTGGGAAGAGT<br>TCCTTTCACTCTTGTTATCTATATTGTCAGCGTGGACTGT<br>TTATAACTGTACCAACTTAGTTTCTTTCAACTCCAGGTT<br>AAGAGACATAAATGTCCTTTGATGC |
| 48 | DNA encodes Rat GnT II (TC) Codon-optimized | TCCTTGGTTTACCAATTGAACTTCGACCAGATGTTGAGA<br>AACGTTGACAAGGACGGTACTTGGTCTCCTGGTGAGTTG<br>GTTTTGGTTGTTCAGGTTCACAACAGACCAGAGTACTTG<br>AGATTGTTGATCGACTCCTTGAGAAAGGCTCAAGGTATC<br>AGAGAGGTTTTGGTTATCTTCCCCACGATTTCTGGTCT<br>GCTGAGATCAACTCCTTGATCTCCTCCGTTGACTTCTGT<br>CCAGTTTTGCAGGTTTCTTCCCATTCTCCATCCAATTGT<br>ACCCATCTGAGTTCCCAGGTTCTGATCCAAGAGACTGTC<br>CAAGAGACTTGAAGAAGAACGCTGCTTTGAAGTTGGGT<br>TGTATCAACGCTGAATACCCAGATTCTTTCGGTCACTAC<br>AGAGAGGCTAAGTTCTCCCAAACTAAGCATCATTGGTG |

| SEQ ID NO: | Description | Sequence |
|---|---|---|
|  |  | GTGGAAGTTGCACTTTGTTTGGGAGAGAGTTAAGGTTTT<br>GCAGGACTACACTGGATTGATCTTGTTCTTGGAGGAGG<br>ATCATTACTTGGCTCCAGACTTCTACCACGTTTTCAAGA<br>AGATGTGGAAGTTGAAGCAACAAGAGTGTCCAGGTTGT<br>GACGTTTTGTCCTTGGGAACTTACACTACTATCAGATCC<br>TTCTACGGTATCGCTGACAAGGTTGACGTTAAGACTTGG<br>AAGTCCACTGAACACAACATGGGATTGGCTTTGACTAG<br>AGATGCTTACCAGAAGTTGATCGAGTGTACTGACACTTT<br>CTGTACTTACGACGACTACAACTGGGACTGGACTTTGCA<br>GTACTTGACTTTGGCTTGTTTGCCAAAAGTTTGGAAGGT<br>TTTGGTTCCACAGGCTCCAAGAATTTTCCACGCTGGTGA<br>CTGTGGAATGCACCACAAGAAAACTTGTAGACCATCCA<br>CTCAGTCCGCTCAAATTGAGTCCTTGTTGAACAACAACA<br>AGCAGTACTTGTTCCCAGAGACTTTGGTTATCGGAGAGA<br>AGTTTCCAATGGCTGCTATTTCCCCACCAAGAAAGAATG<br>GTGGATGGGGTGATATTAGAGACCACGAGTTGTGTAAA<br>TCCTACAGAAGATTGCAGTAG |
| 49 | DNA encodes Mnn2 leader (54) The last 9 nucleotides are the linker containing the AscI restriction site) | ATGCTGCTTACCAAAAGGTTTTCAAAGCTGTTCAAGCTG<br>ACGTTCATAGTTTTGATATTGTGCGGGCTGTTCGTCATT<br>ACAAACAAATACATGGATGAGAACACGTCGGTCAAGGA<br>GTACAAGGAGTACTTAGACAGATATGTCCAGAGTTACT<br>CCAATAAGTATTCATCTTCCTCAGACGCCGCCAGCGCTG<br>ACGATTCAACCCCATTGAGGGACAATGATGAGGCAGGC<br>AATGAAAAGTTGAAAAGCTTCTACAACAACGTTTTCAA<br>CTTTCTAATGGTTGATTCGCCCGGGCGCGCC |
| 50 | Sequence of the 5'-Region used for knock out of PpARG1: | GATCTGGCCTTCCCTGAATTTTTACGTCCAGCTATACGA<br>TCCGTTGTGACTGTATTTCCTGAAATGAAGTTTCAACCT<br>AAAGTTTTGGTTGTACTTGCTCCACCTACCACGGAAACT<br>AATATCGAAACCAATGAAAAAGTAGAACTGGAATCGTC<br>AATCGAAATTCGCAACCAAGTGGAACCCAAAGACTTGA<br>ATCTTTCTAAAGTCTATTCTAGTGACACTAATGGCAACA<br>GAAGATTTGAGCTGACTTTTCAAATGAATCTCAATAATG<br>CAATATCAACATCAGACAATCAATGGGCTTTGTCTAGTG<br>ACACAGGATCAATTATAGTAGTGTCTTCTGCAGGAAGA<br>ATAACTTCCCCGATCCTAGAAGTCGGGGCATCCGTCTGT<br>GTCTTAAGATCGTACAACGAACACCTTTTGGCAATAACT<br>TGTGAAGGAACATGCTTTTCATGGAATTTAAAGAAGCA<br>AGAATGTGTTCTAAACAGCATTTCATTAGCACCTATAGT<br>CAATTCACACATGCTAGTTAAGAAAGTTGGAGATGCAA<br>GGAACTATTCTATTGTATCTGCCGAAGGAGACAACAAT<br>CCGTTACCCCAGATTCTAGACTGCGAACTTTCCAAAAAT<br>GGCGCTCCAATTGTGGCTCTTAGCACGAAAGACATCTAC<br>TCTTATTCAAAGAAAATGAAATGCTGGATCCATTTGATT<br>GATTCGAAATACTTTGAATTGTTGGGTGCTGACAATGCA<br>CTGTTTGAGTGTGTGGAAGCGCTAGAAGGTCCAATTGG<br>AATGCTAATTCATAGATTGGTAGATGAGTTCTTCCATGA<br>AAACACTGCCGGTAAAAAACTCAAACTTTACAACAAGC<br>GAGTACTGGAGGACCTTTCAAATTCACTTGAAGAACTA<br>GGTGAAAATGCGTCTCAATTAAGAGAGAAACTTGACAA<br>ACTCTATGGTGATGAGGTTGAGGCTTCTTGACCTCTTCT<br>CTCTATCTGCGTTTCTTTTTTTTTTTTTTTTTTTTTTTT<br>CAGTTGAGCCAGACCGCGCTAAACGCATACCAATTGCC<br>AAATCAGGCAATTGTGAGACAGTGGTAAAAAAGATGCC<br>TGCAAAGTTAGATTCACACAGTAAGAGAGATCCTACTC<br>ATAAATGAGGCGCTTATTTAGTAGCTAGTGATAGCCACT<br>GCGGTTCTGCTTTATGCTATTTGTTGTATGCCTTACTATC<br>TTTGTTTGGCTCCTTTTTCTTGACGTTTTCCGTTGGAGGG<br>ACTCCCTATTCTGAGTCATGAGCCGCACAGATTATCGCC<br>CAAAATTGACAAAATCTTCTGGCGAAAAAGTATAAAA<br>GGAGAAAAAGCTCACCCTTTTCCAGCGTAGAAAGTAT<br>ATATCAGTCATTGAAGAC |
| 51 | Sequence of the 3'-Region used for knock out of PpARG1: | GGGACTTTAACTCAAGTAAAAGGATAGTTGTACAATTA<br>TATATACGAAGAATAAATCATTACAAAAAGTATTCGTTT<br>CTTTGATTCTTAACAGGATTCATTTTCTGGGTGTCATCA<br>GGTACAGCGCTGAATATCTTGAAGTTAACATCGAGCTC<br>ATCATCGACGTTCATCACACTAGCCACGTTTCCGCAACG<br>GTAGCAATAATTAGGAGCGGACCACACAGTGACGACAT |

Table of Sequences

| SEQ ID NO: | Description | Sequence |
|---|---|---|
| | | CTTTCTCTTTGAAATGGTATCTGAAGCCTTCCATGACCA<br>ATTGATGGGCTCTAGCGATGAGTTGCAAGTTATTAATGT<br>GGTTGAACTCACGTGCTACTCGAGCACCGAATAACCAG<br>CCAGCTCCACGAGGAGAAACAGCCCAACTGTCGACTTC<br>ATCTGGGTCAGACCAAACCAAGTCACAAAATCCTCCTTC<br>ATGAGGGACCTCTTGCGCTCGGCTGAGAACTCTGATTTG<br>ATCTAACATGCGAATATCGGGAGAGAGACCACCATGGA<br>TACATAATATTTTACCATCAATGATGGCACTAAGGGTTA<br>AAAAGTCGAACACCTGGCAACAGTACTTCCAGACAGTG<br>GTGGAACCATATTTATTGAGACATTCCTCATAAAATCCA<br>TAAACCTGAGTGATCTGTCTGGATTCATGATTTCCCCTT<br>ACCAATGTGATATGTTGAGGAAACTTAATTTTTAAAATC<br>ATGAGTAACGTGAACGTCTCCAACGAGAAATAGCCTCT<br>ATCCACATAGTCTCCTAGGAAGATATAGTTCTGTTTTAT<br>TCCATTAGAGGAGGATCCGGGAAACCCACCACTAATCT<br>TGAAAAGTTCCAGTAGATCGTGAAATTGGCCGTGAATA<br>TCTCCGCATACTGTCACTGGACTCTGCACTGGCTGTATA<br>TTGGATTCCTCCATCAGCAAATCCTTCACCCGTTCGCAA<br>AGATGCTTCATATCATTTTCACTTAAAGCCTTGCAGCTT<br>TTGACTTCTTCAAACCACTGATCTGGTCCTCTTTCTGGCA<br>TGATTAAGGTCTATAATATTTCTGAGCTGAGATGTAAAA<br>AAAAATAATAAAAATGGGGAGTGAAAAAGTGTGTAGCT<br>TTTAGGAGTTTGGGATTGATACCCCAAAATGATCTTTAT<br>GAGAATTAAAAGGTAGATACGCTTTTAATAAGAACACC<br>TATCTATAGTACTTTGTGGTCTTGAGTAATTGAGATGTT<br>CAGCTTCTGAGGTTTGCCGTTATTCTGGGATAGTAGTGC<br>GCGACCAAACAACCCGCCAGGCAAAGTGTGTTGTGCTC<br>GAAGACGATTGCCAGAAGAGTAAGTCCGTCCTGCCTCA<br>GATGTTACACACTTTCTTCCCTAGACAGTCGATGCATCA<br>TCGGATTTAAACCTGAAACTTTGATGCCATGATACGCCT<br>AGTCACGTCGACTGAGATTTTAGATAAGCCCCGATCCCT<br>TTAGTACATTCCTGTTATCCATGGATGGAATGGCCTGATA |
| 52 | HYG$^R$ resistance cassette | GATCTGTTTAGCTTGCCTCGTCCCCGCCGGGTCACCCGG<br>CCAGCGACATGGAGGCCCAGAATACCCTCCTTGACAGT<br>CTTGACGTGCGCAGCTCAGGGGCATGATGTGACTGTCG<br>CCCGTACATTTAGCCCATACATCCCCATGTATAATCATT<br>TGCATCCATACATTTTGATGGCCGCACGGCGCGAAGCA<br>AAAATTACGGCTCCTCGCTGCGGACCTGCGAGCAGGGA<br>AACGCTCCCCTCACAGACGCGTTGAATTGTCCCCACGCC<br>GCGCCCCTGTAGAGAAATATAAAAGGTTAGGATTTGCC<br>ACTGAGGTTCTTCTTTCATATACTTCCTTTTAAAATCTTG<br>CTAGGATACAGTTCTCACATCACATCCGAACATAAACA<br>ACCATGGGTAAAAAGCCTGAACTCACCGCGACGTCTGT<br>CGAGAAGTTTCTGATCGAAAAGTTCGACAGCGTCTCCG<br>ACCTGATGCAGCTCTCGGAGGGCGAAGAATCTCGTGCT<br>TTCAGCTTCGATGTAGGAGGGCGTGGATATGTCCTGCGG<br>GTAAATAGCTGCGCCGATGGTTTCTACAAAGATCGTTAT<br>GTTTATCGGCACTTTGCATCGGCCGCGCTCCCGATTCCG<br>GAAGTGCTTGACATTGGGGAATTCAGCGAGAGCCTGAC<br>CTATTGCATCTCCCGCCGTGCACAGGGTGTCACGTTGCA<br>AGACCTGCCTGAAACCGAACTGCCCGCTGTTCTGCAGCC<br>GGTCGCGGAGGCCATGGATGCGATCGCTGCGGCCGATC<br>TTAGCCAGACGAGCGGGTTCGGCCCATTCGGACCGCAA<br>GGAATCGGTCAATACACTACATGGCGTGATTTCATATGC<br>GCGATTGCTGATCCCCATGTGTATCACTGGCAAACTGTG<br>ATGGACGACACCGTCAGTGCGTCCGTCGCGCAGGCTCT<br>CGATGAGCTGATGCTTTGGGCCGAGGACTGCCCCGAAG<br>TCCGGCACCTCGTGCACGCGGATTTCGGCTCCAACAATG<br>TCCTGACGGACAATGGCCGCATAACAGCGGTCATTGAC<br>TGGAGCGAGGCGATGTTCGGGATTCCCAATACGAGGT<br>CGCCAACATCTTCTTCTGGAGGCCGTGGTTGGCTTGTAT<br>GGAGCAGCAGACGCGCTACTTCGAGCGGAGGCATCCGG<br>AGCTTGCAGGATCGCCGCGGCTCCGGGCGTATATGCTCC<br>GCATTGGTCTTGACCAACTCTATCAGAGCTTGGTTGACG<br>GCAATTTCGATGATGCAGCTTGGGCGCAGGGTCGATGC<br>GACGCAATCGTCCGATCCGGAGCCGGGACTGTCGGGCG<br>TACACAAATCGCCCGCAGAAGCGCGGCCGTCTGGACCG<br>ATGGCTGTGTAGAAGTACTCGCCGATAGTGGAAACCGA<br>CGCCCCAGCACTCGTCCGAGGGCAAAGGAATAATCAGT<br>ACTGACAATAAAAAGATTCTTGTTTTCAAGAACTTGTCA<br>TTTGTATAGTTTTTTTTATATTGTAGTTGTTCTATTTTAAT<br>CAAATGTTAGCGTGATTTATATTTTTTTTCGCCTCGACAT<br>CATCTGCCCAGATGCGAAGTTAAGTGCGCAGAAAGTAA |

-continued

Table of Sequences

| SEQ ID NO: | Description | Sequence |
|---|---|---|
| | | TATCATGCGTCAATCGTATGTGAATGCTGGTCGCTATAC<br>TGCTGTCGATTCGATACTAACGCCGCCATCCAGTGTCGA<br>AAACGAGCT |
| 53 | *Ashbya gossypii* TEF1 promoter | GATCTGTTTAGCTTGCCTCGTCCCCGCCGGGTCACCCGG<br>CCAGCGACATGGAGGCCCAGAATACCCTCCTTGACAGT<br>CTTGACGTGCGCAGCTCAGGGGCATGATGTGACTGTCG<br>CCCGTACATTTAGCCCATACATCCCCATGTATAATCATT<br>TGCATCCATACATTTTGATGGCCGCACGGCGCGAAGCA<br>AAAATTACGGCTCCTCGCTGCAGACCTGCGAGCAGGGA<br>AACGCTCCCCTCACAGACGCGTTGAATTGTCCCCACGCC<br>GCGCCCCTGTAGAGAAATATAAAAGGTTAGGATTTGCC<br>ACTGAGGTTCTTCTTTCATATACTTCCTTTTAAAATCTTG<br>CTAGGATACAGTTCTCACATCACATCCGAACATAAACA<br>ACC |
| 54 | *Ashbya gossypii* TEF1 termination sequence | TAATCAGTACTGACAATAAAAAGATTCTTGTTTTCAAGA<br>ACTTGTCATTTGTATAGTTTTTTTATATTGTAGTTGTTCT<br>ATTTTAATCAAATGTTAGCGTGATTTATATTTTTTTTCGC<br>CTCGACATCATCTGCCCAGATGCGAAGTTAAGTGCGCA<br>GAAAGTAATATCATGCGTCAATCGTATGTGAATGCTGGT<br>CGCTATACTGCTGTCGATTCGATACTAACGCCGCCATCC<br>AGTGTCGAAAAC |
| 55 | SH512 | GAGACGATAGACGGTGAGGATTCAGAAGATCCTG |
| 56 | SH97 | GGGGAGAAGGTACCGAAGCCGGAG |
| 57 | SH515 | CCATACACCAGATGTATCTCAAAAATGTCAAC |
| 58 | SH379 | CATGCCCCTGAGCTGCGCACGTCAAG |
| 59 | SH520 | CAACTTGGCTCTGGGCTCGTTTGTATTG |
| 60 | SH521 | GGTGTCTTCAGGGAAGTTCTGAGCTATG |
| 61 | Pp AOX1 promoter | AACATCCAAAGACGAAAGGTTGAATGAAACCTTTTTGC<br>CATCCGACATCCACAGGTCCATTCTCACACATAAGTGCC<br>AAACGCAACAGGAGGGGATACACTAGCAGCAGACCGTT<br>GCAAACGCAGGACCTCCACTCCTCTTCTCCTCAACACCC<br>ACTTTTGCCATCGAAAAACCAGCCCAGTTATTGGGCTTG<br>ATTGGAGCTCGCTCATTCCAATTCCTTCTATTAGGCTAC<br>TAACACCATGACTTTATTAGCCTGTCTATCCTGGCCCCC<br>CTGGCGAGGTTCATGTTTGTTTATTTCCGAATGCAACAA<br>GCTCCGCATTACACCCGAACATCACTCCAGATGAGGGC<br>TTTCTGAGTGTGGGGTCAAATAGTTTCATGTTCCCCAAA<br>TGGCCCAAAACTGACAGTTTAAACGCTGTCTTGGAACCT<br>AATATGACAAAAGCGTGATCTCATCCAAGATGAACTAA<br>GTTTGGTTCGTTGAAATGCTAACGGCCAGTTGGTCAAAA<br>AGAAACTTCCAAAAGTCGGCATACCGTTTGTCTTGTTTG<br>GTATTGATTGACGAATGCTCAAAAATAATCTCATTAATG<br>CTTAGCGCAGTCTCTCTATCGCTTCTGAACCCCGGTGCA<br>CCTGTGCCGAAACGCAAATGGGGAAACACCCGCTTTTT<br>GGATGATTATGCATTGTCTCCACATTGTATGCTTCCAAG<br>ATTCTGGTGGGAATACTGCTGATAGCCTAACGTTCATGA<br>TCAAAATTTAACTGTTCTAACCCCTACTTGACAGCAATA<br>TATAAACAGAAGGAAGCTGCCCTGTCTTAAACCTTTTTT<br>TTTATCATCATTATTAGCTTACTTTCATAATTGCGACTGG<br>TTCCAATTGACAAGCTTTTGATTTTAACGACTTTTAACG<br>ACAACTTGAGAAGATCAAAAAACAACTAATTATTCGAA<br>ACG |
| 62 | Sequence of the Sh ble ORF (Zeocin resistance marker): | ATGGCCAAGTTGACCAGTGCCGTTCCGGTGCTCACCGCG<br>CGCGACGTCGCCGGAGCGGTCGAGTTCTGGACCGACCG<br>GCTCGGGTTCTCCCGGGACTTCGTGGAGGACGACTTCGC<br>CGGTGTGGTCCGGGACGACGTGACCCTGTTCATCAGCG<br>CGGTCCAGGACCAGGTGGTGCCGGACAACACCCTGGCC<br>TGGGTGTGGGTGCGCGGCCTGGACGAGCTGTACGCCGA<br>GTGGTCGGAGGTCGTGTCCACGAACTTCCGGGACGCCT<br>CCGGGCCGGCCATGACCGAGATCGGCGAGCAGCCGTGG<br>GGGCGGGAGTTCGCCCTGCGCGACCCGGCCGGCAACTG<br>CGTGCACTTCGTGGCCGAGGAGCAGGACTGA |

Table of Sequences

| SEQ ID NO: | Description | Sequence |
|---|---|---|
| 63 | ScTEF1 promoter | GATCCCCCACACACCATAGCTTCAAAATGTTTCTACTCC<br>TTTTTTACTCTTCCAGATTTTCTCGGACTCCGCGCATCGC<br>CGTACCACTTCAAAACACCCAAGCACAGCATACTAAAT<br>TTCCCCTCTTTCTTCCTCTAGGGTGTCGTTAATTACCCGT<br>ACTAAAGGTTTGGAAAAGAAAAAAGAGACCGCCTCGTT<br>TCTTTTTCTTCGTCGAAAAAGGCAATAAAAATTTTTATC<br>ACGTTTCTTTTTCTTGAAAATTTTTTTTTTTGATTTTTTC<br>TCTTTCGATGACCTCCCATTGATATTTAAGTTAATAAAC<br>GGTCTTCAATTTCTCAAGTTTCAGTTTCATTTTTCTTGTT<br>CTATTACAACTTTTTTTACTTCTTGCTCATTAGAAAGAA<br>AGCATAGCAATCTAATCTAAGTTTTAATTACAAA |
| 64 | PpTHR1 | GGCCAGCCCATCACCATGAATGCTTAAAACGCCAACTC<br>CTTCCATCTCATTTTCGTACCAGATTATGACTCTTAGGC<br>GGGGAGAATCCCGTCCAGCATAGCGAACATTTCTTTTTT<br>TTTTTTTTTTCGTTTCGCATCTCTCTATCGCATTCAGAAA<br>AAAATACATATAATTCTTCCAGTTTCCGTCATTCATTAC<br>GTTTAAAACTACGAAAGTTTTAGCTCTCTTTTGTTTTTGT<br>TTCCTAGATTCGAAATATTTTCTTTATTGAGTTTAATTTG<br>TGTGGCAGACAATGGTTAGATCTTTCACCATCAAAGTGC<br>CTGCTTCCTCAGCAAATATAGGACCGGGGTTTGACGTTC<br>TGGGAATTGGTCTCAACCTTTACTTGGAACTACAAGTCA<br>CCATTGATCCCAAAATTGATACCTCAAGCGATCCAGAA<br>AATGTGTTATTGTCGTATGAAGGTGAGGGGGCTGATGA<br>GGTGTCATTGAAAAGTGACGAAAACTTGATTACGCGCA<br>CAGCTCTCTATGTTCTACGTTGTGACGACGTCAGGACTT<br>TCCCTAAGGGAACCAAGATTCACGTCATTAACCCTATTC<br>CTCTAGGAAGAGGCTTGGGATCTTCGGGTGCTGCAGTTG<br>TCGCCGGTGCATTGCTCGGAAATTCCATCGGACAGCTTG<br>GATACTCCAAACAACGTTTACTGGATTACTGTTTGATGA<br>TAGAACGTCATCCAGATAACATCACCGCAGCTATGGTG<br>GGTGGTTTCGTTGGATCTTATCTTAGAGATCTTTCACCA<br>GAAGACACCCAGAGAAAAGAGATTCCATTAGCAGAAGT<br>CCTGCCAGAACCTCAAGGTGGTATTAACACCGGTCTCA<br>ACCCACCAGTGCCTCCAAAAAACATTGGGCACCACATC<br>AAATACGGCTGGGCAAAAGAGATCAAATGTATTGCCAT<br>TATTCCAGACTTTGAAGTATCAACCGCTTCATCTAGAGG<br>CGTTCTTCCAACCACTTACGAGAGACATGACATTATTTT<br>CAACCTGCAAAGGATAGCCGTTCTTACCACTGCCCTGAC<br>ACAATCTCCACCAGATCCAAGCTTGATATACCCAGCTAT<br>GCAGGACAGGATTCACCAACCTTACAGGAAAACTTTGA<br>TCCACGGACTGACTGAAATACTGTCTTCATTCACCCCAG<br>AATTACACAAAGGTTTGTTGGGAATCTGTCTTTCCGGTG<br>CTGGGCCCACAATATTAGCCCTCGCAACTGAAAACTTCG<br>ATCAGATTGCTAAGGACATCATTGCCAGATTTGCTGTCG<br>AAGACATCACCTGTAGTTGGAAACTCTTGACCCCAGCTC<br>TTGAAGGTTCTGTTGTTGAGGAGCTTGCTTAATAGAAAT<br>TAGAACATCCTCTTTAGATTATGATAATACGTTTTTAAC<br>TTTTCCCCTAACTGTAGTGATGGTATCGACCCTCTTAG<br>ACCTTAGGTTGGACCTTCTCGAATTTCCTGCCTCTATCA<br>AAAATCCGACCCTCGACATCGTTTACGTACTTTGCAACC<br>AATTAACTAGTACCGGCAGACGTTCAGTGATCATGGCTC<br>TCTATACAAATACCCTGATAACGTTTGCATTCCTGACAG<br>TCGGAGGATGTACGTGCTTATTTTCTTGCTAGTCCCAAA<br>TGTTTTGAGATTGCTCCAATCGTTTTTTCAACAATACTA<br>ACTGCCAACAAATAGATCTTTTATTCAACGGAAATGGG<br>GAACAATTCAACGTGGGTGACTTTTTGGAGACTACATCT<br>CCCTATATGTGGGCAAATCTGGGTATAGCAAGTTGCATT<br>GGATTCTCGGTCATTGGTGCTGCATGGGGAATTTTCATA<br>ACAGGTTCTTCGATCATCGGTGCAGGTGTCAAAGCTCCC<br>AGAATCACAACAAAAAATTTAATCTCCATCATTTTCTGT<br>GAGGTGGTGGCTATTTATGGGCTTATTATGGCC |
| 65 | PpTRP1 5' region and ORF | GCGGAAACGGCAGTAAACAATGGAGCTTCATTAGTGGG<br>TGTTATTATGGTCCCTGGCCGGGAACGAACGGTGAAAC<br>AAGAGGTTGCGAGGGAAATTTCGCAGATGGTGCGGGAA<br>AAGAGAATTTCAAAGGGCTCAAAATACTTGGATTCCAG<br>ACAACTGAGGAAAGAGTGGGACGACTGTCCTCTGGAAG<br>ACTGGTTTGAGTACAACGTGAAAGAAATAAACAGCAGT<br>GGTCCATTTTTAGTTGGAGTTTTTCGTAATCAAAGTATA<br>GATGAAATCCAGCAAGCTATCCACACTCATGGTTTGGAT<br>TTCGTCCAACTACATGGGTCTGAGGATTTTGATTCGTAT<br>ATACGCAATATCCCAGTTCCTGTGATTACCAGATACACA |

| SEQ ID NO: | Description | Sequence |
|---|---|---|
| | | GATAATGCCGTCGATGGTCTTACCGGAGAAGACCTCGC TATAAATAGGGCCCTGGTGCTACTGGACAGCGAGCAAG GAGGTGAAGGAAAAACCATCGATTGGGCTCGTGCACAA AAATTTGGAGAACGTAGAGGAAAATATTTACTAGCCGG AGGTTTGACACCTGATAATGTTGCTCATGCTCGATCTCA TACTGGCTGTATTGGTGTTGACGTCTCTGGTGGGGTAGA AACAAATGCCTCAAAAGATATGGACAAGATCACACAAT TTATCAGAAACGCTACATAA |
| 66 | PpTRP1 3' region | AAGTCAATTAAATACACGCTTGAAAGGACATTACATAG CTTTCGATTTAAGCAGAACCAGAAATGTAGAACCACTT GTCAATAGATTGGTCAATCTTAGCAGGAGCGGCTGGGC TAGCAGTTGGAACAGCAGAGGTTGCTGAAGGTGAGAAG GATGGAGTGGATTGCAAAGTGGTGTTGGTTAAGTCAAT CTCACCAGGGCTGGTTTTGCCAAAAATCAACTTCTCCCA GGCTTCACGGCATTCTTGAATGACCTCTTCTGCATACTT CTTGTTCTTGCATTCACCAGAGAAAGCAAACTGGTTCTC AGGTTTTCCATCAGGGATCTTGTAAATTCTGAACCATTC GTTGGTAGCTCTCAACAAGCCCGGCATGTGCTTTTCAAC ATCCTCGATGTCATTGAGCTTAGGAGCCAATGGGTCGTT GATGTCGATGACGATGACCTTCCAGTCAGTCTCTCCCTC ATCCAACAAAGCCATAACACCGAGGACCTTGACTTGCT TGACCTGTCCAGTGTAACCTACGGCTTCACCAATTTCGC AAACGTCCAATGGATCATTGTCACCCTTGGCCTTGGTCT CTGGATGAGTGACGTTAGGGTCTTCCCATGTCTGAGGGA AGGCACCGTAGTTGTGAATGTATCCGTGGTGAGGGAAA CAGTTACGAACGAAACGAAGTTTTCCCTTCTTTGTGTCC TGAAGAATTGGGTTCAGTTTCTCCTCCTTGGAAATCTCC AACTTGGCGTTGGTCCAACGGGGACTTCAACAACCAT GTTGAGAACCTTCTTGGATTCGTCAGCATAAAGTGGGAT GTCGTGGAAAGGAGATACGACTT |
| 67 | NatR expression cassette NatR ORF 494-1066 Ashbya gossypii TEF1 promoter 106-493 Ashbya gossypii TEF1 termination sequence 1067-1313 | GAGTTAGGTTCACATACGATTTAGGTGACACTATAGAA CGCGGCCGCCAGCTGAAGCTTCGTACGCTGCAGGTCGA CGGATCCCCGGGTTAATTAAGGCGCGCC<u>AGATCTGTTTA GCTTGCCTCGTCCCCGCCGGGTCACCCGGCCAGCGACAT GGAGGCCCAGAATACCCTCCTTGACAGTCTTGACGTGC GCAGCTCAGGGGCATGATGTGACTGTCGCCCGTACATTT AGCCCATACATCCCCATGTATAATCATTTGCATCCATAC ATTTTGATGGCCGCACGGCGCGAAGCAAAAATTACGGC TCCTCGCTGCAGACCTGCGAGCAGGGAAACGCTCCCCT CACAGACGCGTTGAATTGTCCCCACGCCGCGCCCCTGTA GAGAAATATAAAAGGTTAGGATTTGCCACTGAGGTTCT TCTTTCATATACTTCCTTTTAAAATCTTGCTAGGATACAG TTCTCACATCACATCCGAACATAAACAACCATGGGTACC</u> ACTCTTGACGACACGGCTTACCGGTACCGCACCAGTGTC CCGGGGGACGCCGAGGCCATCGAGGCACTGGATGGGTC CTTCACCACCGACACCGTCTTCCGCGTCACCGCCACCGG GGACGGCTTCACCCTGCGGGAGGTGCCGGTGGACCCGC CCCTGACCAAGGTGTTCCCCGACGACGAATCGGACGAC GAATCGGACGACGGGGAGGACGGCGACCCGGACTCCCG GACGTTCGTCGCGTACGGGGACGACGGCGACCTGGCGG GCTTCGTGGTCATCTCGTACTCGGCGTGGAACCGCCGGC TGACCGTCGAGGACATCGAGGTCGCCCCGGAGCACCGG GGGCACGGGGTCGGGCGCGCGTTGATGGGGCTCGCGAC GGAGTTCGCCGGCGAGCGGGGCGCCGGGCACCTCTGGC TGGAGGTCACCAACGTCAACGCACCGGCGATCCACGCG TACCGGCGGATGGGGTTCACCCTCTGCGGCCTGGACAC CGCCCTGTACGACGGCACCGCCTCGGACGGCGAGCGGC AGGCGCTCTACATGAGCATGCCCTGCCCCT<u>AATCAGTAC TGACAATAAAAAGATTCTTGTTTTCAAGAACTTGTCATT TGTATAGTTTTTTTATATTGTAGTTGTTCTATTTTAATCA AATGTTAGCGTGATTTATATTTTTTTTCGCCTCGACATCA TCTGCCCAGATGCGAAGTTAAGTGCGCAGAAAGTAATA TCATGCGTCAATCGTATGTGAATGCTGGTCGCTATACTG CTGTCGATTCGATACTAACGCCGCCATCCAGTGTCGAAA AC</u>GAGCTCGAATTCATCGATGATATCAGATCCACTAGTG GCCTATGCGGCCGCGGATCTGCCGGTCTCCCTATAGTGA GTCGTATTCAC |
| 68 | SH1406 | GTTTCGCGTTCTCACTTAGATGGAG |
| 69 | SH1420 | CCATTTCTCCGTCAATCCGATTCTCGC |

Table of Sequences

| SEQ ID NO: | Description | Sequence |
|---|---|---|
| 70 | SH1407 | CCACTCGCCAGATCGGAGCTGCAAACACTC |
| 71 | SH1421 | CCGCCCTGTACGACGGCACCGCCTC |
| 72 | SH1417 | CGAACCTTTTCCCCAACATATTTGGCAAACG |
| 73 | SH1418 | GCAAGGTGATGGTTCAAATCTCCAGCTCCAC |
| 74 | Pichia pastoris ATT1 5' region in pGLY5933 | GGCCGGGACTACATGAGGCCGATTCTTCAAGCCAGGGA<br>AATTAATTGCTTGAACCGGAAAATCATTAAGGCAGGCA<br>ACGAAAAATCCAACTCCTTGGTTGAATTGACTCAAAAG<br>TTTATCTTACGGAGAAAAGCTAAAGACATCAATACGAA<br>TTTCCTTCCGCCAAAAACTGAACTGATACTGATGGTTCC<br>AATGACTGAATTACAACAGGAGCTATACAAGGATATAA<br>TTGAAACTAACCAAGCCAAGCTTGGCTTGATCAACGAC<br>AGAAACTTTTTCTTCAAAAAATTTTGATTCTTCGTAAA<br>ATATGCAATTCACCCTCCCTGCTGAAAGACGAACCTGAT<br>TTTGCCAGATACAATCTCGGCAATAGATTCAATAGCGGT<br>AAGATCAAGCTAACAGTACTGCTTTTACGAAAGCTGTTT<br>GAAACCACCAATGAGAAGTGTGTGATTGTTTCAAACTTC<br>ACTAAAACTTTGGACGTACTTCAGCTAATCATAGAGCAC<br>AACAATTGGAAATACCACCGACTAGATGGTTCGAGTAA<br>AGGACGGGACAAATCGTACGAGATTTTAACGAGTCGC<br>CTCAAAAAGATCGATTCATCATGTTGCTTTCTTCCAAGG<br>CAGGGGAGTGGGGCTCAACTTAATTGGAGCCTCACGC<br>TTAATTCTTTTTGATAACGACTGGAATCCCAGTGTTGAC<br>ATTCAAGCAATGGCTAGAGTGCATCGAGACGGGCAGAA<br>AAGGCACACCTTTATCTATCGTTTGTATACGAAAGGCAC<br>AATTGACGAAAAGATCCTACAAAGGCAATTGATGAAAC<br>AAAATCTGAGCGACAAATTCCTGGATGATAATGATAGC<br>AGCAAGGATGATGTGTTTAACGACTACGATCTCAAAGA<br>TTTGTTTACTGTAGATCTTGACACGAATTGTAGTACACA<br>CGATTTGATGGAATGTTTATGTAATGGGCGGCTGAGAG<br>ATCCGACTCCCGTCTTGGAAGCAGAAGAATGCAAGACA<br>AAACCGTTGGAGGCCGTTGACGACACGGATGATGGTTG<br>GATGTCAGCTCTGGATTTCAAACAGTTATCACAAAAAG<br>AGGAGACAGGTGCTGTGTCAACAATGCGTCAATGTCTG<br>CTCGGATATCAACACATTGATCCAAAGATTTTGGAACCA<br>ACAGAACCTGTAGGGGACGATTTGGTATTGGCAAACAT<br>CCTCGCGGAGTCCTCAGGCTTGGCTAAATCTGCATTGTC<br>ATCTGAAAAGAAACCCAAGAAACCAGTGGTGAACTTTA<br>TCTTTGTGTCAGGCCAAGACTAAGCTGGAAGAACGGAA<br>CTTTAATCGAAGGAAAAATTAAATGTCAAAGTGGGTCG<br>ATCAGGAGATAATCCATGCTTCACGTGATTTTTCTTAAT<br>AAACGCCGGAAAACTTTCTTTTTTGTGACCAAAATTAT<br>CCGATCTGAAAAAAAATTACGCATGCGTGAAGTAGGAT<br>GAGAGACTTACTGTTGAACTTTGTGAGACGAGGGGAAA<br>AGGAATATCCTGATCGTAAACAAAAAGTTTTCCAGCC<br>CAATCGGGAACATCTGCGAAGTGTTGGAATTCAACCCC<br>TCTTTCGAAAATGTTCCATTTTACCCAAAATTATTGTTAT<br>TAAATAATACATGTGTTACTAGCAAAGTCTGCGCTTTCC<br>ATGTCTCAGATTCGGCAGATAACAAAGTTGACACGTTCT<br>TGCGAGATACGCATGAATCTTTTGGCTGCTTTTTGTGAA<br>AGAGAAATGGTGCCATATATTGCAGACGCCCCTGAAAG<br>ATTAGTGTGCGGCTGAGTCTTTTTTTTTTCTCAACCAGCT<br>TTTTCTTTTTATTGGGTACCATCGCGCACGCAGGACTCA<br>TGCTCCATTAGACTTCTGAACCACCTGACTTAATATTCA<br>TGGACGGACGCTTTTATCCTTAAATTGTTCATCCATTCCT<br>CAATTTTTCCGTTTGCCCTCCCTGTACTATTAAATTACAA<br>AAGCTGATCTTTTTCAAGTGTTTCTCTTTGAATCGCTC |
| 75 | Pichia pastoris ATT1 3' region in pGLY5933: | GGACCCTGAAGACGAAGACATGTCTGCCTTAGAGTTTA<br>CCGCAGTTCGATTCCCCAACTTTTCAGCTACGACAACAG<br>CCCCGCCTCCTACTCCAGTCAATTGCAACAGTCCTGAAA<br>ACATCAAGACCTCCACTGTGGACGATTTTTTGAAAGCTA<br>CTCAAGATCCAAATAACAAAGAGATACTCAACGACATT<br>TACAGTTTGATTTTGATGACTCCATGGATCCTATGAGC<br>TTCGGAAGTATGGAACCAAGAAACGATTTGGAAGTTCC<br>GGACACTATAATGGATTAATTTGCAGCGGGCCTGTTTGT<br>ATAGTCTTTGATTGTGTATAATAGAATTACTACGCGTAT<br>ATCCCGATCTGGAAGTAACATGGAAGTTTCCCATTTTCG<br>CGCAGTCTCCTACTCGTATCCTCCCCACCCCCTTACCGAT<br>GACGCAAAAGGTCACTAGATAAGCATAGCATAGTTTCA<br>TCCCTTGCTCTTTCCTTGTACCAACAGATCATGGCTGGG |

| SEQ ID NO: | Description | Sequence |
|---|---|---|
| | | AATCTCAAGGATATTCTATCCTTGTCGAGGAAGACAGC<br>AAGGAATCTGAAGCAGGCTCTGGATGAGCTTGCGGAGC<br>AGGTGATCAACCACCAACGGAGACGACCAGCTCTGGTC<br>CGAGTTCCTATCAACAACAACCTTAGGCGCAAGAGCCA<br>GCAGTCCTTTTTGAATCGCAGGTCATTCCATCTTTGGAC<br>CAGCAAGTACAACCCATACTTTTGGAGGGGAGGCAGAA<br>GCAACGTTCTGGACCAGCTTAACCGTGAAGCTTTAAGGT<br>ACAGATCGTCTTTTGCGAAACCCGGATTTTATCCAAGTG<br>GGCTGTATCAGTCAACTTTCCCTCAAAGAGGTAGTAGG<br>ATGTTTTCCACCTGCGCCTACTCATGTCAGCAGGAGGCA<br>GTCAAAAACTTGACTTCCGCTGTTCGTGCTTTGTTACAA<br>AGTGGTGCTAATTTCGGCAGTCAAATGAAACAAATGAA<br>ACACTGTTCGCAAAAGAAGAAGCACTTCTCTAAATTTTC<br>TAAGAGGCTTACTTCTTCCACTGCCGCTGGGTCTGGCAA<br>GAATGCTGAACAAGCTCCTTCTGGTTTGGCCGAAGGATC<br>CGCTGTTGTTTTAGCCTTGAACGTCAAAGTCACAATAC<br>TGAGTTGGAAGGAATCTTGGATCAAGAAACTTCTTCCAT<br>TCTCGAGGAAGAAATGGTTCAACATGAGCGTCACCTGG<br>CTATTATTAGAGAAGAAATCCAGAGAATTAGTGAGAAT<br>CTAGGATCATTACCATTAATCATGTCTGGTCACAAGATT<br>GAGGTATTTTTCCCCAATTGTGACACTGTTAAATGTGAG<br>CAACTGATGAGAGATTTGGCTATTACGAAAGGGGTTGT<br>GAGGCGTCATGATTCTACTGCTGAGCATTCAAGCTCCAG<br>GTCATTTGTTCCAGAAGATTGCTTGTATTCCTCAGGGTC<br>AAGTTCACCGAATCCTTTATCCTCAACTTCTTCGAAATC<br>ATTTGATAGAGTCTCATTGGACTACATTTCCTCTCGGTC<br>TACATCTGATCAAACCACTGGTTCTGAGTACACATCTCT<br>GTCTCAACAATATCACCTGGTTAGCAATTACAACCCTGT<br>ACTATCCTCAGCCCCGGGTTCTTCGAGGGTCTTGGAGCT<br>GAATACTCCCGAGTCCACTATGGAAGGCAGTACAGATC<br>TGGAGTATTTAACGCGAGACGATGTGTTGCTGTTAAATG<br>TCTAATCTAGACCTATCCTTCATTCTATATAGCTTAGTTG<br>AGTTTTACGTAAGCCCTAGTTTTTGTTAATTCTTATCGAT<br>TTATGGTTAGTGTACCACTCAACTCACGATGATATATCC<br>CAGGAGCTGTTTGTGCATTATAACTACCAATCCT |
| 76 | ORF encoding *Pichia pastoris* Vrg4p | ATGGCTGACAAAGGATCGGTAGCGGCTAAATCGCTTAC<br>CAACTCTGCACCCTTATCCATCTTTTCTTACTGTGCTGCA<br>TCAATTCTGATGACAGTTACCAATAAGTATGCCGTGTCC<br>GGTGTCGATTTCAACTTTAACTTCTTTTTGCTTGCCGTTC<br>AGGGAATCGTTTGTATTACCTTGATTAGCTCGTTGAAGC<br>AATTGAATGTTATCACCTTTAGAGAGTTCAACAAGGTTG<br>AAGCAAAGAAATGGTTCCCAATCGCCGTGCTGTTAGTT<br>GTCATGATTTATACCTCCTCCAAGGCTCTACAGTATCTG<br>AGCATTCCAATTTACACGATATTCAAAAACTTGACCATT<br>ATCCTTATTGCTTATGGTGAAGTCATCTGGTTCGGAGGC<br>CGTGTGACCAACTTGGCTCTGGGCTCGTTTGTATTGATG<br>GTGCTCTCCTCTGCAGTGGCTTCTTATGGTGATTCTAAT<br>GTTGACACTGGTAAACTCAATTTTAACATTGGCTATTTC<br>TGGATGTTCACCAACTGTTTCTCCTCTGCCGCATTTGTGT<br>TGTTCATGAGAAAGAGAATAAAGTTGACCAACTTCAAA<br>GACTTTGACACCATGTATTACAACAACCTTCTCTCCATT<br>CCAATTTTGCTCTTTGCATCTTTGACTACTGAAGACTGG<br>TCCGCTAAAAACATAGCTCAGAACTTCCCTGAAGACAC<br>CAAATACGCTGTCATCGCTTCCATGATTATTTCAGGAAT<br>GTCTGCCGTGGGTATCTCATACACATCTGCATGGTGTGT<br>CCGTGTGACATCTTCCACGACATACTCGATGGTTGGTGC<br>TTTGAACAAGCTTCCAATTGCCCTGTCTGGTTTGCTATTT<br>TTCAAGGCTCCTATCAACTTCTATTCTATCAGCTCTATCT<br>TTATTGGTTTTGCCGCTGGTCTAGTCTATGCCATTGCCA<br>AGCAGAAGCAAAAGAAGGAAGACGAGTTGCAGTTACC<br>AACTGACAAGAGC |
| 77 | *Pichia pastoris* Vrg4p | MADKGSVAAKSLTNSAPLSIFSYCAASILMTVTNKYAVSG<br>VDFNFNFFLLAVQGIVCITLISSLKQLNVITFREFNKVEAKK<br>WFPIAVLLVVMIYTSSKALQYLSIPIYTIFKNLTIILIAYGEVI<br>WFGGRVTNLALGSFVLMVLSSAVASYGDSNVDTGKLNFN<br>IGYFWMFTNCFSSAAFVLFMRKRIKLTNFKDFDTMYYNNL<br>LSIPILLFASLTTEDWSAKNIAQNFPEDTKYAVIASMIISGM |

| Table of Sequences | | |
|---|---|---|
| SEQ ID NO: | Description | Sequence |
| | | SAVGISYTSAWCVRVTSSTTYSMVGALNKLPIALSGLLFFK<br>APINFYSISSIFIGFAAGLVYAIAKQKQKKEDELQLPTDKS |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A *Pichia pastoris* host cell comprising:
   (a) a disruption of Vanadate Resistance Glycosylation (VRG4) gene expression and Acquired Thermo-Tolerance (ATT1) gene expression; and
   (b) a nucleic acid molecule encoding a recombinant glycoprotein, wherein the host cell is viable.

2. The host cell of claim 1, wherein the host cell further includes a disruption of Outer Chain 1 (OCH1) gene expression.

3. The host cell of claim 1, wherein the host cell has been genetically engineered to produce human-like N- and/or O-glycans.

4. A method for producing a recombinant glycoprotein in a *Pichia pastoris* host cell comprising:
   expressing a nucleic acid molecule encoding the recombinant glycoprotein in a *Pichia pastoris* host cell in which expression of the Vanadate Resistance Glycosylation (VRG4) gene encoding the GDP-mannose transmembrane transporter and the gene encoding Acquired Thermo-Tolerance (ATT1) have been disrupted.

5. The method of claim 4, wherein the host cell further includes a disruption of Outer Chain 1 (OCH1) gene expression.

6. The method of claim 4, wherein the host cell has been genetically engineered to produce human-like N- and/or O-glycans.

7. A method for reducing the amount of phosphomannosylation of N- and O-glycans of a recombinant glycoprotein produced in a *Pichia pastoris* host cell comprising:
   expressing a nucleic acid molecule encoding the recombinant glycoprotein in a *Pichia pastoris* host cell in which expression of the Vanadate Resistance Glycosylation (VRG4) gene encoding the GDP-mannose transmembrane transporter and the gene encoding Acquired Thermo-Tolerance (ATT1) have been disrupted,
   wherein the amount of phosphomanosylation is less than the phosphomannosylation on the recombinant glycoprotein produced in a *Pichia pastoris* host cell that expresses the GDP-mannose transmembrane transporter.

8. The method of claim 7, wherein the host cell further includes a disruption of Outer Chain 1 (OCH 1) gene expression.

9. The method of claim 7, wherein the host cell has been genetically engineered to produce human-like N- and/or O-glycans.

10. A method for reducing the amount of α-linked mannose on a recombinant glycoprotein produced in a *Pichia pastoris* host cell comprising:
    expressing a nucleic acid molecule encoding the recombinant glycoprotein in a *Pichia pastoris* host cell in which expression of the Vanadate Resistance Glycosylation (VRG4) gene encoding the GDP-mannose transmembrane transporter and the gene encoding Acquired Thermo-Tolerance (ATT1) have been disrupted, wherein the amount of α-linked mannose is less than the amount of α-linked mannose on the recombinant glycoprotein produced in a *Pichia pastoris* host cell that expresses the GDP-mannose transmembrane transporter.

11. The method of claim 10, wherein the host cell further includes a disruption of Outer Chain 1 (OCH1) gene expression.

12. The method of claim 10, wherein the host cell has been genetically engineered to produce human-like N-glycans.

13. A method for reducing the amount of β-linked mannose on a recombinant glycoprotein produced in a *Pichia pastoris* host cell comprising:

expressing a nucleic acid molecule encoding the recombinant glycoprotein in a *Pichia pastoris* host cell in which expression of the Vanadate Resistance Glycosylation (VRG4) gene encoding the GDP-mannose transmembrane transporter and the gene encoding Acquired Thermo-Tolerance (ATT1) have been disrupted, wherein the amount of β-linked mannose is less than the amount of β-linked mannose on the recombinant glycoprotein produced in a *Pichia pastoris* host cell that expresses the GDP-mannose transmembrane transporter.

14. The method of claim 13, wherein the host cell further includes a disruption of Outer Chain 1 (OCH1) gene expression.

15. The method of claim 13, wherein the host cell has been genetically engineered to produce human-like N-glycans.

* * * * *